US010428362B2

(12) United States Patent
Nagy et al.

(10) Patent No.: US 10,428,362 B2
(45) Date of Patent: *Oct. 1, 2019

(54) ENZYMATIC HYDROLYSIS OF DISACCHARIDES AND OLIGOSACCHARIDES USING ALPHA-GLUCOSIDASE ENZYMES

(71) Applicant: E I DU PONT DE NEMOURS AND COMPANY, Wilmington, DE (US)

(72) Inventors: Kevin D. Nagy, Wilmington, DE (US); Erwin F. Columbus-Hago, Sunnyvale, CA (US); Jayarama K. Shetty, Palo Alto, CA (US); Susan Marie Hennessey, Avondale, PA (US); Robert Dicosimo, Chadds Ford, PA (US); Ling Hua, Hockessin, DE (US); Rodrigo Ramirez, Campinas (BR); Zhongmei Tang, Shanghai (CN); Zheyong Yu, Shanghai (CN)

(73) Assignee: E. I. DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,246

(22) Filed: May 10, 2018

(65) Prior Publication Data
US 2018/0273999 A1    Sep. 27, 2018

Related U.S. Application Data

(63) Continuation of application No. 14/631,931, filed on Feb. 26, 2015, now Pat. No. 9,982,284.

(60) Provisional application No. 62/004,290, filed on May 29, 2014, provisional application No. 62/004,300, filed on May 29, 2014, provisional application No. 62/004,305, filed on May 29, 2014, provisional application No. 62/004,308, filed on May 29, 2014, provisional application No. 61/945,233, filed on Feb. 27, 2014, provisional application No. 61/945,241, filed on Feb. 27, 2014, provisional application No. 62/004,312, filed on May 29, 2014, provisional application No. 62/004,314, filed on May 29, 2014.

(30) Foreign Application Priority Data

Feb. 25, 2015 (WO) ................ PCT/CN2015/073269

(51) Int. Cl.
| | |
|---|---|
| C12P 19/14 | (2006.01) |
| C12P 7/14 | (2006.01) |
| C12P 19/02 | (2006.01) |
| C12P 19/18 | (2006.01) |
| C12P 19/04 | (2006.01) |
| C12P 19/16 | (2006.01) |
| C12P 7/06 | (2006.01) |

(52) U.S. Cl.
CPC ................ *C12P 19/14* (2013.01); *C12P 7/06* (2013.01); *C12P 7/14* (2013.01); *C12P 19/02* (2013.01); *C12P 19/04* (2013.01); *C12P 19/16* (2013.01); *C12P 19/18* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,247,637 A | 1/1981 | Tamura et al. | |
| 4,618,579 A | 10/1986 | Dwiggins et al. | |
| 4,689,296 A | 8/1987 | Chiang et al. | |
| 4,713,333 A | 12/1987 | Chiang et al. | |
| 4,794,175 A | 12/1988 | Nunberg et al. | |
| 4,863,864 A | 9/1989 | Ashikari et al. | |
| 5,024,941 A | 6/1991 | Maine et al. | |
| 5,141,858 A | 8/1992 | Paul et al. | |
| 5,541,097 A * | 7/1996 | Lantero .................. | C12N 11/14 435/175 |
| 5,763,252 A | 6/1998 | Skadsen et al. | |
| 5,770,437 A | 6/1998 | Lantero et al. | |
| 5,795,766 A | 8/1998 | Suzuki et al. | |
| 5,922,580 A | 7/1999 | Maruta et al. | |
| 5,952,205 A | 9/1999 | Catani et al. | |
| 6,242,225 B1 | 6/2001 | Catani et al. | |
| 6,255,084 B1 | 7/2001 | Nielsen et al. | |
| 6,355,467 B1 | 3/2002 | Kelly et al. | |
| 6,660,502 B2 | 12/2003 | Catani et al. | |
| 7,000,000 B1 | 2/2006 | O'Brien | |
| 7,413,887 B2 | 8/2008 | Dunn-Coleman et al. | |
| 7,638,151 B2 | 12/2009 | Duan et al. | |
| 8,633,006 B2 | 1/2014 | Otani et al. | |

(Continued)

FOREIGN PATENT DOCUMENTS

| | | |
|---|---|---|
| EP | 2292803 B1 | 2/2013 |
| JP | 4595074 B2 | 12/2010 |

(Continued)

OTHER PUBLICATIONS

Shiroza T et al. Sequence analysis of the gtfB gene from *Streptococcus mutans*. 1987. Journal of Bacteriology. vol. 169, No. 9. p. 4263-4270. (Year: 1987).*

(Continued)

*Primary Examiner* — Paul J Holland

(57) ABSTRACT

A method is disclosed for hydrolyzing an alpha-1,5 glucosyl-fructose linkage in a saccharide (disaccharide or oligosaccharide) such as leucrose. This method comprises contacting the saccharide with an alpha-glucosidase enzyme such as transglucosidase or glucoamylase under suitable conditions, during which contacting step the enzyme hydrolyzes at least one alpha-1,5 glucosyl-fructose linkage of the saccharide. This method is useful for reducing the amount of leucrose in a filtrate isolated from a glucan synthesis reaction, for example.

17 Claims, 2 Drawing Sheets

Figure 1:
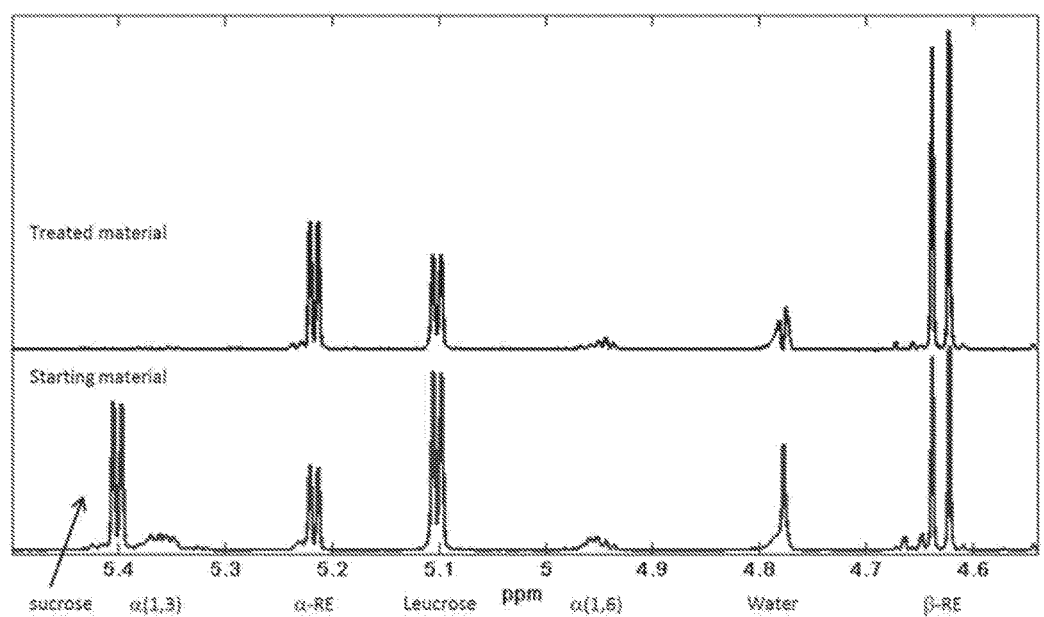

Specification includes a Sequence Listing.

(56) References Cited

U.S. PATENT DOCUMENTS

| | | |
|---|---|---|
| 2003/0167929 A1 | 9/2003 | Brier et al. |
| 2008/0229514 A1 | 9/2008 | Poulose et al. |
| 2011/0076240 A1 | 3/2011 | Day |
| 2011/0136197 A1 | 6/2011 | Dodge et al. |
| 2011/0201059 A1 | 8/2011 | Hall et al. |
| 2013/0102035 A1 | 4/2013 | Degn et al. |
| 2013/0244288 A1 | 9/2013 | O'Brien et al. |
| 2013/0323822 A1 | 12/2013 | Brevnova et al. |
| 2014/0087431 A1 | 3/2014 | Payne et al. |

FOREIGN PATENT DOCUMENTS

| | | |
|---|---|---|
| WO | 2005001036 A2 | 1/2005 |
| WO | 2006028897 A2 | 3/2006 |
| WO | 2013036918 A2 | 3/2013 |
| WO | 2013096511 A1 | 6/2013 |

OTHER PUBLICATIONS

Fukui K et al. Purification and Properties of Glucosyltransferase Responsible for Water-Insoluble Glucan Synthesis from *Streptococcus mutans*. 1982. Infection and Immunity. vol. 37, No. 1. p. 1-9 (Year: 1982).*

Related U.S. Appl. No. 14/631,962, Nagy et al.), filed Feb. 26, 2015.

Corresponding PCT Application No. PCT/US2015/017648, filed Feb. 26, 2015.

Related PCT Application No. PCT/US2015/017644 filed Feb. 26, 2015.

Danisco Technical Brochure, Transglucosylation of Malto-Oligosacharides, Process for Producing Isomalto-Oligosaccharides, A New Class of Oligosaccharides, 12 Pages Total, Published Before Feb. 2014 (Actual Publication Date Unknown).

Abo et al., Peptide Sequences for Sucrose Splitting and Glucan Binding Within *Streptococcus sobrinus* Glucosyltransferase (Water-Insoluble Glucan Synthetase), Journal of Bacteriology, vol. 173, No. 3 (1991), pp. 989-996.

Alarico et al., Molecular and Physiological Role of the Trehalose-Hydrolyzing α-Glucosidase From Thermus Thermophilus HB27, Journal of Bacteriology, vol. 190, No. 7 (2008), pp. 2298-2305.

Anindyawati et al., Synthesis of Novel Oligosaccharides From Leucrose by an α-Glucosidase, Bioscience, Biotechnology and Biochemistry, vol. 59, No. 11 (1995), pp. 2146-2148.

Ashikari et al., Rhizopus Raw-Starch-Degrading Glucoamylase: Its Cloning and Expression in Yeast, Agric. Biol. Chem., vol. 50, No. 4 (1986), pp. 957-964.

Ashikari et al., Direct Fermentation of Raw Corn to Ethanol by Yeast Transformants Containing a Modified Rhizopus Glucoamylase Gene, Appl. Microbiol. Biotechnol., vol. 32 (1989), pp. 129-133.

Boel et al., Glucoamylases G1 and G2 From Aspergillus niger Are Synthesized From Two Different but Closely Related MRNAS, The EMBO Journal, vol. 3, No. 5 (1984), pp. 1097-1102.

Cantarel et al., The Carbohydrate-Active Enzymes Database (CAZY): An Expert Resource for Glycogenomics, Published On-Line, Nucleic Acids Research, vol. 37 (2009), Database Issue D233-238.

Cote et al., Some Structural Features of an Insoluble α-D-Glucan From a Mutant Strain of Leuconostoc Mesenteroides NRRL B-1355, Journal of Industrial Microbiology & Biotechnology, vol. 23 (1999), pp. 656-660.

Cote et al., Isolation and Partial Characterization of an Extracellular Glucansucrase From Leuconostoc Mesenteroides NRRL B-1355 That Synthesizes an Alternating (1-->6), (1->3)-α-D-Glucan, Carbohydrate Research, vol. 101 (1982), pp. 57-74.

Fleetwood et al., Chemistry: Substrate Cleavage Point With Glucamylase, Nature, vol. 196 (1962), p. 984.

Giffard et al., Molecular Characterization of a Cluster of at Least Two Glucosyltransferase Genes in *Streptococcus salivarius* ATCC 25975, Journal of Gneeral Microbiology, vol. 137 (1991), pp. 2577-2593.

Gunther et al., Di- and Oligosaccharide Substrate Specificities and Subsite Binding Energies of Pig Intestinal Glucoamylase-Maltase, Arches of Biochemistry and Biophysics, vol. 354, No. 1 (1998), pp. 111-116.

Hayashida et al., Molecular Cloning of the Glucoamylase 1 Gene of Aspergillus awamori var. *kawachi* for Localization of the Raw-Starch-Affinity Site, Agric. Biol. Chem., vol. 53, No. 4 (1989), pp. 923-929.

Hodoniczky et al., Oral and Intestinal Digestion of Oligosaccharides as Potential Sweeteners: A Systematic Evaluation, Food Chemistry, vol. 132 (2012), pp. 1951-1958.

Houghton-Larsen et al., Cloning and Characterization of a Glucoamylase Gene (GLAM) From the Dimorphic Zygomycete Mucor Circinelloides, Appl. Microbiol. Biotechnol., vol. 62 (2003), pp. 210-217.

Iizuka et al., Susceptibility of Leucrose to Carbohydrases, Journal of Fermentation and Bioengineering, vol. 70, No. 4 (1990), pp. 277-279.

Jeanes et al., Characterization and Classification of Dextrans From Ninety-Six Strains of Bacteria, Contribution From the Starch and Dextrose Section, Northern Utilization Research Branch, vol. 76 (1954), pp. 5041-5052.

Joucla et al., Construction of a Fully Active Truncated Alternansucrase Partially Deleted of its Carboxy-Terminal Domain, FEBS Letters, vol. 580 (2006), pp. 763-768.

Konishi et al., Structure and Enzymatic Properties of Genetically Truncated Forms of the Water-Insoluble Glucan-Synthesizing Glucosyltransferase From *Streptococcus sobrinus*, J. Biochem., vol. 126 (1999), pp. 287-295.

Kingston et al., Role of the C-Terminal YG Repeats of the Primer-Dependent Streptococcal Glucosyltransferase, GTFJ, in Binding to Dextran and Mutan, Microbiology, vol. 148 (2002), pp. 549-558.

Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.

Misaki et al., Structure of the Dextran of Leuconostoc Mesenteroides B-1355, Carbohydrate Research, vol. 84 (1980), pp. 273-285.

Monchois et al., Glucansucrases: Mechanism of Action and Structure-Function Relationships, FEMS Microbiology Reviews, vol. 23 (1999), pp. 131-151.

Monchois et al., Cloning and Sequencing of a Gene Coding for a Novel Dextransucrase From Leuconostoc Mesenteroides NRRL B-1299 Synthesizing Only α(1-6) and α(1-3) Linkages, Gene, vol. 182 (1996), pp. 23-32.

Monchois et al., Isolation of an Active Catalytic Core of *Streptococcus downei* MFE28 GTF-I Glucosyltransferase, Journal of Bacteriology, vol. 181, No. 7 (1999), pp. 2290-2292.

Nakamura et al., Cloning and Sequencing of an α-Glucosidase Gene From Aspergillus niger and its Expression in A. nidulans, Journal of Biotechnology, vol. 53 (1997), pp. 75-84.

Pazur et al., Communications to the Editor: The Transglucosidase of Aspergillus oryzae, J. Amer. Chem. Soc., vol. 73 (1951), p. 3536.

Pazur et al., The Glycoprotein Nature and Antigenicity of a Fungal D-Glucosyltransferase, Carbohydrate Research, vol. 149 (1986), pp. 137-147.

Pazur et al., The Hydrolysis of Glucosyl Oligosaccharides With α-D-(1-->4) and α-D-(1-->6) Bonds by Fungal Amyloglucosidase, The Journal of Biological Chemistry, vol. 235, No. 2 (1960), pp. 297-302.

Peltroche-Llacsahuanga et al., Assessment of Acid Production by Various Human Oral Micro-Organisms When Palatinose or Leucrose is Utilized, J. Dent. Res., vol. 80, No. 1 (2001), pp. 378-384.

Pokusaeva et al., Characterization of Two Novel α-Glucosidases From Bifidobacterium Breve UCC2003, Applied and Environmental Microbiology, vol. 75, No. 4 (2009), pp. 1135-1143.

Remaud-Simeon et al., Production and Use of Glucosyltransferases From Leuconostoc Mesenteroides NRRL B-1299 for the Synthesis of Oligosaccharides Containing α-(1-->2) Linkages, Applied Biochemistry and Biotechnology, vol. 44 (1994), pp. 101-117.

Rutloff et al., Zur Enzymatischen Spaltung Von Leucrose [Enzymatic Cleavage of Leucrose], Naturwissenschaften, vol. 51, No. 7 (1964), p. 163. (English translation provided in parent U.S. Appl. No. 14/631,931).

(56) References Cited

OTHER PUBLICATIONS

Simpson et al., Four Glucosyltransferases, GTFJ, GTFK, GTFL, and GTFM, From *Streptococcus salivarius* ATCC 25975, Microbiology, vol. 141 (1995), pp. 1451-1460.
Van Den Broek et al., Cloning and Characterization of Two α-Glucosidases From Bifidobacterium Adolescentis DSM20083, Appl. Microbiol. Biotechnol., vol. 61 (2003), pp. 55-60.
Yoshimi et al., Functional Analysis of the α-1,3-Glucan Synthase Genes AGSA and AGSB in Aspergillus nidulans: AGSB is the Major α-1,3-Glucan Synthase in This Fungus, PloS One, vol. 8, No. 1 (2013), ES4893, pp. 1-16.
Ziesenitz et al., Nutritional Assessment in Humans and Rats of Leucrose [D-Glucopyranosyl-α(1-->5)-D-Fructopyranose] as a Sugar Substitute, Carbohydrates and Fibers, J. Nutrition, vol. 119 (1989), pp. 971-978.
Parthasarathi and Jayakrishnan, Dextran and Pentosan Sulfate—Clinical Applications, In: Biodegradable Polymers in Clinical Use and Clinical Development, Eds. Domb et al., Wiley, 2011.
Pharmacosmos technical brochure, Dextran Chemistry—Dextran Properties, 4 pages total, published before Sep. 2017 (actual publication date unknown).
Synytsya and Novak, 2014, Structural analysis of glucans, Annals of Translational Medicine, 2(2):17 (14 pages).
Wolski et al., 2007, Cell wall alpha-1,3-glucans from a biocontrol isolate of Rhizoctonia: immunocytolocalization and relationship with alpha-glucanase activity from potato sprouts, Mycological Research, 111:976-984.
Paulo, Elinalva M., Production, extraction and characterization of exopolysaccharides produced by the native Leuconostoc pseudomesenteroides R2 strain, *Anais Da Academia Brasileira De Ciencias*, 2012, 84(2), pp. 495-507.
EC (Enzyme Commission) No. 2.4.1.5, dextransucrase, KEGG Enzyme Database, retrieved online Oct. 2018.

* cited by examiner

ENZYMATIC HYDROLYSIS OF DISACCHARIDES AND OLIGOSACCHARIDES USING ALPHA-GLUCOSIDASE ENZYMES

This application is a continuation of U.S. application Ser. No. 14/631,931 (filed Feb. 26, 2015, now U.S. Pat. No. 9,982,284), which claims the benefit of U.S. Provisional Application Nos. 61/945,233 (filed Feb. 27, 2014), 61/945,241 (filed Feb. 27, 2014), 62/004,290 (filed May 29, 2014), 62/004,308 (filed May 29, 2014), 62/004,312 (filed May 29, 2014), 62/004,300 (filed May 29, 2014), 62/004,314 (filed May 29, 2014), and 62/004,305 (filed May 29, 2014), and of International Appl. No. PCT/CN2015/073269 (filed Feb. 25, 2015). All of these prior applications are incorporated herein by reference in their entireties.

FIELD OF INVENTION

The invention is in the field of enzymatic hydrolysis of small sugar polymers. Specifically, this invention pertains to hydrolyzing disaccharides and oligosaccharides comprising one or more alpha-1,5 glucosyl-fructose linkages with an alpha-glucosidase enzyme.

REFERENCE TO SEQUENCE LISTING SUBMITTED ELECTRONICALLY

The official copy of the sequence listing is submitted electronically via EFS-Web as an ASCII formatted sequence listing with a file named CL6115USNP_Sequence Listing_ST25.txt created on Feb. 10, 2015, and having a size of 266 kilobytes and is filed concurrently with the specification. The sequence listing contained in this ASCII-formatted document is part of the specification and is herein incorporated by reference in its entirety.

BACKGROUND

Glucoamylases (EC 3.2.1.3, alpha-1,4-glucan glucohydrolase) are exo-acting enzymes that catalyze hydrolysis of both alpha-1,4 and alpha-1,6 glycosidic linkages from non-reducing ends of glucose-containing di-, oligo- and polysaccharides, releasing glucose units one at a time (1960, Pazur and Ando, *J. Biol. Chem.* 235:297-302). Cleavage occurs at the glycosidic bond connecting the anomeric carbon with oxygen (1962, Fleetwood and Weigel, *Nature* 196:984). Alpha-1,4, alpha-1,6, and alpha-1,3 bonds are the only linkages hydrolyzed at significant rates by glucoamylase (1957, Barker et al., *J. Chem. Soc.* 4865-4871).

Glucoamylase is also capable of hydrolyzing the glycosidic bond between the two glucosyl units linked by alpha-1,2 (e.g., Kojibiose) or alpha-1,1 (e.g., trehalose). However, this enzymatic activity occurs at a much lower rate and at more dilute substrate concentrations compared to glucoamylase activity toward disaccharides with alpha-1,4 (maltose) or alpha-1,6 (isomaltose) linkages.

Glucoamylase has been widely used for producing high-glucose syrup from starch. High-glucose syrup is useful as a feedstock for producing various value-added compounds such as fuel alcohol, high-fructose corn syrup, organic acids, amino acids and vitamins. Glucoamylase has been isolated from numerous microorganisms, animals and plants, and among microorganisms, many fungi are good sources of this enzyme. Glucoamylase produced in fungal organisms, such as *Aspergillus niger*, is commonly used for commercial applications such as high-glucose syrup production.

Transglucosidases (EC.2.4.1.24, 1,4-alpha-glucan 6-alpha-glucosyltransferase) are D-glucosyltransferase enzymes that catalyze both hydrolytic and transfer reactions on incubation with alpha-D-gluco-oligosaccharides (1951, Pazur and French, *J. Amer. Chem. Soc.* 73:3536). Maltose is the most preferred substrate for transglucosylation reactions with this enzyme. Transfer occurs most frequently to HO-6, producing isomaltose from D-glucose, or panose (6-O-alpha-glucosyl maltose) from maltose. Transglucosidase can also transfer a glucosyl residue to the HO-2 or HO-3 of another D-glucosyl unit to form Kojibiose or Nigerose. This enzyme can further transfer a D-glucosyl unit back to HO-4 to reform maltose.

As a result of transglucosylation reactions with transglucosidase, malto-oligosaccharide residues are converted to isomalto-oligosaccharides (IMO) containing a higher proportion of glucosyl residues linked by alpha-D-1,6 glycosidic linkages from the non-reducing end. IMO sugars are used in many food and beverage formulations in Asia. Brier et al. (U.S. Patent Appl. Publ. No. 2003/0167929) disclosed using transglucosidase to produce IMO from barley wort.

Poulose et al. (U.S. Patent Appl. Publ. No. 2008/0229514) disclosed using transglucosidase to degrade polysaccharides such as xanthan and guar gums. Xanthan gum comprises a cellulosic backbone in which alternate glucoses are 1,3-linked to branches containing mannose and glucuronic acid. The backbone of guar gum comprises beta-1,4-linked mannose residues to which galactose residues are alpha-1,6-linked at every other mannose.

Lantero et al. (U.S. Pat. No. 5,770,437) disclosed using a transglucosidase to degrade sucrose, melezitose and trehalulose. These sugars comprise glucose linked to fructose via 1,2-(sucrose), 1,3-(melezitose), or 1,1-(trehalulose) linkages.

Although various hydrolytic activities of glucoamylase and transglucosidase have been disclosed, these enzymes are generally considered to be alpha-glucosidases, given their ability to hydrolyze alpha-linkages between two glucosyl residues. For example, both glucoamylase and transglucosidase are associated with having maltase activity (hydrolysis of the alpha-1,4 glycosidic link between the two glucosyl residues of maltose), which is a type of alpha-glucosidase activity.

Notwithstanding the foregoing disclosures, surprisingly, it has now been found that alpha-glucosidases such as transglucosidase (EC 2.4.1.24), glucoamylase (EC 3.2.1.3), and other alpha-glucosidases can hydrolyze alpha-1,5 glycosidic linkage of glucosyl-fructose. Alpha-glucosidases are disclosed herein as being useful for degrading disaccharides and oligosaccharides containing glucosyl-alpha-1,5-fructose.

SUMMARY OF INVENTION

In one embodiment, the invention concerns a method of hydrolyzing an alpha-1,5 glucosyl-fructose linkage in a saccharide comprising at least one alpha-1,5 glucosyl-fructose linkage, wherein the saccharide is a disaccharide or oligosaccharide, and wherein the method comprises: contacting the saccharide with an alpha-glucosidase enzyme under suitable conditions, wherein the alpha-glucosidase enzyme hydrolyzes at least one alpha-1,5 glucosyl-fructose linkage of the saccharide, and wherein the amount of the saccharide is reduced compared to the amount of the saccharide that was present prior to the contacting step.

In another embodiment, the alpha-glucosidase enzyme of the hydrolysis method is immobilized.

In another embodiment, the saccharide of the hydrolysis method is leucrose. In another embodiment, the concentration of leucrose after the contacting step is less than 50% of the concentration of leucrose that was present prior to the contacting step.

In another embodiment, the suitable conditions of the hydrolysis method comprise (i) a glucan synthesis reaction, or (ii) a fraction obtained from the glucan synthesis reaction; wherein the saccharide is a byproduct of the glucan synthesis reaction. The glucan synthesis reaction produces at least one insoluble alpha-glucan product in another embodiment. The fraction is a filtrate of the glucan synthesis reaction in another embodiment. In another embodiment, the glucan synthesis reaction produces at least one soluble alpha-glucan product that is (i) a product of a glucosyltransferase, or (ii) a product of the concerted action of both a glucosyltransferase and an alpha-glucanohydrolase capable of hydrolyzing glucan polymers having one or more alpha-1,3-glycosidic linkages or one or more alpha-1,6-glycosidic linkages. The fraction is a chromatographic fraction of the glucan synthesis reaction in another embodiment in which the glucan synthesis reaction produces at least one soluble alpha-glucan product.

In another embodiment, the alpha-glucosidase enzyme is a transglucosidase or glucoamylase. In another embodiment, (i) the transglucosidase comprises an amino acid sequence that is at least 90% identical to SEQ ID NO:1; or (ii) the glucoamylase comprises an amino acid sequence that is at least 90% identical to SEQ ID NO:2.

In another embodiment, the invention concerns a composition produced by contacting a saccharide with an alpha-glucosidase enzyme, wherein the saccharide is a disaccharide or oligosaccharide and comprises at least one alpha-1,5 glucosyl-fructose linkage, wherein the alpha-glucosidase enzyme hydrolyzes at least one alpha-1,5 glucosyl-fructose linkage of the saccharide, and wherein the composition comprises a reduced amount of the saccharide compared to the amount of the saccharide that was present prior to the contacting step.

In another embodiment, the saccharide of the composition is leucrose. The concentration of the leucrose in the composition is less than 50% of the concentration of leucrose that was present prior to the contacting, for example.

In another embodiment, the saccharide of the composition is in (i) a glucan synthesis reaction, or (ii) a fraction obtained from the glucan synthesis reaction; wherein the saccharide is a byproduct of the glucan synthesis reaction. In another embodiment, the fraction is a filtrate of the glucan synthesis reaction or a chromatographic fraction of the glucan synthesis reaction.

In another embodiment, the invention concerns a method of enriching fructose present in a fraction of a glucan synthesis reaction, comprising: (a) contacting a fraction obtained from a glucan synthesis reaction with an alpha-glucosidase enzyme under suitable conditions, wherein the alpha-glucosidase enzyme hydrolyzes at least one alpha-1,5 glucosyl-fructose linkage of a disaccharide or oligosaccharide comprised within the fraction; and (b) separating fructose from the hydrolyzed fraction of step (a) to obtain a composition having a higher concentration of fructose compared to the fructose concentration of the fraction of step (a).

In another thirteenth embodiment, the invention concerns a fermentation method comprising: (a) contacting a fraction obtained from a glucan synthesis reaction with an alpha-glucosidase enzyme under suitable conditions, wherein the alpha-glucosidase enzyme hydrolyzes at least one alpha-1,5 glucosyl-fructose linkage of a disaccharide or oligosaccharide comprised within the fraction; (b) fermenting the fraction of step (a) with a microbe to yield a product, wherein the fermenting can be performed after step (a) or simultaneously with step (a); and (c) optionally, isolating the product of (b); wherein the yield of the product of (b) is increased compared to the product yield of fermenting a fraction of the glucan synthesis reaction that has not been contacted with the alpha-glucosidase enzyme.

BRIEF DESCRIPTION OF THE DRAWINGS AND SEQUENCES

FIG. 1: $^1$H NMR spectra of glucan reaction filtrate material before (starting material) and after (treated material) hydrolysis treatment with NOVO 188 enzyme (see Examples 2-3).

Figure 2:
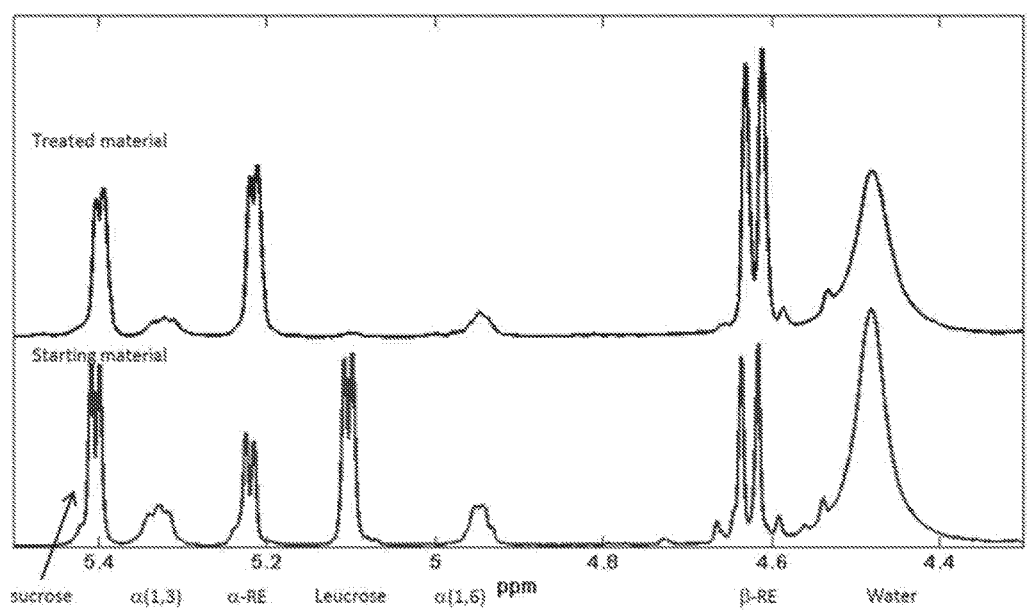

FIG. 2: $^1$H NMR spectra of glucan reaction filtrate material before (starting material) and after (treated material) hydrolysis treatment with TG L-2000 transglucosidase (see Examples 2-3).

TABLE 1

Summary of Nucleic Acid and Protein Sequence Identification Numbers

| Description | Nucleic acid SEQ ID NO. | Protein SEQ ID NO. |
|---|---|---|
| "TG L-2000", *A. niger* transglucosidase (mature form without signal peptide) | | 1 (965 aa) |
| "GC 321 Glucoamylase", *T. reesei* glucoamylase (TrGA) (mature form without signal peptide) | | 2 (599 aa) |
| "gtfJ", *Streptococcus salivarius* glucosyltransferase. The first 42 amino acids of the protein are deleted compared to GENBANK Identification No. 47527; a start methionine is included. | | 3 (1477 aa) |
| "Aclglu1", *Aspergillus clavatus* alpha-glucosidase, full-length precursor form including signal peptide. | 4 (3147 bases) | 5 (990 aa) |
| "Aclglu1", *Aspergillus clavatus* alpha-glucosidase, mature form lacking signal peptide. | | 6 (971 aa) |
| "Nfiglu1", *Neosartorya fischeri* alpha-glucosidase, full-length precursor form including signal peptide. | 7 (3158 bases) | 8 (988 aa) |
| "Nfiglu1", *Neosartorya fischeri* alpha-glucosidase, mature form lacking signal peptide. | | 9 (969 aa) |
| "Ncrglu1", *Neurospora crassa* alpha-glucosidase, full-length precursor form including signal peptide. | 10 (3385 bases) | 11 (1044 aa) |
| "Ncrglu1", *Neurospora crassa* alpha-glucosidase, mature form lacking signal peptide. | | 12 (1022 aa) |
| "TauSec098", *Rasamsonia composticola* alpha-glucosidase, full-length precursor form including signal peptide. | 13 (3293 bases) | 14 (1035 aa) |
| "TauSec098", *Rasamsonia composticola* alpha-glucosidase, mature form lacking signal peptide. | | 15 (1013 aa) |
| "TauSec099", *Rasamsonia composticola* alpha-glucosidase, full-length precursor form including signal peptide. | 16 (3162 bases) | 17 (990 aa) |
| "TauSec099", *Rasamsonia composticola* alpha-glucosidase, mature form lacking signal peptide. | | 18 (973 aa) |
| "BloGlu1", *Bifidobacterium longum* (subsp. *longum* JDM301) alpha-glucosidase (wild type). | 19 (1815 bases) | 20 (604 aa) |
| "BloGlu1", *Bifidobacterium longum* (subsp. *longum* JDM301) alpha-glucosidase, codon-optimized sequence. | 21 (1812 bases) | |

TABLE 1-continued

Summary of Nucleic Acid and Protein Sequence Identification Numbers

| Description | Nucleic acid SEQ ID NO. | Protein SEQ ID NO. |
|---|---|---|
| "BloGlu2", *Bifidobacterium longum* alpha-glucosidase (wild type). | | 22 (604 aa) |
| "BloGlu2", *Bifidobacterium longum* alpha-glucosidase, codon-optimized sequence encoding amino acid sequence. | 23 (1812 bases) | 24 (604 aa) |
| "BloGlu3", *Bifidobacterium longum* (subsp. F8) alpha-glucosidase (wild type) | 25 (1815 bases) | 26 (604 aa) |
| "BloGlu3", *Bifidobacterium longum* (subsp. F8) alpha-glucosidase, codon-optimized sequence encoding amino acid sequence. | 27 (1812 bases) | |
| "BpsGlu1", *Bifidobacterium pseudolongum* alpha-glucosidase (wild type). | | 28 (585 aa) |
| "BpsGlu1", *Bifidobacterium pseudolongum* alpha-glucosidase, codon-optimized sequence encoding amino acid sequence. | 29 (1755 bases) | 30 (586 aa) |
| "BthGlu1", *Bifidobacterium thermophilum* RBL67 alpha-glucosidase (wild type). | 31 (1806 bases) | 32 (601 aa) |
| "BthGlu1", *Bifidobacterium thermophilum* RBL67 alpha-glucosidase, codon-optimized sequence. | 33 (1803 bases) | |
| "BbrGlu2", *Bifidobacterium breve* alpha-glucosidase (wild type). | | 34 (662 aa) |
| "BbrGlu2", *Bifidobacterium breve* alpha-glucosidase, codon-optimized sequence encoding amino acid sequence. | 35 (1812 bases) | 36 (604 aa) |
| "BbrGlu5", *Bifidobacterium breve* ACS-071-V-Sch8b alpha-glucosidase (wild type). | 37 (1821 bases) | 38 (606 aa) |
| "BbrGlu5", *Bifidobacterium breve* ACS-071-V-Sch8b alpha-glucosidase, codon-optimized sequence. | 39 (1818 bases) | |
| "Gtf-S", *Streptococcus* sp. C150 glucosyltransferase, GENBANK GI No. 321278321. | | 40 (1570 aa) |
| "GTF0459", *Streptococcus* sp. C150 glucosyltransferase, N-terminal-truncated version of GENBANK GI No. 321278321. | 41 (4179 bases) | 42 (1392 aa) |
| "Gtf-C", *Streptococcus mutans* MT-4239 glucosyltransferase, GENBANK GI No. 3130088. | | 43 (1455 aa) |
| "GTF0088BsT1", *Streptococcus mutans* MT-4239 glucosyltransferase, N- and C-terminal-truncated version of GENBANK GI No. 3130088. | 44 (2715 bases) | 45 (904 aa) |
| "MUT3325", *Penicillium marneffei* ATCC 18224 mutanase, GENBANK GI No. 212533325. | 46 (1308 bases) | 47 (435 aa) |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The terms "saccharide", "saccharide molecule" and "carbohydrate" are used interchangeably herein and refer to a disaccharide or oligosaccharide, unless otherwise noted. A "disaccharide" herein refers to a carbohydrate having two monosaccharides joined by a glycosidic linkage. An "oligosaccharide" herein refers to a carbohydrate that consists of 2 to 9 monosaccharides, for example, joined by glycosidic linkages. An oligosaccharide can also be referred to herein as an "oligomer". Monosaccharides that are comprised within a disaccharide or oligosaccharide can be referred to as "monosaccharide units" or "monomeric units", for example. Preferred monosaccharides herein are fructose and glucose.

The terms "glycosidic linkage" and "glycosidic bond" are used interchangeably herein and refer to the type of covalent bond that joins a carbohydrate molecule to another carbohydrate molecule.

The terms "alpha-1,3 glucosyl-glucose linkage", "alpha-1,3 glucose-glucose linkage" and "glucose-alpha 1,3-glucose" herein refers to an alpha-1,3-glycosidic linkage between two alpha-D-glucose molecules. The terms "alpha-1,6 glucosyl-glucose linkage", "alpha-1,6 glucose-glucose linkage" and "glucose-alpha 1,6-glucose" herein refers to an alpha-1,6-glycosidic linkage between two alpha-D-glucose molecules. Alpha-1,3 glucosyl-glucose linkage(s) and/or alpha-1,6 glucosyl-glucose linkage(s) herein are comprised within a disaccharide or oligosaccharide in certain embodiments.

The terms "alpha-1,5 glucosyl-fructose linkage", "alpha-1,5 glucose-fructose linkage" and "glucose-alpha-1,5-fructose" herein refers to an alpha-1,5-glycosidic linkage between an alpha-D-glucose molecule and a fructose molecule. An alpha-1,5 glucosyl-fructose linkage herein is comprised within a disaccharide or oligosaccharide in certain embodiments.

"Alpha-D-glucose" herein can also be referred to as "glucose".

A disaccharide containing an alpha-1,5 glucosyl-fructose linkage is referred to herein as leucrose. The terms "leucrose" and "D-glucopyranosyl-alpha(1-5)-D-fructopyranose" are used interchangeably herein. Leucrose has the following structure:

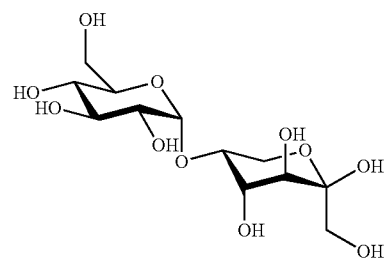

The terms "alpha-glucosidase", "alpha-1,4-glucosidase", and "alpha-D-glucoside glucohydrolase" are used interchangeably herein. Alpha-glucosidases (EC 3.2.1.20) ("EC" refers to Enzyme Commission number) have previously been recognized as enzymes that catalyze hydrolytic release of terminal, non-reducing (1,4)-linked alpha-D-glucose residues from oligosaccharide (e.g., disaccharide) and polysaccharide substrates. Alpha-glucosidases are now disclosed herein to also have hydrolytic activity toward alpha-1,5 glucosyl-fructose linkages, and hydrolytic activity toward alpha-1,3 and alpha-1,6 glucosyl-glucose linkages. Transglucosidase and glucoamylase enzymes are examples of alpha-glucosidases with such activity.

The terms "transglucosidase" (TG), "transglucosidase enzyme", and "1,4-alpha-glucan 6-alpha-glucosyltransferase" are used interchangeably herein. Transglucosidases (EC 2.4.1.24) have previously been recognized as D-glucosyltransferase enzymes that catalyze both hydrolytic and transfer reactions on incubation with certain alpha-D-gluco-oligosaccharides. Transglucosidases are now disclosed herein to also have hydrolytic activity toward alpha-1,5 glucosyl-fructose linkages, and hydrolytic activity toward alpha-1,3 and alpha-1,6 glucosyl-glucose linkages.

The terms "glucoamylase" (GA), "glucoamylase enzyme", and "alpha-1,4-glucan glucohydrolase" are used interchangeably herein. Glucoamylases (EC 3.2.1.3) have previously been recognized as exo-acting enzymes that catalyze hydrolysis of both alpha-1,4 and alpha-1,6 glycosidic linkages from non-reducing ends of glucose-containing di-, oligo- and poly-saccharides. Glucoamylases are now disclosed herein to also have hydrolytic activity toward alpha-1,5 glucosyl-fructose linkages.

Enzymatic hydrolysis is a process in which an enzyme facilitates the cleavage of bonds in molecules with the addition of the elements of water. "Hydrolyzing", "hydrolysis of", or "hydrolytic activity toward" an alpha-1,5 glucosyl-fructose linkage herein refers to enzymatic hydrolysis of the alpha-1,5 glycosidic linkage between glucose and fructose by an alpha-glucosidase such as a glucoamylase or transglucosidase. Such hydrolysis occurs when contacting a disaccharide or oligosaccharide containing an alpha-1,5 glucosyl-fructose linkage with an alpha-glucosidase herein under suitable conditions. Thus, a "hydrolysis reaction" herein comprises at least (i) a disaccharide or oligosaccharide containing an alpha-1,5 glucosyl-fructose linkage, and (ii) an alpha-glucosidase.

The term "saccharification" herein refers to a process of breaking a saccharide (disaccharide or oligosaccharide) into its monosaccharide components. A saccharide can be saccharified in a hydrolysis reaction herein.

"Suitable conditions" for contacting a saccharide (disaccharide or oligosaccharide) comprising at least one alpha-1,5 glucosyl-fructose linkage with an alpha-glucosidase herein refer to those conditions (e.g., temperature, pH, time) that support the hydrolysis of one or more alpha-1,5 glucosyl-fructose linkages in the saccharide by the alpha-glucosidase. Suitable conditions can comprise "aqueous conditions", for example, comprising at least 20 wt % water. Aqueous conditions may characterize a solution or mixture. The solution or mixture in which a saccharide comprising at least one alpha-1,5 glucosyl-fructose linkage is contacted with an alpha-glucosidase can be referred to as an alpha-glucosidase reaction, for example (e.g., a transglucosidase or glucoamylase reaction).

An "immobilized" enzyme herein refers to an enzyme that is attached to an inert, insoluble material. Methods for preparing immobilized enzymes are disclosed, for example, in U.S. Pat. No. 5,541,097, which is incorporated herein by reference.

The terms "glucan" and "glucan polymer" are used interchangeably herein and refer to a polysaccharide of glucose monomers linked by glycosidic bonds. An "alpha-glucan" herein refers to a glucan polymer comprising at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages.

An "insoluble glucan" herein refers to a glucan polymer that is not soluble in aqueous conditions. An example of insoluble glucan herein is poly alpha-1,3-glucan with a DP of at least 8 or 9. A glucosyltransferase reaction in certain embodiments as presently disclosed produces at least one insoluble glucan product.

The terms "soluble glucan", "soluble alpha-glucan", "soluble fiber", "soluble glucan fiber", "soluble dietary fiber" and the like are used interchangeably herein to refer to a glucan polymer that is soluble in aqueous conditions. Examples of soluble glucan herein are certain oligosaccharides, such as poly alpha-1,3-glucan with a DP less than 8, and certain oligosaccharides disclosed in the Examples provided below. A glucosyltransferase reaction in certain embodiments as presently disclosed produces at least one soluble glucan product. Another set of features that characterizes soluble alpha-glucan compounds in certain embodiments herein is that they are (i) water-soluble glucose oligomers having a degree of polymerization of 3 or more, (ii) digestion-resistant (i.e., exhibit very slow or no digestibility) with little or no absorption in the human small intestine, and (iii) at least partially fermentable in the lower gastrointestinal tract. Digestibility of a soluble glucan fiber composition can be measured using AOAC method 2009.01, for example.

The terms "poly alpha-1,3-glucan" and "alpha-1,3-glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. The term "alpha-1,3-glycosidic linkage" as used herein refers to the type of covalent bond that joins alpha-D-glucose molecules to each other through carbons 1 and 3 on adjacent alpha-D-glucose rings.

The "molecular weight" of a glucan herein can be represented as number-average molecular weight ($M_n$) or as weight-average molecular weight ($M_w$). Alternatively, molecular weight can be represented as Daltons, grams/mole, $DP_w$ (weight average degree of polymerization), or $DP_n$ (number average degree of polymerization). Various means are known in the art for calculating these molecular weight measurements such as with high-pressure liquid chromatography (HPLC), size exclusion chromatography (SEC), or gel permeation chromatography (GPC).

The terms "glucosyltransferase enzyme", "gtf enzyme", "gtf enzyme catalyst", "gtf", "glucansucrase" and the like are used interchangeably herein. The activity of a gtf enzyme herein catalyzes the reaction of sucrose substrate to make the products glucan and fructose. Other products (byproducts) of a gtf reaction can include glucose (results from when glucose is hydrolyzed from the glucosyl-gtf enzyme intermediate complex), various soluble oligosaccharides (e.g., DP2-DP7), and leucrose (results from when glucose of the glucosyl-gtf enzyme intermediate complex is linked to fructose). Wild type forms of glucosyltransferase enzymes generally contain (in the N-terminal to C-terminal direction) a signal peptide, a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "glucan synthesis reaction", "glucan reaction" "gtf reaction" and the like are used interchangeably herein and refer to a reaction that is performed by a glucosyltransferase enzyme. A glucan synthesis reaction as used herein generally refers to a solution comprising at least one active glucosyltransferase enzyme in a solution comprising sucrose and water, and optionally other components. Other components that can be in a glucan synthesis reaction herein include fructose, glucose, leucrose, soluble oligosaccharides (e.g., DP2-DP7), and soluble glucan product(s), for example. Also, one or more alpha-glucanohydrolase enzymes can be comprised in a glucan synthesis reaction in some aspects. It would be understood that certain glucan products, such as poly alpha-1,3-glucan with a degree of polymerization (DP) of at least 8 or 9, are water-insoluble and thus are not dissolved in a glucan synthesis reaction, but rather may be present out of solution.

The terms "alpha-glucanohydrolase" and "glucanohydrolase" are used interchangeably herein and refer to an enzyme capable of hydrolyzing an alpha-glucan oligomer. An alpha-glucanohydrolase can be defined by its endohydrolysis activity towards certain alpha-D-glycosidic linkages. Examples of alpha-glucanohydrolase enzymes herein include dextranases (EC 3.2.1.11; capable of endohydrolyzing alpha-1,6-linked glycosidic bonds), mutanases (EC 3.2.1.59; capable of endohydrolyzing alpha-1,3-linked glycosidic bonds), and altemanases (EC 3.2.1.-; capable of endohydrolytically cleaving alteman). Various factors including, but not limited to, level of branching, the type of branching, and the relative branch length within certain alpha-glucans may adversely impact the ability of an alpha-glucanohydrolase to endohydrolyze some glycosidic linkages.

The "percent dry solids" of a glucan synthesis reaction refers to the wt % of all the sugars in a glucan synthesis reaction. The percent dry solids of a gtf reaction can be calculated, for example, based on the amount of sucrose used to prepare the reaction.

A "fraction" of a glucan synthesis reaction herein refers to a liquid solution portion of a glucan synthesis reaction. A fraction can be a portion of, or all of, the liquid solution from a glucan synthesis reaction, and has been separated from a soluble or insoluble glucan product synthesized in the reaction. A fraction can optionally be referred to as a "mother liquor" in embodiments in which the product is an insoluble (solid) glucan product. An example of a fraction is a filtrate of a glucan synthesis reaction. Since a fraction can contain dissolved sugars such as sucrose, fructose, glucose, leucrose, soluble oligosaccharides (e.g., DP2-DP7), a fraction can also be referred to as a "mixed sugar solution" derived from a glucan synthesis reaction. A "hydrolyzed fraction" herein refers to a fraction that has been treated with an alpha-glucosidase herein to hydrolyze leucrose and/or oligosaccharides present in the fraction.

The terms "filtrate", "glucan reaction filtrate", "glucan filtrate" and the like are used interchangeably herein and refer to a fraction that has been filtered away from a solid glucan product synthesized in a glucan synthesis reaction. A "hydrolyzed filtrate" herein refers to a filtrate that has been treated with an alpha-glucosidase herein to hydrolyze leucrose and/or oligosaccharides present in the filtrate.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution. All percentages herein are weight percentages, unless otherwise noted.

As used herein, "polydispersity index", "PDI", "heterogeneity index", "dispersity" and the like refer to a measure of the distribution of molecular mass in a given polymer (e.g., a glucose oligomer such as a soluble alpha-glucan) sample and can be calculated by dividing the weight average molecular weight by the number average molecular weight ($PDI = M_w/M_n$).

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences are disclosed herein as features of certain embodiments. Variants of these sequences that are at least about 70-85%, 85-90%, or 90%-95% identical to the sequences disclosed herein can be used. Alternatively, a variant amino acid sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. A variant amino acid sequence herein has the same function/activity of a disclosed sequence, or at least about 85%, 86%, 87%, 88%, 89%, 90%, 91%, 92%, 93%, 94%, 95%, 96%, 97%, 98%, or 99% of the function/activity of a disclosed sequence.

The term "isolated" as used in certain embodiments refers to any cellular component that is completely separated from its native source (e.g., an isolated polynucleotide or polypeptide molecule). In some instances, an isolated polynucleotide or polypeptide molecule is part of a greater composition, buffer system or reagent mix. For example, the isolated polynucleotide or polypeptide molecule can be comprised within a cell or organism in a heterologous manner. Another example is an isolated alpha-glucosidase (e.g., glucoamylase, transglucosidase), or glucosyltransferase enzyme. The enzyme reactions (e.g., alpha-glucosidase reaction, glucosyltransferase reaction) disclosed herein are synthetic, non-naturally occurring processes.

Embodiments of the disclosed invention concern a method of hydrolyzing an alpha-1,5 glucosyl-fructose linkage in a saccharide comprising at least one alpha-1,5 glucosyl-fructose linkage. The saccharide is a disaccharide or oligosaccharide. This method comprises contacting the saccharide with an alpha-glucosidase enzyme under suitable conditions. In the contacting step, the alpha-glucosidase enzyme hydrolyzes at least one alpha-1,5 glucosyl-fructose linkage of the saccharide. Due to this hydrolysis, the amount of the saccharide is reduced compared to the amount of the saccharide that was present prior to the contacting step. Thus, this hydrolysis method can alternatively be referred to as a method of reducing the amount of a saccharide in a composition.

Significantly, it is believed to be previously unknown that alpha-glucosidase enzymes can hydrolyze alpha-1,5 glucosyl-fructose linkages. Alpha-glucosidase reactions following this hydrolysis method can thus be used to remove leucrose and other oligosaccharide byproducts containing alpha-1,5 glucosyl-fructose linkages from a glucan synthesis reaction and/or a fraction obtained therefrom. Such removal represents an improvement over chemical processes of byproduct removal, such as acid hydrolysis, which can result in 10 degradation of glucan product. Finally, a glucan reaction fraction that is treated according to the above hydrolysis method is better-suited for downstream applications such as fermentation, for example, since the level of glucose and fructose monosaccharides is increased in the fraction. Monosaccharides are generally more tractable for downstream processes compared to leucrose and oligosaccharide byproducts.

An alpha-glucosidase (EC 3.2.1.20) is used in embodiments herein to hydrolyze an alpha-1,5 glucosyl-fructose linkage in a saccharide comprising at least one alpha-1,5 glucosyl-fructose linkage. Alpha-glucosidase enzymes have previously been recognized to catalyze hydrolytic release of terminal, non-reducing (1,4)-linked alpha-D-glucose residues from oligosaccharide (e.g., disaccharide) and polysaccharide substrates. These enzymes are now disclosed herein to also have hydrolytic activity toward alpha-1,5 glucosyl-fructose linkages, for example.

An alpha-glucosidase can be from any source (e.g., plant, animal, microbe such as a bacteria or fungus/yeast), for example, such as those sources disclosed below from which a transglucosidase and/or glucoamylase can be derived. For example, an alpha-glucosidase can be a fungal alpha-glucosidase. Other examples of suitable alpha-glucosidases herein include those disclosed in U.S. Pat. Nos. 6,355,467, 5,922,580, 5,795,766, 5,763,252, and 8,633,006, which are all incorporated herein by reference.

An alpha-glucosidase enzyme in certain embodiments herein may comprise the amino acid sequence of SEQ ID NO:5, 6, 8, 9, 11, 12, 14, 15, 17, 18, 20, 22, 24, 26, 28, 30, 32, 34, 36, 38, or that of DIAZYME RDF ULTRA (DuPont Industrial Biosciences). Alternatively, an alpha-glucosidase enzyme may comprise an amino acid sequence that is at least about 90%, 91%, 92%, 93%, 94%, 95%, 96%, 97%, 98%, or 99% identical to SEQ ID NO:5, 6, 8, 9, 11, 12, 14, 15, 17, 18, 20, 22, 24, 26, 28, 30, 32, 34, 36, 38, or to the amino acid sequence of DIAZYME RDF ULTRA, and have hydrolytic activity toward alpha-1,5 glucosyl-fructose linkages in saccharides. Several of the foregoing sequences, for example, are mature alpha-glucosidases that lack an N-terminal signal peptide. For such sequences, it would be understood that an N-terminal start-methionine would typically be added (if necessary) (directly or via an intervening heterologous amino acid sequence such as an epitope) if expressing it without using a signal peptide (such as with an expression system where the enzyme is expressed intracellularly and obtained from a cell lysate).

A transglucosidase (EC 2.4.1.24; 1,4-alpha-glucan 6-alpha-glucosyltransferase) can be used in certain embodiments herein as an alpha-glucosidase to hydrolyze an alpha-1,5 glucosyl-fructose linkage in a saccharide comprising at least one alpha-1,5 glucosyl-fructose linkage. This class of enzymes has previously been recognized as D-glucosyltransferase enzymes that catalyze hydrolytic and transfer reactions on incubation with certain alpha-D-gluco-oligosaccharides. Transglucosidases as now disclosed herein also have hydrolytic activity toward alpha-1,5 glucosyl-fructose linkages.

A transglucosidase enzyme herein may be derived from any microbial source, such as a bacteria or fungus. Examples of fungal transglucosidases include, but are not limited to, those of *Trichoderma* species (e.g., *T. reesei*), *Aspergillus* species and *Neosartorya* species (e.g., *N. fischen*). Examples of *Aspergillus* species from which a transglucosidase may be derived include, but are not limited to, *A. niger, A. awamori, A. oryzae, A. terreus, A. clavatus, A. fumigatus* and *A. nidulans*. Other examples of transglucosidase enzymes useful herein are described in Barker et al. (1953, *J. Chem. Soc.* 3588-3593); Pazur et al. (1986, *Carbohydr. Res.* 149:137-147), Nakamura et al. (1997, *J. Biotechnol.* 53:75-84), and U.S. Patent Appl. Publ. No. 2008/0229514, all of which are incorporated herein by reference. Still other examples of transglucosidase enzymes useful herein are those that are thermostable; U.S. Pat. No. 4,689,296, which is incorporated herein by reference, discloses a process for producing thermostable transglucosidase. Yet more examples of transglucosidase enzymes useful herein may be any of those in the GENBANK database (NCBI), such as accession numbers: D45356 (GID:2645159, *A. niger*), BAD06006.1 (GID:4031328, *A. awamon*), BAA08125.1 (GID:1054565, *A. oryzae*), XP_001210809.1 (GID:115492363, *A. terreus*), XP_001216899.1 (GID:115433524, *A. terreus*), XP_001271891.1 (GID:121707620, *A. clavatus*), XP_751811.1 (GID:70993928, *A. fumigatus*), XP_659621.1 (GID:67523121, *A. nidulans*), XP_001266999.1 (GID:119500484, *N. fischen*) and XP_001258585.1 (GID:119473371, *N. fischen*), which are all incorporated herein by reference. Alternatively, a transglucosidase herein may have an amino acid sequence that is at least 90% or 95% identical with the amino acid sequence of any of the foregoing disclosed transglucosidase sequences, and have hydrolytic activity toward alpha-1,5 glucosyl-fructose linkages in saccharides. All of the foregoing transglucosidases, when used in a hydrolysis reaction herein, are preferably in a mature form lacking an N-terminal signal peptide.

A transglucosidase enzyme in certain embodiments herein may comprise the amino acid sequence of SEQ ID NO:1 (Transglucosidase L-2000), which is an *A. niger* transglucosidase (U.S. Patent Appl. Publ. No. 2008/0229514). Alternatively, a transglucosidase may comprise an amino acid sequence that is at least about 90%, 91%, 92%, 93%, 94%, 95%, 96%, 97%, 98%, or 99% identical to SEQ ID NO:1 and have hydrolytic activity toward alpha-1,5 glucosyl-fructose linkages in saccharides. Any of SEQ ID NO:1 or variants thereof can be produced following the disclosure of U.S. Patent Appl. Publ. No. 2008/0229514, for example, which is incorporated herein by reference. SEQ ID NO:1 is a mature transglucosidase that lacks an N-terminal signal peptide. Since SEQ ID NO:1 does not begin with a methionine residue, it would be understood that an N-terminal start-methionine would typically be added to SEQ ID NO:1 (directly or via an intervening heterologous amino acid sequence such as an epitope) if expressing it without using a signal peptide (such as with an expression system where the enzyme is expressed intracellularly and obtained from a cell lysate).

A glucoamylase (EC 3.2.1.3; alpha-1,4-glucan glucohydrolase) can be used in certain embodiments herein as an alpha-glucosidase to hydrolyze an alpha-1,5 glucosyl-fructose linkage in a saccharide comprising at least one alpha-1,5 glucosyl-fructose linkage. This class of enzymes has previously been recognized as exo-acting enzymes that catalyze hydrolysis of both alpha-1,4 and alpha-1,6 glycosidic linkages from non-reducing ends of glucose-containing di-, oligo- and poly-saccharides. Glucoamylases as now disclosed herein also have hydrolytic activity toward alpha-1,5 glucosyl-fructose linkages. In certain embodiments, an alpha-glucosidase is not a glucoamylase.

A glucoamylase enzyme herein may be derived from any microbial source, such as a bacteria or fungus. Examples of bacterial glucoamylases include, but are not limited to, those of *Bacillus* species (e.g., *B. alkalophilus, B. amyloliquefaciens, B. lentus, B. licheniformis, B. stearothermophilus, B. subtilis, B. thuringiensis*) and *Streptomyces* species (e.g., *S. lividans*). Examples of fungal glucoamylases include, but are not limited to, those of *Trichoderma* species (e.g., *T. reesei, T. longibrachiatum, T. strictipilis, T. asperellumi, T. konilangbra, T. hazianum*), *Aspergillus* species (e.g., *A. niger, A. oryzae, A. terreus, A. clavatus, A. nidulans, A. kawachii, A. awamon*), *Rhizopus* species (e.g., *R. oryzae, R. niveus*), *Talaromyces* species (e.g., *T. emersonii, T. thermophilus, T. duponti*), *Mucor* species, *Hypocrea* species (e.g., *H. gelatinosa, H. orientalis, H. vinosa, H. citrina*), *Fusarium* species (e.g., *F. oxysporum, F. roseum, F. venenatum*), *Neurospora* species (e.g., *N. crassa*), *Humicola* species (e.g., *H. grisea, H. insolens, H. lanuginose*), *Penicillium* species (e.g., *P. notatum, P. chrysogenum*) and *Saccharomycopsis* species (e.g., *S. fibuligera*). Examples of these bacterial and fungal glucoamylases for use herein are disclosed in U.S. Pat. Appl. Publ. No. 2013/0102035, which is incorporated herein by reference. Other examples of glucoamylase enzymes useful herein are described in Svensson et al. (1983, *Carlsberg Res. Commun.* 48:529-544), Boel et al. (1984, *EMBO J.* 3:1097-1102); Hayashida et al. (1989, *Agric. Biol. Chem.* 53:923-929); U.S. Pat. Nos. 5,024,941, 4,794,175, 4,247,637, 6,255,084, 6,620,924, Ashikari et al. (1986, *Agric. Biol. Chem.* 50:957-964), Ashikari et al. (1989, *Appl. Microbiol. Biotechnol.* 32:129-133), U.S. Pat. Nos. 4,863,864; 4,618,579, Houghton-Larsen et al. (2003, *Appl. Microbiol. Biotechnol.* 62:210-217) and U.S. Pat. No. 7,413,887, all of which are incorporated herein by reference. Alternatively, a glucoamylase herein may have an amino acid sequence that is at least 90% or 95% identical with the amino acid sequence of any of the foregoing disclosed glucoamylase sequences, and have hydrolytic activity toward alpha-1,5 glucosyl-fructose linkages in saccharides. All of the foregoing glucoamylases, when used in a hydrolysis reaction herein, are preferably in a mature form lacking an N-terminal signal peptide. Commercially available glucoamylases useful herein include OPTIDEX L-400, GC 147, GC 321, G ZYME G990 4X, OPTIMAX 7525, DEXTROZYME, DISTILLASE and GLUCZYME, for example.

A glucoamylase enzyme in certain embodiments herein may comprise the amino acid sequence of SEQ ID NO:2 (GC 321), which is a *T. reesei* glucoamylase. Alternatively, a glucoamylase may comprise an amino acid sequence that is at least about 90%, 91%, 92%, 93%, 94%, 95%, 96%, 97%, 98%, or 99% identical to SEQ ID NO:2 and have hydrolytic activity toward alpha-1,5 glucosyl-fructose linkages in saccharides. Any of SEQ ID NO:2 or variants thereof can be produced following the disclosures of U.S. Pat. No. 7,413,887 or U.S. Pat. Appl. Publ. No. 2013/0102035, for example, which are incorporated herein by reference. SEQ ID NO:2 is a mature glucoamylase that lacks an N-terminal signal peptide. Since SEQ ID NO:2 does not begin with a methionine residue, it would be understood that an N-terminal start-methionine would typically be added to SEQ ID NO:2 (directly or via an intervening heterologous amino acid sequence such as an epitope) if expressing it without using a signal peptide (such as with an expression system where the enzyme is expressed intracellularly and obtained from a cell lysate).

An alpha-glucosidase enzyme herein such as a transglucosidase or glucoamylase may be from a commercial source (e.g., DuPont Industrial Biosciences/Genencor, USA; Megazyme International, Ireland; Amano Enzyme Inc., Japan). Alternatively, such an enzyme may be produced by any means known in the art, such as described in U.S. Pat. Appl. Publ. No. 2008/0229514, U.S. Pat. No. 7,413,887 or U.S. Pat. Appl. Publ. No. 2013/0102035, which are incorporated herein by reference. For example, an alpha-glucosidase may be produced recombinantly in a heterologous expression system, such as a microbial or fungal heterologous expression system. Examples of heterologous expression systems include bacterial (e.g., *E. coli, Bacillus* sp.) and eukaryotic systems. Eukaryotic systems can employ yeast (e.g., *Pichia* sp., *Saccharomyces* sp.) or fungal (e.g., *Trichoderma* sp. such as *T. reesei*, *Aspergillus* species such as *A. niger*) expression systems, for example. The transglucosidase of SEQ ID NO:1 and glucoamylase of SEQ ID NO:2, and variants thereof, can be expressed in a *T. reesei* host, for example.

An alpha-glucosidase enzyme when used in a hydrolysis reaction herein is preferably in a mature form lacking an N-terminal signal peptide. An expression system for producing a mature alpha-glucosidase enzyme herein may employ an enzyme-encoding polynucleotide that further comprises sequence encoding an N-terminal signal peptide to direct extra-cellular secretion. The signal peptide in such embodiments is cleaved from the enzyme during the secretion process. The signal peptide may either be native or heterologous to the transglucosidase or glucoamylase. Alternatively, an alpha-glucosidase enzyme in a mature form can be provided by expressing it without using a signal peptide, such as with an expression system where the enzyme is expressed intracellularly and obtained from a cell lysate. In either scenario (secretion or intracellularly expressed), a heterologous amino acid sequence such as an epitope can optionally be included at the N-terminus of the alpha-glucosidase.

An alpha-glucosidase enzyme in certain embodiments may be provided in a hydrolysis reaction herein by direct use of a cell that expresses the enzyme(s). In other words, an alpha-glucosidase that is contacted with a saccharide can be present by virtue of its expression from a cell placed in the suitable conditions for hydrolysis. Such a cell could thus be used in place of adding an isolated alpha-glucosidase preparation to the hydrolysis reaction. A cell for this purpose can be a bacterial, yeast, or fungal cell, for example. Examples of yeast include those from the genera *Saccharomyces* (e.g., *S. cerevisiae*), *Kluyveromyces*, *Candida*, *Pichia*, *Schizosaccharomyces*, *Hansenula*, *Kloeckera*, and *Schwanniomyces*. Other expression systems useful herein are disclosed in U.S. Patent. Appl. Publ. No. 2013/0323822, which is incorporated herein by reference.

A saccharide herein comprises at least one alpha-1,5 glucosyl-fructose linkage. Thus, depending on the length of the saccharide, it may contain 1, 2, 3, 4, 5, 6, 7, or 8 alpha-1,5 glucosyl-fructose linkages, for example. A saccharide preferably contains 1, 2, or 3 linkages of this type.

Since a saccharide herein comprises at least one alpha-1,5 glucosyl-fructose linkage, the saccharide comprises at least one glucose unit and at least one fructose unit. In certain embodiments, a saccharide herein comprises only glucose and fructose units. Such a composition may characterize the disaccharide and oligosaccharide byproducts of a glucan synthesis reaction. Alternatively, a saccharide herein may contain other monosaccharides in addition to glucose and fructose, such as galactose, ribose and xylose.

A saccharide hydrolyzed in certain embodiments of the disclosed invention can be an oligosaccharide. An oligosaccharide herein can have, for example, 2, 3, 4, 5, 6, 7, 8, or 9 monosaccharide units. As would be understood in the art, an oligosaccharide herein can be referenced with respect to its degree of polymerization (DP) number, which specifies the number of monomeric units in the oligosaccharide. A DP3 oligosaccharide has 3 monomeric units, for example. Thus, the oligosaccharide can be a DP3, DP4, DP5, DP6, DP7, DP8, or DP9 oligosaccharide, for example. The DP of a saccharide in certain embodiments is 3 to 7 (i.e., DP 3-7).

An oligosaccharide herein with 3 or more monosaccharide units can comprise other linkages in addition to at least one alpha-1,5 glucosyl-fructose linkage (note that an oligosaccharide with 2 monosaccharide units—i.e., a disaccharide—is leucrose given that a saccharide in a hydrolysis method herein has at least one alpha-1,5 glucosyl-fructose linkage). For example, there may also be alpha-1,3, alpha-1,6, and/or alpha-1,4 linkages in the oligosaccharide, which are also susceptible to hydrolysis by alpha-glucosidases as shown herein.

An oligosaccharide in certain embodiments comprises only glucose monomers linked by alpha-1,3 and/or alpha-1,6 glycosidic linkages. Thus, such oligosaccharides comprise only alpha-1,3 glucosyl-glucose and/or alpha-1,6 glucosyl-glucose linkages. Examples of such an oligosaccharide contain only alpha-1,3 linkages or alpha-1,6 linkages. An oligosaccharide can comprise at least 85%, 86%, 87%, 88%, 89%, 90%, 91%, 92%, 93%, 94%, 95%, 96%, 97%, 98%, or 99% glucosyl-glucose linkages in certain embodiments. In other embodiments, there can be about 75-85% alpha-1,3 glucosyl-glucose linkages and about 15-25% alpha-1,6 glucosyl-glucose linkages in oligosaccharides herein. Alternatively, oligosaccharides herein can comprise any percentage (any integer value between 1% and 99%) of alpha-1,3 glucosyl-glucose linkages and any percentage (any integer value between 1% and 99%) of alpha-1,6 glucosyl-glucose linkages, just so long that the total of these percentages is not greater than 100%. Any of these oligosaccharides can be in a fraction from a glucan synthesis reaction that produces (i) an insoluble alpha-glucan (e.g., poly alpha-1,3-glucan), or (ii) a soluble alpha-glucan product, for example. This linkage content can characterize (i) each oligosaccharide individually, or (ii) a group of oligosaccharides (i.e., average linkage content). Oligosaccharides comprising only glucose monomers linked by alpha-1,3 and/or alpha-1,6 glycosidic linkages can be DP2-DP7, or DP3-DP7, for example. It should be understood that the exact distribution of linkages in oligosaccharides can vary depending on the conditions of the glucan synthesis reaction (e.g., gtf enzyme) producing oligosaccharide byproducts. It should further be understood that the exact linkage distribution is not critical to the presently disclosed methods.

The Examples herein demonstrate that alpha-glucosidases (e.g., transglucosidase and glucoamylase enzymes) can hydrolyze both (i) leucrose, which comprises an alpha-1,5 glucosyl-fructose linkage, and (ii) oligosaccharides comprising only alpha-1,3 glucosyl-glucose and/or alpha-1,6 glucosyl-glucose linkages. Therefore, an alpha-glucosidase can be used, for example, in a reaction for hydrolyzing alpha-1,5 glucosyl-fructose linkages, alpha-1,3 glucosyl-glucose linkages and/or alpha-1,6 glucosyl-glucose linkages.

At least one alpha-1,5 glucosyl-fructose linkage in a saccharide herein can be hydrolyzed by an alpha-glucosidase herein. Alternatively, it is believed that 2, 3, 4, 5, or more alpha-1,5 glucosyl-fructose linkages in a saccharide can be hydrolyzed by an alpha-glucosidase, for example. Hydrolysis of at least one alpha-1,5 glucosyl-fructose linkage can occur at the non-reducing-end of the saccharide in certain embodiments. For example, where the saccharide is the disaccharide, leucrose, the non-reducing end glucose is cleaved from fructose yielding free glucose and fructose. As another example, where the saccharide is an oligosaccharide with a non-reducing end glucose that is alpha-1,5-linked to fructose, it is believed that this glucose can be cleaved off, leaving a fructose residue at the non-reducing end of the oligosaccharide.

The amount of a saccharide is reduced in the disclosed hydrolysis method compared to the amount of the saccharide that was present prior to the contacting step. This reduction results from hydrolytic cleavage of at least one alpha-1,5 glucosyl-fructose linkage in the saccharide. The amount (e.g., concentration) of a saccharide after the contacting step in a hydrolysis method herein can be less than about 1%, 2%, 3%, 4%, 5%, 10%, 20%, 30%, 40%, 50%, 60%, 70%, 80%, or 90% (or any integer value between 1% and 90%) of the amount of the saccharide that was present prior to the contacting step (prior to contacting an alpha-glucosidase herein with a saccharide under suitable conditions).

A saccharide hydrolyzed in certain embodiments of the disclosed invention is leucrose, which is a disaccharide with an alpha-1,5 glucosyl-fructose linkage. The concentration of leucrose after the contacting step in a hydrolysis method herein can be less than about 1%, 2%, 3%, 4%, 5%, 10%, 20%, 30%, 40%, 50%, 60%, 70%, 80%, or 90% (or any integer value between 1% and 90%) of the concentration of leucrose that was present prior to the contacting step (prior to contacting an alpha-glucosidase herein with leucrose under suitable conditions). A hydrolysis method in some aspects herein can alternatively be referred to as a method of reducing the amount of a leucrose in a composition.

Leucrose can be contacted with a transglucosidase such as one comprising SEQ ID NO:1 (Transglucosidase L-2000), for example, in a hydrolysis method herein. The concentration of leucrose after completing such a method can be less than about 1-3% of the original leucrose concentration in certain embodiments.

The amount of a saccharide is reduced in the disclosed hydrolysis method compared to the amount of the saccharide that was present prior to the contacting step. It would be understood that such a comparison can be made in any number of ways. For example, the saccharide concentration can be measured both before and after performing the hydrolysis method. Alternatively, the comparison can be made with respect to a control reaction having the same conditions, except that no alpha-glucosidase as presently disclosed is added to the control reaction.

An alpha-glucosidase in certain embodiments herein may be immobilized. The enzyme may be immobilized using any method and/or means known in the art, such as those disclosed in U.S. Pat. Nos. 5,541,097 and 4,713,333, both of which are incorporated herein by reference. For example, one or more enzymes can be immobilized by contacting the enzyme(s) with a solution of an amine-reactive material (e.g., glutaraldehyde) to form an adduct (e.g., enzyme-glutaraldehyde adduct), after which the adduct is bonded to a solid carrier that has been treated with a polyamine (e.g., a polyethylenimine such as EPOMIN P-1050).

A solid carrier (solid support) to which an alpha-glucosidase enzyme can be immobilized in certain embodiments can be an inorganic or organic material. Such materials include, for example, gamma-alumina, titania, activated granular carbon, granular diatomaceous earth, glass beads, porous glass, pumice-stone, silica gel, metal oxide and aluminum oxide.

A polyamine can be used to treat a solid carrier such that subsequent exposure of the solid carrier to an adduct comprising an enzyme and amine-reactive material leads to attachment of the enzyme to the solid carrier. Examples of polyamines useful herein include polyethylenediamine, a polyethylenimine (e.g., polydiethylenetriamine, polytriethylenetetramine, polypentaethylenehexam ine, polyhexamethylenediamine), polymethylenedicyclohexylam ine, polymethylenedianiline, polytetraethylenepentamine, polyphenylenediamine and blends of two or more of these polyamine compounds. Preferred polyamines are water-soluble and/or have a molecular weight of about from 500 to 100,000 Daltons. A polyethylenimine such as EPOMIN P-1050 can be used in certain embodiments.

An amine-reactive material useful for preparing an adduct comprising an enzyme herein can be, for example, an aldehyde, organic halide, anhydride, azo compound, isothiocyanate, and/or isocyanate. Examples of these amine-reactive materials include glutaraldehyde, succindialdehyde, terephthaldehyde, bis-diazobenzidine-2,2'-disulfonic acid, 4,4'-difluoro-3,3'-dinitrodiphenylsulfone, diphenyl-4,4'-dithiocyanate-2,2'-disulfonic acid, 3-methoxydiphenylmethane-4,4'-diisocyanate, toluene-2-isocyanate-4-isothiocyanate, toluene-2,-4-diisothiocyanate, diazobenzidine, diazobenzidine-3,3'-dianisidine, N,N'-hexamethylene bisiodoacetamide, hexamethylene diisocyanate, cyanuric chloride, and/or 1,5-difluoro-2,4-dinitrobenzene. Preferably, the amine-reactive material is an aldehyde such as glutaraldehyde.

An alpha-glucosidase enzyme adducted with an amine-reactive compound can be contacted with a polyamine-treated solid carrier, thereby immobilizing the enzyme onto the solid carrier. An immobilized enzyme herein can be employed in various reactor systems, such as in a column (e.g., packed column) or stirred tank reactor, for performing hydrolysis reaction as disclosed herein.

Suitable conditions for contacting a saccharide herein with an alpha-glucosidase herein (e.g., transglucosidase or glucoamylase) are those conditions that support the hydrolysis of one or more alpha-1,5 glucosyl-fructose linkages in the saccharide by the alpha-glucosidase. Examples of suitable conditions are disclosed in the below Examples. Conditions (e.g., temperature, pH, time) for contacting an alpha-glucosidase herein with a sugar substrate are also disclosed in U.S. Pat. Appl. Publ. No. 2008/0229514, U.S. Pat. No. 7,413,887 and U.S. Pat. Appl. Publ. No. 2013/0102035 (all of which are incorporated herein by reference), and may also be applicable to the disclosed hydrolysis method.

The disaccharides and oligosaccharides in the disclosed hydrolysis method are typically soluble in water or an aqueous solution. Thus, contacting a saccharide herein with an alpha-glucosidase is preferably performed under suitable conditions that are aqueous, in which the saccharide is dissolved. Aqueous conditions can characterize a solution or mixture comprising at least about 20 wt % water. Alternatively, aqueous conditions herein are at least about 20, 30, 40, 50, 60, 70, 80, 85, 90, or 95 wt % water (or any integer value between 20 and 95 wt %), for example. Aqueous conditions can further comprise a buffer, for example, such as an acidic, neutral, or alkaline buffer, at a suitable concentration and selected based on the pH range provided by the buffer. Examples of buffers/buffering agents include citrate, acetate (e.g., sodium acetate), $KH_2PO_4$, MOPS, CHES, borate, sodium carbonate, and sodium bicarbonate.

The pH of a hydrolysis reaction herein can be about 3.0 to 9.0, for example. Hydrolysis reaction pH can be, for example, about 3.0, 3.5, 4.0, 4.5, 5.0, 5.5, 6.0, 6.5, 7.0, 7.5, 8.0, 8.5, or 9.0. Alternatively, the pH can be about 4-5. Techniques for setting pH include the use of buffers, alkalis, and/or acids, for example, and are well known in the art.

The temperature of a hydrolysis reaction herein can be about 20° C. to about 80° C., for example. Hydrolysis reaction temperature can be, for example, about 20, 30, 40, 50, 60, 70, or 80° C. (or any integer value between 20 and 80° C.). A hydrolysis temperature of about 60° C., 65° C., or 60-65° C. is preferred in certain embodiments.

A hydrolysis reaction herein can be performed for a period of at least about 10 minutes to about 90 hours, for example. The time of a hydrolysis reaction can be, for example, at least about 0.5, 1, 2, 3, 4, 8, 12, 16, 20, 24, 30, 36, 42, 48, 54, 60, 66, 72, 78, 84, or 90 hours (or any integer value between 0.5 and 72 hours). In certain embodiments, such as for hydrolyzing leucrose, a hydrolysis reaction can be performed in less than 4 hours (e.g., 0.5-4 hours) for example. The time period required to achieve a desired level of hydrolysis will vary on the exact conditions used, and would be understood by one skilled in the art. For example, increasing the amount of enzyme added to a reaction or immobilized on a solid support used in a reaction will reduce the contact time.

One or more of alpha-glucosidase enzymes herein may be used in a hydrolysis reaction in certain embodiments. Both a transglucosidase and glucoamylase can be used in a reaction, for example. The amount of an alpha-glucosidase in a hydrolysis reaction herein can be plus/minus 10% to 20% (or 5% to 10%) from any of the amounts used in the Examples below (e.g., Example 2), for example. Alternatively, about 0.1-0.5 vol % or 0.1-1.0 vol % of alpha-glucosidase can be used in a hydrolysis reaction. Alternatively still, an alpha-glucosidase herein can be used at about, or at least about, 1, 2, 3, 4, 5, 6, 7, 8, 9, 10, 11, 12, 13, 14, or 15 ppm in a hydrolysis reaction. A transglucosidase unit (TGU) can be defined as the amount of a transglucosidase enzyme that will produce one micromole of panose per minute under the conditions of the following assay, for example. Transglucosidase activity can be assayed as follows, for example: a transglucosidase is brought up in 100 mM sodium acetate buffer, pH 4.5, containing 4 mM para-nitrophenyl-alpha-glucoside and 1 mg/ml bovine serum albumin (BSA). After 30 min incubation at 30° C., the reaction is terminated by the addition of an equal volume 1 M sodium carbonate and $OD_{405}$ is recorded. A glucoamylase unit (GAU) can be defined, for example, as the amount of glucoamylase enzyme that will produce 1 g of reducing sugar calculated as glucose per hour from a soluble starch substrate (4% DS [degree of substitution]) at pH 4.2 and 60° C.

The initial concentration of a saccharide in a hydrolysis reaction in certain embodiments of the disclosed invention can be about 1 wt % to 50 wt %, for example. For example, the concentration of leucrose can be about 5, 10, 15, 20, 25, 30, 35, or 40 wt % (or any integer value between 5 and 40 wt %). As another example, the concentration of one or more oligosaccharides (e.g., DP2, DP3, DP4, DP2-DP7, DP3-DP7) in a hydrolysis reaction herein can be about 1, 2, 3, 4, 5, 6, 7, 8, 9, 10, 11, 12, 13, 14, or 15 wt %. Those skilled in the art would recognize that the concentration of total sugars (which includes disaccharides and oligosaccharides) can have an impact on the activity of alpha-glucosidase enzymes; preferred concentrations of total sugars in a hydrolysis reaction to maximize enzyme activity can be less than 50 wt % dry solids (DS), with a most preferred concentration of 20-35 wt % DS in some aspects.

Suitable conditions in certain embodiments for contacting a saccharide with an alpha-glucosidase herein can comprise (i) a glucan synthesis reaction, or (ii) a fraction obtained from a glucan synthesis reaction, where the saccharide is a byproduct of the glucan synthesis reaction. In other words, a hydrolysis reaction herein may be conducted in the context of a glucan synthesis reaction or a fraction of a glucan synthesis reaction, though it is typically conducted in the latter. A glucan synthesis reaction herein can produce one or more insoluble and/or soluble alpha-glucan products, for example. Thus, a glucan synthesis reaction can be characterized in some embodiments herein as an "alpha-glucan synthesis reaction".

A glucan synthesis reaction generally refers to a solution comprising at least sucrose, water and one active glucosyltransferase enzyme, and optionally other components. Other components that can be in a glucan synthesis reaction include fructose, glucose, leucrose, soluble oligosaccharides (e.g., DP2-DP7), and soluble glucan product(s). Also, one or more alpha-glucanohydrolase enzymes can be comprised in a glucan synthesis reaction in some aspects. It would be understood that certain glucan products, such as poly alpha-1,3-glucan with a DP of at least 8 or 9, may be water-insoluble and thus are not dissolved in a glucan synthesis reaction, but rather may be present out of solution. Thus, a glucan produced by glucan synthesis reaction herein can be insoluble. An alpha-glucosidase enzyme herein can be added to a glucan synthesis reaction at any stage thereof, such as during initial preparation of the reaction or when the reaction is near (e.g., 80 to 90% complete) or at completion, where the latter two time points are preferred.

A glucan synthesis reaction herein may be one that, in addition to producing a glucan product, produces byproducts such as leucrose and/or soluble oligosaccharides. A glucan in some aspects is a poly alpha-glucan. Thus, a glucan synthesis reaction herein can be for producing poly alpha-1,3-glucan or mutan, for example, which are typically co-produced with at least leucrose and/or oligosaccharide byproducts in a glucan synthesis reaction.

A glucan synthesis reaction in certain embodiments comprises a glucosyltransferase enzyme that produces a poly alpha-glucan such as poly alpha-1,3-glucan. Examples of such glucosyltransferase enzymes useful herein are disclosed in U.S. Pat. No. 7,000,000, and U.S. Pat. Appl. Publ. Nos. 2013/0244288, 2013/0244287 and 2014/0087431 (all of which are incorporated herein by reference.

A glucosyltransferase enzyme herein may be derived from any microbial source, such as a bacteria or fungus. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneni, L. fermentum* and *L. reuteri*.

A glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Primers that can be used in certain embodiments include dextran and other carbohydrate-based primers, such as hydrolyzed glucan, for example. U.S. Appl. Publ. No. 2013/0244287, which is incorporated herein by reference, discloses preparation of hydrolyzed glucan using poly alpha-1,3-glucan as the starting material. Dextran for use as a primer can be dextran T10 (i.e., dextran having a molecular weight of 10 kD), for example.

A glucosyltransferase enzyme for a glucan synthesis reaction herein may be produced by any means known in the art. For example, a glucosyltransferase enzyme may be produced recombinantly in a heterologous expression system, such as a microbial heterologous expression system. Examples of heterologous expression systems include bacterial (e.g., *E. coli* such as TOP10 or MG1655; *Bacillus* sp.) and eukaryotic (e.g., yeasts such as *Pichia* sp. and *Saccharomyces* sp.) expression systems.

A glucosyltransferase enzyme described herein may be used in any purification state (e.g., pure or non-pure). For example, a glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v), for example, in a reaction solution for producing a poly alpha-glucan such as poly alpha-1,3-glucan from sucrose.

The temperature of a glucan synthesis reaction herein can be controlled, if desired. In certain embodiments, the temperature of the reaction is between about 5° C. to about 50° C. The temperature in certain other embodiments is between about 20° C. to about 40° C.

The initial concentration of sucrose in a glucan synthesis reaction herein can be about 20 g/L to about 400 g/L, for example. Alternatively, the initial concentration of sucrose can be about 75 g/L to about 175 g/L, or from about 50 g/L to about 150 g/L. Alternatively still, the initial concentration of sucrose can be about 40, 50, 60, 70, 80, 90, 100, 110, 120, 130, 140, 150, or 160 g/L (or any integer value between 40 and 160 g/L), for example. "Initial concentration of sucrose" refers to the sucrose concentration in a gtf reaction solution just after all the reaction solution components have been added (at least water, sucrose, gtf enzyme).

Sucrose used in a glucan synthesis reaction herein can be highly pure (>99.5%) or be of any other purity or grade. For example, sucrose can have a purity of at least 99.0%, or can be reagent grade sucrose. As another example, incompletely refined sucrose can be used. Incompletely refined sucrose herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. The ICUMSA (International Commission for Uniform Methods of Sugar Analysis) of incompletely refined sucrose herein can be greater than 150, for example. Sucrose herein may be derived from any renewable sugar source such as sugar cane, sugar beets, cassava, sweet sorghum, or corn. Suitable forms of sucrose useful herein are crystalline form or non-crystalline form (e.g., syrup, cane juice, beet juice), for example. Additional suitable forms of incompletely refined sucrose are disclosed in U.S. Appl. No. 61/969,958.

Methods of determining ICUMSA values for sucrose are well known in the art and disclosed by the International Commission for Uniform Methods of Sugar Analysis in *ICUMSA Methods of Sugar Analysis: Official and Tentative Methods Recommended by the International Commission for Uniform Methods of Sugar Analysis* (ICUMSA) (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0—Official*, Verlag Dr Albert Bartens, 2011 revision), which is incorporated herein by reference.

The pH of a glucan synthesis reaction in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a glucan synthesis reaction can be from 0 mM to about 100 mM, or about 10, 20, or 50 mM, for example.

Poly alpha-1,3-glucan produced in a glucan synthesis reaction herein may have at least about 50%, 60%, 70%, 80%, 90%, 95%, 96%, 97%, 98%, 99%, or 100% (or any integer value between 50% and 100%) glycosidic linkages that are alpha-1,3. In such embodiments, accordingly, the poly alpha-1,3-glucan has less than about 50%, 40%, 30%, 20%, 10%, 5%, 4%, 3%, 2%, 1%, or 0% (or any integer value between 0% and 50%) of glycosidic linkages that are not alpha-1,3.

Poly alpha-1,3-glucan herein preferably has a backbone that is linear/unbranched. In certain embodiments, the poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points.

The molecular weight of poly alpha-1,3-glucan produced in a glucan synthesis reaction herein can be measured as number-average molecular weight ($M_n$) or weight-average molecular weight ($M_w$). Alternatively, molecular weight can be measured in Daltons or grams/mole. It may also be useful to refer to the $DP_w$ (weight average degree of polymerization) or $DP_n$ (number average degree of polymerization) of the poly alpha-1,3-glucan polymer.

The $M_n$ or $M_w$ of poly alpha-1,3-glucan herein may be at least about 1000. Alternatively, the $M_n$ or $M_w$ can be at least about 1000 to about 600000 (or any integer value between 1000 and 600000), for example. Alternatively still, poly alpha-1,3-glucan in can have a molecular weight in $DP_n$ or $DP_w$ of at least about 100, or of at least about 100 to 1000 (or any integer value between 100 and 1000).

A fraction of a glucan synthesis reaction may constitute suitable conditions for contacting a saccharide with an alpha-glucosidase as presently disclosed. A fraction can be a portion of, or all of, the liquid solution from a glucan synthesis reaction. Typically, a fraction has been separated from soluble or insoluble glucan product(s) synthesized in the reaction. For example, a fraction can be separated from one or more glucan products that are insoluble in water (e.g., poly alpha-1,3-glucan) which fall out of solution during their synthesis. A fraction in certain preferred embodiments of the present disclosure is from a poly alpha-1,3-glucan synthesis reaction.

The volume of a fraction (before optionally diluting or concentrating the fraction, see below) in certain embodiments can be at least about 10%, 20%, 30%, 40%, 50%, 60%, 70%, 80%, or 90% (or any integer value between 10% and 90%) of the volume of the glucan synthesis reaction from which it is obtained. Typically, in glucan synthesis reactions producing an insoluble glucan (e.g., poly alpha-1,3-glucan), the fraction will be a portion of (not all of) the liquid solution component of the reaction. A fraction can be obtained at any stage of a glucan synthesis reaction, but is preferably obtained near (e.g., greater than 80 or 90% complete) or after completion of the reaction.

Examples of a fraction of a glucan synthesis reaction in certain embodiments include filtrates and supernatants. Thus, in those embodiments in which an insoluble glucan product is synthesized, a fraction herein can be obtained (separated) from a glucan synthesis reaction using a funnel, filter (e.g., press filter), centrifuge, or any other method or equipment known in the art that allows removal of some or all liquids from solids. Filtration can be by gravity, vacuum, or press filtration, for example. Filtration preferably removes all or most of an insoluble glucan; any filter material (e.g., filter paper) with an average pore size (e.g., ~40-50 micron) sufficient to remove solids from liquids can be used. A fraction typically retains all or most of its dissolved components, such as byproducts of the glucan synthesis reaction. Leucrose is a preferred saccharide in a filtrate herein.

A fraction herein can optionally be diluted or concentrated, if desired. Concentration of a fraction can be performed using any other method or equipment known in the art suitable for concentrating a solution. For example, a fraction can be concentrated by evaporation, such as with a rotary evaporator (e.g., set at a temperature of about 40-50° C.). A fraction in some aspects herein can be concentrated down to a volume that is about 75%, 80%, 85%, 90%, or 95% of the original fraction volume. A concentrated fraction (e.g., concentrated filtrate) can optionally be referred to as a syrup.

A fraction in some aspects can comprise water that replaces the water that was present in the composition from which the fraction was obtained. For example, saccharide byproduct(s) from a glucan synthesis reaction can be separated in certain chromatographic methods in which the original solvent is replaced with another solvent (e.g., saccharide byproducts that are bound to a column [thus removed from the original solvent] can be eluted into a new solvent).

A fraction in some aspects may be treated in a manner to have any of the suitable conditions (e.g., temperature, pH and time) disclosed above for contacting a saccharide with an alpha-glucosidase. For example, a fraction can be modified to have a pH of about 4 to 5 before an alpha-glucosidase is added to the fraction. As another example, the temperature of a hydrolysis reaction with a fraction can be about 55-65° C. (e.g., about 60° C.). A fraction that has been concentrated down to a syrup can be used in a hydrolysis reaction in yet another example.

A fraction in certain preferred embodiments herein is from a poly alpha-1,3-glucan synthesis reaction; such a fraction is preferably a filtrate. A fraction of a poly alpha-1,3-glucan synthesis reaction herein comprises at least water, fructose and one or more types of saccharide (leucrose and/or oligosaccharides such as DP2-DP7). Other components that may be in this type of fraction include sucrose (i.e., residual sucrose not consumed in the gtf reaction), one or more gtf enzymes, glucose, buffer, salts, FermaSure®, borates, sodium hydroxide, hydrochloric acid, cell lysate components, proteins and/or nucleic acids, for example. Minimally, the components of a fraction from a poly alpha-1,3-glucan synthesis reaction include water, fructose, glucose, one or more types of saccharide (leucrose and/or oligosaccharides such as DP2-DP7), and optionally sucrose, for example. It would be understood that the composition of a fraction depends, in part, on the conditions of the glucan synthesis reaction from which the fraction is obtained. In those fractions containing one or more gtf enzymes, it is preferable that such one or more gtf enzymes are deactivated (e.g., heat-deactivated) before using the fraction in a hydrolysis reaction herein.

It should be understood that the exact distribution of sugar byproducts produced via polymerization of sucrose in a glucan synthesis reaction can vary based on the reaction conditions and gtf enzyme used, especially on temperature and sucrose concentration. It should also be understood that the exact composition of sugars in a fraction of a glucan synthesis reaction is not critical to the disclosed hydrolysis process. Generally, as the amount of sucrose is increased, the selectivity of the reaction towards both leucrose and oligosaccharides will increase. Conversely, as the temperature increases, the selectivity of the reaction towards leucrose tends to decrease, while the selectivity towards oligosaccharides is largely unaffected. It should also be understood that the ratio of sugars to water, i.e., wt % dry solids (DS), which is calculated by dividing the mass of sugar to total solution weight, can be adjusted either by evaporating water, preferably at temperatures below 50° C. under vacuum, or addition of water, without significant impact to the relative distribution of sugars in a fraction of a glucan synthesis reaction. It is also possible to increase the percentage of sucrose in a fraction by stopping the gtf reaction before complete conversion (to glucan) is achieved, either by reducing the pH below the active range for the gtf enzyme or by thermal deactivation of the gtf enzyme.

In certain embodiments, a glucan synthesis reaction herein can produce one or more soluble alpha-glucan products. A soluble alpha-glucan product ("soluble fiber", alternatively) can be (i) a direct product of a glucosyltransferase, or (ii) a product of the concerted action of both a glucosyltransferase and an alpha-glucanohydrolase capable of hydrolyzing glucan polymers having one or more alpha-1,3-glycosidic linkages or one or more alpha-1,6-glycosidic linkages.

A soluble alpha-glucan herein can comprise, for example:
a) at least 75% alpha-1,3-glycosidic linkages;
b) less than 25% alpha-1,6-glycosidic linkages;
c) less than 10% alpha-1,3,6-glycosidic linkages;
d) an $M_w$ of less than 5000 Daltons;
e) a viscosity of less than 0.25 Pascal second (Pa·s) at 12 wt % in water at 20° C.;
f) a dextrose equivalence (DE) in the range of 4 to 40;
g) a digestibility of less than 10% as measured by the Association of Analytical Communities (AOAC) method 2009.01;
h) a solubility of at least 20% (w/w) in pH 7 water at 25° C.; and
i) a polydispersity index (PDI) of less than 5.

Such a soluble alpha-glucan can be produced as disclosed in U.S. Appl. No. 62/004,290.

As an example, a soluble alpha-glucan fiber composition can comprise at least 75%, preferably at least 80%, more preferably at least 85%, even more preferably at least 90%, and most preferably at least 95% alpha-(1,3) glycosidic linkages.

As another example, in addition to the alpha-(1,3) glycosidic linkage embodiments described above, a soluble alpha-glucan fiber composition can further comprise less than 25%, preferably less than 10%, more preferably 5% or less, and even more preferably less than 1% alpha-(1,6) glycosidic linkages.

As another example, in addition to the alpha-(1,3) and alpha-(1,6) glycosidic linkage content embodiments described above, a soluble alpha-glucan fiber composition can further comprise less than 10%, preferably less than 5%, and most preferably less than 2.5% alpha-(1,3,6) glycosidic linkages.

As another example, a soluble alpha-glucan fiber composition can comprise 93 to 97% alpha-(1,3) glycosidic linkages and less than 3% alpha-(1,6) glycosidic linkages and has a weight-average molecular weight corresponding to a DP of 3 to 7 mixture. In a further embodiment, a soluble alpha-glucan fiber composition can comprise about 95% alpha-(1,3) glycosidic linkages and about 1% alpha-(1,6) glycosidic linkages and has a weight-average molecular weight corresponding to a DP of 3 to 7 mixture. In a further aspect of the above embodiment, a soluble alpha-glucan fiber composition can further comprise 1 to 3% alpha-(1,3,6) linkages or preferably about 2% alpha-(1,3,6) linkages.

As another example, in addition to the above-mentioned glycosidic linkage content embodiments, a soluble alpha-glucan fiber composition can further comprise less than 5%, preferably less than 1%, and most preferably less than 0.5% alpha-(1,4) glycosidic linkages.

As another example, in addition the above-mentioned glycosidic linkage content embodiments, a soluble alpha-glucan fiber composition can comprise a weight average molecular weight ($M_w$) of less than 5000 Daltons, preferably less than 2500 Daltons, more preferably between 500 and 2500 Daltons, and most preferably about 500 to about 2000 Daltons.

As another example, in addition to any of the above features, a soluble alpha-glucan fiber composition can comprise a viscosity of less than 250 centipoise (0.25 Pa·s), preferably less than 10 cP (0.01 Pa·s), preferably less than 7 cP (0.007 Pa·s), more preferably less than 5 cP (0.005 Pa·s), more preferably less than 4 cP (0.004 Pa·s), and most preferably less than 3 cP (0.003 Pa·s) at 12 wt % in water at 20° C.

A soluble alpha-glucan fiber composition can have, in certain embodiments, a digestibility of less than 10%, or preferably less than 9%, 8%, 7%, 6%, 5%, 4%, 3%, 2%, or 1% digestibility as measured by the Association of Analytical Communities (AOAC) method 2009.01. In another aspect, the relative level of digestibility may alternatively be determined using AOAC 2011.25 (Integrated Total Dietary Fiber Assay) (McCleary et al., 2012, *J. AOAC Int.*, 95 (3), 824-844).

In addition to any of the above embodiments, a soluble alpha-glucan fiber composition can have a solubility of at least 20% (w/w), preferably at least 30%, 40%, 50%, 60%, or 70% in pH 7 water at 25° C.

In one embodiment, a soluble alpha-glucan fiber composition can comprise a reducing sugar content of less than 10 wt %, preferably less than 5 wt %, and most preferably 1 wt % or less.

In one embodiment, a soluble alpha-glucan fiber composition can comprise a caloric content of less than 4 kcal/g, preferably less than 3 kcal/g, more preferably less than 2.5 kcal/g, and most preferably about 2 kcal/g or less.

As another example, a soluble alpha-glucan herein can comprise:
  a) 10% to 30% alpha-1,3-glycosidic linkages;
  b) 65% to 87% alpha-1,6-glycosidic linkages;
  c) less than 5% alpha-1,3,6-glycosidic linkages;
  d) a weight average molecular weight (Mw) of less than 5000 Daltons;
  e) a viscosity of less than 0.25 Pascal second (Pa·s) at 12 wt % in water at 20° C.;
  f) a dextrose equivalence (DE) in the range of 4 to 40, preferably 10 to 40;
  g) a digestibility of less than 10% as measured by the Association of Analytical Communities (AOAC) method 2009.01;
  h) a solubility of at least 20% (w/w) in pH 7 water at 25° C.; and
  i) a polydispersity index (PDI) of less than 5.

Such a soluble alpha-glucan can be produced as disclosed in U.S. Appl. No. 62/004,308.

As another example, a soluble alpha-glucan herein can comprise:
  a) 25-35 alpha-1,3-glycosidic linkages;
  b) 55-75% alpha-1,6-glycosidic linkages;
  c) 5-15% alpha-1,3,6-glycosidic linkages;
  d) a weight average molecular weight of less than 5000 Daltons;
  e) a viscosity of less than 0.25 Pascal second (Pa·s) at 12 wt % in water at 20° C.;
  f) a dextrose equivalence (DE) in the range of 4 to 40;
  g) a digestibility of less than 10% as measured by the Association of Analytical Communities (AOAC) method 2009.01;
  h) a solubility of at least 20% (w/w) in water at 25° C.; and
  i) a polydispersity index of less than 5.

Such a soluble alpha-glucan can be produced as disclosed in U.S. Appl. No. 62/004,312.

As another example, a soluble alpha-glucan herein can comprise:
  a) at least 95% alpha-1,6-glycosidic linkages;
  b) 1% or less alpha-1,3-glycosidic linkages;
  c) less than 2% alpha-1,3,6-glycosidic linkages;
  d) less than 1.5% alpha-1,4-glycosidic linkages;
  e) a weight average molecular weight of less than 20000 Daltons;
  f) a viscosity of less than 0.25 Pascal second (Pa·s) at 12 wt % in water at 20° C.;
  g) a dextrose equivalence (DE) in the range of 1 to 30;
  h) a digestibility of less than 10% as measured by the Association of Analytical Communities (AOAC) method 2009.01;
  i) a solubility of at least 20% (w/w) in pH 7 water at 25° C.; and
  j) a polydispersity index of less than 5.

Such a soluble alpha-glucan can be produced as disclosed in U.S. Appl. No. 62/004,314.

As another example, a soluble alpha-glucan herein can comprise:
  a) a range of:
    i) 1% to 50% of alpha-1,3-glycosidic linkages; or
    ii) greater than 10% but less than 40% alpha-1,4-glycosidic linkages; or
    iii) any combination of i) and ii);
  b) 1 to 50% alpha-1,2-glycosidic linkages;
  c) 0-25% alpha-1,3,6-glycosidic linkages;
  d) less than 98% alpha-1,6-glycosidic linkages;
  e) a weight average molecular weight of less than 300 kDa;
  f) a viscosity of less than 0.25 Pascal second (Pa·s) at 12 wt % in water at 20° C.;
  g) a digestibility of less than 20% as measured by the Association of Analytical Communities (AOAC) method 2009.01;
  h) a solubility of at least 20% (w/w) in pH 7 water at 25° C.; and
  i) a polydispersity index of less than 26, preferably less than 5.

Such a soluble alpha-glucan can be produced as disclosed in U.S. Appl. No. 62/004,305.

In certain embodiments, a soluble alpha-glucan is a direct product of a glucosyltransferase. Such a glucosyltransferase, and conditions for use thereof in a suitable glucan synthesis reaction, can be as disclosed herein, or as disclosed in any of U.S. Patent Appl. Nos. 62/004,290, 62/004,308, 62/004,312, 62/004,314, and/or 62/004,305, for example.

A soluble alpha-glucan can alternatively be a product, for example, of the concerted action of both a glucosyltransferase and an alpha-glucanohydrolase that is capable of hydrolyzing glucan polymers having one or more alpha-1,3-glycosidic linkages or one or more alpha-1,6-glycosidic linkages. In some aspects, a glucan synthesis reaction for producing a soluble alpha-glucan product can comprise both at least one glucosyltransferase and at least one alpha-glucanohydrolase. In other aspects, a glucan synthesis reaction can initially comprise one or more glucosyltransferases as the only enzyme component(s). Such a reaction produces a first alpha-glucan product that has not yet been subject to modification by an alpha-glucanohydrolase. Then, at least one alpha-glucanohydrolase is added to the reaction for a suitable period of time to allow modification of the first product to a soluble alpha-glucan product. Thus, there are different ways by which to synthesize a soluble alpha-glucan product through the concerted action of both a glucosyltransferase and an alpha-glucanohydrolase. Conditions for performing a glucan synthesis reaction in which one or more alpha-glucanohydrolase enzymes are included during glucan synthesis reaction and/or after glucan synthesis can be as disclosed herein, or as disclosed in any of U.S. Patent Appl. Nos. 62/004,290, 62/004,308, 62/004,312, 62/004,314, and/or 62/004,305, for example.

An alpha-glucanohydrolase herein can be, for example, a dextranase (capable of hydrolyzing alpha-1,6-linked glycosidic bonds; E.C. 3.2.1.11), a mutanase (capable of hydrolyzing alpha-1,3-linked glycosidic bonds; E.C. 3.2.1.59), a mycodextranase (capable of endohydrolysis of (1-4)-alpha-D-glucosidic linkages in alpha-D-glucans containing both (1-3)- and (1-4)-bonds; EC 3.2.1.61), a glucan 1,6-alpha-glucosidase (EC 3.2.1.70), and an alternanase (capable of endohydrolytically cleaving alternan; E.C. 3.2.1.—; see U.S. Pat. No. 5,786,196).

A mutanase comprising SEQ ID NO:47 can be used in certain aspects. Alternatively, a mutanase can comprise an amino acid sequence that is at least 90%, 91%, 92%, 93%, 94%, 95%, 96%, 97%, 98%, or 99% identical to SEQ ID NO:47 and have mutanase activity, for example.

A glucan synthesis reaction as presently disclosed for producing one or more soluble alpha-glucan products can serve directly as suitable conditions in which to perform a hydrolysis reaction herein in which an alpha-glucosidase is used to hydrolyze an alpha-1,5 glucosyl-fructose linkage. Such hydrolysis can be performed following any of the conditions disclosed above regarding hydrolytic treatment of a glucan synthesis reaction that produces poly alpha-1,3-glucan, for example. Alternatively, a fraction (e.g., chromatographic fraction) of a glucan synthesis reaction for producing one or more soluble alpha-glucan products can be used as suitable conditions in which to perform alpha-glucosidase-mediated hydrolysis of alpha-1,5 glucosyl-fructose linkages.

A fraction in certain embodiments herein can be a chromatographic fraction of a glucan synthesis reaction. For example, a fraction can be a chromatographic fraction of a glucan synthesis reaction that produces one or more soluble alpha-glucan products as disclosed herein. Such a reaction can optionally include one or more alpha-glucanohydrolases during glucan synthesis, and/or after completion of glucan synthesis. A fraction in any of these types of embodiments typically has been obtained for the purpose of separating all of, or most of (e.g., at least about 60%, 70%, 80%, 90%, 95%), a soluble alpha-glucan product from a reaction composition from which it was produced. Once separated from all or most of a soluble alpha-glucan product, a fraction can be subjected to any of the alpha-1,5 glucosyl-fructose hydrolysis processes disclosed herein using one or more alpha-glucanases.

A chromatographic fraction herein can typically be obtained using a suitable type of liquid chromatography. Liquid chromatography can be performed using size-exclusion chromatography (SEC), column chromatography, high-performance liquid chromatography (HPLC), ion-exchange chromatography, affinity chromatography, ultrafiltration, microfiltration, or dialysis, for example.

The present disclosure also concerns a composition produced by contacting a saccharide with an alpha-glucosidase enzyme (e.g., transglucosidase or glucoamylase), wherein (i) the saccharide is a disaccharide or oligosaccharide comprising at least one alpha-1,5 glucosyl-fructose linkage, and (ii) the alpha-glucosidase enzyme hydrolyzes at least one alpha-1,5 glucosyl-fructose linkage of the saccharide. The composition produced in this manner comprises a reduced amount of the saccharide compared to the amount of the saccharide that was present prior to the contacting. Examples of the composition include any of those disclosed herein, such as a hydrolyzed filtrate from a glucan synthesis reaction, or a hydrolyzed fraction of a glucan synthesis reaction used to produce soluble alpha-glucan. Any of the features disclosed above and in the Examples regarding a hydrolysis method and products thereof can characterize the composition. The following features of the composition are examples.

An alpha-glucosidase enzyme in certain embodiments of the composition can comprise an amino acid sequence that is at least 90%, 91%, 92%, 93%, 94%, 95%, 96%, 97%, 98%, or 99% identical to SEQ ID NO:5, 6, 8, 9, 11, 12, 14, 15, 17, 18, 20, 22, 24, 26, 28, 30, 32, 34, 36, 38, or that of DIAZYME RDF ULTRA (DuPont Industrial Biosciences). A transglucosidase in certain embodiments of the composition can comprise an amino acid sequence that is at least 90% identical to SEQ ID NO:1. A glucoamylase in certain embodiments of the composition can comprise an amino acid sequence that is at least 90% identical to SEQ ID NO:2. Alternatively, any of the alpha-glucosidase enzymes disclosed herein can be used to produce the disclosed composition.

A composition produced by a hydrolysis method herein can have, for example, a concentration of a saccharide such as leucrose that is less than 50% of the concentration of leucrose that was present prior to contacting the saccharide with an alpha-glucosidase.

A composition produced by a hydrolysis method in certain embodiments herein can be a glucan synthesis reaction, or a fraction thereof, in which a saccharide byproduct of the glucan synthesis reaction is contacted with an alpha-glucosidase. A fraction in this embodiment can be a filtrate of the glucan synthesis reaction, or a fraction of a glucan synthesis reaction used to produce soluble alpha-glucan, for example. A saccharide in this embodiment can be leucrose, for example.

It would be understood by a skilled artisan that the presently disclosed embodiments are useful, in part, for saccharifying disaccharides and oligosaccharides that can otherwise be difficult to breakdown. This feature can be taken advantage of to perform enhanced methods of (i) fructose enrichment and (ii) fermentation, for example.

Example 6 below demonstrates that fructose enrichment by chromatography is enhanced when using a glucan filtrate hydrolyzed by an alpha-glucosidase (transglucosidase), as compared to using a filtrate that was not hydrolyzed.

Thus, the disclosed invention further concerns a method of enriching fructose that is present in a fraction of a glucan synthesis reaction. This method comprises (a) contacting a fraction obtained from a glucan synthesis reaction with an alpha-glucosidase enzyme (e.g., transglucosidase or glucoamylase) under suitable conditions, wherein the enzyme hydrolyzes at least one alpha-1,5 glucosyl-fructose linkage of a disaccharide or oligosaccharide comprised within the fraction; and (b) separating fructose from the hydrolyzed fraction of step (a) to obtain a composition having a higher concentration of fructose compared to the fructose concentration of the fraction of step (a).

The features of the disclosed fructose enrichment method regarding alpha-glucosidase (e.g., transglucosidase or glucoamylase) enzymes, and fractions of a glucan synthesis reaction, for example, can be according to any of the disclosures provided herein concerning each of these features.

Step (b) of separating fructose can be performed by any means known in the art. For example, chromatography can be employed as disclosed in the below Examples, or by following the disclosure of European Patent Publ. No. EP2292803B1, which is incorporated herein by reference.

A composition (e.g., fructose solution or fructose syrup) having a higher concentration of fructose resulting from the disclosed enrichment method can have at least about 90, 91, 92, 93, 94, 95, 96, 97, 98, or 99 wt % fructose.

A fructose enrichment method herein can perform better than one which utilizes a filtrate that has not been hydrolyzed with an alpha-glucosidase as presently disclosed. Such increased performance can be measured in terms of a percent fructose recovery of at least 40%, 45%, or 50%.

The present disclosure further concerns a fermentation method comprising (a) contacting a fraction obtained from a glucan synthesis reaction with an alpha-glucosidase enzyme (e.g., transglucosidase or glucoamylase) under suitable conditions, wherein the alpha-glucosidase enzyme hydrolyzes at least one alpha-1,5 glucosyl-fructose linkage of a disaccharide or oligosaccharide comprised within the fraction; (b) fermenting the fraction of step (a) with a microbe to yield a product; and (c) optionally, isolating the product of (b). The fermenting step of (b) can be performed after step (a) or simultaneously with step (a). Significantly, this method can be used to produce ethanol, for example, by fermenting a hydrolyzed filtrate of a glucan synthesis reaction. The ethanol yield from such a process is higher than the ethanol yield obtained when fermenting a glucan filtrate that has not been hydrolyzed.

The features of the disclosed fermentation method regarding alpha-glucosidase (e.g., transglucosidase or glucoamylase) enzymes, disaccharides and oligosaccharides, fractions of a glucan synthesis reaction, and suitable contacting conditions, for example, can be according to any of the disclosures provided herein concerning each of these features.

A microbe for use in a fermentation method herein can be a bacteria, yeast, or fungus, for example. Examples of bacteria useful herein include *Lactobacillus* species, *Streptococcus* species, *Bifidobactenium* species, *Leuconostoc* species, *Eschenchia* species (e.g., *E. coli*) and *Bacillus* species. Examples of yeast useful herein include *Saccharomyces* species such as *S. cerevisiae* and *S. bayanus*.

A fermentation method herein can yield a product such as ethanol or an acid (e.g., lactic acid). It is believed, however, that other products can be produced if desired. It would be understood by one of skill in the art that production of certain products using a fermentation method as disclosed would depend on various conditions such as the microbe(s) used in the fermentation. Conditions for fermentation herein can be as disclosed in the below Examples, or as disclosed in El-Mansi et al. (2006, *Fermentation Microbioloyav and Biotechnology*, Second Edition, CRC Press) and Stanbury et al. (1999, *Principles of Fermentation Technology*, Second Edition, Butterworth-Heinemann), for example, which are both incorporated herein by reference.

The yield of a product in certain embodiments of a fermentation method herein is higher than the product yield obtained when fermenting a glucan filtrate that has not been hydrolyzed with an alpha-glucosidase herein. This comparison can be with respect to a control fermentation, for example, which used a non-hydrolyzed fraction of a glucan synthesis reaction. Product yield of a fermentation herein can be increased by at least about 10%, 20%, 40%, 60%, 80%, or 100% (or any integer value between 10% and 100%), for example. In addition, the rate of product formation by a fermentation herein can be increased.

Example 7 below demonstrates that leucrose can be fermented to ethanol by yeast provided a feed comprising glucan filtrate that had not been hydrolyzed. Thus, further disclosed herein is a method of using a microbe to ferment leucrose to a product (e.g., ethanol). Such a method can comprise fermenting a glucan filtrate that (i) has, or (ii) has not been, hydrolyzed with an alpha-glucosidase as disclosed herein. Regardless of whether the leucrose is provided in a glucan filtrate or another form (e.g., semi-purified or enriched form), a method for fermenting leucrose can comprise adapting a microbe (e.g., yeast such as *S. cerevisiae*) for utilizing leucrose. Such adaptation can comprise growing a microbe in the presence of leucrose, and optionally other sugars, over at least 2 or 3 growth cycles, for example, after which the microbe utilizes more leucrose for fermenting a product. In certain embodiments, a microbe can be (i) grown in a first feed comprising leucrose (1 cycle complete), (ii) removed from the first feed, (iii) grown in a second feed comprising leucrose (two cycles complete), (iv) optionally removed from the second feed, and (v) optionally grown in a third feed (three cycles complete). A microbe adapted in this manner can have an increased capacity to ferment leucrose in certain embodiments.

Example 9 below demonstrates that almost all (e.g., >98% or >99%) the leucrose present in a glucan filtrate can be used for fermentation by yeast when the glucan filtrate is hydrolyzed with a transglucosidase while at the same time fermented with yeast. Thus, an enhanced leucrose fermentation method herein can comprise hydrolysis of leucrose with an alpha-glucosidase (e.g., transglucosidase or glucoamylase) while simultaneously fermenting the leucrose with a microbe.

Non-limiting examples of compositions and methods disclosed herein include:

1. A method of hydrolyzing an alpha-1,5 glucosyl-fructose linkage in a saccharide comprising at least one alpha-1,5 glucosyl-fructose linkage, wherein the saccharide is a disaccharide or oligosaccharide, and wherein the method comprises:
    contacting the saccharide with an alpha-glucosidase enzyme under suitable conditions, wherein the alpha-glucosidase enzyme hydrolyzes at least one alpha-1,5 glucosyl-fructose linkage of the saccharide, and wherein the amount of the saccharide is reduced compared to the amount of the saccharide that was present prior to the contacting.
2. The method of embodiment 1, wherein the alpha-glucosidase enzyme is immobilized.
3. The method of embodiment 1 or 2, wherein the saccharide is leucrose.
4. The method of embodiment 3, wherein the concentration of leucrose after the contacting step is less than 50% of the concentration of leucrose that was present prior to the contacting.
5. The method of embodiment 1, 2, 3, or 4, wherein the suitable conditions comprise:
    (i) a glucan synthesis reaction, or
    (ii) a fraction obtained from the glucan synthesis reaction; wherein the saccharide is a byproduct of the glucan synthesis reaction.
6. The method of embodiment 5, wherein the glucan synthesis reaction produces at least one insoluble alpha-glucan product.
7. The method of embodiment 6, wherein the fraction is a filtrate of the glucan synthesis reaction.

8. The method of embodiment 5, wherein the glucan synthesis reaction produces at least one soluble alpha-glucan product that is
   (i) a product of a glucosyltransferase, or
   (ii) a product of the concerted action of both a glucosyltransferase and an alpha-glucanohydrolase capable of hydrolyzing glucan polymers having one or more alpha-1,3-glycosidic linkages or one or more alpha-1,6-glycosidic linkages.
9. The method of embodiment 8, wherein the fraction is a chromatographic fraction of the glucan synthesis reaction.
10. The method of any one of embodiments 1-9, wherein the alpha-glucosidase enzyme is a transglucosidase or glucoamylase.
11. A composition produced by contacting a saccharide with an alpha-glucosidase enzyme,
   wherein the saccharide is a disaccharide or oligosaccharide and comprises at least one alpha-1,5 glucosyl-fructose linkage,
   wherein the enzyme hydrolyzes at least one alpha-1,5 glucosyl-fructose linkage of the saccharide,
   and wherein the composition comprises a reduced amount of the saccharide compared to the amount of the saccharide that was present prior to the contacting.
12. The composition of embodiment 11, wherein the saccharide is leucrose.
13. The composition of embodiment 11 or 12, wherein the saccharide is in (i) a glucan synthesis reaction, or (ii) a fraction obtained from the glucan synthesis reaction; wherein the saccharide is a byproduct of the glucan synthesis reaction.
14. A method of enriching fructose present in a fraction of a glucan synthesis reaction, comprising:
   (a) contacting a fraction obtained from a glucan synthesis reaction with an alpha-glucosidase enzyme under suitable conditions, wherein the alpha-glucosidase enzyme hydrolyzes at least one alpha-1,5 glucosyl-fructose linkage of a disaccharide or oligosaccharide comprised within the fraction; and
   (b) separating fructose from the hydrolyzed fraction of step (a) to obtain a composition having a higher concentration of fructose compared to the fructose concentration of the fraction of step (a).
15. A fermentation method comprising:
   (a) contacting a fraction obtained from a glucan synthesis reaction with an alpha-glucosidase enzyme under suitable conditions, wherein the alpha-glucosidase enzyme hydrolyzes at least one alpha-1,5 glucosyl-fructose linkage of a disaccharide or oligosaccharide comprised within the fraction;
   (b) fermenting the fraction of step (a) with a microbe to yield a product, wherein the fermenting is performed after step (a) or simultaneously with step (a); and
   (c) optionally, isolating the product of (b);
   wherein the yield of the product of (b) is increased compared to the product yield of fermenting a fraction of the glucan synthesis reaction that has not been contacted with the alpha-glucosidase enzyme.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meaning of some of the abbreviations used herein is as follows: "g" means gram(s), "h" means hour(s), "mL" means milliliter(s), "psi" means pound(s) per square inch, "wt %" means weight percentage, "µm" means micrometer(s), "%" means percent, "° C." means degrees Celsius, "mg" means milligram(s), "mm" means millimeter(s), "mL/min" means milliliters per minute, "m" means meter(s), "µL" means microliter(s), "mmol" means millimole(s), "min" means minute(s), "mol %" means mole percent, "M" means molar, "mg/g" means milligram per gram, "rpm" means revolutions per minute, "MPa" means megaPascals.

General Methods

All reagents were obtained from Sigma-Aldrich (St. Louis, Mo.) unless stated otherwise. Sucrose was obtained from VWR (Radnor, Pa.).

Preparation of Crude Extracts of Glucosyltransferase (gtf) Enzymes

The *Streptococcus salivarius* gtfJ enzyme (SEQ ID NO:3) was expressed in *E. coli* strain DH10B using an isopropyl beta-D-1-thiogalactopyranoside (IPTG)-induced expression system. SEQ ID NO:3 has an N-terminal 42-residue deletion compared to the *S. salivarius* gtfJ amino acid sequence in GENBANK Identification No. 47527, but includes a start methionine. Briefly, *E. coli* DH10B cells were transformed to express SEQ ID NO:3 from a DNA sequence codon-optimized to express the gtfJ enzyme in *E. coli*. This DNA sequence was contained in the expression vector, pJexpress404® (DNA 2.0, Menlo Park Calif.). The transformed cells were inoculated to an initial optical density (OD at 600 nm) of 0.025 in LB medium (10 g/L Tryptone; 5 g/L yeast extract, 10 g/L NaCl) and allowed to grow at 37° C. in an incubator while shaking at 250 rpm. The cultures were induced by addition of 1 mM IPTG when they reached an $OD_{600}$ of 0.8-1.0. Induced cultures were left on the shaker and harvested 3 hours post induction.

GtfJ enzyme (SEQ ID NO:3) was harvested by centrifuging cultured cells (25° C., 16000 rpm) in an Eppendorf® centrifuge, re-suspending the cells in 5.0 mM phosphate buffer (pH 7.0) and cooling to 4° C. on ice. The cells were broken using a bead beater with 0.1-mm silica beads, and then centrifuged at 16000 rpm at 4° C. to pellet the unbroken cells and cell debris. The crude extract (containing soluble GtfJ enzyme, SEQ ID NO:3) was separated from the pellet and analyzed by Bradford protein assay to determine protein concentration (mg/mL).

The *Streptococcus* sp. C150 gtf-S enzyme (SEQ ID NO:40) was prepared as follows. SG1184 is a *Bacillus subtilis* expression strain that expresses a truncated version of the glycosyltransferase Gtf-S("GTF0459") from *Streptococcus* sp. C150 (GENBANK® GI:321278321). The gene (SEQ ID NO:41) encoding an N-terminal truncated protein GTF0459 (SEQ ID NO:42) from *E. coli* expression plasmid pMP79 was cloned into the NheI and HindIII sites of the *Bacillus subtilis* integrative expression plasmid p4JH under the aprE promoter and fused with the *B. subtilis* AprE signal peptide on the vector. The construct was first transformed into *E. coli* DH10B and selected on LB with ampicillin (100 µg/mL) plates. The confirmed construct pDCQ984 expressing GTF0459 was then transformed into *B. subtilis* BG6006 containing nine protease deletions (amyE::xyIRPxyl-AcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB) and selected on LB plates with chloramphenicol (5 μg/mL). The colonies grown on LB plates with 5 μg/mL chloramphenicol were streaked several times onto LB plates with 25 μg/mL chloramphenicol. The resulting *B. subtilis* expression strain, SG1184, was first grown in LB medium with 25 μg/mL chloramphenicol and then subcultured into GrantsII medium containing 25 μg/mL chloramphenicol grown at 30° C. for 2-3 days. The cultures were spun at 15,000 g for 30 min at 4° C. and the supernatant was filtered through 0.22-μm filters. The filtered supernatant was aliquoted and frozen at −80° C.

*B. subtilis* SG1184 strain, expressing GTF0459 (SEQ ID NO:42), was grown under an aerobic submerged condition by conventional fed-batch fermentation. A nutrient medium was used containing 0-0.25% corn steep solids (Roquette), 5-25 g/L sodium and potassium phosphate, a solution of 0.3-0.6 M ferrous sulfate, manganese chloride and calcium chloride, 0.5-4 g/L magnesium sulfate, and a solution of 0.01-3.7 g/L zinc sulfate, cuprous sulfate, boric acid and citric acid. An antifoam agent, FOAMBLAST 882, at 2-4 mL/L was added to control foaming. A 10-L fermentation was fed with 50% (w/w) glucose feed when initial glucose in batch was non-detectable. The glucose feed rate was ramped over several hours. The fermentation was controlled at 30° C. and 20% DO, and at initial agitation of 750 rpm. The pH was controlled at 7.2 using 50% (v/v) ammonium hydroxide. Fermentation parameters such as pH, temperature, airflow, and DO % were monitored throughout the entire 2-day fermentation run. The culture broth was harvested at the end of the run and centrifuged to obtain supernatant. The supernatant containing GTF0459 (SEQ ID NO:42) was then stored frozen at −80° C.

The *S. mutans* MT-4239 gtf-C enzyme (SEQ ID NO:43) was prepared as follows. A gene encoding a truncated version of a glucosyltransferase (gtf) enzyme identified in GENBANK® as GI:3130088 (SEQ ID NO:43; gtf-C from *S. mutans* MT-4239) was synthesized using codons optimized for expression in *Bacillus subtilis* and synthesized by GenScript. The gene (SEQ ID NO:44) encoding GTF0088BsT1 with an N-terminal truncation and a C-terminal T1 truncation (SEQ ID NO:45) was amplified from the GENSCRIPT plasmid and cloned into the NheI and HindIII sites of the *Bacillus subtilis* integrative expression plasmid p4JH under the aprE promoter and fused with the *B. subtilis* AprE signal peptide on the vector. The construct was first transformed into *E. coli* DH10B and selected on LB with ampicillin (100 μg/mL) plates. The confirmed construct pDCQ1021 expressing GTF0088BsT1 was then transformed into *B. subtilis* BG6006 containing nine protease deletions (amyE::xyIR-PxylAcomK-ermC, degUHy32, oppA, AspoIIE3501, ΔaprE, ΔnprE, Δepr, ΔispA, Δbpr, Δvpr, ΔwprA, Δmpr-ybfJ, ΔnprB) and selected on the LB plates with chloramphenicol (5 μg/mL). The colonies grown on LB plates with 5 μg/mL chloramphenicol were streaked several times onto LB plates with 25 μg/mL chloramphenicol. The resulting *B. subtilis* expression strain SG1221 was first grown in LB medium with 25 μg/mL chloramphenicol and then subcultured into GrantsII medium containing 25 μg/mL chloramphenicol grown at 30° C. for 2-3 days. The cultures were spun at 15,000 g for 30 min at 4° C. and the supernatant was filtered through 0.22-μm filters. The filtered supernatant was aliquoted and frozen at −80° C.

*B. subtilis* SG1221 strain, expressing GTF0088BsT1 (SEQ ID NO:45), was grown under an aerobic submerged condition by conventional fed-batch fermentation. A nutrient medium was used containing 0-0.25% corn steep solids (Roquette), 5-25 g/L sodium and potassium phosphate, a solution of 0.3-0.6 M ferrous sulfate, manganese chloride and calcium chloride, 0.5-4 g/L magnesium sulfate, and a solution of 0.01-3.7 g/L zinc sulfate, cuprous sulfate, boric acid and citric acid. An antifoam agent, FOAMBLAST 882, at 2-4 mL/L was added to control foaming. A 2-L fermentation was fed with 50% (w/w) glucose feed when initial glucose in batch was non-detectable. The glucose feed rate was ramped over several hours. The fermentation was controlled at 30° C. and 20% DO, and at an initial agitation of 400 rpm. The pH was controlled at 7.2 using 50% (v/v) ammonium hydroxide. Fermentation parameters such as pH, temperature, airflow, and DO % were monitored throughout the entire 2-day fermentation run. The culture broth was harvested at the end of run and centrifuged to obtain supernatant. The supernatant containing GTF0088BsT1 (SEQ ID NO:45) was then stored frozen at −80° C.

Determination of the Glucosyltransferase GTF0459 and GTF0088BsT1 Activity

Glucosyltransferase activity assay was performed by incubating 1-10% (v/v) crude protein extract containing GTF enzyme with 200 g/L sucrose in 25 mM or 50 mM sodium acetate buffer at pH 5.5 in the presence or absence of 25 g/L dextran (MW ~1500, Sigma-Aldrich, Cat. #31394) at 37° C. and 125 rpm orbital shaking. One aliquot of reaction mixture was withdrawn at 1 h, 2 h and 3 h and heated at 90° C. for 5 min to inactivate the GTF. The insoluble material was removed by centrifugation at 13,000×g for 5 min, followed by filtration through 0.2-μm RC (regenerated cellulose) membrane. The resulting filtrate was analyzed by HPLC using two AMINEX HPX-87C columns series at 85° C. (Bio-Rad, Hercules, Calif.) to quantify sucrose concentration. The sucrose concentration at each time point was plotted against the reaction time and the initial reaction rate was determined from the slope of the linear plot. One unit of GTF activity was defined as the amount of enzyme needed to consume one micromole of sucrose in one minute under the assay conditions.

Preparation of a Crude Extract of Alpha-(1,3)-Glucanohydrolase (Mutanase)

A gene encoding the *Penicillium marneffei* ATCC® 18224™ mutanase identified in GENBANK® as GI:212533325 was synthesized by GenScript (Piscataway, N.J.). The nucleotide sequence (SEQ ID NO:46) encoding protein sequence (MUT3325; SEQ ID NO:47) was subcloned into plasmid pTrex3 at SacII and AscI restriction sites, a vector designed to express the gene of interest in *Trichoderma reesei*, under control of CBHI promoter and terminator, with *Aspergillus niger* acetamidase for selection. The resulting plasmid was transformed into *T. reesei* by biolistic injection. The detailed method of biolistic transformation is described in International PCT Patent Application Publication WO2009/126773 A1, which is incorporated herein by reference. A 1-cm² agar plug with spores from a stable clone, TRM05-3, was used to inoculate the production media (described below). The culture was grown in shake flasks for 4-5 days at 28° C. and 220 rpm. To harvest the secreted proteins, the cell mass was first removed by centrifugation at 4000 g for 10 min and the supernatant was filtered through 0.2-μm sterile filters. The expression of mutanase MUT3325 (SEQ ID NO:47) was confirmed by SDS-PAGE.

The production media component is listed below.

NREL-Trich Lactose Defined

| Formula | Amount | Units |
|---|---|---|
| ammonium sulfate | 5 | g |
| PIPPS | 33 | g |
| BD BACTO casamino acid | 9 | g |
| KH₂PO₄ | 4.5 | g |

-continued

| Formula | Amount | Units |
| --- | --- | --- |
| CaCl$_2$•2H$_2$O | 1.32 | g |
| MgSO$_4$•7H$_2$O | 1 | g |
| *T. reesei* trace elements | 2.5 | mL |
| NaOH pellet | 4.25 | g |
| Adjust pH to 5.5 with 50% NaOH | | |
| Bring volume to | 920 | mL |
| Add to each aliquot: FOAM BLAST | 5 | drops |
| Autoclave, then add 20% lactose filter sterilized | 80 | mL |

*T. reesei* Trace Elements

| Formula | Amount | Units |
| --- | --- | --- |
| citric acid•H$_2$O | 191.41 | g |
| FeSO$_4$•7H$_2$O | 200 | g |
| ZnSO$_4$•7H$_2$O | 16 | g |
| CuSO$_4$•5H$_2$O | 3.2 | g |
| MnSO$_4$•H$_2$O | 1.4 | g |
| H$_3$BO$_3$ (boric acid) | 0.8 | g |
| Bring volume to | 1 | L |

Fermentation seed culture was prepared by inoculating 0.5 L of minimal medium in a 2-L baffled flask with 1.0 mL frozen spore suspension of the MUT3325 expression strain TRM05-3 (The minimal medium was composed of 5 g/L ammonium sulfate, 4.5 g/L potassium phosphate monobasic, 1.0 g/L magnesium sulfate heptahydrate, 14.4 g/L citric acid anhydrous, 1 g/L calcium chloride dihydrate, 25 g/L glucose and trace elements including 0.4375 g/L citric acid, 0.5 g/L ferrous sulfate heptahydrate, 0.04 g/L zinc sulfate heptahydrate, 0.008 g/L cupric sulfate pentahydrate, 0.0035 g/L manganese sulfate monohydrate and 0.002 g/L boric acid. The pH was 5.5.). The culture was grown at 32° C. and 170 rpm for 48 hours before being transferred to 8 L of the production medium in a 14-L fermenter. The production medium was composed of 75 g/L glucose, 4.5 g/L potassium phosphate monobasic, 0.6 g/L calcium chloride dehydrate, 1.0 g/L magnesium sulfate heptahydrate, 7.0 g/L ammonium sulfate, 0.5 g/L citric acid anhydrous, 0.5 g/L ferrous sulfate heptahydrate, 0.04 g/L zinc sulfate heptahydrate, 0.00175 g/L cupric sulfate pentahydrate, 0.0035 g/L manganese sulfate monohydrate, 0.002 g/L boric acid and 0.3 mL/L FOAMBLAST 882.

The fermentation was first run with batch growth on glucose at 34° C., 500 rpm for 24 h. At the end of 24 h, the temperature was lowered to 28° C. and the agitation speed was increased to 1000 rpm. The fermenter was then fed with a mixture of glucose and sophorose (62% w/w) at a specific feed rate of 0.030 g glucose-sophorose solids/g biomass/hr. At the end of run, the biomass was removed by centrifugation and the supernatant containing the MUT3325 mutanase (SEQ ID NO:47) was concentrated about 10-fold by ultrafiltration using 10-kD Molecular Weight Cut-Off ultrafiltration cartridge (UFPii-10-E-35; GE Healthcare, Little Chalfont, Buckinghamshire, UK). The concentrated protein was stored at −80° C.

Determination of Alpha-Glucanohydrolase (Mutanase) Activity

Insoluble mutan polymers required for determining mutanase activity were prepared using secreted enzymes produced by *Streptococcus sobrinus* ATCC®33478™. Specifically, one loop of glycerol stock of *S. sobrinus* ATCC® 33478™ was streaked on a BHI agar plate (Brain Heart Infusion agar, Teknova, Hollister, Calif.), and the plate was incubated at 37° C. for 2 days. A few colonies were picked using a loop to inoculate 2×100 mL BHI liquid medium in the original medium bottle from Teknova, and the culture was incubated at 37° C., held static for 24 h. The resulting cells were removed by centrifugation and the resulting supernatant was filtered through a 0.2-µm sterile filter; 2×101 mL of filtrate was collected. To the filtrate was added 2×11.2 mL of 200 g/L sucrose (final sucrose 20 g/L). The reaction was incubated at 37° C. with no agitation for 67 h. The resulting polysaccharide polymers were collected by centrifugation at 5000×g for 10 min. The supernatant was carefully decanted. The insoluble polymers were washed 4 times with 40 mL of sterile water. The resulting mutan polymers were lyophilized for 48 h. Mutan polymer (390 mg) was suspended in 39 mL of sterile water to make a 10 mg/mL suspension. The mutan suspension was homogenized by sonication (40% amplitude until large lumps disappear, ~10 min in total). The homogenized suspension was aliquoted and stored at 4° C.

A mutanase assay was initiated by incubating an appropriate amount of enzyme with 0.5 mg/mL mutan polymer (prepared as described above) in 25 mM KOAc buffer at pH 5.5 and 37° C. At various time points, an aliquot of reaction mixture was withdrawn and quenched with equal volume of 100 mM glycine buffer (pH 10). The insoluble material in each quenched sample was removed by centrifugation at 14,000×g for 5 min. The reducing ends of oligosaccharide and polysaccharide polymer produced at each time point were quantified by the p-hydroxybenzoic acid hydrazide solution (PAHBAH) assay (Lever M., *Anal. Biochem.*, (1972) 47:273-279) and the initial rate was determined from the slope of the linear plot of the first three or four time points of the time course. The PAHBAH assay was performed by adding 10 µL of reaction sample supernatant to 100 µL of PAHBAH working solution and heated at 95° C. for 5 min. The working solution was prepared by mixing one part of reagent A (0.05 g/mL p-hydroxy benzoic acid hydrazide and 5% by volume of concentrated hydrochloric acid) and four parts of reagent B (0.05 g/mL NaOH, 0.2 g/mL sodium potassium tartrate). The absorption at 410 nm was recorded and the concentration of the reducing ends was calculated by subtracting appropriate background absorption and using a standard curve generated with various concentrations of glucose as standards.

Analysis of Reaction Profiles by HPLC

Periodic samples from reactions were taken and analyzed using an Agilent® 1260 HPLC equipped with a refractive index detector. An Aminex® HP-87C column (BioRad, Hercules, Calif.) having deionized water at a flow rate of 0.6 mL/min and 85° C. was used to quantitate the level of sucrose, glucose, leucrose and fructose in gtf reactions. An Aminex® HP-42A column (BioRad) having deionized water at a flow rate of 0.6 mL/min and 85° C. was used to quantitate soluble oligosaccharide byproducts (DP2-DP7) in gtf reactions.

A Dionex® UltiMate™ 3000 HPLC (Thermo Scientific) equipped with a refractive index detector was used for samples involving immobilized enzymes (Example 4). A Phenomenex® Rezex™ calcium monosaccharide column having deionized water at a flow rate of 0.3 mL/min and 85° C. was used to analyze the sugars.

Analysis of Oligosaccharide Linkage by NMR

NMR data were acquired on an Agilent DD2 spectrometer operating at 500 MHz for $^1$H using a 5-mm cryogenic triple-resonance pulsed-field gradient (PFG) probe. Water suppression was obtained by carefully placing the observe transmitter frequency on resonance for the residual water signal in a "presat" experiment, and then using the first slice of a NOESY experiment with a full phase cycle (multiple of 32) and a mix time of 10 ms. One-dimensional $^1$H spectra were acquired with a spectral width of 6410 Hz, acquisition time of 5.1 s, 65536 data points, 4 s presaturation and a 90-degree pulse of 5.85 μs. Sample temperature was maintained at 25° C. Samples were prepared by adding 50 μL to a 5-mm NMR tube along with 450 μL of D20 and 60 μL of D20 containing 12.4 mM DSS (4,4-dimethyl-4-silapentane-1-sulfonic acid sodium salt) internal reference with the methyl resonance set to 0 ppm. Chemical shift assignments for different anomeric linkages were taken from: Goffin et al. (2009, *Bull Korean Chem. Soc.* 30:2535-2541. Peak assignments were 5.35 ppm for alpha(1,3) linkages, 5.1 ppm for leucrose, and 4.95 for alpha(1,6) linkages. Reducing ends (RE) were assigned to be 5.2 for alpha RE and 4.65 for beta RE.

Example 1

Production of Sugar Syrup by Polymerization of Sucrose

This example discloses the general manner in which a mixture of soluble sugars was produced by polymerization of sucrose with a gtf enzyme in a glucan synthesis reaction. Specifically, a filtrate of a glucan synthesis reaction was prepared, which was then concentrated to a syrup.

Sucrose (3000 g) was added to a clean 5-gallon polyethylene bucket. Water (18.1 L) and Fermasure™ (10 mL) were added to the bucket, and the pH was adjusted to 7.0 by addition of 5 vol % NaOH and 5 vol % $H_2SO_4$. The final volume was ~20 L and the initial concentration of sucrose as measured by HPLC was 152.5 g/L. The glucan polymerization reaction was initiated by adding 0.3 vol % of crude gtf enzyme (SEQ ID NO:3) extract prepared as described in the General Methods section. This extract contained about 2.9 mg/mL of protein. Agitation to the reaction solution was provided using an overhead mechanical motor equipped with a glass shaft and PTFE blade.

After 48 hours, HPLC analysis revealed that 96% of the sucrose had been consumed and the reaction was deemed to be complete. The insoluble poly-alpha-1,3-glucan product of the reaction was removed by filtration with a Buchner filter funnel using 325-mesh steel screen and 40-micron filter paper. The mother liquor (filtrate) was then concentrated using a rotary evaporator (bath temp of 40-50° C.) to a total sugar concentration of about 320 g/L sugars. The composition of the concentrated filtrate is provided in Table 2.

TABLE 2

Composition of a Concentrated Filtrate of a Glucan Synthesis Reaction

|  | Sucrose | Leucrose | Glucose | Fructose | DP2 | DP3+ | Total |
|---|---|---|---|---|---|---|---|
| g/L | 13.5 | 130.6 | 25.5 | 103.8 | 18.3 | 28.3 | 320.1 |
| wt % | 4.2 | 40.8 | 8 | 32.4 | 5.7 | 8.9 | 100 |

Table 2 indicates that the concentrated filtrate of the glucan synthesis reaction contains sucrose, fructose, glucose, leucrose and oligosaccharides of DP2-DP7.

Example 2

Effect of Enzymes on Hydrolysis of Sugars in a Filtrate of a Glucan Synthesis Reaction This example measures the activity of various glucoamylase (EC 3.2.1.3), transglucosidase (EC 2.4.1.24), beta-glucosidase (EC 3.2.1.21), alpha-amylase (EC 3.2.1.1) and glucosidase (EC 3.2.1) enzymes for the purpose of reducing the concentration of leucrose and/or oligosaccharide byproducts in a concentrated filtrate of a glucan synthesis reaction. Certain enzymes such as DIAZYME RDF ULTRA, transglucosidase (EC 2.4.1.24) and glucoamylase (EC 3.2.1.3), which are all alpha-glucosidase, were found to be particularly effective at reducing the amount of these byproducts, resulting in a corresponding increase in monosaccharides (glucose and fructose) in the treated filtrate.

A filtrate of a glucan synthesis reaction was first prepared and concentrated to a syrup according to the procedure outline in Example 1. The composition of this concentrated filtrate is provided in Table 3. NMR analysis revealed that the ratio of alpha(1,3) to alpha (1,6) linkages present in the syrup was 78:22.

TABLE 3

Composition of a Concentrated Filtrate of a Glucan Synthesis Reaction

|  | Sucrose | Leucrose | Glucose | Fructose | DP2 | DP3+ | Total |
|---|---|---|---|---|---|---|---|
| g/L | 161 | 210 | 93 | 302 | 33 | 61 | 860 |
| wt % | 18.7 | 24.4 | 10.8 | 35.1 | 3.8 | 7.1 | 100.0 |

The syrup of Table 3 was used to test the hydrolytic activity of various enzymes against leucrose and oligosaccharide byproducts of the glucan synthesis reaction. It was not obvious at the outset of these experiments what enzyme could be used to hydrolyze both these byproducts, given that leucrose contains an unusual linkage [alpha(1,5)-glucosyl fructose] and that the oligosaccharides comprise primarily alpha(1,3) and alpha(1,6) glucosyl-glucose linkages. Enzymes with various activities were selected for this analysis (Table 4).

TABLE 4

Enzymes Evaluated for Leucrose and Oligosaccharide Hydrolysis

| Enzyme | Source | Function | Activity or protein concentration |
|---|---|---|---|
| DIAZYME RDF ULTRA | DuPont IB$^a$ | 1,4-alpha-glucosidase | 710 U/g |
| Oligo-1,6-glucosidase | Megazyme | 1,6-alpha-glucosidase | 320 U/mg |
| SPEZYME FRED | DuPont IB | Alpha-amylase | 1-5% |
| SPEZYME RSL | DuPont IB | Alpha-amylase | 1-5% |
| OPTIMAX L-1000 | DuPont IB | Pullulanase | 1-5% |
| TRANSGLUCOSIDASE L-2000 | DuPont IB | Trans-glucosidase | >1700 TGU/g |
| purified TRANSGLUCOSIDASE L-2000 | DuPont IB | Trans-glucosidase | 22.7 mg/mL |
| ACCELLERASE BG | DuPont IB | Beta-glucosidase | 3000 U/g |
| NOVO 188 | Sigma-Aldrich | Beta-glucosidase | >250 U/g |
| SUMIZYME BFS-L | Shin Nihon Chemical | Beta-glucosidase | 100 U/g |
| SUMIZYME BGA | Shin Nihon Chemical | Beta-glucosidase | 2000 U/g |

TABLE 4-continued

Enzymes Evaluated for Leucrose and Oligosaccharide Hydrolysis

| Enzyme | Source | Function | Activity or protein concentration |
|---|---|---|---|
| ACCELERASE TRIO | DuPont IB | Cellulase | 5-10% |
| ACCELERASE 1500 | DuPont IB | Cellulase/Beta-glucosidase | 5-10%/0.5-4% |
| OPTIDEX L-400 | DuPont IB | Glucoamylase | >350 GAU/g |
| GC 147 | DuPont IB | Glucoamylase | 400 GAU/g |
| GC 321 | DuPont IB | Glucoamylase | >350 GAU/g |

[a]DuPont Industrial Biosciences

Conditions for treating the syrup of Table 3 with each of the above enzymes are provided in Table 5 (enzyme loading, time, temperature, pH, sugar concentration). The syrup was diluted with water to reach the sugar concentration used in each hydrolysis reaction. Table 5 further provides the percent hydrolysis of the leucrose and DP3+(at least DP3-DP7) oligosaccharides by each enzyme. Percent DP3+ hydrolysis was calculated as (1−(wt % DP3+ oligosaccharides in the final syrup)/(wt % DP3+ oligosaccharides in the initial syrup)). Similarly, percent leucrose hydrolysis was calculated as (1−(wt % leucrose in the final syrup)/(wt % leucrose in the initial syrup)).

TABLE 5

Hydrolysis of Leucrose and Oligosaccharides in a Concentrated Filtrate by Various Enzymes

| Example | Enzyme | Enzyme loading (vol %) | Temp (° C.) | Time (hr) | pH | Sugar concentration (g/L)[a] | DP3+[b] hydrolysis (%) | Leucrose hydrolysis (%) |
|---|---|---|---|---|---|---|---|---|
| 2.1 | DIAZYME RDF ULTRA | 0.5 | 60 | 88 | 4.0 | 300 | 36 | 13 |
| 2.2 | Oligo-1,6-glucosidase | 5 | 40 | 72 | 5.5 | 400 | 43 | <2 |
| 2.3 | SPEZYME FRED | 0.5 | 60 | 66 | 4.0 | 280 | <2 | <2 |
| 2.4 | SPEZYME RSL | 0.5 | 60 | 48 | 4 | 290 | <2 | <2 |
| 2.5 | OPTIMAX L-1000 | 0.5 | 60 | 48 | 4 | 290 | <2 | <2 |
| 2.6 | TG L-2000 | 0.25 | 60 | 70 | 4.0 | 260 | 54 | >98 |
| 2.7 | TG L-2000 | 2 | 60 | 48 | 4.5 | 300 | 96 | >98 |
| 2.8 | PURIFIED TG L-2000 | 0.5 | 60 | 48 | 4.5 | 260 | 56 | >98 |
| 2.9 | ACCELERASE BG | 0.5 | 60 | 70 | 4 | 300 | 11 | <2 |
| 2.10 | NOVO 188 | 0.25 | 60 | 70 | 4 | 300 | 49 | 36 |
| 2.11 | NOVO 188 | 5 | 60 | 40 | 5.5 | 340 | 93 | 29 |
| 2.12 | SUMIZYME BFS-L | 0.5 | 60 | 48 | 4.5 | 260 | 55 | 46 |
| 2.13 | SUMIZYME BGA | 0.1 wt % | 60 | 48 | 4.5 | 260 | 26 | 77 |
| 2.14 | ACCELERASE TRIO | 0.5 | 60 | 48 | 4 | 290 | 28 | 6.6 |
| 2.15 | ACCELERASE 1500 | 0.5 | 60 | 66 | 4 | 280 | 26 | 4 |
| 2.16 | GC 147 | 0.5 | 60 | 40 | 4 | 300 | 55 | 12 |
| 2.17 | GC 321 | 5 | 60 | 72 | 5.5 | 400 | 74 | 64 |
| 2.18 | OPTIDEX L-400 | 0.5 | 60 | 70 | 4 | 300 | 27 | 25 |

[a]Sugar concentration (total concentration of sucrose, glucose, fructose, leucrose and oligosaccharides) measured by HPLC; reported values are rounded to nearest 10 g/L increment.
[b]DP3+ contains DP3-DP7, but may also contain larger soluble oligosaccharides that have a high ratio of alpha-1,6 linkages to alpha-1,3 linkages, when produced using certain gtf enzymes.

Table 5 indicates that 1,4-alpha-glucosidase and 1,6-alpha-glucosidase showed some (Example 2.1) or very little (Example 2.2) hydrolysis of leucrose, but did release some glucose from the oligosaccharides. Use of alpha-amylase (Example 2.3 and Example 2.4) showed very little activity against the compounds of interest. Similarly, use of a pullulanase (Example 2.5) showed very little activity. Cellulases (Examples 2.14 and 2.15) were largely ineffective at hydrolyzing leucrose, but did hydrolyze some of the oligosaccharides.

Although the oligosaccharides did not contain beta linkages, surprisingly, beta-glucosidase enzymes also showed a range of hydrolytic conversion from very low (ACCELERASE BG, Example 2.9) to very high (NOVO 188, Examples 2.10 and 2.11). The relative efficacy of these enzymes varied quite dramatically. In some cases, the amount of oligosaccharide that was hydrolyzed greatly exceeded (Example 2.11), or was close to (Example 2.12), the percentage of leucrose that was hydrolyzed. In other cases, leucrose was highly hydrolyzed by beta-glucosidase while the oligosaccharides were moderately hydrolyzed (Example 2.13). The high disparity amongst the results observed with beta-glucosidase suggests that the presence of other enzymes in the tested beta-glucosidase formulations, such as glucoamylase or another type of alpha-glucosidase, could be responsible for the observed activity.

Conversely, the results in Table 5 indicate that transglucosidase (TG L-2000, Example 2.6) showed very high activity at hydrolyzing both the oligosaccharides and leucrose. Leucrose hydrolysis by transglucosidase appeared quantitative under certain circumstances, and greater than 95% of the DP3+ material was hydrolyzed to glucose and DP2 at high enzyme loadings (Example 2.7). Use of a purified version of transglucosidase revealed similar activity (Example 2.8), indicating that the observed hydrolysis is due to the transglucosidase enzyme and not background activity.

Glucoamylases (Examples 2.16-2.18) showed a range of activity against leucrose and the oligosaccharides. Only one tested glucoamylase (Example 2.18) gave less than 30% hydrolysis of both the leucrose and oligosaccharides.

The results in Table 5 indicate that alpha-glucosidases such as DIAZYME RDF ULTRA, glucoamylase and transglucosidase can hydrolyze leucrose byproduct present in a glucan reaction filtrate. The ability of alpha-glucosidases to hydrolyze leucrose indicates that these enzymes can hydrolyze alpha-1,5 glucosyl-fructose linkages. While this activity was shown above using leucrose as a substrate, it is believed that this activity can also be extended to oligosaccharides comprising alpha-1,5 glucosyl-fructose linkages.

The results in Table 5 further indicate that alpha-glucosidases such as glucoamylase and transglucosidase can hydrolyze oligosaccharide byproducts present in a glucan reaction filtrate. Since these oligosaccharides are mostly comprised of glucose monomer units linked by alpha-1,3 and/or alpha-1,6 linkages (Example 3), the data in Table 5 indicate that alpha-glucosidase enzymes can hydrolyze alpha-1,3 glucosyl-glucose and/or alpha-1,6 glucosyl-glucose linkages.

Since alpha-glucosidase enzymes were generally effective at hydrolyzing the leucrose and/or oligosaccharide byproducts of a glucan synthesis reaction, these enzymes can be used alone or in combination to reduce the processing time necessary to generate a high purity syrup from a glucan reaction filtrate containing an increased amount of monosaccharides and reduced amount of sugar byproducts. An example of an effective enzyme combination could be a transglucosidase such as TG L-2000, for leucrose hydrolysis, and a glucoamylase (e.g., GC 321) enzyme that efficiently hydrolyzes oligosaccharide byproducts.

Thus, alpha-glucosidase enzymes can individually hydrolyze (i) alpha-1,5 glucosyl-fructose linkages and (ii) alpha-1,3 and alpha-1,6 glucosyl-glucose linkages in certain saccharides.

Example 3

Comparison of Linkage Distributions of Glucan Reaction Filtrate Components Before and After Enzyme Hydrolysis This example measures the hydrolytic activity of transglucosidase (EC 2.4.1.24) and beta-glucosidase (EC 3.2.1.21) enzymes against leucrose and oligosaccharide byproducts present in a concentrated filtrate of a glucan synthesis reaction. Transglucosidase was found to reduce the amount of these byproducts, resulting in a corresponding increase in monosaccharides (glucose and fructose) in the treated filtrate.

The oligosaccharide byproducts present in the filtrate of the above glucan synthesis reaction comprise >90% glucose-glucose linkages, as determined by NMR (General Methods). Of the glucose-glucose linkages, ~78% represent alpha-1,3 linkages and ~22% represent alpha-1,6 linkages.

NMR was used to determine the linkage profile of material generated in Example 2.11 above after hydrolysis. As shown in FIG. 1, the peak corresponding to alpha-1,3 linkages was reduced by 86%, the peak corresponding to alpha-1,6 linkages was reduced by only 2.3%, and the peak corresponding to leucrose peaks was reduced by 21%. While sucrose was very nearly quantitatively hydrolyzed by this enzyme, Novo 188 does not appear to be capable of hydrolyzing alpha-1,6 linkages.

NMR was similarly used to determine the linkage profile of material generated using TG L-2000 (SEQ ID NO:1) transglucosidase (FIG. 2). 210 µL of concentrated filtrate from the material in Table 3, 300 µL of D20, and 90 µL of D20 containing 12.4 mM DSS as internal reference were mixed in an NMR tube to give a total sugar concentration of 300 g/L and heated to 60° C. A time zero spectrum (starting material in FIG. 2) was acquired after thermal equilibration at 60° C., and then 0.5 vol % of enzyme was added. The sample was re-equilibrated in the probe at 60° C. and shimmed, and measurements were taken within a few minutes of analysis. After 10 hours of treatment with TG L-2000 enzyme (treated material in FIG. 2), the peaks corresponding to alpha-1,3 linkages were reduced by 41%, the peaks corresponding to alpha-1,6 linkages were reduced by 36%, and the peak corresponding to leucrose was reduced by >95% (FIG. 2). An increase in both the alpha-reducing end and beta-reducing end peaks was observed, which corresponds to an increase in fructose and glucose (FIG. 2).

These results demonstrate that a transglucosidase can convert oligosaccharides containing alpha-1,3 and alpha-1,6 linkages into glucose and can convert leucrose into fructose and glucose. Thus, transglucosidase can hydrolyze (i) alpha-1,5 glucosyl-fructose linkages and (ii) alpha-1,3 and alpha-1,6 glucosyl-glucose linkages in certain saccharides.

Example 4

Hydrolysis of Leucrose and Oligosaccharides in Glucan Reaction Filtrate Using Immobilized Enzymes This Example describes using immobilized glucoamylase (EC 3.2.1.3) and transglucosidase (EC 2.4.1.24) to hydrolyze leucrose and other oligosaccharides present in filtrate obtained from a glucan synthesis reaction. Specifically, the effect of immobilized transglucosidase TG L-2000 (SEQ ID NO:1, obtained from Genencor/DuPont Industrial Biosciences) and immobilized glucoamylase GC-147 (obtained from Genencor/DuPont Industrial Biosciences) on the hydrolysis of leucrose and oligosaccharides DP2, DP3 and HS (higher sugars, DP4+) in a filtrate of a glucan synthesis reaction was studied.

Immobilization of the glucoamylase and transglucosidase enzymes was carried out according to the method described in U.S. Pat. No. 5,541,097, which is incorporated herein by reference.

In a typical process for immobilizing the glucoamylase or transglucosidase, two batches of about 8.0 g/batch of porous granular diatomaceous earth (EP Minerals, Reno, Nev.) were hydrated with distilled water and then transferred to a glass column reactor of 1.5-cm diameter and 30-cm height. Water was pumped upflow at about 6-7 mL/min to remove fines from all three columns. Generally, within an hour the water effluent was free of fines. Water was drained from the column to the top of the granular diatomaceous earth beds and replaced with 0.1% w/v aqueous solution of polyethylenimine (PEI, EPOMIN P-1050). 3500 mL of the PEI solution was then pumped upflow and effluent was recycled through the beds for 2 hours. The granular diatomaceous earth beds were then washed upflow with distilled water for 2 hours to remove free PEI at room temperature. In this manner, granular diatomaceous earth-PEI carriers were obtained.

In the meantime, 3.5 mL of glucoamylase GC-147 having activity defined in Table 4 was added to 315 ml of 0.02 M acetate buffer (pH 4.5). 1.575 g of 50% w/w glutaraldehyde (Protectol® GA-50) was then slowly added to the aqueous solution of glucoamylase with gentle mixing, and the glutaraldehyde was allowed to react with the aqueous glucoamylase solution for 4 hours at a temperature of 20-25° C. with gentle agitation, which resulted in formation of a treated enzyme-glutaraldehyde adduct containing treated glucoamylase. Separately, these steps were repeated using the transglucosidase TG L-2000 having activity defined in Table 4 instead of the glucoamylase, thereby resulting in the formation of a treated enzyme-glutaraldehyde adduct containing treated transglucosidase.

Each of the treated enzyme-glutaraldehyde adducts was then circulated for 4 hours (20-25° C.) in its own column prepared as above containing granular diatomaceous earth-PEI carrier. Excess treated adduct was then washed out of the carriers with water. Columns with immobilized glucoamylase or transglucosidase were thus prepared.

A glucan filtrate having the composition defined in Table 3 was diluted to 180 g/L, adjusted to pH 4.5, and passed through a column containing an immobilized enzyme. Column temperature was controlled to 60° C. After 16 hours of column equilibration, samples were taken periodically at different flow rates. Sugar compositions of hydrolysis reaction products were determined by HPLC (Table 6). Every time the flow rate setting was changed, the column was allowed to re-equilibrate for at least 1-2 bed volumes before sampling. The degree of hydrolysis of leucrose and oligosaccharides was calculated using the manner described in Example 2. Three column configurations were tested: 1) immobilized glucoamylase, 2) immobilized transglucosidase, and 3) immobilized glucoamylase followed by immobilized transglucosidase.

TABLE 6

Application of Immobilized Glucoamylase and Transglucosidase Enzymes to Hydrolyze Oligosaccharides and Leucrose

| Immobilized Enzyme | Mean contact time (hr) | DP3+ hydrolysis (%) | Leucrose hydrolysis (%) |
|---|---|---|---|
| GC 147 | 0.7 | 16 | 17 |
| GC 147 | 1.0 | 20 | 22 |
| GC 147 | 1.3 | 25 | 29 |
| GC 147 | 3.0 | 39 | 47 |
| TG L-2000 | 0.7 | 28 | >95 |
| TG L-2000 | 1.0 | 32 | >95 |
| TG L-2000 | 1.3 | 37 | >95 |
| TG L-2000 | 3.0 | 47 | >95 |
| GC 147 + TG L-2000 | 6.0 | 55 | >95 |

Table 6 indicates that, as the mean contact time (defined as the nominal column volume divided by the mean flow rate) was increased, the degree of hydrolysis of leucrose and oligosaccharides generally increased. Use of the immobilized transglucosidase to hydrolyze leucrose was particularly effective, as no significant difference was observed even using the fastest flow rate that was tested. While each column individually showed reasonable conversion, the combination of the glucoamylase and transglucosidase gave the highest hydrolysis of oligosaccharides.

Thus, use of an immobilized glucoamylase or transglucosidase, or both types of immobilized enzymes, represents an effective technique to hydrolyze oligosaccharides containing alpha-1,3 and alpha-1,6 glucosyl-glucose linkages, as well as leucrose. These results are consistent with those of Example 2.

Immobilization of other alpha-glucosidase enzymes should give similar results.

Example 5

Enrichment of Fructose from a Glucan Reaction Filtrate by Chromatography

This example discloses how fructose in a glucan reaction filtrate can be further enriched through chromatography.

Generally, when separating sugar molecules by chromatography, components elute inversely to molecular size so that the largest molecules elute first. Thus, with respect to a filtrate of a glucan synthesis reaction, oligosaccharides elute first, followed by disaccharides, and then monosaccharides. Separations using a sodium cation resin did not separate fructose and glucose well, and all of leucrose, sucrose, and DP2 co-eluted. Use of ion exchange resins where the cation is calcium are preferred to separate glucose and fructose.

A filtrate of a glucan synthesis reaction was first prepared and concentrated to a syrup according to the procedure outline in Example 1. The composition of this concentrated filtrate is provided in Table 7.

TABLE 7

Composition of a Concentrated Filtrate of a Glucan Synthesis Reaction

|  | Sucrose | Leucrose | Glucose | Fructose | DP2 | DP3+ | Total |
|---|---|---|---|---|---|---|---|
| g/L | 126 | 202 | 93 | 295 | 40 | 65 | 821 |
| wt % | 15.4 | 24.6 | 11.3 | 36.0 | 4.8 | 7.9 | 100 |

The syrup of Table 7 was filtered and diluted to 25 g dry solids/100 g solution with ion-exchanged water, and fed to a column containing a crosslinked strong acid ion exchange resin in the calcium form. The physical parameters of this column appear in Table 8. Diluted syrup (15.8 L) was fed to the column, which was maintained at 65° C., after which the column was eluted using water at a flow rate of 30 L/hr.

TABLE 8

Physical Parameters of the Column

| Resin Type | FINEX CS11GC |
|---|---|
| Ion form | $Ca^{2+}$ |
| Crosslinking, % divinyl benzene | 5.5 |
| Particle size (mm) | 0.34 |
| Bed length (m) | 5.0 |
| Column diameter (m) | 0.225 |

In this separation, leucrose remained in the column longer than sucrose, perhaps due to complexation of leucrose with the calcium cation, and in fact, co-eluted with glucose. Two fractions containing fructose were isolated. Fraction 5.1 eluted between 47 and 120 minutes, and fraction 5.2 eluted between 120 and 172 minutes. Of the fructose fed to the chromatographic separation, 95.7% of the fructose was isolated in >90% purity. The product distribution in each fraction (5.1 and 5.2) as measured by HPLC appears in Table 9.

TABLE 9

Product Distribution of Chromatographic Fractions Containing Significant Amounts of Fructose

| Fraction | Sucrose | Leucrose | Glucose | Fructose | DP3+ | Others | Total | % Fructose recovered |
|---|---|---|---|---|---|---|---|---|
| 5.1 | 31.9 | 34.8 | 20.8 | 3.9 | 5.4 | 4.8 | 100 | 3.9 |
| 5.2 | 0.0 | 1.0 | 0.8 | 97.7 | 0.0 | 0.6 | 100 | 95.7 |

As the feed composition for this separation comprised 36.0% fructose, a total of 34.5% of the total stream was recovered as a fructose syrup with >90 wt % DS fructose. If the sucrose in the feed is neglected, 40.7% of the sugars were recovered as a fructose syrup with >90 wt % DS fructose.

Thus, fructose in a glucan reaction filtrate can be further enriched through chromatography. Example 6 below demonstrates that this process can be enhanced using glucan filtrate hydrolyzed with a transglucosidase.

Example 6

Enrichment of Fructose from a Hydrolyzed Glucan Reaction Filtrate by Chromatography This example demonstrates that fructose isolation from a glucan filtrate in which the oligosaccharides and leucrose have been hydrolyzed results in an increased yield of high purity fructose syrup compared to when isolating fructose from a non-hydrolyzed glucan filtrate.

A syrup was prepared by concentrating (vacuum at 50° C.) a glucan filtrate that had been treated with 1 vol % of transglucosidase TG L-2000 (SEQ ID NO:1) for 24 hr at 60° C. and pH 4.5. Some oligosaccharide formation was observed during the concentration process, which was expected since transglucosidase enzymes are known to create oligosaccharides at high concentrations of monosaccharides. The syrup had the final product distribution described in Table A.

TABLE A

Composition of a Concentrated Glucan Filtrate that Was Hydrolyzed before Concentration

|  | Sucrose | Leucrose | Glucose | Fructose | DP2 | DP3+ | Total |
|---|---|---|---|---|---|---|---|
| g/L | 3 | <10 | 294 | 409 | 73 | 81 | ~870 |
| wt % | 0.3 | 1.1 | 33.7 | 47.0 | 8.4 | 9.3 | 100 |

The syrup described in Table A was filtered and diluted to 25.4 g DS/100 g solution with ion-exchanged water and was fed to a column containing a crosslinked strong acid cation exchange resin in the calcium form. The physical parameters of the column appear in Table B. Diluted syrup (169 g) was then fed to the column, which was maintained at 65° C., after which the column was eluted using water at a flow rate of 50 mL/min.

TABLE B

Physical Parameters of the Column

| Resin Type | FINEX CS11GC |
|---|---|
| Ion form | Ca$^{2+}$ |
| Crosslinking, % divinyl benzene | 5.5 |

TABLE B-continued

Physical Parameters of the Column

| Resin Type | FINEX CS11GC |
|---|---|
| Particle size (mm) | 0.34 |
| Bed length (m) | 1.69 |
| Column diameter (m) | 0.093 |

Two fractions containing fructose were isolated. Fraction 6.1 eluted between 73 and 103 minutes, and fraction 6.2 eluted between 103 and 120 minutes. Of the fructose fed to the chromatographic separation, 93.0% of the fructose fed to the column was isolated in fraction 6.2 in >90% purity. The product distribution in each fraction (6.1 and 6.2) as measured by HPLC appears in Table C.

TABLE C

Product Distribution of Chromatographic Fractions Containing Fructose from a Hydrolyzed Glucan Filtrate

| Fraction | Sucrose | Leucrose | Glucose | Fructose | DP3+ | Others | Total | % Fructose recovered |
|---|---|---|---|---|---|---|---|---|
| 6.1 | 7.7 | 13.9 | 63.9 | 7.3 | 1.5 | 5.7 | 100 | 5.9 |
| 6.2 | 0.0 | 0.6 | 3.0 | 91.8 | 0.0 | 4.6 | 100 | 93.0 |

The reduced separation efficiency in this example compared to Example 5 can be attributed to differences in the scale of the column and the higher glucose fraction of the sample. Even so, chromatographic purification of this material resulted in an increased yield of high purity fructose syrup compared to that achieved in Example 5, in which syrup was chromatographically prepared from a glucan filtrate that had not been hydrolyzed by a transglucosidase. As the feed composition for this separation comprised 47% fructose (Table A), 43.7% of the total stream was recovered as a fructose syrup with >90 wt % DS fructose. This 43.7% recovery is significantly better than the 34.5% recovery in Example 5.

Thus, fructose isolation from a glucan filtrate that has been hydrolyzed with transglucosidase results in an increased yield of fructose compared to when isolating fructose from a non-hydrolyzed glucan filtrate.

Example 7

Production of Ethanol by Fermenting a Filtrate of a Glucan Synthesis Reaction

This example discloses yeast fermentation of glucan filtrate to ethanol.

Yeast (S. cerevisiae) cream (Tonon mill, Brazil) was washed by suspending the cream in tap water (2.4 L, optical density of 65 at 600 nm) and then centrifuging the yeast cream for 5 minutes using a LEGEND XTR centrifuge (Thermo Scientific) at 4500 g. After decanting the supernatant, the yeast cells were resuspended and concentrated by centrifugation two additional times. After the third wash, the pH was adjusted to 2 by addition of 5 wt % sulfuric acid. The optical density was measured using a GENESYS 20 4001 spectrophotometer (Thermo Scientific) and adjusted to 100 at 600 nm by addition of tap water. The adjusted yeast cream (1.5 L) was added to a 7.5-L BIOFLO310 fermenter vessel (New Brunswick). The fermenter was set to maintain temperature at 30° C. and agitation at 100 rpm. Although pH was measured during fermentation, it was not controlled by the addition of acid or base solutions.

A feed solution containing yeast extract (10 g/L), peptone (20 g/L), and 200 g/L of sugars from a glucan filtrate was prepared and sterilized using a PHOENIX AV-250 PLUS autoclave at 121° C. for 15 minutes. The feed solution was allowed to cool to 25° C. (room temperature) before the fermentation began. The sterilized feed solution (3.5 L) was added to the fermenter over approximately 5 hours at a rate of 684 mL/hr, and the fermentation was allowed to proceed for 22 hours.

Periodic samples were taken during the fermentation and analyzed for optical density using a GENESYS 20 4001 spectrophotometer, Brix using a PAL-3 refractometer (Atago), and sugar and ethanol concentrations by HPLC (General Methods). These results are summarized in Table 10.

TABLE 10

Feed and Time Course Fermentation Profiles for the First Ethanol Fermentation

| Time (hr) | Sucrose | Leucrose | Glucose | Fructose | DP2 | DP3+ | Total Sugar | EtOH |
|---|---|---|---|---|---|---|---|---|
| Feed | 9 | 70 | 19 | 76 | 7 | 19 | 200 | 0 |
| 0 | 0.2 | 0.0 | 0.0 | 0.1 | — | — | — | 7 |
| 1 | <1 | 18 | 0.3 | <1 | — | — | — | 15 |
| 2 | <1 | 30 | 0.4 | <1 | — | — | — | 21 |
| 3 | <1 | 40 | 0.0 | <1 | — | — | — | 25 |
| 4 | <1 | 46 | 0.0 | <1 | — | — | — | 28 |
| 5 | <1 | 49 | 0.0 | <1 | — | — | — | 29 |
| 6 | <1 | 53 | 0.0 | <1 | — | — | — | 32 |
| 8 | <1 | 53 | 0.0 | <1 | — | — | — | 33 |
| 22 | <1 | 53 | 0.0 | <1 | 5 | 18 | 76 | 33 |

Concentrations (g/L) of ethanol (EtOH) and sugar compounds in the feed and at various fermentation time points (0-22 hours) are listed.

When the fermentation was over, the yeast cells were separated by centrifugation using a LEGEND XTR centrifuge at 4500 g for 5 minutes. After decanting the supernatant, the yeast were resuspended and concentrated by centrifugation two additional times. After the third wash, the pH was adjusted to 2 by addition of 5 wt % sulfuric acid. The optical density was measured using a GENESYS 20 4001 spectrophotometer and adjusted to 100 at 600 nm by addition of tap water. Two additional fermentation cycles, each using fresh feed, were performed using recycled yeast cells from the previous fermentation following the same conditions described above. The fermentation results obtained using first-time and second-time recycled yeast are provided in Tables 11 and 12, respectively.

TABLE 11

Feed and Time Course Fermentation Profiles Using the First Recycle of Yeast Cells

| Time (hr) | Sucrose | Leucrose | Glucose | Fructose | DP2 | DP3+ | Total Sugar | EtOH |
|---|---|---|---|---|---|---|---|---|
| Feed | 13 | 69 | 21 | 77 | 7 | 18 | 206 | 0 |
| 0 | 0 | 4 | 0 | 0 | — | — | — | 5 |
| 1 | <1 | 19 | 0 | <1 | — | — | — | 18 |
| 4 | <1 | 35 | 0 | <1 | — | — | — | 23 |
| 4 | <1 | 40 | 0 | <1 | — | — | — | 26 |
| 5 | <1 | 45 | 0 | <1 | — | — | — | 29 |
| 6 | <1 | 53 | 0 | <1 | — | — | — | 32 |
| 7 | <1 | 50 | 0 | <1 | — | — | — | 32 |
| 7 | <1 | 51 | 0 | <1 | — | — | — | 33 |
| 21 | <1 | 42 | 0 | <1 | 6 | 18 | 65 | 37 |

Concentrations (g/L) of ethanol (EtOH) and sugar compounds in the feed and at various fermentation time points (0-21 hours) are listed.

TABLE 12

Feed and Time Course Fermentation Profiles Using the Second Recycle of Yeast Cells

| Time (hr) | Sucrose | Leucrose | Glucose | Fructose | DP2 | DP3+ | Total Sugar | EtOH |
|---|---|---|---|---|---|---|---|---|
| Feed | 10 | 70 | 19 | 76 | 6 | 19 | 201 | 0 |
| 0 | <1 | 0 | 0 | <1 | — | — | — | 11 |
| 1 | <1 | 32 | 0 | <1 | — | — | — | 24 |
| 4 | <1 | 40 | 0 | <1 | — | — | — | 29 |
| 4 | <1 | 45 | 0 | <1 | — | — | — | 31 |
| 5 | <1 | 46 | 0 | <1 | — | — | — | 33 |
| 6 | <1 | 45 | 0 | <1 | — | — | — | 34 |
| 6 | <1 | 16 | 0 | <1 | — | — | — | 48 |
| 7 | <1 | 7 | 0 | <1 | — | — | — | 52 |
| 21 | <1 | 5 | 0 | <1 | 5 | 16 | 27 | 54 |

Concentrations (g/L) of ethanol (EtOH) and sugar compounds in the feed and at various fermentation time points (0-21 hours) are listed.

Very little leucrose was consumed in the first fermentation, although the yeast cells started to acclimate and consume leucrose by the second recycle. Ethanol fermentation titers increased from 33 g/L (Table 10, 22 hours) to 54 g/L (Table 12, 21 hours) after three fermentation cycles with recycled yeast, although significant amounts of leucrose were present in the medium, even after the last cycle.

Thus, glucan filtrate can be used in a fermentation process to produce ethanol.

Example 8

Production of Ethanol by Fermenting Hydrolyzed Glucan Filtrate

This example demonstrates that fermenting a glucan filtrate in which the leucrose and oligosaccharide byproduct components have previously been saccharified results in increased ethanol yields.

Fermentations were performed following the procedure outlined in Example 7, but using a glucan filtrate that was previously treated with a transglucosidase (TG L-2000, SEQ ID NO: 1). Hydrolyzed glucan filtrate was prepared as follows. Glucan filtrate was adjusted to 300 g sugars/L and then the pH was adjusted to 4.0 using 1.0 M sodium hydroxide and 5 wt % sulfuric acid. The final volume of this preparation was 6.75 L. The filtrate solution was then sterilized using a PHOENIX AV-250 PLUS autoclave at 121° C. for 15 minutes, and then the temperature was adjusted to 60° C. TG L-2000 enzyme extract as described in Table 4 (135 mL) was mixed with the sterilized filtrate and the solution was incubated in an incubator-shaker (IKA KS4000) at 60° C. and 100 rpm for 72 hours. Hydrolyzed glucan filtrate was thus prepared.

Yeast (S. cerevisiae) cream (Bom Retiro mill, Brazil) was washed by suspending the cream in tap water (2.4 L, optical density of 65 at 600 nm) and then centrifuging the yeast cream for 5 minutes using a LEGEND XTR centrifuge at 4500 g. After decanting the supernatant, the yeast were resuspended and concentrated by centrifugation two additional times. After the third wash, the pH was adjusted to 4.5 by addition of 5 wt % sulfuric acid and the optical density was measured using a GENESYS 20 4001 spectrophotometer and adjusted to 100 at 600 nm by addition of tap water. The adjusted yeast cream (1.5 L) was added to a 7.5-L BIOFLO310 fermenter vessel. The fermenter was set to maintain temperature at 30° C., agitation at 100 rpm, and pH at 4.5 using 4 M aqueous ammonium hydroxide or 5 wt % aqueous sulfuric acid.

A feed solution containing yeast extract (10 g/L), peptone (20 g/L), and 200 g/L of sugars from the hydrolyzed filtrate was prepared and sterilized using a PHOENIX AV-250 Plus autoclave at 121° C. for 15 minutes. The feed solution was allowed to cool to 25° C. (room temperature) before the fermentation began. The sterilized feed solution (3.5 L) was added to the fermenter over approximately 5 hours at a rate of 684 mL/hr, and the fermentation was allowed to proceed for 22 hours.

Periodic samples were taken during the fermentation and analyzed for optical density using a GENESYS 20 4001 spectrophotometer, Brix using a PAL-3 refractometer, and sugar and ethanol concentrations by HPLC (General Methods). These results are summarized in Table 13.

TABLE 13

Feed and Time Course Fermentation Profiles for the First Ethanol Fermentation Using Hydrolyzed Glucan Filtrate

| Time (hr) | Sucrose | Leucrose | Glucose | Fructose | DP2 | DP3+ | Total Sugar | EtOH |
|---|---|---|---|---|---|---|---|---|
| Feed | 7 | 4 | 65 | 97 | 11 | 3 | 186 | 0 |
| 0 | 0 | 0 | 0 | 0 | — | — | — | 7 |
| 1 | <1 | 1 | <1 | <1 | — | — | — | 20 |
| 2 | <1 | 3 | <1 | <1 | — | — | — | 32 |
| 3 | <1 | 4 | <1 | <1 | — | — | — | 40 |
| 4 | <1 | 4 | <1 | <1 | — | — | — | 49 |
| 5 | <1 | 4 | <1 | <1 | — | — | — | 53 |
| 6 | <1 | 5 | <1 | <1 | — | — | — | 55 |
| 8 | <1 | 5 | <1 | <1 | — | — | — | 57 |
| 22 | <1 | 5 | <1 | <1 | 8 | 3 | 16 | 54 |

Concentrations (g/L) of ethanol (EtOH) and sugar compounds in the feed and at various fermentation time points (0-22 hours) are listed.

When the fermentation was over, the yeast cells were separated by centrifugation using a LEGEND XTR centrifuge at 4500 g for 5 minutes. After decanting the supernatant, the yeast cells were resuspended and concentrated by centrifugation two additional times. After the third wash, the pH was adjusted to 2 by addition of 5 wt % sulfuric acid. The optical density was measured using a GENESYS 20 4001 spectrophotometer and adjusted to 100 at 600 nm by addition of tap water. Two additional fermentation cycles, each using fresh feed, were performed using recycled yeast cells from the previous fermentation following the same conditions described above. The fermentation results obtained using first-time and second-time recycled yeast cells are provided in Tables 14 and 15, respectively.

TABLE 14

Feed and Time Course Fermentation Profiles Using the First Recycle of Yeast Cells with Hydrolyzed Glucan Filtrate

| Time (hr) | Sucrose | Leucrose | Glucose | Fructose | DP2 | DP3+ | Total Sugar | EtOH |
|---|---|---|---|---|---|---|---|---|
| Feed | 7 | 4 | 69 | 104 | 7 | 4 | 194 | 0 |
| 0 | <1 | 0 | <1 | <1 | — | — | — | 10 |
| 1 | <1 | 7 | <1 | <1 | — | — | — | 25 |
| 4 | <1 | 5 | <1 | <1 | — | — | — | 39 |
| 4 | <1 | 4 | <1 | <1 | — | — | — | 45 |
| 5 | <1 | 5 | <1 | <1 | — | — | — | 51 |
| 6 | <1 | 5 | <1 | <1 | — | — | — | 57 |
| 6.2 | <1 | 5 | <1 | <1 | — | — | — | 60 |
| 7 | <1 | 5 | <1 | <1 | — | — | — | 59 |
| 21 | <1 | 5 | <1 | <1 | 9 | 5 | 19 | 58 |

Concentrations (g/L) of ethanol (EtOH) and sugar compounds in the feed and at various fermentation time points (0-21 hours) are listed.

TABLE 15

Feed and Time Course Fermentation Profiles Using the Second Recycle of Yeast Cells with Hydrolyzed Glucan Filtrate

| Time (hr) | Sucrose | Leucrose | Glucose | Fructose | DP2 | DP3+ | Total Sugar | EtOH |
|---|---|---|---|---|---|---|---|---|
| Feed | 7 | 4 | 70 | 105 | 7 | 5 | 197 | 0 |
| 0 | 0 | 0 | 0 | 0 | — | — | — | 10 |
| 1 | <1 | 7 | <1 | <1 | — | — | — | 25 |
| 3.5 | <1 | 5 | <1 | <1 | — | — | — | 39 |
| 4 | <1 | 4 | <1 | <1 | — | — | — | 45 |
| 5 | <1 | 5 | <1 | <1 | — | — | — | 51 |
| 6 | <1 | 5 | <1 | <1 | — | — | — | 57 |
| 6.2 | <1 | 5 | <1 | <1 | — | — | — | 60 |
| 7 | <1 | 5 | <1 | <1 | — | — | — | 59 |
| 21 | <1 | 5 | <1 | <1 | 9 | 5 | 19 | 58 |

Concentrations (g/L) of ethanol (EtOH) and sugar compounds in the feed and at various fermentation time points (0-21 hours) are listed.

All of the fermentations were essentially complete within about six hours of initiating fermentation, and resulted in ethanol titers of 57-60.0 g/L. Comparing these fermentations with those in Example 7 demonstrates that hydrolyzing a glucan filtrate before subjecting it to fermentation results in faster and greater ethanol yields than those obtained from fermentations using non-hydrolyzed glucan filtrate.

Thus, fermenting a glucan filtrate in which the leucrose and oligosaccharide byproduct components have been saccharified results in increased ethanol yields at faster rates. This saccharification can be done using a transglucosidase, for example.

Example 9

Simultaneous Saccharification and Fermentation of a Glucan Filtrate Solution

This example discloses that simultaneous saccharification and fermentation of a feed containing glucan filtrate can result in enhanced fermentation properties.

Yeast (S. cerevisiae) cream (Bom Retiro mill, Brazil) was washed by suspending the cream in tap water (2.4 L, optical density of 65 at 600 nm) and then centrifuging the yeast cream for 5 minutes using a LEGEND XTR centrifuge at 4500 g. After decanting the supernatant, the yeast cells were resuspended and concentrated by centrifugation two additional times. After the third wash, the pH was adjusted to 4.5 by addition of 5 wt % sulfuric acid and the optical density was measured using a GENESYS 20 4001 spectrophotometer and adjusted to 100 at 600 nm by addition of tap water. The adjusted yeast cream (1.5 L) was added to a 7.5-L BIOFLO310 fermenter vessel. The fermenter was set to maintain temperature at 30° C., agitation at 100 rpm, and pH at 4.5 using 4 M aqueous ammonium hydroxide or 5 wt % aqueous sulfuric acid.

A feed solution containing yeast extract (10 g/L), peptone (20 g/L), and 200 g/L of sugars from a glucan filtrate was prepared and sterilized using a PHOENIX AV-250 PLUS autoclave at 121° C. for 15 minutes. The feed solution was allowed to cool to 25° C. (room temperature) before the fermentation began. TG L-2000 transglucosidase enzyme extract as described in Table 4 (1% v/v) was added to the sterilized feed solution immediately before adding the solution to the fermenter. The feed solution (3.5 L) containing TG L-2000 enzyme was added to the fermenter over approximately 5 hours at 684 mL/hr, and the fermentation was allowed to proceed for 48 hours.

Periodic samples were taken during the fermentation and analyzed for optical density using a GENESYS 20 400I spectrophotometer, Brix using a PAL-3 refractometer (Atago), and sugar and ethanol concentrations by HPLC (General Methods). These results are summarized in Table 16.

TABLE 16

Feed and Time Course Fermentation Profiles for Simultaneous Saccharification and Ethanol Fermentation of Glucan Filtrate

| Time (hr) | Sucrose | Leucrose | Glucose | Fructose | DP2 | DP3+ | Total Sugar | EtOH |
|---|---|---|---|---|---|---|---|---|
| Feed | 7 | 82 | 12 | 79 | 6 | 20 | 206 | 0 |
| 0 | 0 | 0 | 0 | 0 | 0 | 0 | 0 | 2 |
| 1 | <1 | 13 | <1 | 3 | — | — | — | 11 |
| 2 | <1 | 21 | <1 | 4 | — | — | — | 30 |
| 3 | <1 | 21 | <1 | 3 | — | — | — | 38 |
| 4 | <1 | 20 | <1 | 3 | 11 | 16 | 50 | 43 |
| 5 | <1 | 14 | <1 | 2 | — | — | — | 45 |
| 6 | <1 | <1 | <1 | 2 | — | — | — | 59 |
| 22 | <1 | <1 | <1 | 1 | — | — | — | 62 |
| 25 | <1 | <1 | <1 | <1 | — | — | — | 63 |
| 27 | <1 | <1 | <1 | <1 | — | — | — | 63 |
| 31 | <1 | <1 | <1 | <1 | — | — | — | 57 |
| 46 | <1 | <1 | <1 | <1 | — | — | — | 57 |
| 48 | <1 | <1 | <1 | <1 | 1 | 11 | 12 | 62 |

Concentrations (g/L) of ethanol (EtOH) and sugar compounds in the feed and at various fermentation time points (0-48 hours) are listed.

The fermentation was nominally complete in 6 hours, similar to the fermentations where the filtrate was hydrolyzed prior to the fermentation step (Example 8), and gave a slightly superior titer of ethanol (62 g/L) compared to using unhydrolyzed filtrate (Example 7). In addition, almost all of the leucrose was consumed by 6 hours (compare Table 16 with Tables 13-15). In addition to adding a saccharifying enzyme, such as TG L-2000, to a feed containing glucan filtrate just prior to fermentation, similar results should be obtained if the saccharifying enzyme is added to the fermentation directly.

Thus, simultaneous saccharification and fermentation of a feed containing glucan filtrate can result in enhanced fermentation properties such as increased (i) consumption of glucan filtrate components (e.g., leucrose) and (ii) ethanol yield and rate of production.

Example 10

Preparation of Various Alpha-Glucosidases

This example discloses preparing various alpha-glucosidases in addition to those alpha-glucosidases (transglucosidase, glucoamylase, DIAZYME RDF ULTRA) used in some of the foregoing Examples. These additional alpha-glucosidases were tested for hydrolytic activity against oligosaccharides comprising alpha-1,5 glucosyl-fructose linkages or alpha-1,3 and/or alpha-1,6 glucosyl-glucose linkages in Examples 11, 12, 15 and 16 provided below.

Discovery of an *Aspergillus clavatus* Alpha-Glucosidase (Aclglu1)

A strain of *Aspergillus clavatus* was selected as a potential source of other enzymes that may be useful in various industrial applications. One of the genes identified in *Aspergillus clavatus* encodes an alpha-glucosidase and the sequence of this gene, called "Aclglu1", is provided in SEQ ID NO:4. The corresponding protein encoded by SEQ ID NO:4 is provided in SEQ ID NO:5. Aclglu1 belongs to Glycosyl hydrolase family 31 based on a PFAM search (pfam.sanger.ac.uk web link). At the N-terminus, the protein (SEQ ID NO:5) has a signal peptide with a length of 19 amino acids as predicted by SignalP version 4.0 (Nordahl Petersen et al., 2011, *Nature Methods*, 8:785-786). The presence of a signal sequence suggests that Aclglu1 is a secreted enzyme. The amino acid sequence of the predicted mature form of Aclglu1 is set forth as SEQ ID NO:6.

Expression of *Aspergillus Clavatus* Alpha-Glucosidase Aclglu1

A synthetic Aclglu1 gene was cloned into pTrex3gM expression vector (described in U.S. Patent Appl. Publ. No. 2011/0136197, incorporated herein by reference) and the resulting plasmid was designated as pJG294. The sequence of the Aclglu1 gene was confirmed by DNA sequencing.

Plasmid pJG294 was transformed into a quad deleted *Trichoderma reesei* strain (described in WO05/001036) using a biolistic method (Te'o V S et al., J Microbiol Methods, 51:393-9, 2002). The protein, which was predicted to comprise SEQ ID NO:6, was secreted into the extracellular medium and filtered culture medium was used to perform SDS-PAGE and alpha-glucosidase activity assays to confirm enzyme expression.

Discovery of *Neosartorya fischeri* Alpha-Glucosidase Nfiglu1

A strain of *Neosartorya fischeri* was selected as a potential source of other enzymes that may be useful in various industrial applications. One of the genes identified in *Neosartorya fischeri* encodes an alpha-glucosidase and the sequence of this gene, called "Nfiglu1", is provided in SEQ ID NO:7. The corresponding protein encoded by SEQ ID NO:7 is provided in SEQ ID NO:8. Nfiglu1 belongs to Glycosyl hydrolase family 31 based on a PFAM search (pfam.sanger.ac.uk web link). At the N-terminus, the protein (SEQ ID NO:8) has a signal peptide with a length of 19 amino acids as predicted by SignalP version 4.0 (Nordahl Petersen et al., 2011, *Nature Methods*, 8:785-786). The presence of a signal sequence suggests that Nfiglu1 is a secreted enzyme. The amino acid sequence of the predicted mature form of Nfiglu1 is set forth as SEQ ID NO: 9.

Expression of *Neosartorya fischen* Alpha-Glucosidase Nfiglu1

A synthetic Nfiglu1 gene was cloned into pTrex3gM expression vector (described in U.S. Patent Appl. Publ. No. 2011/0136197) and the resulting plasmid was designated as pJG295. The sequence of the Nfiglu1 gene was confirmed by DNA sequencing.

Plasmid pJG295 was transformed into a quad deleted *Trichoderma reesei* strain (described in WO05/001036) using a biolistic method (Te'o V S et al., J Microbiol Methods, 51:393-9, 2002). The protein, which was predicted to comprise SEQ ID NO:9, was secreted into the extracellular medium and filtered culture medium was used to perform SDS-PAGE and alpha-glucosidase activity assays to confirm enzyme expression.

Discovery of *Neurospora crassa* Alpha-Glucosidase Ncrglu1

A strain of *Neurospora crassa* was selected as a potential source of other enzymes that may be useful in various industrial applications. One of the genes identified in *Neurospora crassa* encodes an alpha-glucosidase and the sequence of this gene, called "Ncrglu1", is provided in SEQ ID NO:10. The corresponding protein encoded by SEQ ID NO:10 is provided in SEQ ID NO:11. Ncrglu1 belongs to Glycosyl hydrolase family 31 based on a PFAM search (pfam.sanger.ac.uk web link). At the N-terminus, the protein (SEQ ID NO:11) has a signal peptide with a length of 22 amino acids as predicted by SignalP version 4.0 (Nordahl Petersen et al., 2011, *Nature Methods*, 8:785-786). The presence of a signal sequence suggests that Ncrglu1 is a secreted enzyme. The amino acid sequence of the predicted mature form of Ncrglu1 is set forth as SEQ ID NO:12.

Expression of *Neurospora crassa* Alpha-Glucosidase Ncrglu1

A synthetic Ncrglu1 gene was cloned into pTrex3gM expression vector (described in U.S. Patent Appl. Publ. No. 2011/0136197) and the resulting plasmid was designated as pJG296. The sequence of the Ncrglu1 gene was confirmed by DNA sequencing.

Plasmid pJG296 was transformed into a quad deleted *Trichoderma reesei* strain (described in WO05/001036) using a biolistic method (Te'o V S et al., J Microbiol Methods, 51:393-399, 2002). The protein, which was predicted to comprise SEQ ID NO:12, was secreted into the extracellular medium and filtered culture medium was used to perform SDS-PAGE and alpha-glucosidase activity assays to confirm enzyme expression.

Discovery of *Rasamsonia composticola* alpha-glucosidase TauSec098

A strain of *Rasamsonia composticola* was selected as a potential source of other enzymes that may be useful in various industrial applications. One of the genes identified in *Rasamsonia composticola* encodes an alpha-glucosidase and the sequence of this gene, called "TauSec098", is provided in SEQ ID NO:13. The corresponding protein encoded by SEQ ID NO:13 is provided in SEQ ID NO:14. TauSec098 belongs to Glycosyl hydrolase family 31 and contains an N-terminal CBM 20 domain based on a PFAM search (pfam.sanger.ac.uk web link). At the N-terminus, the protein (SEQ ID NO:14) has a signal peptide with a length of 22 amino acids as predicted by SignalP version 4.0 (Nordahl Petersen et al., 2011, *Nature Methods*, 8:785-786). The presence of a signal sequence suggests that TauSec098 is a secreted enzyme. The amino acid sequence of the predicted mature form of TauSec098 is set forth as SEQ ID NO:15.

Expression of *Rasamsonia composticola* Alpha-Glucosidase TauSec098

A synthetic TauSec098 gene was cloned into the *Trichoderma reesei* expression vector pGXT (a pTTT-derived plasmid) by Generay Biotech Co. (Shanghai, China) and the resulting plasmid was designated as pGX256-TauSec098. The sequence of the TauSec098 gene was confirmed by DNA sequencing.

Plasmid pGX256-TauSec098 was transformed into a quad-deleted *Trichoderma reesei* strain (described in WO05/001036) using protoplast transformation (Te'o et al., J. Microbiol. Methods 51:393-399, 2002). Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week. After growth on acetamide plates, the spores of transformants were collected and transferred into new acetamide agar plates. After 5 days of growth on acetamide plates, $1 \times 10^8$ spores were inoculated into 30 ml Glucose/Sophorose defined media in a 250-mL shake flask. The shake flask was shook at 28° C. for 5 days. Supernatants from these cultures were used to confirm expression (SDS PAGE) and activity of mature TauSec098 enzyme (SEQ ID NO:15).

Discovery of *Rasamsonia composticola* Alpha-Glucosidase TauSec099

A strain of *Rasamsonia composticola* was selected as a potential source of other enzymes that may be useful in various industrial applications. One of the genes identified in *Rasamsonia composticola* encodes an alpha-glucosidase and the sequence of this gene, called "TauSec099", is provided in SEQ ID NO:16. The corresponding protein encoded by SEQ ID NO:16 is provided in SEQ ID NO:17. TauSec099 belongs to Glycosyl hydrolase family 31 based on a PFAM search (pfam.sanger.ac.uk web link). At the N-terminus, the protein (SEQ ID NO:17) has a signal peptide with a length of 17 amino acids as predicted by SignalP version 4.0 (Nordahl Petersen et al., 2011, *Nature Methods*, 8:785-786). The presence of a signal sequence suggests that TauSec099 is a secreted enzyme. The amino acid sequence of the predicted mature form of TauSec099 is set forth as SEQ ID NO:18.

Expression of *Rasamsonia composticola* Alpha-Glucosidase TauSec099

A synthetic TauSec099 gene was cloned into the *Trichoderma reesei* expression vector pGXT (a pTTT-derived plasmid) by Generay Biotech Co. (Shanghai, China) and the resulting plasmid was designated as pGX256-TauSec099. The sequence of the TauSec0998 gene was confirmed by DNA sequencing.

Plasmid pGX256-TauSec099 was transformed into a quad-deleted *Trichoderma reesei* strain (described in WO05/001036) using protoplast transformation (Te'o et al., J. Microbiol. Methods 51:393-399, 2002).

Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week. After growth on acetamide plates, the spores of transformants were collected and transferred into new acetamide agar plates. After 5 days of growth on acetamide plates, $1 \times 10^8$ spores were inoculated into 30 ml Glucose/Sophorose defined media in a 250-mL shake flask. The shake flask was shook at 28° C. for 5 days. Supernatants from these cultures were used to confirm expression (SDS PAGE) and activity of mature TauSec099 enzyme (SEQ ID NO:18).

Sequences of *Bifidobacteurim longum* alpha-glucosidase BloGlu1

An alpha-glucosidase gene, "BloGlu1", was identified from *Bifidobacterium longum* subsp. *longum* JDM301. The nucleic acid sequence for the BloGlu1 gene (SEQ ID NO:19, GENBANK Acc. No. NC014169.1, complement sequence from positions 140600 to 142414) and the amino acid sequence of the hypothetical protein (SEQ ID NO:20) encoded by SEQ ID NO:19 were found in GENBANK Acc. No. YP_003660432.1.

Expression of *Bifidobacteurim longum* Alpha-Glucosidase BloGlu1

The DNA sequence encoding the entire BloGlu1 protein (SEQ ID NO:20) was optimized for expression in *B. subtilis*, then synthesized (yielding SEQ ID NO:21) and inserted into the p3JM plasmid by Generay Biotech Co. (Shanghai, China), resulting in p3JM-BloGlu1. The p3JM-BloGlu1 plasmid contains an aprE promoter to drive expression of the optimized BloGlu1 sequence (SEQ ID NO:21).

Plasmid p3JM-BloGlu1 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express BloGlu1 protein (SEQ ID NO:20).

Sequences of *Bifidobacteurim longum* Alpha-Glucosidase BloGlu2

An alpha-glucosidase, BloGlu2, was identified from *Bifidobacterium longum*. The amino acid sequence (SEQ ID NO:22) of BloGlu2 was found in the NCBI database (GENBANK Acc. No. WP_007054665.1).

Expression of *Bifidobacteurim longum* Alpha-Glucosidase BloGlu2

A DNA sequence encoding BloGlu2 protein was optimized for expression in *B. subtilis*, then synthesized (yielding SEQ ID NO:23) and inserted into the p3JM plasmid by Generay Biotech Co., resulting in p3JM-BloGlu2. SEQ ID NO:23 encodes the amino acid sequence of SEQ ID NO:24. The p3JM-BloGlu2 plasmid contains an aprE promoter to drive expression of the optimized BloGlu2 sequence (SEQ ID NO:23).

Plasmid p3JM-BloGlu2 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express BloGlu2 protein (SEQ ID NO:24).

Sequences of *Bifidobacterium* Longum Alpha-Glucosidase BloGlu3

An alpha-glucosidase gene, "BloGlu3", was identified from *Bifidobacterium longum* subsp. *longum* F8. The nucleic acid sequence for the BloGlu3 gene (SEQ ID NO:25), GENBANK Acc. No. NC_021008.1, positions 2130627 to 2132441), and the amino acid sequence of the hypothetical protein (SEQ ID NO:26) encoded by SEQ ID NO:25 were found in GENBANK Acc. No. YP_007768249.1.

Expression of *Bifidobacteurim longum* Alpha-Glucosidase BloGlu3

The DNA sequence encoding the entire BloGlu3 protein (SEQ ID NO:26) was optimized for expression in *B. subtilis*, then synthesized (yielding SEQ ID NO:27) and inserted into the p3JM plasmid by Generay Biotech Co., resulting in p3JM-BloGlu3. The p3JM-BloGlu3 plasmid contains an aprE promoter to drive expression of the optimized BloGlu3 sequence (SEQ ID NO:27).

Plasmid p3JM-BloGlu3 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express BloGlu3 protein (SEQ ID NO:26).

Sequences of *Bifidobacterium pseudolongum* Alpha-Glucosidase BpsGlu1

An alpha-glucosidase, BpsGlu1, was identified from *Bifidobacterium pseudolongum*. The amino acid sequence (SEQ ID NO:28) of BpsGlu1 was found in the NCBI database (GENBANK Acc. No. WP_022858408.1).

Expression of *Bifidobacterium pseudolongum* Alpha-Glucosidase BpsGlu1

A DNA sequence encoding BpsGlu1 protein was optimized for expression in *B. subtilis*, then synthesized (yielding SEQ ID NO:29) and inserted into the p3JM plasmid by Generay Biotech Co., resulting in p3JM-BpsGlu1. SEQ ID NO:29 encodes the amino acid sequence of SEQ ID NO:30. The p3JM-BpsGlu1 plasmid contains an aprE promoter to drive expression of the optimized BpsGlu1 sequence (SEQ ID NO:29)

Plasmid p3JM-BpsGlu1 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express BpsGlu1 protein (SEQ ID NO:30).

Sequences of *Bifidobacterium thermophilum* alpha-glucosidase BthGlu1

An alpha-glucosidase gene, "BthGlu1", was identified from *Bifidobacterium thermophilum* RBL67. The nucleic acid sequence of the BthGlu1 gene (SEQ ID NO:31, GENBANK Acc. No. NC_020546.1, positions 150690 to 152495), and the amino acid sequence of the hypothetical protein (SEQ ID NO:32) encoded by SEQ ID NO:31 were found in GENBANK Acc. No. YP_007592840.1.

Expression of *Bifidobacterium thermophilum* Alpha-Glucosidase BthGlu1

The DNA sequence encoding the entire BthGlu1 protein (SEQ ID NO:32) was optimized for expression in *B. subtilis*, then synthesized (yielding SEQ ID NO:33) and inserted into the p3JM plasmid by Generay Biotech Co., resulting in p3JM-BthGlu1. The p3JM-BthGlu1 plasmid contains an aprE promoter to drive expression of the optimized BthGlu1 sequence (SEQ ID NO:33).

Plasmid p3JM-BthGlu1 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express BthGlu1 protein (SEQ ID NO:32).

Sequences of *Bifidobacterium breve* Alpha-Glucosidase BbrGlu2

An alpha-glucosidase, BbrGlu2, was identified from *Bifidobacterium breve*. The amino acid sequence (SEQ ID NO:34) of BbrGlu2 was found in the NCBI database (GENBANK Acc. No. WP_003827971.1).

Expression of *Bifidobacterium breve* Alpha-Glucosidase BbrGlu2

A DNA sequence encoding BbrGlu2 protein was optimized for expression in *B. subtilis*, then synthesized (yielding SEQ ID NO:35) and inserted into the p3JM plasmid by Generay Biotech Co., resulting in p3JM-BbrGlu2. SEQ ID NO:35 encodes the amino acid sequence of SEQ ID NO:36. The p3JM-BbrGlu2 plasmid contains an aprE promoter to drive expression of the optimized BbrGlu2 sequence (SEQ ID NO:35)

Plasmid p3JM-BbrGlu2 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express SEQ ID NO:36.

Sequences of *Bifidobacterium breve* Alpha-Glucosidase BbrGlu5

An alpha-glucosidase gene, "BbrGlu5", was identified from *Bifidobacterium breve* ACS-071-V-Sch8b. The nucleic acid sequence of the BbrGlu5 gene (SEQ ID NO:37, GENBANK Acc. No. NC_017218.1, complement of sequence from positions 2241075 to 2242895), and the amino acid sequence of the hypothetical protein (SEQ ID NO:38) encoded by SEQ ID NO:37 were found in GENBANK Acc. No. YP_005583701.1.

Expression of *Bifidobacterium breve* Alpha-Glucosidase BbrGlu5

The DNA sequence encoding the entire BbrGlu5 protein (SEQ ID NO:38) was optimized for expression in *B. subtilis*, then synthesized (yielding SEQ ID NO:39) and inserted into the p3JM plasmid by Generay Biotech Co., resulting in p3JM-BbrGlu5. The p3JM-BbrGlu5 plasmid contains an aprE promoter to drive expression of the optimized BbrGlu5 sequence (SEQ ID NO:39).

Plasmid p3JM-BbrGlu5 was used to transform *B. subtilis* cells (degUHy32, ΔnprB, Δvpr, Δepr, ΔscoC, ΔwprA, Δmpr, ΔispA, Δbpr), and the transformed cells were spread on Luria Agar plates supplemented with 5 ppm chloramphenicol. A colony with correct insertion, as confirmed by PCR and sequencing, was selected and subjected to fermentation in a 250-mL shake flask with MBD medium (a MOPS-based defined medium supplemented with an additional 5 mM $CaCl_2$) to express BbrGlu5 protein (SEQ ID NO:38).

Purification of alpha-glucosidases from expression cultures

AclGlu1 and NcrGlu1

Both AclGlu1 (SEQ ID NO:6) and NcrGlu1 (SEQ ID NO:12) alpha-glucosidases were purified using two chromatography steps. For each purification, the crude broth from the shake flask was concentrated, after which ammonium sulfate was added to a final concentration of 2 M. The solution was loaded onto a 50-mL phenyl HP column pre-equilibrated with 20 mM Tris pH 8.0, 2 M ammonium sulfate. The target protein (SEQ ID NO:6 or SEQ ID NO:12) was eluted from the column with 1 M ammonium sulfate, 20 mM Tris pH 8.0. Respective fractions were pooled, concentrated and buffer-exchanged into 20 mM Tris pH 8.0 (buffer A), using a VIVAFLOW 200 ultrafiltration device (Sartorius Stedim). The resulting solution was applied to a 40-mL Q HP column pre-equilibrated with buffer A. The target protein was eluted from the column with 0.3 M NaCl in buffer A. The fractions containing target protein were then pooled and concentrated using 10K AMICON ULTRA-15 devices, and stored in 40% glycerol at −20° C. until usage.

NfiGlu1

NfiGlu1 alpha-glucosidase (SEQ ID NO:9) was purified using two hydrophobic interaction chromatography steps. The crude broth from the shake flask was concentrated, after which ammonium sulfate was added to a final concentration of 1 M. The solution was loaded onto a 50-mL phenyl HP column pre-equilibrated with 20 mM Tris pH 8.0, 1 M ammonium sulfate. The target protein (SEQ ID NO:9) flowed through the column. Flow-through fractions were pooled, after which ammonium sulfate was added to a final concentration of 2 M. The solution was loaded onto the same phenyl HP column pre-equilibrated with 20 mM Tris pH 8.0, 2 M ammonium sulfate. The target protein was eluted from the column with 1 M ammonium sulfate, 20 mM Tris pH 8.0. The fractions containing target protein were then pooled and concentrated using 10K AMICON ULTRA-15 devices, and stored in 40% glycerol at −20° C. until usage.

TauSec098 and TauSec099

Both TauSec098 (SEQ ID NO:15) and TauSec099 (SEQ ID NO:18) alpha-glucosidases were purified via hydrophobic interaction chromatography. For each purification, ammonium sulphate was added to about 180 mL of concentrated crude broth from a 7-L fermenter to a final concentration of 1 M. This solution was then loaded onto a 50-mL HIPREP phenyl-FF Sepharose column (GE Healthcare) pre-equilibrated with 20 mM sodium acetate pH 5.0, 1 M ammonium sulphate (buffer A). After washing with the same buffer with three column volumes (CVs), the column was eluted stepwise with 75%, 50% and 0% buffer A using three CVs each, followed by two CVs of MILLIQ $H_2O$. All fractions were analyzed by SDS-PAGE. The target protein (SEQ ID NO:15 or SEQ ID NO: 18) was mainly present in the flow-through fraction, which was concentrated and buffer-exchanged to remove excess ammonium sulfate using 10 KDa AMICON ULTRA-15 devices. The final product, which was greater than 90% pure, was stored in 40% glycerol at −80° C. until usage.

BloGlu1, BloGlu2 and BloGlu3

BloGlu1 (SEQ ID NO:20), BloGlu2 (SEQ ID NO:24) and BloGlu3 (SEQ ID NO:26) alpha-glucosidases were all purified in three steps. For each purification, the crude broth from a 1-L DASGIP fermenter was concentrated, after which ammonium sulfate was added to 60% saturation. The solution was stirred at 4° C. for 1 hr, and then centrifuged at 8000×g for 30 min. The resulting pellet was re-suspended in 20 mM Tris pH 8.0 (buffer A). Ammonium sulfate was added to the resulting solution to a final concentration of 1 M; this preparation was then loaded onto a 40-mL HiPrep™ Phenyl FF column pre-equilibrated with 20 mM Tris pH 8.0, 1 M ammonium sulfate (buffer B). After washing, the column was eluted stepwise with 75%, 50%, and 0% buffer B and $H_2O$ in three column volumes each. All fractions were analyzed using SDS-PAGE and activity assays. The fractions containing target protein (SEQ ID NO:20, SEQ ID NO:24, or SEQ ID NO:26) were pooled, concentrated and subsequently loaded onto a HiLoad™ 26/60 Superdex™ 75 column pre-equilibrated with 20 mM sodium phosphate pH 7.0, 0.15 M NaCl. Flow-through fractions containing the target protein were then pooled and concentrated using 10K AMICON ULTRA-15 devices, and stored in 40% glycerol at −20° C. until usage.

BpsGlu1 and BthGlu1

Both BpsGlu1 (SEQ ID NO:30) and BthGlu1 (SEQ ID NO:32) alpha-glucosidases were purified in two steps. For each purification, the crude broth from a 1-L DASGIP fermenter was concentrated, after which ammonium sulfate was added to 60% saturation. The solution was stirred at 4°

C. for 1 hr, and then centrifuged at 8000×g for 30 min. The resulting pellet was re-suspended in 20 mM Tris pH 8.0 (buffer A). Ammonium sulfate was added to the resulting solution to a final concentration of 1 M; this preparation was then loaded onto a 40-mL HiPrep™ Phenyl FF column pre-equilibrated with 20 mM Tris pH 8.0, 1 M ammonium sulfate (buffer B). After washing, the column was eluted stepwise with 75%, 50%, and 0% buffer B and H₂O in three column volumes each. All fractions were analyzed using SDS-PAGE and activity assays. The target protein (SEQ ID NO:30 or SEQ ID NO:32) was present in the eluate from the 0% buffer B elution step; this eluate was pooled and concentrated using 10K AMICON ULTRA-15 devices. The final product, which was greater than 95% pure, was stored in 40% glycerol at −20° C. until usage.

BbrGlu2 and BbrGlu5

Both BbrGlu2 (SEQ ID NO:36) and BbrGlu5 (SEQ ID NO:38) alpha-glucosidases were purified in four steps. For each purification, the crude broth from a 1-L DASGIP fermenter was concentrated, after which ammonium sulfate was added to 60% saturation. The solution was stirred at 4° C. for 1 hr, and then centrifuged at 8000×g for 30 min. The resulting pellet was re-suspended in 20 mM HEPES pH 7.0 (buffer A). Ammonium sulfate was added to the resulting solution to a final concentration of 1 M; this preparation was then loaded onto a HiPrep™ Phenyl FF column pre-equilibrated with 20 mM HEPES pH 7.0, 1 M ammonium sulfate. The target protein (SEQ ID NO:36 or SEQ ID NO:38) was eluted from the column with 0.5 M ammonium sulfate. Respective fractions were pooled, concentrated and buffer-exchanged into buffer A using a VIVAFLOW 200 ultrafiltration device (Sartorius Stedim). The resulting solution was applied to a HiPrep™ Q FF 16/10 column pre-equilibrated with buffer A. Target protein was eluted from the column with a linear gradient of 0-0.5 M NaCl in buffer A. Fractions containing target protein were pooled, concentrated and subsequently loaded onto a HiLoad™ 26/60 Superdex™ 75 column pre-equilibrated with 20 mM HEPES pH 7.0, 0.15 M NaCl. The fractions containing target protein were then pooled and concentrated using 10K AMICON ULTRA-15 devices, and stored in 40% glycerol at −20° C. until usage.

Thus, various additional alpha-glucosidases were expressed and purified. These alpha-glucosidases were tested for hydrolytic activity against alpha-1,5 glucosyl-fructose linkages and alpha-1,3 and/or alpha-1,6 glucosyl-glucose linkages in Examples 11, 12, 15 and 16 provided below.

Example 11

Testing Alpha-Glucosidases for Hydrolytic Activity Against Various Glycosidic Linkages This example discloses testing whether alpha-glucosidases have hydrolytic activity beyond that previously associated with this class of enzymes (EC 3.2.1.20). Alpha-glucosidases from Example 10 were shown to have hydrolytic activity against alpha-1,5 glucosyl-fructose linkages and alpha-1,3 and alpha-1,6 glucosyl-glucose linkages.

Substrate Specificity of Alpha-Glucosidases

The substrate specificity of each alpha-glucosidase disclosed in Example 10 was assayed based on the release of glucose from a particular substrate (isomaltose, maltose, panose, leucrose, or nigerose) when the substrate was incubated with alpha-glucosidase. The rate of glucose release was measured using a coupled glucose oxidase/peroxidase (GOX/HRP) method (1980, *Anal. Biochem.* 105:389-397). Glucose release was quantified as the rate of oxidation of 2,2'-azino-bis 3-ethylbenzothiazoline-6-sulfonic acid (ABTS) by peroxide that was generated from coupled GOX/HRP enzymes reacted with glucose.

Individual substrate solutions were prepared by mixing a 9 mL solution of substrate (1% in water, w/v) with 1 mL of 0.5 M pH 5.0 sodium acetate buffer and 40 µL of 0.5 M calcium chloride in a 15-mL conical tube. Coupled enzyme (GOX/HRP) solution with ABTS was prepared in 50 mM sodium acetate buffer (pH 5.0), with the final concentrations of 2.74 mg/mL ABTS, 0.1 U/mL HRP, and 1 U/mL GOX. Serial dilutions of individual alpha-glucosidase samples and glucose standard were prepared in MILLIQ water. For nigerose, alpha-glucosidase samples were tested with only one dosage at 10 ppm due to a limited stock of substrate solutions. Each alpha-glucosidase sample (10 µL) was transferred into a new microtiter plate (Corning 3641) containing 90 µL of substrate solution pre-incubated at 50° C. for 5 min at 600 rpm. Reactions were carried out at 50° C. for 10 min (for isomaltose, maltose, panose, and nigerose substrates), or for 60 min (for leucrose substrate) with shaking (600 rpm) in a THERMOMIXER (Eppendorf). 10 µL of each reaction mix, as well as 10 µL of serial dilutions of glucose standard, were then quickly transferred to new microtiter plates (Corning 3641), respectively, to which 90 µL of ABTS/GOX/HRP solution was then added accordingly. The microtiter plates containing reaction mixes were immediately measured at 405 nm at 11 second intervals for 5 min using a SOFTMAX PRO plate reader (Molecular Devices). The output was the reaction rate, $V_o$, for each enzyme concentration. Linear regression was used to determine the slope of the plot $V_o$ vs. enzyme dose. The specific activity of each alpha-glucosidase was calculated based on the glucose standard curve using Equation 1:

$$\text{Specific Activity(Unit/mg)}=\text{Slope(enzyme)/slope(std)} \times 1000 \quad (1),$$

where 1 Unit=1 µmol glucose/min.

For nigerose, the value of the reaction rate with enzyme dosage at 10 ppm was directly used to indicate enzyme activity.

Using the foregoing method, the specificity of each alpha-glucosidase was determined against each substrate. The activities of an oligo-1,6-glucosidase (purchased from Megazyme, see Table 4) and a transglucosidase (TG L-2000, see Table 4) against each substrate were also measured. The results of this analysis are provided in Table 17.

TABLE 17

Activity of Various Alpha-Glucosidases Against Different Substrates

| Enzyme | SEQ ID NO. | Enzyme Activity (U/mg) as Measured on: | | | | |
|---|---|---|---|---|---|---|
| | | Iso-maltose | Maltose | Panose | Leucrose | Nigerose[a] |
| Oligo-1,6-glucosidase | | 118.2 | 0.0 | 54.3 | 1.3 | 19.6 |
| TG L-2000 | 1 | 194.0 | 235.6 | 127.7 | 68.9 | 254.0 |
| AclGlu1 | 6 | 255.7 | 401.9 | 180.9 | 113.7 | 315.1 |
| NfiGlu1 | 9 | 521.2 | 360.0 | 126.9 | 89.4 | 264.3 |
| NcrGlu1 | 12 | 282.7 | 34.9 | 15.9 | 61.6 | 200.4 |
| TauSec098 | 15 | 54.9 | 123.8 | 23.8 | 1.8 | 305.6 |
| TauSec099 | 18 | 244.0 | 97.7 | 50.8 | 70.6 | 184.8 |
| BloGlu1 | 20 | 71.1 | 66.9 | 23.1 | 2.5 | 165.0 |
| BloGlu2 | 24 | 65.9 | 86.7 | 19.9 | 3.5 | 217.9 |
| BloGlu3 | 26 | 120.1 | 175.5 | 31.4 | 9.0 | 272.6 |
| BspGlu1 | 30 | 64.2 | 247.9 | 60.8 | 27.3 | 254.6 |

TABLE 17-continued

Activity of Various Alpha-Glucosidases Against Different Substrates

| Enzyme | SEQ ID NO. | Enzyme Activity (U/mg) as Measured on: | | | | |
|---|---|---|---|---|---|---|
| | | Iso-maltose | Maltose | Panose | Leucrose | Nigerose[a] |
| BthGlu1 | 32 | 108.3 | 93.3 | 21.1 | 68.4 | 128.5 |
| BbrGlu2 | 36 | 106.6 | 167.5 | 26.9 | 6.1 | 258.8 |
| BbrGlu5 | 38 | 925.8 | 0.0 | 279.7 | 2.8 | 22.1 |

[a]Each enzyme was used at one (10 ppm) against nigerose.

Interestingly, it was found that alpha-glucosidases, besides exhibiting hydrolytic activity against alpha-1,4 glucosyl-glucose linkage (maltose), also exhibit hydrolytic activity against alpha-1,6 glucosyl-glucose linkage (isomaltose), alpha-1,3 glucosyl-glucose linkage (nigerose), and alpha-1,5 glucosyl-fructose linkage (leucrose) (Table 17).

Thus, alpha-glucosidases have hydrolytic activity beyond that previously associated with EC 3.2.1.20 enzymes. Specifically, alpha-glucosidases have hydrolytic activity against alpha-1,5 glucosyl-fructose linkages and alpha-1,3 and alpha-1,6 glucosyl-glucose linkages.

Example 12

Hydrolysis of Leucrose and Oligosaccharides in Glucan Reaction Filtrate Using Alpha-Glucosidase This Example describes using alpha-glucosidase to hydrolyze leucrose and other oligosaccharides present in filtrate obtained from a glucan synthesis reaction. Specifically, the effect of alpha-glucosidases disclosed in Example 10 on the hydrolysis of leucrose and oligosaccharides DP2, DP3 and HS (higher sugars, DP4+) in a filtrate of an insoluble glucan (poly alpha-1,3-glucan) synthesis reaction was studied.

Isolation and Analysis of Oligosaccharides for Testing Against Alpha-Glucosidase Activity First, a concentrated filtrate of a glucan synthesis reaction was prepared as per Example 1.

Briefly, oligosaccharides were isolated from the concentrated filtrate by chromatographic separation, and analyzed for glycosidic linkage profile. Chromatographic separation employing a strong acid cation-exchange resin was used to isolate the oligosaccharide fraction of the concentrated filtrate. The physical parameters of the column used for this separation were as follows: FINEX CS11GC, #227 resin; Na$^+$ ion form; 5% divinyl benzene (crosslinking); 0.34 mm particle size; 1.64 m bed length; 0.093 m column diameter.

In more detail, the concentrated sugar solution (i.e., concentrated filtrate) described in Table 3 was filtered and diluted to 25 g dry solids/100 g solution using tap water. Prior to addition of this sugar solution to the column resin, the resin was washed with six bed volumes (BV) of sodium chloride solution (three BV at 10 wt % sodium chloride followed by three BV at 5 wt % sodium chloride) to convert the resin to the sodium form. The sugar solution (0.6 L) was then fed to the column, after which the column was eluted using water at a flow rate of 50 mL/min. The run conditions of the chromatographic separation are summarized as follows: 0.6 L feed size, 25 g dry solids/100 g solution, 65° C. column temperature, 50 mL/min flow rate. An oligosaccharide solution was eluted between 11 and 21 minutes. A small amount of salts—indicated by an increase in conductivity—was eluted at the same time. The oligosaccharide fraction thus prepared was analyzed by HPLC to determine its product distribution. In total, the fraction contained >89% of oligosaccharides containing three or more hexose units and less than 1.5% of identifiable mono- and di-saccharides. This fraction was concentrated to a total dry weight of 317 g/L using a thin film evaporator (LCI Corporation, Charlotte, N.C.) followed by rotary evaporation with a ROTAVAPOR (R-151; Buchi, New Castle, Del.). The product distribution of the concentrated fraction as measured by HPLC appears in Table 18.

TABLE 18

Product Distribution of Concentrated Oligosaccharide Fraction

| | Sucrose | Leucrose | Glucose | Fructose | DP2 | DP3 | DP4 | DP5 | DP6 | DP7 | Total |
|---|---|---|---|---|---|---|---|---|---|---|---|
| g/L | 0.0 | 2.5 | 0.0 | 0.7 | 31.5 | 75.9 | 101.8 | 62.1 | 28.9 | 15.3 | 316.7 |
| wt % | 0.0 | 0.8 | 0.0 | 0.2 | 9.9 | 23.9 | 32.1 | 19.8 | 8.5 | 4.8 | 100 |

Primary Screening of Alpha-Glucosidases on Glucan Oligomer Hydrolysis

The activities of eleven different alpha-glucosidases (Example 10), as well as the activities of two benchmark enzymes, oligo-1,6-glucosidase (purchased from Megazyme) and transglucosidase (TG L-2000), were individually evaluated against the purified oligosaccharide fraction prepared above (Table 18). Each alpha-glucosidase (dosed at 1 mg/mL) was incubated in a solution containing oligosaccharide substrates (2.9% dry solids) and 2 mM calcium chloride at pH 5.0 at 60° C. Each reaction was quenched after 24 hours of incubation by adding 50 μL of 0.5 M NaOH.

The oligosaccharide/monosaccharide contents of the quenched reactions were determined as follows. A sample of each reaction was diluted 5-fold in water for HPLC analysis. HPLC separation was done using an Agilent 1200 series HPLC system with an AMINEX HPX-42A column (300 mm×7.8 mm) at 85° C. The sample (10 μL) was applied to the HPLC column and separated with an isocratic gradient of MILLI-Q water as the mobile phase at a flow rate of 0.6 mL/min. Oligosaccharide products were detected using a refractive index detector. The numbers provided in Table 19 below reflect the average of peak area percentages (from duplication of each sample) of each $DP_n$ as a fraction of the total from DP1 to DP7.

TABLE 19

Analysis Glucan Filtrate Oligosaccharides
Following Treatment with Alpha-Glucosidase

| Enzyme | SEQ ID NO | DP7 % | DP6 % | DP5 % | DP4 % | DP3 % | DP2 % | DP1 % |
|---|---|---|---|---|---|---|---|---|
| Oligo-1,6-glucosidase | | 0.0 | 0.6 | 8.7 | 27.9 | 21.9 | 12.2 | 28.7 |
| TG L-2000 | 1 | 0.0 | 0.0 | 0.0 | 0.0 | 0.0 | 3.0 | 97.0 |
| Nfiglu1 | 9 | 0.0 | 0.0 | 0.0 | 0.0 | 0.0 | 1.9 | 98.1 |
| Ncrglu1 | 12 | 0.0 | 0.0 | 0.0 | 2.8 | 1.6 | 7.0 | 88.6 |
| TauSec098 | 15 | 0.0 | 0.0 | 0.0 | 15.3 | 0.0 | 4.5 | 80.2 |
| TauSec099 | 18 | 0.0 | 0.0 | 0.0 | 15.7 | 0.0 | 0.5 | 83.7 |
| BloGlu1 | 20 | 0.0 | 0.0 | 6.7 | 36.3 | 35.6 | 0.0 | 21.3 |
| BloGlu2 | 24 | 0.0 | 0.7 | 8.6 | 31.2 | 34.9 | 14.0 | 10.7 |
| BloGlu3 | 26 | 0.0 | 0.6 | 8.0 | 28.4 | 33.5 | 13.9 | 15.6 |
| BspGlu1 | 30 | 0.0 | 0.5 | 5.2 | 15.4 | 16.2 | 8.2 | 54.5 |
| BthGlu1 | 32 | 0.0 | 0.0 | 13.0 | 12.6 | 2.0 | 1.9 | 70.5 |
| BbrGlu2 | 36 | 0.0 | 0.0 | 21.5 | 30.7 | 24.6 | 0.0 | 23.3 |
| BbrGlu5 | 38 | 0.0 | 0.0 | 8.1 | 23.8 | 12.1 | 15.5 | 40.5 |
| Blank | | 0.0 | 0.0 | 16.2 | 38.6 | 30.4 | 0.0 | 14.8 |

As indicated in Table 19, the oligosaccharide content of the reactions generally shifted toward smaller sized sugars, in comparison with the control reaction ("Blank") in which there was no enzyme. These results indicate that alpha-glucosidase can be used to hydrolyze oligosaccharides comprised within a glucan synthesis reaction and a fraction thereof. Also, given the linkage profile of the oligosaccharides (Examples 3 and 4), and the activity of alpha-glucosidase against various glycosidic linkages in addition to alpha-1,4 linkages (Example 11), it is apparent that alpha-glucosidase can be used to break down oligosaccharides with alpha-1,5 glucosyl-fructose linkages and/or alpha-1,3 and alpha-1,6 glucosyl-glucose linkages. The results provided in Table 19 also suggest that fungal alpha-glucosidases have better hydrolytic activity towards soluble oligosaccharides compared with the bacterial alpha-glucosidases.

Confirmation of Alpha-Glucosidase Hydrolytic Activity Toward Oligosaccharide Products of Glucan Synthesis Reactions Reactions were prepared comprising one or two alpha-glucosidases and a concentrated filtrate obtained from a poly alpha-1,3-glucan synthesis reaction (Table 3). Alpha-glucosidase reactions were dosed with enzyme at 4 ppm, or for blends, each enzyme was used at a 1:1 ratio with a final dosage of 4 ppm. The concentrated filtrate was loaded in each reaction at 10% dry solids. Each reaction further comprised 2 mM calcium chloride at pH 5.0, and was carried out at 60° C. or 65° C. The reactions were quenched by adding 50 μL of 0.5 M NaOH after a 23-hour incubation.

The oligosaccharide/monosaccharide contents of the quenched reactions were determined as follows. A sample of each reaction diluted 25-fold in water for HPLC analysis. HPLC separation was done using an Agilent 1200 series HPLC system with an AMINEX HPX-42A column (300 mm×7.8 mm) at 85° C. The sample (10 μL) was applied to the HPLC column and separated with an isocratic gradient of MILLI-Q water as the mobile phase at a flow rate of 0.6 mL/min. Oligosaccharide products were detected using a refractive index detector. The numbers provided in Table 20 below reflect the average of peak area percentages (from duplication of each sample) of each $DP_n$ as a fraction of the total. The results provided in Table 20 generally confirm the activity of certain alpha-glucosidases as discussed above regarding the results provided in Table 19.

TABLE 20

Analysis Glucan Filtrate Sugars Following Treatment with Alpha-Glucosidase

| Temp. | Enzyme | SEQ ID NO | DP7+ % | DP7 % | DP6 % | DP5 % | DP4 % | DP3 % | DP2 % | Leucrose % | Glucose % | Fructose % |
|---|---|---|---|---|---|---|---|---|---|---|---|---|
| 60° C. | TG L-2000 | 1 | 5.8 | 0.2 | 0.4 | 1.2 | 1.8 | 2.0 | 6.2 | 0.0 | 32.0 | 50.4 |
| | TauSec098 | 15 | 5.4 | 0.0 | 0.1 | 0.2 | 0.3 | 1.9 | 3.4 | 25.4 | 26.2 | 37.1 |
| | TauSec099 | 18 | 6.0 | 0.2 | 0.5 | 1.2 | 1.8 | 2.3 | 6.8 | 0.0 | 30.4 | 50.8 |
| | TauSec098 + TauSec099 | 15, 18 | 6.4 | 0.1 | 0.1 | 0.2 | 0.5 | 2.2 | 8.1 | 0.0 | 32.4 | 50.0 |
| | TauSec098 + TG L-2000 | 15, 1 | 6.3 | 0.1 | 0.1 | 0.2 | 0.4 | 1.8 | 8.1 | 0.0 | 32.9 | 50.1 |
| | Blank | | 5.4 | 0.2 | 0.4 | 1.0 | 1.6 | 2.4 | 2.9 | 25.1 | 22.7 | 38.2 |
| 65° C. | TG L-2000 | 1 | 6.3 | 0.1 | 0.4 | 1.1 | 1.7 | 2.2 | 6.7 | 0.0 | 31.6 | 49.8 |
| | TauSec098 | 15 | 5.8 | 0.1 | 0.2 | 0.2 | 0.3 | 1.6 | 3.3 | 24.5 | 27.2 | 36.7 |
| | TauSec099 | 18 | 6.3 | 0.2 | 0.5 | 1.1 | 1.7 | 2.1 | 6.1 | 0.0 | 32.3 | 49.7 |
| | TauSec098 + TauSec099 | 15, 18 | 6.7 | 0.0 | 0.1 | 0.2 | 0.4 | 1.7 | 7.8 | 0.0 | 34.0 | 49.2 |
| | TauSec098 + TG L-2000 | 15, 1 | 6.8 | 0.1 | 0.2 | 0.2 | 0.4 | 1.8 | 7.6 | 0.0 | 33.9 | 49.1 |
| | Blank | | 6.0 | 0.1 | 0.3 | 0.9 | 1.4 | 2.1 | 3.0 | 24.5 | 23.8 | 37.7 |

Thus, alpha-glucosidase can be used to hydrolyze leucrose and other oligosaccharides present in a fraction (e.g., filtrate) obtained from a glucan synthesis reaction, such as a poly alpha-1,3-glucan synthesis reaction.

Example 13

Isolation of Oligomer/Leucrose Fraction from Gtf-S/MUT3325 Reaction

Sucrose (4.50 kg) was dissolved in distilled deionized water to a final total volume of 9.5 L and the resulting solution was heated with stirring at 80° C. for 5 minutes and then cooled to 47° C. With stirring, 500 grams of a crude extract containing 0.6 g/L of gtf-S enzyme (GTF0459, SEQ ID NO:42) and 15.0 mL of a crude extract containing 10 g/L of mutanase (MUT3325, SEQ ID NO:47) was added with stirring (see General Methods for enzyme preparations). The pH of the resulting mixture was immediately adjusted to between pH 5.5 to pH 6.0 by slowly adding a 1:10 (v/v) dilution of 37 wt % HCl with stirring. The reaction temperature and pH were maintained at 47° C. and pH 5.5-6.0, respectively, until sucrose conversion was >95% per HPLC analysis, after which the reaction mixture was immediately adjusted to pH 7.0 to 7.5 and heated to 90° C. for 20 min, then cooled to 25° C. for immediate filtration to remove particulates and precipitate. The resulting filtrate was held at 5° C. prior to IEX/SEC column chromatography using the following resin and conditions: FINEX CS 11 GC SAC in $Ca^{2+}$ form, column i.d=9.3 cm, resin bed height 1.58 m, T=70° C., flow rate=51 mL/min, linear flow rate=0.44 m/h, feed size=0.6 L=171 g, feed RI-DS=25.1 g/100 g, sample interval=3 min. The column fractions collected between 30 min and 67 min were combined, concentrated by evaporation to 66% dissolved solids and analyzed by HPLC as described in the General Methods. Table 21 indicates the oligosacharide and monosaccharide components of the isolated fraction thus prepared.

Example 14

Isolation of Oligomer/Leucrose Fraction from Gtf-C Reaction

Sucrose (4.50 kg) was dissolved in distilled deionized water to a final total volume of 9.5 L and the resulting solution was heated with stirring at 80° C. for 5 minutes and then cooled to 47° C. With stirring, 500 grams of a crude extract containing 0.41 g/L of gtf-C enzyme (GTF0088BsT1, SEQ ID NO:45) was added with stirring (see General Methods for enzyme preparation). The pH of the resulting mixture was immediately adjusted to between pH 5.5 to pH 6.0 by slowly adding a 1:10 (v/v) dilution of 37 wt % HCl with stirring. The reaction temperature and pH were maintained at 47° C. and pH 5.5-6.0, respectively, until sucrose conversion was >95% per HPLC analysis, after which the reaction mixture was immediately adjusted to pH 7.0 to 7.5 and heated to 90° C. for 20 min, then cooled to 25° C. for immediate filtration to remove particulates and precipitate. The resulting filtrate held at 5° C. prior to IEX/SEC column chromatography using the following resin and conditions: FINEX CS 11 GC SAC in $Ca^{2+}$ form, column i.d=9.3 cm, resin bed height 1.58 m, T=70° C., flow rate=50 mL/min, linear flow rate=0.44 m/h, feed size=0.6 L=171 g, feed RI-DS=25.8 g/100 g, sample interval=3 min. The column fractions collected between 34 min and 72 min were combined, concentrated by evaporation to 67% dissolved solids and analyzed by HPLC as described in the General Methods. Table 22 indicates the oligosacharide and mono-

TABLE 21

Analysis of Oligomer/Leucrose Fraction from gtf-S/MUT3325 Reaction

| DP7+ (% DS) | DP6 (% DS) | DP5 (% DS) | DP4 (% DS) | DP3 (% DS) | DP2 (% DS) | sucrose (% DS) | leucrose (% DS) | glucose (% DS) | fructose (% DS) |
|---|---|---|---|---|---|---|---|---|---|
| 0 | 1.1 | 2.9 | 7.2 | 16.2 | 12.7 | 13.5 | 30.7 | 7.9 | 7.9 |

In this Example, a glucan synthesis reaction was used to produce at least one soluble alpha-glucan product. This soluble product resulted from the concerted action of both a glucosyltransferase (GTF0459, SEQ ID NO:42) and an alpha-glucanohydrolase (MUT3325, SEQ ID NO:47) that were both present in the glucosyltransferase reaction. This Example also demonstrated the preparation of a chromatographic fraction from the glucan synthesis reaction. This fraction was used in Examples 15 and 16 below to test the activity of alpha-glucosidases thereupon.

saccharide components of the isolated fraction thus prepared.

TABLE 22

Analysis of Oligomer/Leucrose Fraction from Gtf-C Reaction

| DP7+ (% DS) | DP6 (% DS) | DP5 (% DS) | DP4 (% DS) | DP3 (% DS) | DP2 (% DS) | sucrose (% DS) | leucrose (% DS) | glucose (% DS) | fructose (% DS) |
|---|---|---|---|---|---|---|---|---|---|
| 1.2 | 0.9 | 1.5 | 2.6 | 5.4 | 13.2 | 2.5 | 59.9 | 6.9 | 5.7 |

In this Example, a glucan synthesis reaction was used to produce at least one soluble alpha-glucan product. This Example also demonstrated the preparation of a chromatographic fraction from a glucan synthesis reaction that produced a soluble alpha-glucan product. This fraction was used in Examples 15 and 16 below to test the activity of alpha-glucosidases thereupon.

Example 15

Primary Screening of Alpha-Glucosidases Using Oligomer/Leucrose Fractions from Gtf-S/MUT3325 and Gtf-C Reactions This Example describes using alpha-glucosidase to hydrolyze leucrose and other oligosaccharides present in chromatographic fractions obtained from glucan synthesis reactions that produced soluble alpha-glucan product. Specifically, study was made on the effect of alpha-glucosidases disclosed in Example 10 on the hydrolysis of leucrose and oligosaccharides in the fractions prepared in Examples 13 and 14.

A total of twelve alpha-glucosidases and two benchmark enzymes (oligo-1,6-glucosidase and TG L-2000 transglucosidase) were screened using oligomer/leucrose fractions from gtf-S/MUT3325 (Example 13) and gtf-C (Example 14) reactions as substrate material. All the enzymes (alpha-glucosidases and benchmark enzymes) were dosed at equal protein concentrations. Each alpha-glucosidase (dosed at 100 ppm) was incubated in a solution containing oligomer/leucrose substrates (10% dry solids) and 2 mM calcium chloride at pH 5.5 at 47° C. Each reaction was quenched after 21 hours of incubation by adding 50 μL of 0.5 M NaOH.

The oligosaccharide/monosaccharide contents of the quenched reactions were determined as follows. A sample from each reaction was centrifuged and supernatant therefrom was diluted 25-fold in water for HPLC analysis (General Methods). The percentages reported in Table 23 reflect the average of peak area percentages (from duplicate analyses of each sample) of each $DP_n$ as a fraction of the total. The results indicate that the fungal alpha-glucosidases had better hydrolytic activity towards glucan oligomers when compared to the bacterial alpha-glucosidases.

As indicated in Table 23, the oligosaccharide content of the reactions generally shifted toward smaller sized sugars, in comparison with the control reactions ("Blank") in which there was no enzyme. These results indicate that alpha-glucosidase can be used to hydrolyze oligosaccharides comprised within a glucan synthesis reaction and a fraction thereof, particularly a chromatographic fraction of a glucan synthesis reaction that produced soluble alpha-glucan product. Also, given the linkage profile of the oligosaccharides (Examples 13 and 14), and the activity of alpha-glucosidase against various glycosidic linkages in addition to alpha-1,4 linkages (Example 11), it is apparent that alpha-glucosidase can be used to break down oligosaccharides with alpha-1,5 glucosyl-fructose linkages and also likely alpha-1,3 and alpha-1,6 glucosyl-glucose linkages. The results provided in Table 23 also suggest that fungal alpha-glucosidases have better hydrolytic activity towards soluble oligosaccharides compared with the bacterial alpha-glucosidases.

Thus, alpha-glucosidase can be used to hydrolyze leucrose and other oligosaccharides present in a fraction (e.g., chromatographic fraction) obtained from a glucan synthesis reaction, such as one that synthesizes a soluble alpha-glucan product.

Example 16

Select Screening of Alpha-Glucosidases Using Oligomer/Leucrose Fractions from Gtf-S/MUT3325 and Gtf-C Reactions This Example is further to Example 15, describing the use of alpha-glucosidase to hydrolyze leucrose and other oligosaccharides present in chromatographic fractions obtained from glucan synthesis reactions that produced soluble alpha-glucan product.

TABLE 23

Sugar Composition Analysis of Primary Screening of Alpha-Glucosidases Using Oligomer/Leucrose Fractions from Gtf-S/MUT3325 and Gtf-C reactions

| Substrate | Enzyme | SEQ ID NO | DP6+ % | DP6 % | DP5 % | DP4 % | DP3 % | DP2 % | Leucrose % | Glucose % | Fructose % |
|---|---|---|---|---|---|---|---|---|---|---|---|
| oligomer/leucrose fraction from Gtf-C reaction | Oligo-1,6-glucosidase | | 8 | 0.1 | 0.2 | 0.4 | 1.1 | 6.8 | 50.7 | 19.6 | 13.1 |
| | TG L-2000 | 1 | 0.7 | 0.1 | 0.2 | 0.5 | 1.1 | 5.7 | 3.8 | 48.6 | 39.3 |
| | Aclglu1 | 6 | 0.8 | 0.1 | 0.2 | 0.4 | 1 | 4.2 | 0 | 51.8 | 41.6 |
| | Nfiglu1 | 9 | 0.7 | 0.1 | 0.2 | 0.4 | 1 | 3.6 | 0 | 52.2 | 41.7 |
| | Ncrglu1 | 12 | 0.7 | 0 | 0.2 | 0.4 | 1 | 3.6 | 4 | 49.9 | 40.2 |
| | BloGlu1 | 20 | 0.1 | 0.3 | 0.4 | 0.7 | 0.6 | 2.9 | 20.6 | 40.7 | 33.6 |
| | BloGlu2 | 24 | 0.8 | 0.2 | 0.6 | 1 | 0.9 | 4 | 30.9 | 34 | 27.5 |
| | BloGlu3 | 26 | 1.1 | 0.3 | 0.5 | 1 | 1 | 4 | 28.8 | 35.4 | 28.1 |
| | BspGlu1 | 30 | 0.9 | 0.1 | 0.1 | 0.1 | 0.3 | 2.5 | 27.9 | 39.5 | 28.7 |
| | BthGlu1 | 32 | 0.8 | 0.2 | 0.5 | 0.7 | 0.7 | 2.9 | 28.6 | 37.1 | 28.4 |
| | BbrGlu2 | 36 | 1.1 | 0.1 | 0.6 | 1.1 | 1.2 | 4.7 | 36.8 | 30.7 | 23.7 |
| | BbrGlu5 | 38 | 1.4 | 0.1 | 0.2 | 0.5 | 0.9 | 4 | 44.6 | 29.1 | 19.4 |
| | TauSec098 | 15 | 3.1 | 0.2 | 0.4 | 0.7 | 1.7 | 4.9 | 59.3 | 17.9 | 11.8 |
| | TauSec099 | 18 | 0.1 | 0 | 0.1 | 0.4 | 1 | 3.3 | 0 | 51.2 | 43.6 |
| | blank | | 1.1 | 0.3 | 0.6 | 1.5 | 2.9 | 7.9 | 65.4 | 11.7 | 8.5 |
| oligomer/leucrose fraction from Gtf-S/MUT3325 reaction | Oligo-1,6-glucosidase | | 10.8 | 0.8 | 2.8 | 7.5 | 15.7 | 0 | 27.8 | 18.9 | 15.6 |
| | TG L-2000 | 1 | 1.4 | 0.8 | 2.7 | 7.3 | 13.2 | 2.3 | 0 | 43.8 | 28.6 |
| | Aclglu1 | 6 | 1.8 | 0.8 | 2.5 | 6.9 | 12.3 | 1.2 | 0 | 45.6 | 29 |
| | Nfiglu1 | 9 | 1.8 | 0.8 | 2.6 | 7 | 13.6 | 0.9 | 0 | 44.4 | 29.1 |
| | Ncrglu1 | 12 | 2.1 | 0.7 | 2.2 | 6.6 | 13.9 | 0 | 0 | 45.2 | 29.3 |
| | BloGlu1 | 20 | 3.5 | 0.7 | 2.4 | 6.5 | 11.7 | 2.1 | 14.8 | 35.6 | 22.6 |
| | BloGlu2 | 24 | 1.5 | 0.8 | 2.6 | 7 | 14.6 | 2.8 | 24.9 | 28 | 17.8 |
| | BloGlu3 | 26 | 2 | 0.8 | 2.5 | 6.9 | 14.1 | 2.9 | 22.4 | 29.9 | 18.6 |
| | BspGlu1 | 30 | 1.7 | 0.6 | 1.5 | 3 | 3.4 | 2 | 18.8 | 48.3 | 20.8 |
| | BthGlu1 | 32 | 1.4 | 0.7 | 2.5 | 6.2 | 12.2 | 2.1 | 16.3 | 36.7 | 21.9 |
| | BbrGlu2 | 36 | 1.5 | 0.8 | 2.6 | 7 | 14.7 | 3 | 25 | 28 | 17.6 |
| | BbrGlu5 | 38 | 2.7 | 0.7 | 2.5 | 5.9 | 17.2 | 0 | 23.9 | 26.6 | 20.5 |
| | TauSec098 | 15 | 2.9 | 0 | 0.1 | 0.3 | 1.1 | 3.6 | 37.1 | 41.8 | 13.1 |
| | TauSec099 | 18 | 1.4 | 0.8 | 2.8 | 7.6 | 16.2 | 0 | 0 | 40.8 | 30.4 |
| | blank | | 1.4 | 0.9 | 3.1 | 8.7 | 19.4 | 0 | 37.1 | 15.6 | 13.8 |

Evaluation of alpha-glucosidases that were most active for hydrolysis of oligomer/leucrose fractions from gtf-S/MUT3325 and gtf-C reactions (Example 15) was performed by analyzing sugar compositions resulting in reactions containing enzymes dosed at equal protein concentrations. Incubations of alpha-glucosidases (dosed at 4 ppm; for blends, the ratio of the two enzymes was 1:1 and total dosage was 4 ppm) and oligomer/leucrose substrate (10% ds) were performed at pH 5.5 in the presence of 2 mM calcium chloride at 60° C. and 65° C., respectively. The reactions were quenched by adding 50 μL of 0.5 M NaOH after 23 hours of incubation.

The oligosaccharide/monosaccharide contents of the quenched reactions were determined as follows. A sample from each reaction was centrifuged and supernatant therefrom was diluted 25-fold in water for HPLC analysis (General Methods). The percentages reported in Table 24 (below) reflect the average of peak area percentages (from duplicate analyses of each sample) of each $DP_n$ as a fraction of the total. The results indicate that TauSec098 was efficacious for hydrolysis of DP2 to DP7 oligomers and TauSec099 outperformed TG L-2000 for leucrose hydrolysis when the incubation was performed at 65° C. The blends of TauSec098 with TauSec099 (or TG L-2000) were effective for hydrolysis of oligomers and leucrose for DP1 production.

Thus, alpha-glucosidase can be used to hydrolyze leucrose and other oligosaccharides present in a fraction (e.g., chromatographic fraction) obtained from a glucan synthesis reaction, such as one that synthesizes a soluble alpha-glucan product.

TABLE 24

Sugar Composition Analysis of Select Screening of Alpha-Glucosidases Using Oligomer/Leucrose Fractions from Gtf-S/MUT3325 and Gtf-C reactions

| Temp | Substrate | Enzyme | SEQ ID NO | DP7+ (%) | DP7 (%) | DP6 (%) | DP5 (%) | DP4 (%) | DP3 (%) | DP2 (%) | Leucrose (%) | Glucose (%) | Fructose (%) |
|---|---|---|---|---|---|---|---|---|---|---|---|---|---|
| 60° C. | oligomer/leucrose fraction from Gtf-C reaction | TG L-2000 | 1 | 2.5 | 0.4 | 0.5 | 0.9 | 1.9 | 5.3 | 22.9 | 18.4 | 21.4 | 25.8 |
| | | TauSec098 | 15 | 5.4 | 0.3 | 0.5 | 1.0 | 1.4 | 2.6 | 6.3 | 71.8 | 0.0 | 10.7 |
| | | TauSec099 | 18 | 2.9 | 0.3 | 0.5 | 1.0 | 1.9 | 4.7 | 23.3 | 21.5 | 19.7 | 24.1 |
| | | TauSec098 + TauSec099 | 15, 18 | 2.7 | 0.3 | 0.5 | 0.9 | 1.4 | 3.3 | 19.9 | 34.9 | 18.2 | 17.8 |
| | | TauSec098 + TG L-2000 | 15, 1 | 2.7 | 0.3 | 0.5 | 0.8 | 1.4 | 4.5 | 23.7 | 27.1 | 18.6 | 20.3 |
| | | Blank | | 5.2 | 0.4 | 0.6 | 1.2 | 1.8 | 3.2 | 8.3 | 70.0 | 0.0 | 9.2 |
| | oligomer/leucrose fraction from Gtf-S/MUT3325 reaction | TG L-2000 | 1 | 4.1 | 0.3 | 1.2 | 3.2 | 8.1 | 17.2 | 13.2 | 0.0 | 27.9 | 24.8 |
| | | TauSec098 | 15 | 3.4 | 0.2 | 0.0 | 0.4 | 1.1 | 3.5 | 12.3 | 32.3 | 35.3 | 11.5 |
| | | TauSec099 | 18 | 4.2 | 0.0 | 1.2 | 3.2 | 8.2 | 17.4 | 15.3 | 0.0 | 25.4 | 25.1 |
| | | TauSec098 + TauSec099 | 15, 18 | 3.5 | 0.2 | 0.4 | 0.9 | 2.3 | 6.2 | 16.8 | 21.2 | 31.7 | 16.9 |
| | | TauSec098 + TG L-2000 | 15, 1 | 3.2 | 0.1 | 0.3 | 0.7 | 2.0 | 6.0 | 26.0 | 17.0 | 29.1 | 15.6 |
| | | Blank | | 4.6 | 0.4 | 1.2 | 3.2 | 7.9 | 17.5 | 15.1 | 36.6 | 0.0 | 13.5 |
| 65° C. | oligomer/leucrose fraction from Gtf-C reaction | TG L-2000 | 1 | 2.5 | 0.3 | 0.5 | 1.0 | 1.8 | 4.9 | 24.9 | 26.0 | 17.4 | 20.8 |
| | | TauSec098 | 15 | 2.8 | 0.4 | 0.5 | 1.0 | 1.4 | 2.6 | 6.6 | 73.6 | 0.0 | 11.1 |
| | | TauSec099 | 18 | 2.2 | 0.3 | 0.4 | 1.0 | 2.0 | 4.9 | 23.2 | 17.4 | 21.6 | 27.0 |
| | | TauSec098 + TauSec099 | 15, 18 | 4.5 | 0.3 | 0.5 | 0.9 | 1.4 | 3.4 | 20.3 | 28.6 | 20.1 | 20.1 |
| | | TauSec098 + TG L-2000 | 15, 1 | 5.1 | 0.3 | 0.5 | 0.9 | 1.2 | 2.9 | 21.1 | 34.4 | 18.0 | 15.7 |
| | | Blank | | 7.0 | 0.4 | 0.7 | 1.3 | 1.8 | 3.2 | 7.9 | 68.4 | 0.0 | 9.4 |
| | oligomer/leucrose fraction from Gtf-S/MUT3325 reaction | TG L-2000 | 1 | 2.9 | 0.2 | 1.1 | 3.1 | 8.1 | 18.0 | 11.7 | 16.5 | 19.3 | 19.0 |
| | | TauSec098 | 15 | 2.6 | 0.0 | 0.1 | 0.3 | 0.9 | 3.3 | 12.0 | 33.1 | 36.6 | 11.1 |
| | | TauSec099 | 18 | 4.4 | 0.0 | 1.2 | 3.1 | 7.8 | 16.1 | 14.4 | 0.0 | 27.4 | 25.5 |
| | | TauSec098 + TauSec099 | 15, 18 | 3.9 | 0.2 | 0.4 | 0.8 | 2.1 | 5.7 | 16.2 | 19.4 | 33.7 | 17.6 |
| | | TauSec098 + TG L-2000 | 15, 1 | 3.7 | 0.2 | 0.3 | 0.7 | 1.8 | 5.0 | 24.9 | 20.5 | 29.4 | 13.6 |
| | | Blank | | 3.1 | 0.6 | 1.1 | 2.5 | 6.3 | 13.6 | 13.0 | 31.1 | 17.0 | 11.8 |

What is claimed is:

1. A method of reducing the amount of a saccharide present in (i) a glucan synthesis reaction, or (ii) a fraction thereof, wherein said method comprises:
    contacting said glucan synthesis reaction or fraction thereof with an alpha-glucosidase enzyme, wherein the amount of said saccharide is reduced in said glucan synthesis reaction or said fraction thereof compared to the amount of said saccharide that was present prior to said contacting,
    wherein said glucan synthesis reaction produces an insoluble alpha-glucan product, wherein at least 97% of the glycosidic linkages of said insoluble alpha-glucan product are alpha-1,3-glycosidic linkages, and
    wherein said saccharide is a byproduct of said glucan synthesis reaction and is (a) leucrose or (b) a disaccharide or oligosaccharide that comprises at least one alpha-1,3 or alpha-1,6 glucosyl-glucose linkage.

2. The method of claim 1, wherein said alpha-glucosidase enzyme is immobilized.

3. The method of claim 1, wherein said saccharide is leucrose.

4. The method of claim 1, wherein said saccharide comprises at least one alpha-1,3 or alpha-1,6 glucosyl-glucose linkage.

5. The method of claim 4, wherein said saccharide comprises at least one alpha-1,3 glucosyl-glucose linkage.

6. The method of claim 1, wherein said alpha-glucosidase enzyme is a transglucosidase or glucoamylase.

7. A method of enriching fructose present in a fraction of a glucan synthesis reaction, comprising:
    (a) producing a fraction of said glucan synthesis reaction according to the method of claim 1, thereby providing a hydrolyzed fraction containing fructose; and
    (b) separating fructose from said hydrolyzed fraction of step (a) to obtain a composition having a higher concentration of fructose compared to the fructose concentration of said fraction of step (a).

8. A fermentation method comprising:
    (a) producing a fraction of said glucan synthesis reaction according to the method of claim 1;
    (b) fermenting said fraction of step (a) with a microbe to yield a product, wherein said fermenting is performed after step (a) or simultaneously with step (a); and
    (c) optionally, isolating said product of step (b);
    wherein the yield of said product of (b) is increased compared to the product yield of fermenting a fraction of said glucan synthesis reaction that has not been contacted with said alpha-glucosidase enzyme.

9. The method of claim 1, wherein at least 98% of glycosidic linkages of said insoluble alpha-glucan product are alpha-1,3-glycosidic linkages.

10. The method of claim 9, wherein at least 99% of glycosidic linkages of said insoluble alpha-glucan product are alpha-1,3-glycosidic linkages.

11. The method of claim 10, wherein at least 100% of glycosidic linkages of said insoluble alpha-glucan product are alpha-1,3-glycosidic linkages.

12. The method of claim 1, wherein said insoluble alpha-glucan product has a number average degree of polymerization of at least 100.

13. The method of claim 1, wherein said method comprises contacting said glucan synthesis reaction with said alpha-glucosidase enzyme.

14. The method of claim 1, wherein said method comprises contacting said fraction with said alpha-glucosidase enzyme.

15. The method of claim 14, wherein said fraction is a filtrate of said glucan synthesis reaction.

16. The method of claim 14, wherein said fraction is a supernatant of the glucan synthesis reaction.

17. The method of claim 1, wherein said alpha-glucosidase enzyme is a *Neosartorya fischeri* alpha-glucosidase enzyme, *Rasamsonia composticola* alpha-glucosidase enzyme, *Bifidobacterium longum* alpha-glucosidase enzyme, *Bifidobacterium pseudolongum* alpha-glucosidase enzyme, *Bifidobacterium thermophilum* alpha glucosidase enzyme, or *Bifidobacterium breve* alpha-glucosidase enzyme.

* * * * *

SEQUENCE LISTING

<160> NUMBER OF SEQ ID NOS: 47

<210> SEQ ID NO 1
<211> LENGTH: 965
<212> TYPE: PRT
<213> ORGANISM: Aspergillus niger

<400> SEQUENCE: 1

Ser Gln Ser Leu Leu Ser Thr Thr Ala Pro Ser Gln Pro Gln Phe Thr
1               5                   10                  15

Ile Pro Ala Ser Ala Asp Val Gly Ala Gln Leu Ile Ala Asn Ile Asp
            20                  25                  30

-continued

Asp Pro Gln Ala Ala Asp Ala Gln Ser Val Cys Pro Gly Tyr Lys Ala
         35                  40                  45

Ser Lys Val Gln His Asn Ser Arg Gly Phe Thr Ala Ser Leu Gln Leu
 50                  55                  60

Ala Gly Arg Pro Cys Asn Val Tyr Gly Thr Asp Val Glu Ser Leu Thr
 65                  70                  75                  80

Leu Ser Val Glu Tyr Gln Asp Ser Asp Arg Leu Asn Ile Gln Ile Leu
                 85                  90                  95

Pro Thr His Val Asp Ser Thr Asn Ala Ser Trp Tyr Phe Leu Ser Glu
                100                 105                 110

Asn Leu Val Pro Arg Pro Lys Ala Ser Leu Asn Ala Ser Val Ser Gln
             115                 120                 125

Ser Asp Leu Phe Val Ser Trp Ser Asn Glu Pro Ser Phe Asn Phe Lys
 130                 135                 140

Val Ile Arg Lys Ala Thr Gly Asp Ala Leu Phe Ser Thr Glu Gly Thr
145                 150                 155                 160

Val Leu Val Tyr Glu Asn Gln Phe Ile Glu Phe Val Thr Ala Leu Pro
                165                 170                 175

Glu Glu Tyr Asn Leu Tyr Gly Leu Gly Glu His Ile Thr Gln Phe Arg
                180                 185                 190

Leu Gln Arg Asn Ala Asn Leu Thr Ile Tyr Pro Ser Asp Asp Gly Thr
             195                 200                 205

Pro Ile Asp Gln Asn Leu Tyr Gly Gln His Pro Phe Tyr Leu Asp Thr
 210                 215                 220

Arg Tyr Tyr Lys Gly Asp Arg Gln Asn Gly Ser Tyr Ile Pro Val Lys
225                 230                 235                 240

Ser Ser Glu Ala Asp Ala Ser Gln Asp Tyr Ile Ser Leu Ser His Gly
                245                 250                 255

Val Phe Leu Arg Asn Ser His Gly Leu Glu Ile Leu Leu Arg Ser Gln
            260                 265                 270

Lys Leu Ile Trp Arg Thr Leu Gly Gly Ile Asp Leu Thr Phe Tyr
             275                 280                 285

Ser Gly Pro Ala Pro Ala Asp Val Thr Arg Gln Tyr Leu Thr Ser Thr
 290                 295                 300

Val Gly Leu Pro Ala Met Gln Gln Tyr Asn Thr Leu Gly Phe His Gln
305                 310                 315                 320

Cys Arg Trp Gly Tyr Asn Asn Trp Ser Asp Leu Ala Asp Val Val Ala
                325                 330                 335

Asn Phe Glu Lys Phe Glu Ile Pro Leu Glu Tyr Ile Trp Thr Asp Ile
                340                 345                 350

Asp Tyr Met His Gly Tyr Arg Asn Phe Asp Asn Asp Gln His Arg Phe
                355                 360                 365

Ser Tyr Ser Glu Gly Asp Glu Phe Leu Ser Lys Leu His Glu Ser Gly
 370                 375                 380

Arg Tyr Tyr Val Pro Ile Val Asp Ala Ala Leu Tyr Ile Pro Asn Pro
385                 390                 395                 400

Glu Asn Ala Ser Asp Ala Tyr Ala Thr Tyr Asp Arg Gly Ala Ala Asp
                405                 410                 415

Asp Val Phe Leu Lys Asn Pro Asp Gly Ser Leu Tyr Ile Gly Ala Val
             420                 425                 430

Trp Pro Gly Tyr Thr Val Phe Pro Asp Trp His His Pro Lys Ala Val
 435                 440                 445

Asp Phe Trp Ala Asn Glu Leu Val Ile Trp Ser Lys Lys Val Ala Phe

```
                450                 455                 460
Asp Gly Val Trp Tyr Asp Met Ser Glu Val Ser Ser Phe Cys Val Gly
465                 470                 475                 480

Ser Cys Gly Thr Gly Asn Leu Thr Leu Asn Pro Ala His Pro Ser Phe
                485                 490                 495

Leu Leu Pro Gly Glu Pro Gly Asp Ile Ile Tyr Asp Tyr Pro Glu Ala
                500                 505                 510

Phe Asn Ile Thr Asn Ala Thr Glu Ala Ala Ser Ala Ser Ala Gly Ala
                515                 520                 525

Ser Ser Gln Ala Ala Ala Thr Ala Thr Thr Thr Ser Thr Ser Val Ser
530                 535                 540

Tyr Leu Arg Thr Thr Pro Thr Pro Gly Val Arg Asn Val Glu His Pro
545                 550                 555                 560

Pro Tyr Val Ile Asn His Asp Gln Glu Gly His Asp Leu Ser Val His
                565                 570                 575

Ala Val Ser Pro Asn Ala Thr His Val Asp Gly Val Glu Glu Tyr Asp
                580                 585                 590

Val His Gly Leu Tyr Gly His Gln Gly Leu Asn Ala Thr Tyr Gln Gly
                595                 600                 605

Leu Leu Glu Val Trp Ser His Lys Arg Arg Pro Phe Ile Ile Gly Arg
                610                 615                 620

Ser Thr Phe Ala Gly Ser Gly Lys Trp Ala Gly His Trp Gly Gly Asp
625                 630                 635                 640

Asn Tyr Ser Lys Trp Trp Ser Met Tyr Tyr Ser Ile Ser Gln Ala Leu
                645                 650                 655

Ser Phe Ser Leu Phe Asp Ile Pro Met Phe Gly Ala Asp Thr Cys Gly
                660                 665                 670

Phe Asn Gly Asn Ser Asp Glu Glu Leu Cys Asn Arg Trp Met Gln Leu
                675                 680                 685

Ser Ala Phe Phe Pro Phe Tyr Arg Asn His Asn Glu Leu Ser Thr Ile
                690                 695                 700

Pro Gln Glu Pro Tyr Arg Trp Ala Ser Val Ile Glu Ala Thr Lys Ser
705                 710                 715                 720

Ala Met Arg Ile Arg Tyr Ala Ile Leu Pro Tyr Phe Tyr Thr Leu Phe
                725                 730                 735

Asp Leu Ala His Thr Thr Gly Ser Thr Val Met Arg Ala Leu Ser Trp
                740                 745                 750

Glu Phe Pro Asn Asp Pro Thr Leu Ala Ala Val Glu Thr Gln Phe Met
                755                 760                 765

Val Gly Pro Ala Ile Met Val Val Pro Val Leu Glu Pro Leu Val Asn
                770                 775                 780

Thr Val Lys Gly Val Phe Pro Gly Val Gly His Gly Glu Val Trp Tyr
785                 790                 795                 800

Asp Trp Tyr Thr Gln Ala Ala Val Asp Ala Lys Pro Gly Val Asn Thr
                805                 810                 815

Thr Ile Ser Ala Pro Leu Gly His Ile Pro Val Tyr Val Arg Gly Gly
                820                 825                 830

Asn Ile Leu Pro Met Gln Glu Pro Ala Leu Thr Thr Arg Glu Ala Arg
                835                 840                 845

Gln Thr Pro Trp Ala Leu Leu Ala Ala Leu Gly Ser Asn Gly Thr Ala
                850                 855                 860

Ser Gly Gln Leu Tyr Leu Asp Asp Gly Glu Ser Ile Tyr Pro Asn Ala
865                 870                 875                 880
```

```
Thr Leu His Val Asp Phe Thr Ala Ser Arg Ser Ser Leu Arg Ser Ser
                885                 890                 895

Ala Gln Gly Arg Trp Lys Glu Arg Asn Pro Leu Ala Asn Val Thr Val
            900                 905                 910

Leu Gly Val Asn Lys Glu Pro Ser Ala Val Thr Leu Asn Gly Gln Ala
        915                 920                 925

Val Phe Pro Gly Ser Val Thr Tyr Asn Ser Thr Ser Gln Val Leu Phe
    930                 935                 940

Val Gly Gly Leu Gln Asn Leu Thr Lys Gly Gly Ala Trp Ala Glu Asn
945                 950                 955                 960

Trp Val Leu Glu Trp
                965

<210> SEQ ID NO 2
<211> LENGTH: 599
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
            85                  90                  95

Ser Leu Ala Asp Gly Ser Gly Leu Gly Glu Pro Lys Phe Glu Leu Thr
        100                 105                 110

Leu Lys Pro Phe Thr Gly Asn Trp Gly Arg Pro Gln Arg Asp Gly Pro
    115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
            165                 170                 175

Leu Trp Glu Glu Val Asn Gly Ser Ser Phe Phe Thr Val Ala Asn Gln
        180                 185                 190

His Arg Ala Leu Val Glu Gly Ala Thr Leu Ala Ala Thr Leu Gly Gln
    195                 200                 205

Ser Gly Ser Ala Tyr Ser Ser Val Ala Pro Gln Val Leu Cys Phe Leu
210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
            245                 250                 255

Ile His Thr Phe Asp Pro Asn Leu Gly Cys Asp Ala Gly Thr Phe Gln
        260                 265                 270

Pro Cys Ser Asp Lys Ala Leu Ser Asn Leu Lys Val Val Val Asp Ser
```

275                 280                 285
Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
            325                 330                 335

Tyr Val Trp Lys Lys Thr Gly Ser Ile Thr Val Thr Ala Thr Ser Leu
        340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
            405                 410                 415

Leu His Leu Thr Trp Ser Tyr Ala Ser Phe Leu Thr Ala Thr Ala Arg
        420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
            485                 490                 495

Val Ala Val Thr Phe His Glu Leu Val Ser Thr Gln Phe Gly Gln Thr
        500                 505                 510

Val Lys Val Ala Gly Asn Ala Ala Leu Gly Asn Trp Ser Thr Ser
            515                 520                 525

Ala Ala Val Ala Leu Asp Ala Val Asn Tyr Ala Asp Asn His Pro Leu
530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
            565                 570                 575

Asn His Thr Tyr Thr Val Pro Ala Val Ala Cys Val Thr Gln Val Val
        580                 585                 590

Lys Glu Asp Thr Trp Gln Ser
        595

<210> SEQ ID NO 3
<211> LENGTH: 1477
<212> TYPE: PRT
<213> ORGANISM: Streptococcus salivarius

<400> SEQUENCE: 3

Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

```
Asn Ala Val Glu Thr Ala Thr Thr Asn Thr Gln Ala Thr Ala Glu
 50                  55                  60

Ala Ala Thr Thr Ala Thr Thr Ala Asp Val Ala Val Ala Ala Val Pro
 65              70                  75                  80

Asn Lys Glu Ala Val Val Thr Thr Asp Ala Pro Ala Val Thr Thr Glu
                 85                  90                  95

Lys Ala Glu Glu Gln Pro Ala Thr Val Lys Ala Glu Val Val Asn Thr
                100                 105                 110

Glu Val Lys Ala Pro Glu Ala Ala Leu Lys Asp Ser Glu Val Glu Ala
                115                 120                 125

Ala Leu Ser Leu Lys Asn Ile Lys Asn Ile Asp Gly Lys Tyr Tyr Tyr
130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
                180                 185                 190

Ile Asn Asn Arg Ala Tyr Asp Ser Ser Glu Ala Ser Phe Glu Leu Ile
                195                 200                 205

Asp Gly Tyr Leu Thr Ala Asp Ser Trp Tyr Arg Pro Ala Ser Ile Ile
210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
                260                 265                 270

Asp Lys Gln Glu Thr Leu Lys Val Ala Ala Lys Asp Ile Gln Ile Lys
                275                 280                 285

Ile Glu Gln Lys Ile Gln Ala Glu Lys Ser Thr Gln Trp Leu Arg Glu
290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Gly Glu Asp His Leu Gln Gly Gly Ala
                325                 330                 335

Leu Leu Tyr Val Asn Asp Ser Arg Thr Pro Trp Ala Asn Ser Asp Tyr
                340                 345                 350

Arg Arg Leu Asn Arg Thr Ala Thr Asn Gln Thr Gly Thr Ile Asp Lys
                355                 360                 365

Ser Ile Leu Asp Glu Gln Ser Asp Pro Asn His Met Gly Gly Phe Asp
370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
                420                 425                 430

Asp Asn Val Asp Ala Asp Met Leu Gln Leu Tyr Thr Asn Tyr Phe Arg
                435                 440                 445

Glu Tyr Tyr Gly Val Asn Lys Ser Glu Ala Asn Ala Leu Ala His Ile
                450                 455                 460

Ser Val Leu Glu Ala Trp Ser Leu Asn Asp Asn His Tyr Asn Asp Lys
```

```
              465                 470                 475                 480
        Thr Asp Gly Ala Ala Leu Ala Met Glu Asn Lys Gln Arg Leu Ala Leu
                        485                 490                 495
        Leu Phe Ser Leu Ala Lys Pro Ile Lys Glu Arg Thr Pro Ala Val Ser
                        500                 505                 510
        Pro Leu Tyr Asn Asn Thr Phe Asn Thr Thr Gln Arg Asp Glu Lys Thr
                        515                 520                 525
        Asp Trp Ile Asn Lys Asp Gly Ser Lys Ala Tyr Asn Glu Asp Gly Thr
                        530                 535                 540
        Val Lys Gln Ser Thr Ile Gly Lys Tyr Asn Glu Lys Tyr Gly Asp Ala
        545                 550                 555                 560
        Ser Gly Asn Tyr Val Phe Ile Arg Ala His Asp Asn Asn Val Gln Asp
                                565                 570                 575
        Ile Ile Ala Glu Ile Ile Lys Lys Glu Ile Asn Pro Lys Ser Asp Gly
                        580                 585                 590
        Phe Thr Ile Thr Asp Ala Glu Met Lys Gln Ala Phe Glu Ile Tyr Asn
                        595                 600                 605
        Lys Asp Met Leu Ser Ser Asp Lys Lys Tyr Thr Leu Asn Asn Ile Pro
                        610                 615                 620
        Ala Ala Tyr Ala Val Met Leu Gln Asn Met Glu Thr Ile Thr Arg Val
        625                 630                 635                 640
        Tyr Tyr Gly Asp Leu Tyr Thr Asp Asp Gly His Tyr Met Glu Thr Lys
                        645                 650                 655
        Ser Pro Tyr Tyr Asp Thr Ile Val Asn Leu Met Lys Ser Arg Ile Lys
                        660                 665                 670
        Tyr Val Ser Gly Gly Gln Ala Gln Arg Ser Tyr Trp Leu Pro Thr Asp
                        675                 680                 685
        Gly Lys Met Asp Asn Ser Asp Val Glu Leu Tyr Arg Thr Asn Glu Val
                        690                 695                 700
        Tyr Thr Ser Val Arg Tyr Gly Lys Asp Ile Met Thr Ala Asn Asp Thr
        705                 710                 715                 720
        Glu Gly Ser Lys Tyr Ser Arg Thr Ser Gly Gln Val Thr Leu Val Ala
                        725                 730                 735
        Asn Asn Pro Lys Leu Asn Leu Asp Gln Ser Ala Lys Leu Asn Val Glu
                        740                 745                 750
        Met Gly Lys Ile His Ala Asn Gln Lys Tyr Arg Ala Leu Ile Val Gly
                        755                 760                 765
        Thr Ala Asp Gly Ile Lys Asn Phe Thr Ser Asp Ala Asp Ala Ile Ala
        770                 775                 780
        Ala Gly Tyr Val Lys Glu Thr Asp Ser Asn Gly Val Leu Thr Phe Gly
        785                 790                 795                 800
        Ala Asn Asp Ile Lys Gly Tyr Glu Thr Phe Asp Met Ser Gly Phe Val
                        805                 810                 815
        Ala Val Trp Val Pro Val Gly Ala Ser Asp Asn Gln Asp Ile Arg Val
                        820                 825                 830
        Ala Pro Ser Thr Glu Ala Lys Lys Glu Gly Glu Leu Thr Leu Lys Ala
                        835                 840                 845
        Thr Glu Ala Tyr Asp Ser Gln Leu Ile Tyr Gly Phe Ser Asn Phe
                        850                 855                 860
        Gln Thr Ile Pro Asp Gly Ser Asp Pro Ser Val Tyr Thr Asn Arg Lys
        865                 870                 875                 880
        Ile Ala Glu Asn Val Asp Leu Phe Lys Ser Trp Gly Val Thr Ser Phe
                                885                 890                 895
```

-continued

Glu Met Ala Pro Gln Phe Val Ser Ala Asp Asp Gly Thr Phe Leu Asp
              900                 905                 910

Ser Val Ile Gln Asn Gly Tyr Ala Phe Ala Asp Arg Tyr Asp Leu Ala
              915                 920                 925

Met Ser Lys Asn Lys Tyr Gly Ser Lys Glu Asp Leu Arg Asp Ala
              930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Glu Val Val Thr Ala Thr
              965                 970                 975

Arg Thr Asp Gly Ala Gly Arg Lys Ile Ala Asp Ala Ile Ile Asp His
              980                 985                 990

Ser Leu Tyr Val Ala Asn Ser Lys Ser Ser Gly Lys Asp Tyr Gln Ala
              995                 1000                1005

Lys Tyr Gly Gly Glu Phe Leu Ala Glu Leu Lys Ala Lys Tyr Pro
         1010                1015                1020

Glu Met Phe Lys Val Asn Met Ile Ser Thr Gly Lys Pro Ile Asp
         1025                1030                1035

Asp Ser Val Lys Leu Lys Gln Trp Lys Ala Glu Tyr Phe Asn Gly
         1040                1045                1050

Thr Asn Val Leu Glu Arg Gly Val Gly Tyr Val Leu Ser Asp Glu
         1055                1060                1065

Ala Thr Gly Lys Tyr Phe Thr Val Thr Lys Glu Gly Asn Phe Ile
         1070                1075                1080

Pro Leu Gln Leu Thr Gly Lys Glu Lys Val Ile Thr Gly Phe Ser
         1085                1090                1095

Ser Asp Gly Lys Gly Ile Thr Tyr Phe Gly Thr Ser Gly Thr Gln
         1100                1105                1110

Ala Lys Ser Ala Phe Val Thr Phe Asn Gly Asn Thr Tyr Tyr Phe
         1115                1120                1125

Asp Ala Arg Gly His Met Val Thr Asn Ser Glu Tyr Ser Pro Asn
         1130                1135                1140

Gly Lys Asp Val Tyr Arg Phe Leu Pro Asn Gly Ile Met Leu Ser
         1145                1150                1155

Asn Ala Phe Tyr Ile Asp Ala Asn Gly Asn Thr Tyr Leu Tyr Asn
         1160                1165                1170

Ser Lys Gly Gln Met Tyr Lys Gly Gly Tyr Thr Lys Phe Asp Val
         1175                1180                1185

Ser Glu Thr Asp Lys Asp Gly Lys Glu Ser Lys Val Val Lys Phe
         1190                1195                1200

Arg Tyr Phe Thr Asn Glu Gly Val Met Ala Lys Gly Val Thr Val
         1205                1210                1215

Ile Asp Gly Phe Thr Gln Tyr Phe Gly Glu Asp Gly Phe Gln Ala
         1220                1225                1230

Lys Asp Lys Leu Val Thr Phe Lys Gly Lys Thr Tyr Tyr Phe Asp
         1235                1240                1245

Ala His Thr Gly Asn Gly Ile Lys Asp Thr Trp Arg Asn Ile Asn
         1250                1255                1260

Gly Lys Trp Tyr Tyr Phe Asp Ala Asn Gly Val Ala Ala Thr Gly
         1265                1270                1275

Ala Gln Val Ile Asn Gly Gln Lys Leu Tyr Phe Asn Glu Asp Gly
         1280                1285                1290

```
Ser Gln Val Lys Gly Gly Val Lys Asn Ala Asp Gly Thr Tyr
    1295                1300                1305

Ser Lys Tyr Lys Glu Gly Phe Gly Glu Leu Val Thr Asn Glu Phe
    1310                1315                1320

Phe Thr Thr Asp Gly Asn Val Trp Tyr Tyr Ala Gly Ala Asn Gly
    1325                1330                1335

Lys Thr Val Thr Gly Ala Gln Val Ile Asn Gly Gln His Leu Tyr
    1340                1345                1350

Phe Asn Ala Asp Gly Ser Gln Val Lys Gly Gly Val Val Lys Asn
    1355                1360                1365

Ala Asp Gly Thr Tyr Ser Lys Tyr Asn Ala Ser Thr Gly Glu Arg
    1370                1375                1380

Leu Thr Asn Glu Phe Phe Thr Thr Gly Asp Asn Trp Tyr Tyr
    1385                1390                1395

Ile Gly Ala Asn Gly Lys Ser Val Thr Gly Glu Val Lys Ile Gly
    1400                1405                1410

Asp Asp Thr Tyr Phe Phe Ala Lys Asp Gly Lys Gln Val Lys Gly
    1415                1420                1425

Gln Thr Val Ser Ala Gly Asn Gly Arg Ile Ser Tyr Tyr Tyr Gly
    1430                1435                1440

Asp Ser Gly Lys Arg Ala Val Ser Thr Trp Ile Glu Ile Gln Pro
    1445                1450                1455

Gly Val Tyr Val Tyr Phe Asp Lys Asn Gly Leu Ala Tyr Pro Pro
    1460                1465                1470

Arg Val Leu Asn
    1475

<210> SEQ ID NO 4
<211> LENGTH: 3147
<212> TYPE: DNA
<213> ORGANISM: Aspergillus clavatus

<400> SEQUENCE: 4
atggccagtc tcgtaggcct tcttgccagt gcttggctcc tcccgtcgac ctacggagcg    60
gcggttcact cgtttgctcc tagtacgacg gcaaccgcag cttactcgca gcatactttg   120
ccttcgtcca ttgacaatgg ggctcagttg attgccaata tcgatgaccc cttggcagtg   180
aatgcgcagt ccgtttgtcc aggctataag gcctcggatg tgcaacagac atcacggggt   240
ttcaccgcca gcctgcagct tgcgggcgag ccgtgcaatg cctatgggat tgacgttgac   300
tcgctgagtc tctcggtgga agttctggcg aaggatcgct tgaatatcca gattgtccct   360
acccatgtgg atagctctaa tgcctcttgg tacattcttc cagaggaccg ggtacccaaa   420
gcgcaagcat ctgccgacgc ctccgtctct caaagtgact cgagatcga gtggtccaat   480 gaccccctcgt tcaatatcaa gatcatccgg aaggcaactg gggatgccct gtttgacaca   540
gccgattcgg tcttggtctt tcagaatcag ttcatcgagt ttgtgtctgc tttgcctgag   600
ggttataatc tttatggatt gggggagcgg atggcccagc tgcggcttct gagaaacgct   660 acccctgacca cctacgcggc agatgtcgga gacccgattg atgagtatgt gttagaatct   720
atgaatcctt gatctcgttg gctcacaatg gaccaatagc aacatctatg acagcatcc   780 tttctaccct cgacacgaga tactatacca agatgccaac ggctcatatt ctcttgtgaa   840
caccgatgat gccgatgcgt ctggagatta tgagtcctc tcccacgacg tgttcctgag   900
aaatgcacat ggacaggagg ttattctgca gtctcgcaac attacatggc ggacaatcgg   960
```

```
tggaagcatc gatttgacct tctactcagg tcccactcag gcagatgtca ccaagagcta   1020
ccagctcacc acgattggct tgcctgcgat gcaacagtac agcgcccttg gtttccatca   1080
atgccgctgg ggttaccgca gctggtctga actcgaggaa gtcgtaaaca ccttttgaaca  1140
gtttgagatt cccctcgaat atatctggtg agctcaattc ttcgtaagaa atatgggct    1200
cttggtgtct aacgcatttt cccaggaccg acattgacta catgcgtggt taccgcgatt   1260
tcgataatga ccaagtccat ttcccctacg atgaaggcga ggagttcctc gacagacttc   1320
acaaatcagg gcgtcactgg gtccccatcg tcgactccgc catctacatc cctaaccctg   1380
acaatgcgtc tgacgcgtaa gtcattgtgt cttatttggc cagcttttca aacagatgct   1440
tacagacgtg acttcaggta cgacacctat gctagaggag ccaaggatga tgttttcatc   1500
aagaaccctg atggcagcct ttatatcgga gctgtatggc ccggattcac agtcttccct   1560
gattggcaca accccaaagc agcggaatgg tggagcaacg agcttgtcac ttggttcgag   1620
aaagtgcagt atgatggcat ttggattgac atgagcgaag tctcctcttt ctgcgttggt   1680
agctgcggga caggaaatct gcacctgaac cccgcccacc caccatttca acttcctggc   1740
gagccgggta acattgagta tacctatccc gaggccttca atgtgaccaa ctccactgaa   1800
gctgcttctg cctctgctgc ctccgccagc cagtcctctg cagctgctgc gacccaaacc   1860
gacgtcagct cgaccacgac ctcgtacttg cggacgacac ccactcctgg tgtccgtgat   1920
atcaactatc ccccttacgt gatcaaccat gttcaatctg ccatgatctc gctgtccat    1980
gccatctctc ccaacgccac ccacgtggat ggtgttcagg agtacgatgt gcacagtctg   2040
tggggtcatc agatcctcaa cgccacttat cagggattgc tcgaggtctt cactgagaag   2100
cgacctttca tcatcggccg atccacctt gccggctcag ggaaatgggc cggtcactgg    2160
ggcggtgata caactctag atggggctct atgttccact ccatttcgca ggctctgtcg    2220
ttctctctct ttggcattcc catgtttggt gttgatactt gtggcttcaa tggcaacacc   2280
gacgaggaac tctgcaaccg atggatgcag ctatcggcct tcttcccatt ctaccgaaac   2340
cacaacactc tcgcggctct ttcgcaggag ccctaccggt gggcctccgt cactgaagca   2400
gccaagactg ccatgagcat tcgatatgcc ctcctgccat acttctacac tctgttccac   2460
caggcgcaca ccaccggttc caccgtcatg cgcgccctcg catgggagtt cccgaacgat   2520
ccctcccttg ccgccgtcga cacccagttc atggtcggac catccattct ggtcacgccc   2580
gtcctcgagc ctcttgccaa aacagtcaag ggcgtcttcc ccggcgtcgg caagggtcag   2640
gtctggtatg actggtacac ccaggccgct gtcgacgcca agcccggcgt caacaccacc   2700
atcccggccc cgctgggcca catccccgtc tatgtccgcg gcggcagcat cctgcccatg   2760
caggagcccg ctcttaccac ccgcgacgcc cgcaagaccc cctggtcgct gcttgccgct   2820
ctggacggta accagaccgc ctccggccag ctgtacctcg acgacgggag cagcgtcaac   2880
ccgtcttcga ccctcaacgt ggagttcgcg gctacccact cgagcatcaa ggtctcggcc   2940
aagggtgatt ggcgcgagaa gaatagtctg gatagcgtga ctgttctcgg tgtcgccaag   3000
gagcctgccc gcgtcacctt caaccgccgc agggtccccc ccgagtcggt ggagtataat   3060
gcgacctccc aggttttgac cgtgagcgga ctgcagaagc tgacgccccg cggggcttgg   3120
gctgaggatt ggattctgaa gtggtaa                                       3147
```

<210> SEQ ID NO 5
<211> LENGTH: 990
<212> TYPE: PRT
<213> ORGANISM: Aspergillus clavatus

<400> SEQUENCE: 5

```
Met Ala Ser Leu Val Gly Leu Leu Ala Ser Ala Trp Leu Leu Pro Ser
1               5                   10                  15

Thr Tyr Gly Ala Ala Val His Ser Phe Ala Pro Ser Thr Thr Ala Thr
            20                  25                  30

Ala Ala Tyr Ser Gln His Thr Leu Pro Ser Ser Ile Asp Asn Gly Ala
        35                  40                  45

Gln Leu Ile Ala Asn Ile Asp Asp Pro Leu Ala Val Asn Ala Gln Ser
    50                  55                  60

Val Cys Pro Gly Tyr Lys Ala Ser Asp Val Gln Gln Thr Ser Arg Gly
65                  70                  75                  80

Phe Thr Ala Ser Leu Gln Leu Ala Gly Glu Pro Cys Asn Ala Tyr Gly
                85                  90                  95

Ile Asp Val Asp Ser Leu Ser Leu Ser Val Glu Val Leu Ala Lys Asp
            100                 105                 110

Arg Leu Asn Ile Gln Ile Val Pro Thr His Val Asp Ser Ser Asn Ala
        115                 120                 125

Ser Trp Tyr Ile Leu Pro Glu Asp Arg Val Pro Lys Ala Gln Ala Ser
    130                 135                 140

Ala Asp Ala Ser Val Ser Gln Ser Asp Phe Glu Ile Glu Trp Ser Asn
145                 150                 155                 160

Asp Pro Ser Phe Asn Ile Lys Ile Ile Arg Lys Ala Thr Gly Asp Ala
                165                 170                 175

Leu Phe Asp Thr Ala Asp Ser Val Leu Val Phe Gln Asn Gln Phe Ile
            180                 185                 190

Glu Phe Val Ser Ala Leu Pro Glu Gly Tyr Asn Leu Tyr Gly Leu Gly
        195                 200                 205

Glu Arg Met Ala Gln Leu Arg Leu Leu Arg Asn Ala Thr Leu Thr Thr
    210                 215                 220

Tyr Ala Ala Asp Val Gly Asp Pro Ile Asp Asp Asn Ile Tyr Gly Gln
225                 230                 235                 240

His Pro Phe Tyr Leu Asp Thr Arg Tyr Tyr Thr Lys Asp Ala Asn Gly
                245                 250                 255

Ser Tyr Ser Leu Val Asn Thr Asp Asp Ala Asp Ala Ser Gly Asp Tyr
            260                 265                 270

Glu Ser Phe Ser His Gly Val Phe Leu Arg Asn Ala His Gly Gln Glu
        275                 280                 285

Val Ile Leu Gln Ser Arg Asn Ile Thr Trp Arg Thr Ile Gly Gly Ser
    290                 295                 300

Ile Asp Leu Thr Phe Tyr Ser Gly Pro Thr Gln Ala Asp Val Thr Lys
305                 310                 315                 320

Ser Tyr Gln Leu Thr Thr Ile Gly Leu Pro Ala Met Gln Gln Tyr Ser
                325                 330                 335

Ala Leu Gly Phe His Gln Cys Arg Trp Gly Tyr Arg Ser Trp Ser Glu
            340                 345                 350

Leu Glu Glu Val Val Asn Thr Phe Glu Gln Phe Glu Ile Pro Leu Glu
        355                 360                 365

Tyr Ile Trp Thr Asp Ile Asp Tyr Met Arg Gly Tyr Arg Asp Phe Asp
    370                 375                 380

Asn Asp Gln Val His Phe Pro Tyr Asp Glu Gly Glu Phe Leu Asp
385                 390                 395                 400

Arg Leu His Lys Ser Gly Arg His Trp Val Pro Ile Val Asp Ser Ala
```

```
            405                 410                 415
Ile Tyr Ile Pro Asn Pro Asp Asn Ala Ser Asp Ala Tyr Asp Thr Tyr
            420                 425                 430

Ala Arg Gly Ala Lys Asp Asp Val Phe Ile Lys Asn Pro Asp Gly Ser
            435                 440                 445

Leu Tyr Ile Gly Ala Val Trp Pro Gly Phe Thr Val Phe Pro Asp Trp
            450                 455                 460

His Asn Pro Lys Ala Ala Glu Trp Trp Ser Asn Glu Leu Val Thr Trp
465                 470                 475                 480

Phe Glu Lys Val Gln Tyr Asp Gly Ile Trp Ile Asp Met Ser Glu Val
                485                 490                 495

Ser Ser Phe Cys Val Gly Ser Cys Gly Thr Gly Asn Leu His Leu Asn
                500                 505                 510

Pro Ala His Pro Pro Phe Gln Leu Pro Gly Glu Pro Gly Asn Ile Glu
            515                 520                 525

Tyr Thr Tyr Pro Glu Ala Phe Asn Val Thr Asn Ser Thr Glu Ala Ala
            530                 535                 540

Ser Ala Ser Ala Ala Ser Ala Ser Gln Ser Ser Ala Ala Ala Ala Thr
545                 550                 555                 560

Gln Thr Asp Val Ser Ser Thr Thr Thr Ser Tyr Leu Arg Thr Thr Pro
                565                 570                 575

Thr Pro Gly Val Arg Asp Ile Asn Tyr Pro Pro Tyr Val Ile Asn His
            580                 585                 590

Val Gln Ser Gly His Asp Leu Ala Val His Ala Ile Ser Pro Asn Ala
            595                 600                 605

Thr His Val Asp Gly Val Gln Glu Tyr Asp Val His Ser Leu Trp Gly
610                 615                 620

His Gln Ile Leu Asn Ala Thr Tyr Gln Gly Leu Leu Glu Val Phe Thr
625                 630                 635                 640

Glu Lys Arg Pro Phe Ile Ile Gly Arg Ser Thr Phe Ala Gly Ser Gly
                645                 650                 655

Lys Trp Ala Gly His Trp Gly Gly Asp Asn Asn Ser Arg Trp Gly Ser
            660                 665                 670

Met Phe His Ser Ile Ser Gln Ala Leu Ser Phe Ser Leu Phe Gly Ile
            675                 680                 685

Pro Met Phe Gly Val Asp Thr Cys Gly Phe Asn Gly Asn Thr Asp Glu
            690                 695                 700

Glu Leu Cys Asn Arg Trp Met Gln Leu Ser Ala Phe Phe Pro Phe Tyr
705                 710                 715                 720

Arg Asn His Asn Thr Leu Ala Ala Leu Ser Gln Glu Pro Tyr Arg Trp
                725                 730                 735

Ala Ser Val Thr Glu Ala Ala Lys Thr Ala Met Ser Ile Arg Tyr Ala
            740                 745                 750

Leu Leu Pro Tyr Phe Tyr Thr Leu Phe His Gln Ala His Thr Thr Gly
            755                 760                 765

Ser Thr Val Met Arg Ala Leu Ala Trp Glu Phe Pro Asn Asp Pro Ser
770                 775                 780

Leu Ala Ala Val Asp Thr Gln Phe Met Val Gly Pro Ser Ile Leu Val
785                 790                 795                 800

Thr Pro Val Leu Glu Pro Leu Ala Lys Thr Val Lys Gly Val Phe Pro
                805                 810                 815

Gly Val Gly Lys Gly Gln Val Trp Tyr Asp Trp Tyr Thr Gln Ala Ala
            820                 825                 830
```

```
Val Asp Ala Lys Pro Gly Val Asn Thr Thr Ile Pro Ala Pro Leu Gly
            835                 840                 845

His Ile Pro Val Tyr Val Arg Gly Gly Ser Ile Leu Pro Met Gln Glu
        850                 855                 860

Pro Ala Leu Thr Thr Arg Asp Ala Arg Lys Thr Pro Trp Ser Leu Leu
865                 870                 875                 880

Ala Ala Leu Asp Gly Asn Gln Thr Ala Ser Gly Gln Leu Tyr Leu Asp
                885                 890                 895

Asp Gly Ser Ser Val Asn Pro Ser Ser Thr Leu Asn Val Glu Phe Ala
            900                 905                 910

Ala Thr His Ser Ser Ile Lys Val Ser Ala Lys Gly Asp Trp Arg Glu
        915                 920                 925

Lys Asn Ser Leu Asp Ser Val Thr Val Leu Gly Val Ala Lys Glu Pro
    930                 935                 940

Ala Arg Val Thr Phe Asn Arg Arg Val Pro Pro Glu Ser Val Glu
945                 950                 955                 960

Tyr Asn Ala Thr Ser Gln Val Leu Thr Val Ser Gly Leu Gln Lys Leu
                965                 970                 975

Thr Pro Arg Gly Ala Trp Ala Glu Asp Trp Ile Leu Lys Trp
            980                 985                 990

<210> SEQ ID NO 6
<211> LENGTH: 971
<212> TYPE: PRT
<213> ORGANISM: Aspergillus clavatus

<400> SEQUENCE: 6

Ala Ala Val His Ser Phe Ala Pro Ser Thr Thr Ala Thr Ala Ala Tyr
1               5                   10                  15

Ser Gln His Thr Leu Pro Ser Ser Ile Asp Asn Gly Ala Gln Leu Ile
                20                  25                  30

Ala Asn Ile Asp Asp Pro Leu Ala Val Asn Ala Gln Ser Val Cys Pro
            35                  40                  45

Gly Tyr Lys Ala Ser Asp Val Gln Gln Thr Ser Arg Gly Phe Thr Ala
50                  55                  60

Ser Leu Gln Leu Ala Gly Glu Pro Cys Asn Ala Tyr Gly Ile Asp Val
65                  70                  75                  80

Asp Ser Leu Ser Leu Ser Val Glu Val Leu Ala Lys Asp Arg Leu Asn
                85                  90                  95

Ile Gln Ile Val Pro Thr His Val Asp Ser Ser Asn Ala Ser Trp Tyr
            100                 105                 110

Ile Leu Pro Glu Asp Arg Val Pro Lys Ala Gln Ala Ser Ala Asp Ala
        115                 120                 125

Ser Val Ser Gln Ser Asp Phe Glu Ile Glu Trp Ser Asn Asp Pro Ser
    130                 135                 140

Phe Asn Ile Lys Ile Arg Lys Ala Thr Gly Asp Ala Leu Phe Asp
145                 150                 155                 160

Thr Ala Asp Ser Val Leu Val Phe Gln Asn Gln Phe Ile Glu Phe Val
                165                 170                 175

Ser Ala Leu Pro Glu Gly Tyr Asn Leu Tyr Gly Leu Gly Glu Arg Met
            180                 185                 190

Ala Gln Leu Arg Leu Leu Arg Asn Ala Thr Leu Thr Thr Tyr Ala Ala
        195                 200                 205

Asp Val Gly Asp Pro Ile Asp Asp Asn Ile Tyr Gly Gln His Pro Phe
```

```
                  210                 215                 220
Tyr Leu Asp Thr Arg Tyr Tyr Thr Lys Asp Ala Asn Gly Ser Tyr Ser
225                 230                 235                 240

Leu Val Asn Thr Asp Asp Ala Asp Ala Ser Gly Asp Tyr Glu Ser Phe
                245                 250                 255

Ser His Gly Val Phe Leu Arg Asn Ala His Gly Gln Glu Val Ile Leu
                260                 265                 270

Gln Ser Arg Asn Ile Thr Trp Arg Thr Ile Gly Gly Ser Ile Asp Leu
                275                 280                 285

Thr Phe Tyr Ser Gly Pro Thr Gln Ala Asp Val Thr Lys Ser Tyr Gln
            290                 295                 300

Leu Thr Thr Ile Gly Leu Pro Ala Met Gln Gln Tyr Ser Ala Leu Gly
305                 310                 315                 320

Phe His Gln Cys Arg Trp Gly Tyr Arg Ser Trp Ser Glu Leu Glu Glu
                325                 330                 335

Val Val Asn Thr Phe Glu Gln Phe Glu Ile Pro Leu Glu Tyr Ile Trp
                340                 345                 350

Thr Asp Ile Asp Tyr Met Arg Gly Tyr Arg Asp Phe Asp Asn Asp Gln
                355                 360                 365

Val His Phe Pro Tyr Asp Glu Gly Glu Phe Leu Asp Arg Leu His
                370                 375                 380

Lys Ser Gly Arg His Trp Val Pro Ile Val Asp Ser Ala Ile Tyr Ile
385                 390                 395                 400

Pro Asn Pro Asp Asn Ala Ser Asp Ala Tyr Asp Thr Tyr Ala Arg Gly
                405                 410                 415

Ala Lys Asp Asp Val Phe Ile Lys Asn Pro Asp Gly Ser Leu Tyr Ile
                420                 425                 430

Gly Ala Val Trp Pro Gly Phe Thr Val Phe Pro Asp Trp His Asn Pro
                435                 440                 445

Lys Ala Ala Glu Trp Trp Ser Asn Glu Leu Val Thr Trp Phe Glu Lys
                450                 455                 460

Val Gln Tyr Asp Gly Ile Trp Ile Asp Met Ser Glu Val Ser Ser Phe
465                 470                 475                 480

Cys Val Gly Ser Cys Gly Thr Gly Asn Leu His Leu Asn Pro Ala His
                485                 490                 495

Pro Pro Phe Gln Leu Pro Gly Glu Pro Gly Asn Ile Glu Tyr Thr Tyr
                500                 505                 510

Pro Glu Ala Phe Asn Val Thr Asn Ser Thr Glu Ala Ala Ser Ala Ser
                515                 520                 525

Ala Ala Ser Ala Ser Gln Ser Ser Ala Ala Ala Thr Gln Thr Asp
            530                 535                 540

Val Ser Thr Thr Thr Ser Tyr Leu Arg Thr Thr Pro Thr Pro Gly
545                 550                 555                 560

Val Arg Asp Ile Asn Tyr Pro Pro Tyr Val Ile Asn His Val Gln Ser
                565                 570                 575

Gly His Asp Leu Ala Val His Ala Ile Ser Pro Asn Ala Thr His Val
            580                 585                 590

Asp Gly Val Gln Glu Tyr Asp Val His Ser Leu Trp Gly His Gln Ile
                595                 600                 605

Leu Asn Ala Thr Tyr Gln Gly Leu Leu Glu Val Phe Thr Glu Lys Arg
                610                 615                 620

Pro Phe Ile Ile Gly Arg Ser Thr Phe Ala Gly Ser Gly Lys Trp Ala
625                 630                 635                 640
```

Gly His Trp Gly Gly Asp Asn Asn Ser Arg Trp Gly Ser Met Phe His
                645                 650                 655

Ser Ile Ser Gln Ala Leu Ser Phe Ser Leu Phe Gly Ile Pro Met Phe
            660                 665                 670

Gly Val Asp Thr Cys Gly Phe Asn Gly Asn Thr Asp Glu Glu Leu Cys
        675                 680                 685

Asn Arg Trp Met Gln Leu Ser Ala Phe Phe Pro Phe Tyr Arg Asn His
    690                 695                 700

Asn Thr Leu Ala Ala Leu Ser Gln Glu Pro Tyr Arg Trp Ala Ser Val
705                 710                 715                 720

Thr Glu Ala Ala Lys Thr Ala Met Ser Ile Arg Tyr Ala Leu Leu Pro
                725                 730                 735

Tyr Phe Tyr Thr Leu Phe His Gln Ala His Thr Thr Gly Ser Thr Val
            740                 745                 750

Met Arg Ala Leu Ala Trp Glu Phe Pro Asn Asp Pro Ser Leu Ala Ala
        755                 760                 765

Val Asp Thr Gln Phe Met Val Gly Pro Ser Ile Leu Val Thr Pro Val
    770                 775                 780

Leu Glu Pro Leu Ala Lys Thr Val Lys Gly Val Phe Pro Gly Val Gly
785                 790                 795                 800

Lys Gly Gln Val Trp Tyr Asp Trp Tyr Thr Gln Ala Ala Val Asp Ala
                805                 810                 815

Lys Pro Gly Val Asn Thr Thr Ile Pro Ala Pro Leu Gly His Ile Pro
            820                 825                 830

Val Tyr Val Arg Gly Gly Ser Ile Leu Pro Met Gln Glu Pro Ala Leu
        835                 840                 845

Thr Thr Arg Asp Ala Arg Lys Thr Pro Trp Ser Leu Leu Ala Ala Leu
    850                 855                 860

Asp Gly Asn Gln Thr Ala Ser Gly Gln Leu Tyr Leu Asp Asp Gly Ser
865                 870                 875                 880

Ser Val Asn Pro Ser Ser Thr Leu Asn Val Glu Phe Ala Ala Thr His
                885                 890                 895

Ser Ser Ile Lys Val Ser Ala Lys Gly Asp Trp Arg Glu Lys Asn Ser
            900                 905                 910

Leu Asp Ser Val Thr Val Leu Gly Val Ala Lys Glu Pro Ala Arg Val
        915                 920                 925

Thr Phe Asn Arg Arg Val Pro Pro Glu Ser Val Glu Tyr Asn Ala
    930                 935                 940

Thr Ser Gln Val Leu Thr Val Ser Gly Leu Gln Lys Leu Thr Pro Arg
945                 950                 955                 960

Gly Ala Trp Ala Glu Asp Trp Ile Leu Lys Trp
                965                 970

<210> SEQ ID NO 7
<211> LENGTH: 3158
<212> TYPE: DNA
<213> ORGANISM: Neosartorya fischeri

<400> SEQUENCE: 7
atggccagcc tcctgggcct cgtcgccagt gcttggctcc tccccacggc ctatggtgca      60
agccattcgc ttgcgcctag cacgtccgca acctcagcac acgcgcaata cactttacca     120
tcttctattg acgttggtgc tcaattggtc gccaacatcg acgatcccct gccgtcgac      180 gcacagtctg tgtgtccggg ctacaaagcc tcaaatgtgc accagacatc ccaaggtttc     240

```
accgccagcc tacagctcgc gggcgaccca tgcaacgtgt acgggacaga cgttgattcg    300
ctgtctctga cagtggatta tctggccaag gaccgcctga acatccaaat tgttcctacc    360
tacgtggatg cctccaacgc ttcttggtac ctcctctcgg aagacttggt gccccgggct    420
caaggctctg gcgtgtccgc ctctcaaagc gactttgatg tgaagtggtc caatgagcct    480
tctttcaacc tcaaggtcat tcgcaaggct actggagacg tcctcttcga taccgagggc    540
tccgtcctgt tctttgagaa ccagtttatc gagtttgtct cttcgttgcc cgagggttac    600
aacctgtacg gtttgggaga gcgcatggcc cagctgcggc tcttgagaaa cgcgaccctg    660
accacctatg cagcggatgt gggagacccg attgataggg atgttgctga ccatggttga    720
aacctaatgt acgaagtcga caagcttaca atcggctctc cagcaacatc tatggacagc    780
atccgttcta tctcgacact agatactata ctaaaggcac gaatgggtct tactcgcttg    840
tcaacacgga cgaggcggac ttgtcggagg attatgaatc attctcccac ggtgtctttc    900
tgagaaactc tcatggtcag gaggttcttc tgcaaccccg caacatcacc tggcgcacaa    960
ttggtggtag catcgatttg actttctact ccggtcccac gcaagcggac gtcacaaaga   1020
gctaccagct ctccaccatt ggacttcctg caatgcagca gtacagcacc cttggattcc   1080
accaatgccg ctggggctac cagaattggt ctcagctcga ggaagtggtc aacaactttg   1140
agcgatttga gattcccctg gaatacatct ggtcagtctg atttctgagt ttatacatat   1200
ttcccagttc cttttattta cattccttcc aggagcgaca tcgattacat gcttggctac   1260
cgtgactttg agaatgatcc cgaacggttc tcctacgatg aaggcgagga atttctgaac   1320
aaacttcaca agtcgggacg acactacgtt cctatcgttg actcggcaat ctatattccc   1380
aaccccgaca atgcatcgga tgcgtaagtc cttgttatct tatcctcctt gttagatggt   1440
caagttctca cgaacgtttg aattccaggt acgagcctta tgctcgcggg gcaaaggatg   1500 acgtttteat caagaaccct gatggcaccc tctacatcgg tgcagtgtgg ccgggcttta   1560
ctgtcttccc agattggctc aaccccaagg catttgacta ctgggccaac gaactcgtca   1620
tctggtcaaa gaaggttgcg ttcgatggca tctggattga tatgagcgaa gtatcctctt   1680
tctgcgttgg cagctgtgga acaggaaagc tacatctgaa cccggttcac ccaccattcc   1740
agcttcccgg tgaacctgga atatcggct acgactaccc cgaggccttc aacgtgacga   1800
actctaccga agcggcctct gcctccgccg cctctgccag tcaggcttcg gctgctgctg   1860
ctacccaaac cgccactacg tcaacatcta catcgtatct gcggacgacg cccacgccgg   1920
gcgtccgtga cgtcaactac cctccatatg tgattaatca tgttcaggag ggtcatgacc   1980
ttgccgttca cgccatttct cccaactcta ctcatgcgga cggcgtccag gaatacgatg   2040
ttcacagtct gtggggccac cagatcctca atgccaccta ctacggactg cgccaggtct   2100
tcactgagaa gcgacccttc atcattggtc ggtctacctt tgctggctcg ggcaagtggg   2160
ccggtcactg gggcggtgat aacaactcca aatgggggtc catgttcctg tccatctcgc   2220
agggtctgtc gttctcgctg ttcggtattc ccatgttcgg cgtggatacc tgcggtttca   2280
acggtaacac cgacgaggag ctctgcagcc ggtggatgca gctgtcggcc ttcttcccct   2340
tctaccgcaa ccacaatgtc cttggggcta tcccccagga gccctaccgt tgggcctctg   2400
tcacccaagc ctccaaggct gccatgaaga tccgctattc catcctacct tacttctaca   2460
ctcttttcca ccaggcccac accactggct ctaccgtcat gcgcgctctc gcctgggagt   2520
tccccacgga cccgtccctc gccgccgtcg acacccagtt catggtcggt ccttccatca   2580
```

```
tggtcgtccc cgtgctcgag cccctcgccg ataccgtcaa gggcgcgttc ccaggcgtcg    2640
gcaaaggcga agtctggtac gactggtaca cccagaccgc cgtagacgcc aaacccggcg    2700
tcaacaccac cattcccgct ccgctgggcc acattcccgt ctatgtccgt ggaggcagca    2760
tcctgcccat gcaggaaccc gccctcacga ccagagacgc ccgtaacact ccctggtcgc    2820
tactcgtcgc tctgagcggc aaccagactg cctcgggctc gctgtatctc gacgacggaa    2880
ccagcctcaa cccgtcccgc actctcgatg tcgacttcca ggctaccgcc tggagcatca    2940
aggtctcggt caagggtacc tgggaggaga agaaccgcct ggataaggtg actgtcctcg    3000
gcgtgggtga agccttcc gctgtgacgt tcaacggccg caacgtccac cctggctcgg      3060
tgcactacaa tgctacctcc aaggtgctgt ctgtgcaggg attgcacagc atgacgcccc    3120
atggcgcctg gctggaaac tgggttctga aatggtag                              3158
```

<210> SEQ ID NO 8
<211> LENGTH: 988
<212> TYPE: PRT
<213> ORGANISM: Neosartorya fischeri

<400> SEQUENCE: 8

```
Met Ala Ser Leu Leu Gly Leu Val Ala Ser Ala Trp Leu Leu Pro Thr
 1               5                  10                  15

Ala Tyr Gly Ala Ser His Ser Leu Ala Pro Ser Thr Ser Ala Thr Ser
            20                  25                  30

Ala His Ala Gln Tyr Thr Leu Pro Ser Ser Ile Asp Val Gly Ala Gln
        35                  40                  45

Leu Val Ala Asn Ile Asp Asp Pro Leu Ala Val Asp Ala Gln Ser Val
    50                  55                  60

Cys Pro Gly Tyr Lys Ala Ser Asn Val His Gln Thr Ser Gln Gly Phe
65                  70                  75                  80

Thr Ala Ser Leu Gln Leu Ala Gly Asp Pro Cys Asn Val Tyr Gly Thr
                85                  90                  95

Asp Val Asp Ser Leu Ser Leu Thr Val Asp Tyr Leu Ala Lys Asp Arg
            100                 105                 110

Leu Asn Ile Gln Ile Val Pro Thr Tyr Val Asp Ala Ser Asn Ala Ser
        115                 120                 125

Trp Tyr Leu Leu Ser Glu Asp Leu Val Pro Arg Ala Gln Gly Ser Gly
    130                 135                 140

Val Ser Ala Ser Gln Ser Asp Phe Asp Val Lys Trp Ser Asn Glu Pro
145                 150                 155                 160

Ser Phe Asn Leu Lys Val Ile Arg Lys Ala Thr Gly Asp Val Leu Phe
                165                 170                 175

Asp Thr Glu Gly Ser Val Leu Val Phe Glu Asn Gln Phe Ile Glu Phe
            180                 185                 190

Val Ser Ser Leu Pro Glu Gly Tyr Asn Leu Tyr Gly Leu Gly Glu Arg
        195                 200                 205

Met Ala Gln Leu Arg Leu Leu Arg Asn Ala Thr Leu Thr Thr Tyr Ala
    210                 215                 220

Ala Asp Val Gly Asp Pro Ile Asp Ser Asn Ile Tyr Gly Gln His Pro
225                 230                 235                 240

Phe Tyr Leu Asp Thr Arg Tyr Tyr Thr Lys Gly Thr Asn Gly Ser Tyr
                245                 250                 255

Ser Leu Val Asn Thr Asp Glu Ala Asp Leu Ser Glu Asp Tyr Glu Ser
            260                 265                 270
```

```
Phe Ser His Gly Val Phe Leu Arg Asn Ser His Gly Gln Glu Val Leu
            275                 280                 285

Leu Gln Pro Arg Asn Ile Thr Trp Arg Thr Ile Gly Gly Ser Ile Asp
    290                 295                 300

Leu Thr Phe Tyr Ser Gly Pro Thr Gln Ala Asp Val Thr Lys Ser Tyr
305                 310                 315                 320

Gln Leu Ser Thr Ile Gly Leu Pro Ala Met Gln Gln Tyr Ser Thr Leu
                325                 330                 335

Gly Phe His Gln Cys Arg Trp Gly Tyr Gln Asn Trp Ser Gln Leu Glu
            340                 345                 350

Glu Val Val Asn Asn Phe Glu Arg Phe Glu Ile Pro Leu Glu Tyr Ile
        355                 360                 365

Trp Ser Asp Ile Asp Tyr Met Leu Gly Tyr Arg Asp Phe Glu Asn Asp
370                 375                 380

Pro Glu Arg Phe Ser Tyr Asp Glu Gly Glu Glu Phe Leu Asn Lys Leu
385                 390                 395                 400

His Lys Ser Gly Arg His Tyr Val Pro Ile Val Asp Ser Ala Ile Tyr
                405                 410                 415

Ile Pro Asn Pro Asp Asn Ala Ser Asp Ala Tyr Glu Pro Tyr Ala Arg
                420                 425                 430

Gly Ala Lys Asp Asp Val Phe Ile Lys Asn Pro Asp Gly Thr Leu Tyr
            435                 440                 445

Ile Gly Ala Val Trp Pro Gly Phe Thr Val Phe Pro Asp Trp Leu Asn
        450                 455                 460

Pro Lys Ala Phe Asp Tyr Trp Ala Asn Glu Leu Val Ile Trp Ser Lys
465                 470                 475                 480

Lys Val Ala Phe Asp Gly Ile Trp Ile Asp Met Ser Glu Val Ser Ser
                485                 490                 495

Phe Cys Val Gly Ser Cys Gly Thr Gly Lys Leu His Leu Asn Pro Val
            500                 505                 510

His Pro Pro Phe Gln Leu Pro Gly Glu Pro Gly Asn Ile Gly Tyr Asp
        515                 520                 525

Tyr Pro Glu Ala Phe Asn Val Thr Asn Ser Thr Glu Ala Ala Ser Ala
530                 535                 540

Ser Ala Ser Ala Ser Gln Ala Ser Ala Ala Ala Thr Gln Thr
545                 550                 555                 560

Ala Thr Thr Ser Thr Ser Thr Ser Tyr Leu Arg Thr Pro Thr Pro
                565                 570                 575

Gly Val Arg Asp Val Asn Tyr Pro Pro Tyr Val Ile Asn His Val Gln
            580                 585                 590

Glu Gly His Asp Leu Ala Val His Ala Ile Ser Pro Asn Ser Thr His
        595                 600                 605

Ala Asp Gly Val Gln Glu Tyr Asp Val His Ser Leu Trp Gly His Gln
610                 615                 620

Ile Leu Asn Ala Thr Tyr Tyr Gly Leu Arg Gln Val Phe Thr Glu Lys
625                 630                 635                 640

Arg Pro Phe Ile Ile Gly Arg Ser Thr Phe Ala Gly Ser Gly Lys Trp
                645                 650                 655

Ala Gly His Trp Gly Gly Asp Asn Asn Ser Lys Trp Gly Ser Met Phe
            660                 665                 670

Leu Ser Ile Ser Gln Gly Leu Ser Phe Ser Leu Phe Gly Ile Pro Met
        675                 680                 685

Phe Gly Val Asp Thr Cys Gly Phe Asn Gly Asn Thr Asp Glu Glu Leu
```

```
        690                 695                 700
Cys Ser Arg Trp Met Gln Leu Ser Ala Phe Phe Pro Phe Tyr Arg Asn
705                 710                 715                 720

His Asn Val Leu Gly Ala Ile Pro Gln Glu Pro Tyr Arg Trp Ala Ser
                725                 730                 735

Val Thr Gln Ala Ser Lys Ala Ala Met Lys Ile Arg Tyr Ser Ile Leu
                740                 745                 750

Pro Tyr Phe Tyr Thr Leu Phe His Gln Ala His Thr Thr Gly Ser Thr
                755                 760                 765

Val Met Arg Ala Leu Ala Trp Glu Phe Pro Thr Asp Pro Ser Leu Ala
                770                 775                 780

Ala Val Asp Thr Gln Phe Met Val Gly Pro Ser Ile Met Val Val Pro
785                 790                 795                 800

Val Leu Glu Pro Leu Ala Asp Thr Val Lys Gly Ala Phe Pro Gly Val
                805                 810                 815

Gly Lys Gly Glu Val Trp Tyr Asp Trp Tyr Thr Gln Thr Ala Val Asp
                820                 825                 830

Ala Lys Pro Gly Val Asn Thr Thr Ile Pro Ala Pro Leu Gly His Ile
                835                 840                 845

Pro Val Tyr Val Arg Gly Gly Ser Ile Leu Pro Met Gln Glu Pro Ala
                850                 855                 860

Leu Thr Thr Arg Asp Ala Arg Asn Thr Pro Trp Ser Leu Leu Val Ala
865                 870                 875                 880

Leu Ser Gly Asn Gln Thr Ala Ser Gly Ser Leu Tyr Leu Asp Asp Gly
                885                 890                 895

Thr Ser Leu Asn Pro Ser Arg Thr Leu Asp Val Asp Phe Gln Ala Thr
                900                 905                 910

Ala Trp Ser Ile Lys Val Ser Val Lys Gly Thr Trp Glu Glu Lys Asn
                915                 920                 925

Arg Leu Asp Lys Val Thr Val Leu Gly Val Gly Glu Lys Pro Ser Ala
                930                 935                 940

Val Thr Phe Asn Gly Arg Asn Val His Pro Gly Ser Val His Tyr Asn
945                 950                 955                 960

Ala Thr Ser Lys Val Leu Ser Val Gln Gly Leu His Ser Met Thr Pro
                965                 970                 975

His Gly Ala Trp Ala Gly Asn Trp Val Leu Lys Trp
                980                 985

<210> SEQ ID NO 9
<211> LENGTH: 969
<212> TYPE: PRT
<213> ORGANISM: Neosartorya fischeri

<400> SEQUENCE: 9

Ala Ser His Ser Leu Ala Pro Ser Thr Ser Ala Thr Ser Ala His Ala
1               5                   10                  15

Gln Tyr Thr Leu Pro Ser Ser Ile Asp Val Gly Ala Gln Leu Val Ala
                20                  25                  30

Asn Ile Asp Asp Pro Leu Ala Val Asp Ala Gln Ser Val Cys Pro Gly
                35                  40                  45

Tyr Lys Ala Ser Asn Val His Gln Thr Ser Gln Gly Phe Thr Ala Ser
            50                  55                  60

Leu Gln Leu Ala Gly Asp Pro Cys Asn Val Tyr Gly Thr Asp Val Asp
65                  70                  75                  80
```

```
Ser Leu Ser Leu Thr Val Asp Tyr Leu Ala Lys Asp Arg Leu Asn Ile
                85                  90                  95

Gln Ile Val Pro Thr Tyr Val Asp Ala Ser Asn Ala Ser Trp Tyr Leu
            100                 105                 110

Leu Ser Glu Asp Leu Val Pro Arg Ala Gln Gly Ser Gly Val Ser Ala
        115                 120                 125

Ser Gln Ser Asp Phe Asp Val Lys Trp Ser Asn Glu Pro Ser Phe Asn
    130                 135                 140

Leu Lys Val Ile Arg Lys Ala Thr Gly Asp Val Leu Phe Asp Thr Glu
145                 150                 155                 160

Gly Ser Val Leu Val Phe Glu Asn Gln Phe Ile Glu Phe Val Ser Ser
                165                 170                 175

Leu Pro Glu Gly Tyr Asn Leu Tyr Gly Leu Gly Glu Arg Met Ala Gln
            180                 185                 190

Leu Arg Leu Leu Arg Asn Ala Thr Leu Thr Thr Tyr Ala Ala Asp Val
        195                 200                 205

Gly Asp Pro Ile Asp Ser Asn Ile Tyr Gly Gln His Pro Phe Tyr Leu
    210                 215                 220

Asp Thr Arg Tyr Tyr Thr Lys Gly Thr Asn Gly Ser Tyr Ser Leu Val
225                 230                 235                 240

Asn Thr Asp Glu Ala Asp Leu Ser Glu Asp Tyr Glu Ser Phe Ser His
                245                 250                 255

Gly Val Phe Leu Arg Asn Ser His Gly Gln Glu Val Leu Leu Gln Pro
            260                 265                 270

Arg Asn Ile Thr Trp Arg Thr Ile Gly Gly Ser Ile Asp Leu Thr Phe
        275                 280                 285

Tyr Ser Gly Pro Thr Gln Ala Asp Val Thr Lys Ser Tyr Gln Leu Ser
    290                 295                 300

Thr Ile Gly Leu Pro Ala Met Gln Gln Tyr Ser Thr Leu Gly Phe His
305                 310                 315                 320

Gln Cys Arg Trp Gly Tyr Gln Asn Trp Ser Gln Leu Glu Glu Val Val
                325                 330                 335

Asn Asn Phe Glu Arg Phe Glu Ile Pro Leu Glu Tyr Ile Trp Ser Asp
            340                 345                 350

Ile Asp Tyr Met Leu Gly Tyr Arg Asp Phe Glu Asn Asp Pro Glu Arg
        355                 360                 365

Phe Ser Tyr Asp Glu Gly Glu Glu Phe Leu Asn Lys Leu His Lys Ser
    370                 375                 380

Gly Arg His Tyr Val Pro Ile Val Asp Ser Ala Ile Tyr Ile Pro Asn
385                 390                 395                 400

Pro Asp Asn Ala Ser Asp Ala Tyr Glu Pro Tyr Ala Arg Gly Ala Lys
                405                 410                 415

Asp Asp Val Phe Ile Lys Asn Pro Asp Gly Thr Leu Tyr Ile Gly Ala
            420                 425                 430

Val Trp Pro Gly Phe Thr Val Phe Pro Asp Trp Leu Asn Pro Lys Ala
        435                 440                 445

Phe Asp Tyr Trp Ala Asn Glu Leu Val Ile Trp Ser Lys Lys Val Ala
    450                 455                 460

Phe Asp Gly Ile Trp Ile Asp Met Ser Glu Val Ser Ser Phe Cys Val
465                 470                 475                 480

Gly Ser Cys Gly Thr Gly Lys Leu His Leu Asn Pro Val His Pro Pro
                485                 490                 495

Phe Gln Leu Pro Gly Glu Pro Gly Asn Ile Gly Tyr Asp Tyr Pro Glu
```

```
            500                 505                 510
Ala Phe Asn Val Thr Asn Ser Thr Glu Ala Ser Ala Ser Ala Ala
            515                 520                 525

Ser Ala Ser Gln Ala Ser Ala Ala Ala Thr Gln Thr Ala Thr Thr
            530                 535                 540

Ser Thr Ser Thr Ser Tyr Leu Arg Thr Thr Pro Thr Pro Gly Val Arg
545                 550                 555                 560

Asp Val Asn Tyr Pro Pro Tyr Val Ile Asn His Val Gln Glu Gly His
                565                 570                 575

Asp Leu Ala Val His Ala Ile Ser Pro Asn Ser Thr His Ala Asp Gly
            580                 585                 590

Val Gln Glu Tyr Asp Val His Ser Leu Trp Gly His Gln Ile Leu Asn
            595                 600                 605

Ala Thr Tyr Tyr Gly Leu Arg Gln Val Phe Thr Glu Lys Arg Pro Phe
            610                 615                 620

Ile Ile Gly Arg Ser Thr Phe Ala Gly Ser Gly Lys Trp Ala Gly His
625                 630                 635                 640

Trp Gly Gly Asp Asn Asn Ser Lys Trp Gly Ser Met Phe Leu Ser Ile
                645                 650                 655

Ser Gln Gly Leu Ser Phe Ser Leu Phe Gly Ile Pro Met Phe Gly Val
            660                 665                 670

Asp Thr Cys Gly Phe Asn Gly Asn Thr Asp Glu Glu Leu Cys Ser Arg
            675                 680                 685

Trp Met Gln Leu Ser Ala Phe Phe Pro Phe Tyr Arg Asn His Asn Val
            690                 695                 700

Leu Gly Ala Ile Pro Gln Glu Pro Tyr Arg Trp Ala Ser Val Thr Gln
705                 710                 715                 720

Ala Ser Lys Ala Ala Met Lys Ile Arg Tyr Ser Ile Leu Pro Tyr Phe
            725                 730                 735

Tyr Thr Leu Phe His Gln Ala His Thr Thr Gly Ser Thr Val Met Arg
            740                 745                 750

Ala Leu Ala Trp Glu Phe Pro Thr Asp Pro Ser Leu Ala Ala Val Asp
            755                 760                 765

Thr Gln Phe Met Val Gly Pro Ser Ile Met Val Pro Val Leu Glu
            770                 775                 780

Pro Leu Ala Asp Thr Val Lys Gly Ala Phe Pro Gly Val Gly Lys Gly
785                 790                 795                 800

Glu Val Trp Tyr Asp Trp Tyr Thr Gln Thr Ala Val Asp Ala Lys Pro
                805                 810                 815

Gly Val Asn Thr Thr Ile Pro Ala Pro Leu Gly His Ile Pro Val Tyr
                820                 825                 830

Val Arg Gly Gly Ser Ile Leu Pro Met Gln Glu Pro Ala Leu Thr Thr
            835                 840                 845

Arg Asp Ala Arg Asn Thr Pro Trp Ser Leu Leu Val Ala Leu Ser Gly
850                 855                 860

Asn Gln Thr Ala Ser Gly Ser Leu Tyr Leu Asp Asp Gly Thr Ser Leu
865                 870                 875                 880

Asn Pro Ser Arg Thr Leu Asp Val Asp Phe Gln Ala Thr Ala Trp Ser
                885                 890                 895

Ile Lys Val Ser Val Lys Gly Thr Trp Glu Glu Lys Asn Arg Leu Asp
            900                 905                 910

Lys Val Thr Val Leu Gly Val Gly Glu Lys Pro Ser Ala Val Thr Phe
            915                 920                 925
```

Asn Gly Arg Asn Val His Pro Gly Ser Val His Tyr Asn Ala Thr Ser
        930                 935                 940

Lys Val Leu Ser Val Gln Gly Leu His Ser Met Thr Pro His Gly Ala
945                 950                 955                 960

Trp Ala Gly Asn Trp Val Leu Lys Trp
            965

<210> SEQ ID NO 10
<211> LENGTH: 3385
<212> TYPE: DNA
<213> ORGANISM: Neurospora crassa

<400> SEQUENCE: 10

| | |
|---|---|
| atggccgtct tcacatcggc ttccttcttt cttcttgcgg ctcttgtccc tcaatggaca | 60 |
| tctgctcaac atgtatctgt ggttgcaacg tcatctggac ctggtgtgtt gagcgggacg | 120 |
| gtggcagggg attcccctat gttcactttc ccagcttcgg ctgacatcgg accaaatgtc | 180 |
| ttaccgaaca ttttcgaccc gcaagcagtt aatgttcaaa gcgtctgtcc aggatataca | 240 |
| gctgctaatg cacaaaagac ggagaaggga ctcacggctg acttgaccct tgctggccct | 300 |
| ccctgcaatg tctatggcaa cgacatcgag cacctgaagc ttaccattga gtttcaggcg | 360 |
| gacaatcgga tcaatgtcca gattcaacct cgctatactg gccccggtaa tgaaacctgg | 420 |
| ttcatacttc ctgaggtgct cgtgccacga ccagaggccg agcctgatgc gaatgccgct | 480 |
| agaagcaagc tggaaatctc gtggtcgaat gagcccacct tctccttcac agtgaagcgt | 540 |
| aaggagactg agatgtgtct tgttcacgac cgagggccgtg tccttgttta tgaggatcag | 600 |
| ttcatcgagt tcggctcctc tttacccgag aattcaacc tgtatggtct cggcgaagtt | 660 |
| atgcatggct ttagactggg gaacaatctg acacgtaagt ctctttactt aacatgaatg | 720 |
| tgcatcgtgg attgcatctg actaacacca tctccaggca cgctgttcgc tgcggatgtg | 780 |
| ggcgacaacc tcgatgccaa catctacggc aaccaccga tctatctcga caccagatac | 840 |
| ttcaccaagg acgagtctgg aaaattaagc tacgtttccg acccagcaga caagaatgcc | 900 |
| aaatatgttt cgtatacaaa cggtgtcttc cttcgaaatg ctcatgcaca ggaagtgctc | 960 |
| cttcgacccg aaggtatcac ctggaggact ctcggcggaa gcatcgattt gtacttcttt | 1020 |
| gagggacctt ttgctcagga tatcatcaag tcttatcagc tcagtaccgt tggtcttcct | 1080 |
| gcaatgcagc agtattggac tcttggctt caccaatgtc gctggggata ctcgaactgg | 1140 |
| actgttgtga aggatgtcgt tgacaatttc cgcaagtttg gcatcccgtt ggagacaatc | 1200 |
| tggagtgagt gaacccaagt ccttcagcat cagaatcttc cccatccatg cttttactga | 1260 |
| cttttttaag ccgacattga ttacatgaag ggctatcgtg actttgaaaa cgaccctgat | 1320 |
| cagttcagct acgaggaagg cgccaggttc ctcgaggagc ttcacaagaa tcaccagcac | 1380 |
| tacgtgccga ttgtcgactc ggccatctat gttccaaatc ctgacaagcc agaagatgat | 1440 |
| tacgaacctt accaccgtgg actcgaagct gatgctttca tcatgaaccc agacggttcg | 1500 |
| ctctatatcg gtgcagtgtg gcctggctac accgtgtttc cggactggat tggtgccgcc | 1560 |
| ctcaacggta caggtaccgt cggctggtgg acggacgagt tgttaggta ctataagaag | 1620 |
| gtcgcttttg atggcatctg gattgacatg agcgaggttg cttctttctg catcggaagc | 1680 |
| tgtggcacgg gcaacctgac gctcaatccg gttcatccac catgggtct tcccggtgag | 1740 |
| ccaggcgctc ttgtgctcga ttaccccgaa ggttttgaaa aaccaacgc gagtgaggca | 1800 |
| tcctctgcaa cgtcggttta caaaacgcag aacccagacc ccacgactac agccagcacc | 1860 |

```
actagcacta cttcttacct caggacgaca ccgactcctg gagtgcgcaa tatcaactat    1920
ccaccatatg tcatcaacaa cttccacggc gacattggta ctcacgccct gagcccaat    1980
ggtacccacc atggcggcac agtcgactat gacttccaca acttgttcgg ccatcagatc    2040
ctccacgcaa cctaccaggc acttctcaaa gtctttgagg gcaagcgtcc ttttatcatc    2100
ggccgcagca cctttgcggg ttctggcaaa tgggccggtc actggggtgg tgataactat    2160
tccctatggg cgtttctgta ctttagcatt ccccaggccc tatccttctc catcttcggt    2220
ttccccatgt tcggcgtaga tacctgcggc ttcaatggca acacggacca cgagctgtgc    2280
tcacgatgga tgcagctcag cgcctttttc ccattctacc gcaaccacaa cgtccgtggc    2340
gccatcagcc aggagcccta cgtgtggagc tctgtgatcg atgcgtccaa gaaggcgatg    2400
aggattcgat acctcctgct cccgtacatg tacacactta tggcccaggc cagcctgtct    2460
ggagatacgg tcatgcgcgc actctcgtgg gagttcccgc aagagccgtg gttggcggat    2520
gcggatcgcc agttcatgtt gggcagcgcg gtgatggtga ccatgtctct tgttcaaggg    2580
gccaatacag tggacggcgt gtttcctgga gttggcgatg ggaccatctg gtatgattgg    2640
tatacataca aggccgccag tgagggtgtt cagcctgggg agaatgtaac gatcgatgca    2700
cctctgggac acattccggt ttttctacgg ggtggccatg tcattccagt gcaagagccg    2760
ggcatgacta cgacggagag cagacaaaat gagtggagtg tcatcgttgc tcttgatggt    2820
gcgggtaagg cgaatggtac gttgtatctg gatgatggtg agagtttgga gccgggtgag    2880
aatgtgaagt gggttgatgt gagtcttctt ccgttctttc tatttttctt ctcttttccg    2940
tgagtgttca gtcggtcgat tgccactcgc tcctctcgcg acaaggtcga aagtgctaac    3000
cgggtttggc tgtttctagt tcacggttga gaagaactca tttcgagtga cacctcaggg    3060
caagtacctt gaccgaaact cactggccaa cgtcacgatc ctgggagtgg ccgaggcacc    3120
tctgggagtg gctattaata gtcatctgct cggatcagct tcttggtcct acgactccga    3180
ggggaagttc ctttcggtaa ccgagctgca ggacaacttc aaggaagggg cgtgggcatc    3240
caactgacg ctgtcgtgga actcggcctc aaactcgggc tcgtctcctg ttcagggagg    3300
cggcggcagg ctcgagttca gcacgcccaa tttgctccat gcagctgctt tcggcatcct    3360
ttttggccgc atgtttgtag tttag                                         3385
```

<210> SEQ ID NO 11
<211> LENGTH: 1044
<212> TYPE: PRT
<213> ORGANISM: Neurospora crassa

<400> SEQUENCE: 11

Met Ala Val Phe Thr Ser Ala Ser Phe Phe Leu Leu Ala Ala Leu Val
1               5                   10                  15

Pro Gln Trp Thr Ser Ala Gln His Val Ser Val Ala Thr Ser Ser
            20                  25                  30

Gly Pro Gly Val Leu Ser Gly Thr Val Ala Gly Asp Ser Pro Met Phe
        35                  40                  45

Thr Phe Pro Ala Ser Ala Asp Ile Gly Pro Asn Val Leu Pro Asn Ile
    50                  55                  60

Phe Asp Pro Gln Ala Val Asn Val Gln Ser Val Cys Pro Gly Tyr Thr
65                  70                  75                  80

Ala Ala Asn Ala Gln Lys Thr Glu Lys Gly Leu Thr Ala Asp Leu Thr
                85                  90                  95

```
Leu Ala Gly Pro Pro Cys Asn Val Tyr Gly Asn Asp Ile Glu His Leu
            100                 105                 110
Lys Leu Thr Ile Glu Phe Gln Ala Asp Asn Arg Ile Asn Val Gln Ile
        115                 120                 125
Gln Pro Arg Tyr Thr Gly Pro Gly Asn Glu Thr Trp Phe Ile Leu Pro
    130                 135                 140
Glu Val Leu Val Pro Arg Pro Glu Ala Glu Pro Asp Ala Asn Ala Ala
145                 150                 155                 160
Arg Ser Lys Leu Glu Ile Ser Trp Ser Asn Glu Pro Thr Phe Ser Phe
                165                 170                 175
Thr Val Lys Arg Lys Glu Thr Gly Asp Val Leu Phe Thr Thr Glu Gly
            180                 185                 190
Arg Val Leu Val Tyr Glu Asp Gln Phe Ile Glu Phe Gly Ser Ser Leu
        195                 200                 205
Pro Glu Asn Tyr Asn Leu Tyr Gly Leu Gly Glu Val Met His Gly Phe
    210                 215                 220
Arg Leu Gly Asn Asn Leu Thr Arg Thr Leu Phe Ala Ala Asp Val Gly
225                 230                 235                 240
Asp Asn Leu Asp Ala Asn Ile Tyr Gly Asn His Pro Ile Tyr Leu Asp
                245                 250                 255
Thr Arg Tyr Phe Thr Lys Asp Glu Ser Gly Lys Leu Ser Tyr Val Ser
            260                 265                 270
Asp Pro Ala Asp Lys Asn Ala Lys Tyr Val Ser Tyr Thr Asn Gly Val
        275                 280                 285
Phe Leu Arg Asn Ala His Ala Gln Glu Val Leu Leu Arg Pro Glu Gly
    290                 295                 300
Ile Thr Trp Arg Thr Leu Gly Gly Ser Ile Asp Leu Tyr Phe Phe Glu
305                 310                 315                 320
Gly Pro Phe Ala Gln Asp Ile Ile Lys Ser Tyr Gln Leu Ser Thr Val
                325                 330                 335
Gly Leu Pro Ala Met Gln Gln Tyr Trp Thr Leu Gly Phe His Gln Cys
            340                 345                 350
Arg Trp Gly Tyr Ser Asn Trp Thr Val Val Lys Asp Val Val Asp Asn
        355                 360                 365
Phe Arg Lys Phe Gly Ile Pro Leu Glu Thr Ile Trp Thr Asp Ile Asp
    370                 375                 380
Tyr Met Lys Gly Tyr Arg Asp Phe Glu Asn Asp Pro Asp Gln Phe Ser
385                 390                 395                 400
Tyr Glu Glu Gly Ala Arg Phe Leu Glu Glu Leu His Lys Asn His Gln
                405                 410                 415
His Tyr Val Pro Ile Val Asp Ser Ala Ile Tyr Val Pro Asn Pro Asp
            420                 425                 430
Lys Pro Glu Asp Asp Tyr Glu Pro Tyr His Arg Gly Leu Glu Ala Asp
        435                 440                 445
Ala Phe Ile Met Asn Pro Asp Gly Ser Leu Tyr Ile Gly Ala Val Trp
    450                 455                 460
Pro Gly Tyr Thr Val Phe Pro Asp Trp Ile Gly Ala Ala Leu Asn Gly
465                 470                 475                 480
Thr Gly Thr Val Gly Trp Trp Asp Glu Phe Val Arg Tyr Tyr Lys
                485                 490                 495
Lys Val Ala Phe Asp Gly Ile Trp Ile Asp Met Ser Glu Val Ala Ser
            500                 505                 510
Phe Cys Ile Gly Ser Cys Gly Thr Gly Asn Leu Thr Leu Asn Pro Val
```

```
                515                 520                 525
His Pro Pro Trp Gly Leu Pro Gly Glu Pro Gly Ala Leu Val Leu Asp
    530                 535                 540

Tyr Pro Glu Gly Phe Glu Lys Thr Asn Ala Ser Glu Ala Ser Ser Ala
545                 550                 555                 560

Thr Ser Val Tyr Lys Thr Gln Asn Pro Asp Pro Thr Thr Thr Ala Ser
                565                 570                 575

Thr Thr Ser Thr Thr Ser Tyr Leu Arg Thr Thr Pro Thr Pro Gly Val
            580                 585                 590

Arg Asn Ile Asn Tyr Pro Pro Tyr Val Ile Asn Asn Phe His Gly Asp
        595                 600                 605

Ile Gly Thr His Ala Leu Ser Pro Asn Gly Thr His His Gly Gly Thr
    610                 615                 620

Val Asp Tyr Asp Phe His Asn Leu Phe Gly His Gln Ile Leu His Ala
625                 630                 635                 640

Thr Tyr Gln Ala Leu Leu Lys Val Phe Glu Gly Lys Arg Pro Phe Ile
                645                 650                 655

Ile Gly Arg Ser Thr Phe Ala Gly Ser Gly Lys Trp Ala Gly His Trp
            660                 665                 670

Gly Gly Asp Asn Tyr Ser Leu Trp Ala Phe Leu Tyr Phe Ser Ile Pro
        675                 680                 685

Gln Ala Leu Ser Phe Ser Ile Phe Gly Phe Pro Met Phe Gly Val Asp
    690                 695                 700

Thr Cys Gly Phe Asn Gly Asn Thr Asp His Glu Leu Cys Ser Arg Trp
705                 710                 715                 720

Met Gln Leu Ser Ala Phe Phe Pro Phe Tyr Arg Asn His Asn Val Arg
                725                 730                 735

Gly Ala Ile Ser Gln Glu Pro Tyr Val Trp Ser Ser Val Ile Asp Ala
            740                 745                 750

Ser Lys Lys Ala Met Arg Ile Arg Tyr Leu Leu Leu Pro Tyr Met Tyr
        755                 760                 765

Thr Leu Met Ala Gln Ala Ser Leu Ser Gly Asp Thr Val Met Arg Ala
    770                 775                 780

Leu Ser Trp Glu Phe Pro Gln Glu Pro Trp Leu Ala Asp Ala Asp Arg
785                 790                 795                 800

Gln Phe Met Leu Gly Ser Ala Val Met Val Thr Pro Cys Leu Val Gln
                805                 810                 815

Gly Ala Asn Thr Val Asp Gly Val Phe Pro Gly Val Gly Asp Gly Thr
            820                 825                 830

Ile Trp Tyr Asp Trp Tyr Thr Tyr Lys Ala Ala Ser Glu Gly Val Gln
        835                 840                 845

Pro Gly Glu Asn Val Thr Ile Asp Ala Pro Leu Gly His Ile Pro Val
    850                 855                 860

Phe Leu Arg Gly Gly His Val Ile Pro Val Gln Glu Pro Gly Met Thr
865                 870                 875                 880

Thr Thr Glu Ser Arg Gln Asn Glu Trp Ser Val Ile Val Ala Leu Asp
                885                 890                 895

Gly Ala Gly Lys Ala Asn Gly Thr Leu Tyr Leu Asp Asp Gly Glu Ser
            900                 905                 910

Leu Glu Pro Gly Glu Asn Val Lys Trp Val Asp Phe Thr Val Glu Lys
        915                 920                 925

Asn Ser Phe Arg Val Thr Pro Gln Gly Lys Tyr Leu Asp Arg Asn Ser
    930                 935                 940
```

```
Leu Ala Asn Val Thr Ile Leu Gly Val Ala Glu Ala Pro Leu Gly Val
945                 950                 955                 960

Ala Ile Asn Ser His Leu Leu Gly Ser Ala Ser Trp Ser Tyr Asp Ser
                965                 970                 975

Glu Gly Lys Phe Leu Ser Val Thr Glu Leu Gln Asp Asn Phe Lys Glu
            980                 985                 990

Gly Ala Trp Ala Ser Asn Trp Thr Leu Ser Trp Asn Ser Ala Ser Asn
        995                 1000                1005

Ser Gly Ser Ser Pro Val Gln Gly Gly Gly Arg Leu Glu Phe
    1010                1015                1020

Ser Thr Pro Asn Leu Leu His Ala Ala Ala Phe Gly Ile Leu Phe
    1025                1030                1035

Gly Arg Met Phe Val Val
    1040

<210> SEQ ID NO 12
<211> LENGTH: 1022
<212> TYPE: PRT
<213> ORGANISM: Neurospora crassa

<400> SEQUENCE: 12

Gln His Val Ser Val Val Ala Thr Ser Ser Gly Pro Gly Val Leu Ser
1               5                   10                  15

Gly Thr Val Ala Gly Asp Ser Pro Met Phe Thr Phe Pro Ala Ser Ala
            20                  25                  30

Asp Ile Gly Pro Asn Val Leu Pro Asn Ile Phe Asp Pro Gln Ala Val
        35                  40                  45

Asn Val Gln Ser Val Cys Pro Gly Tyr Thr Ala Ala Asn Ala Gln Lys
    50                  55                  60

Thr Glu Lys Gly Leu Thr Ala Asp Leu Thr Leu Ala Gly Pro Pro Cys
65                  70                  75                  80

Asn Val Tyr Gly Asn Asp Ile Glu His Leu Lys Leu Thr Ile Glu Phe
                85                  90                  95

Gln Ala Asp Asn Arg Ile Asn Val Gln Ile Gln Pro Arg Tyr Thr Gly
            100                 105                 110

Pro Gly Asn Glu Thr Trp Phe Ile Leu Pro Glu Val Leu Val Pro Arg
        115                 120                 125

Pro Glu Ala Glu Pro Asp Ala Asn Ala Ala Arg Ser Lys Leu Glu Ile
    130                 135                 140

Ser Trp Ser Asn Glu Pro Thr Phe Ser Phe Thr Val Lys Arg Lys Glu
145                 150                 155                 160

Thr Gly Asp Val Leu Phe Thr Thr Glu Gly Arg Val Leu Val Tyr Glu
                165                 170                 175

Asp Gln Phe Ile Glu Phe Gly Ser Ser Leu Pro Glu Asn Tyr Asn Leu
            180                 185                 190

Tyr Gly Leu Gly Glu Val Met His Gly Phe Arg Leu Gly Asn Asn Leu
        195                 200                 205

Thr Arg Thr Leu Phe Ala Ala Asp Val Gly Asp Asn Leu Asp Ala Asn
    210                 215                 220

Ile Tyr Gly Asn His Pro Ile Tyr Leu Asp Thr Arg Tyr Phe Thr Lys
225                 230                 235                 240

Asp Glu Ser Gly Lys Leu Ser Tyr Val Ser Asp Pro Ala Asp Lys Asn
                245                 250                 255

Ala Lys Tyr Val Ser Tyr Thr Asn Gly Val Phe Leu Arg Asn Ala His
```

-continued

```
                260             265             270
Ala Gln Glu Val Leu Leu Arg Pro Glu Gly Ile Thr Trp Arg Thr Leu
            275             280             285
Gly Gly Ser Ile Asp Leu Tyr Phe Phe Glu Gly Pro Phe Ala Gln Asp
        290             295             300
Ile Ile Lys Ser Tyr Gln Leu Ser Thr Val Gly Leu Pro Ala Met Gln
305             310             315             320
Gln Tyr Trp Thr Leu Gly Phe His Gln Cys Arg Trp Gly Tyr Ser Asn
                325             330             335
Trp Thr Val Val Lys Asp Val Val Asp Asn Phe Arg Lys Phe Gly Ile
            340             345             350
Pro Leu Glu Thr Ile Trp Thr Asp Ile Asp Tyr Met Lys Gly Tyr Arg
        355             360             365
Asp Phe Glu Asn Asp Pro Asp Gln Phe Ser Tyr Glu Glu Gly Ala Arg
    370             375             380
Phe Leu Glu Glu Leu His Lys Asn His Gln His Tyr Val Pro Ile Val
385             390             395             400
Asp Ser Ala Ile Tyr Val Pro Asn Pro Asp Lys Pro Glu Asp Asp Tyr
                405             410             415
Glu Pro Tyr His Arg Gly Leu Glu Ala Asp Ala Phe Ile Met Asn Pro
            420             425             430
Asp Gly Ser Leu Tyr Ile Gly Ala Val Trp Pro Gly Tyr Thr Val Phe
        435             440             445
Pro Asp Trp Ile Gly Ala Ala Leu Asn Gly Thr Gly Thr Val Gly Trp
    450             455             460
Trp Thr Asp Glu Phe Val Arg Tyr Tyr Lys Lys Val Ala Phe Asp Gly
465             470             475             480
Ile Trp Ile Asp Met Ser Glu Val Ala Ser Phe Cys Ile Gly Ser Cys
                485             490             495
Gly Thr Gly Asn Leu Thr Leu Asn Pro Val His Pro Pro Trp Gly Leu
            500             505             510
Pro Gly Glu Pro Gly Ala Leu Val Leu Asp Tyr Pro Glu Gly Phe Glu
        515             520             525
Lys Thr Asn Ala Ser Glu Ala Ser Ser Ala Thr Ser Val Tyr Lys Thr
    530             535             540
Gln Asn Pro Asp Pro Thr Thr Ala Ser Thr Thr Ser Thr Thr Ser
545             550             555             560
Tyr Leu Arg Thr Thr Pro Thr Pro Gly Val Arg Asn Ile Asn Tyr Pro
                565             570             575
Pro Tyr Val Ile Asn Asn Phe His Gly Asp Ile Gly Thr His Ala Leu
            580             585             590
Ser Pro Asn Gly Thr His His Gly Gly Thr Val Asp Tyr Asp Phe His
        595             600             605
Asn Leu Phe Gly His Gln Ile Leu His Ala Thr Tyr Gln Ala Leu Leu
    610             615             620
Lys Val Phe Glu Gly Lys Arg Pro Phe Ile Ile Gly Arg Ser Thr Phe
625             630             635             640
Ala Gly Ser Gly Lys Trp Ala Gly His Trp Gly Gly Asp Asn Tyr Ser
                645             650             655
Leu Trp Ala Phe Leu Tyr Phe Ser Ile Pro Gln Ala Leu Ser Phe Ser
            660             665             670
Ile Phe Gly Phe Pro Met Phe Gly Val Asp Thr Cys Gly Phe Asn Gly
        675             680             685
```

```
Asn Thr Asp His Glu Leu Cys Ser Arg Trp Met Gln Leu Ser Ala Phe
    690             695                 700

Phe Pro Phe Tyr Arg Asn His Asn Val Arg Gly Ala Ile Ser Gln Glu
705             710             715                 720

Pro Tyr Val Trp Ser Ser Val Ile Asp Ala Ser Lys Lys Ala Met Arg
            725             730                 735

Ile Arg Tyr Leu Leu Leu Pro Tyr Met Tyr Thr Leu Met Ala Gln Ala
            740             745             750

Ser Leu Ser Gly Asp Thr Val Met Arg Ala Leu Ser Trp Glu Phe Pro
        755             760             765

Gln Glu Pro Trp Leu Ala Asp Ala Asp Arg Gln Phe Met Leu Gly Ser
770             775             780

Ala Val Met Val Thr Pro Cys Leu Val Gln Gly Ala Asn Thr Val Asp
785             790             795             800

Gly Val Phe Pro Gly Val Gly Asp Gly Thr Ile Trp Tyr Asp Trp Tyr
            805             810             815

Thr Tyr Lys Ala Ala Ser Glu Gly Val Gln Pro Gly Glu Asn Val Thr
            820             825             830

Ile Asp Ala Pro Leu Gly His Ile Pro Val Phe Leu Arg Gly Gly His
            835             840             845

Val Ile Pro Val Gln Glu Pro Gly Met Thr Thr Thr Glu Ser Arg Gln
850             855             860

Asn Glu Trp Ser Val Ile Val Ala Leu Asp Gly Ala Gly Lys Ala Asn
865             870             875             880

Gly Thr Leu Tyr Leu Asp Asp Gly Glu Ser Leu Glu Pro Gly Glu Asn
            885             890             895

Val Lys Trp Val Asp Phe Thr Val Glu Lys Asn Ser Phe Arg Val Thr
            900             905             910

Pro Gln Gly Lys Tyr Leu Asp Arg Asn Ser Leu Ala Asn Val Thr Ile
            915             920             925

Leu Gly Val Ala Glu Ala Pro Leu Gly Val Ala Ile Asn Ser His Leu
930             935             940

Leu Gly Ser Ala Ser Trp Ser Tyr Asp Ser Glu Gly Lys Phe Leu Ser
945             950             955             960

Val Thr Glu Leu Gln Asp Asn Phe Lys Glu Gly Ala Trp Ala Ser Asn
            965             970             975

Trp Thr Leu Ser Trp Asn Ser Ala Ser Asn Gly Ser Ser Pro Val
            980             985             990

Gln Gly Gly Gly Arg Leu Glu Phe Ser Thr Pro Asn Leu Leu His
        995             1000            1005

Ala Ala Ala Phe Gly Ile Leu Phe Gly Arg Met Phe Val Val
   1010            1015            1020

<210> SEQ ID NO 13
<211> LENGTH: 3293
<212> TYPE: DNA
<213> ORGANISM: Rasamsonia composticola

<400> SEQUENCE: 13
atgcggccaa cttccctcgt caagcacttg gctgcgacca gcctcctctt tctcgcggcg     60
gatgcagctg ctatcgtccg ccgcaacggc gcctctcctt catgccccgg ctataaagcg    120
agtaacgtga agaccgtcga cggtgaaatc gtcagcgcgg atctcaatct cgcgggtccc    180
gcctgcaatg tgtatggcac ggatctggac gatctgaagc tgcaggttga gtaccaatca    240
```

```
ggtaagtcgc acagcatcgc cgtctgcagc ttatcggcag catgtgatcg gcgcctggac    300
tagggcttag ggcctggggt tagggctgac tgcttgctgc cgttcgatgt gactggaact    360
gtacggttgg ttgacaacga tctgacatct gcagaacaac gcctccatgt gaagatctac    420
gatgccgccg agcaggtcta ccaggtgccc accgcggtgc ttccccggcc cagcagcgcc    480
aacatccccc cggccaagtc ggacctgaag ttctccatga ccaacgaccc cttctccttt    540
accatcaagc gcagatcaaa cggcgaaatc ctcttcgaca cctccggcca tccgctgatc    600
ttcgagtcgc agtatctggg cctccgtacc aagctgccgg actcgcccaa catctacggc    660
ctgggagagc acaccggttc tttccgcctg cccaccaaga attacacccg cacgctgtgg    720
tcgcgcgatg cgtacggtac gcccaaagac accaacctgt acggcaacca cccggtgtac    780
ttcgactacc gcggcagcaa cggcacccat ggcgtgttcc tgctgaacag caacggcatg    840
gacgtcgata tcgacgtcga ctcggacgga cagtacctgc agtacaacac cctgggggc    900 gtgctggact tctacttcct cagcgggccg gatcccaagg ccgtcgcgac gcagtatgcc    960
gagacggtcg gaaaaccggt catgatgccc tactgggat tcggcttcca caactgcaga   1020
tatggatacc aggacatcta tgaggttgct gagatcattg ccaactacag tgccgcaaac   1080
attccgcttg agacccaatg gactgatatc ggtatgcttt ccatcccggt gccgtggttt   1140
ttgcttctca gcgtggctga ctgttgcaga ctatatggat ctgaggaaag tgtttacgct   1200 ggaccctat cgctatccat gaagctcgt ccaagaggtt gtctcttatc tccacaagca    1260
caaccagcac tacatcatga tggtggaccc tgcagtggca taccagaact attcagcgtt   1320
caacaacggc gtcgctgccg acgctttcct gaagttctcg aatggctcca tctaccaggg   1380
tgtcgtctgg ccgggggcga cggcgttccc ggactggttc gcaccccaga cacaggagtt   1440
ttggaatagc gagttctcga ccttctttga ccccgcccac ggcgtcgaca tcgatgccct   1500
ttggatcgac atgaacgagg cgtccaactt ctgcgacttt ccctgctcga accccgccgc   1560
gtatgcggca gccaacggcg atccgcccac gcctccgccg gtccgcttga gcccccgag   1620 gccgattcct ggatttggcc ctgacttcca gccgacgtgt gtcgccacgg tgtcgttcga   1680
ttgcgatgcg cagacctact ttggcgagaa catcctcatc ctgggtaact cgacgacact   1740
gggagccggc gacgttcaca tggcgccagt catgagcgcg aacaactacc cgatctggca   1800
gctgaccgtc cagatgccgc cgaatgggac gttctcgtac cagtacgttc gcaaggaatc   1860
ggacggcagt tacatctacg aacagacgaa tcgcacggtc acgacgggcg actgcaccag   1920
cggcacgctt aaggtgtccg acaccatcac caccagctct ggaccgcaca agagatccga   1980
attacggccg ctggtgcgct cgccgttccc ggcggaggac ctgaccaggc gccagtctgg   2040
atcgatgttg ggcctgccca acaggaacct gctgaatccg ccatacacca tccacaatgc   2100
ggctggcaac ctgagtgaga agaccatcaa caccgacctg atccatgcgg gcggatatgc   2160
cgagtacgac acgcacaact gtacggcac gatgatgagc gcgaccagca gggaggcgat   2220
gctgaaccgc agaccagcag tcaggccact tgtgtaagtc atccatcgtc cttaagccag   2280
acacagcatg ttaggggcta acgggcagta gcattacccg gtcgaccttc gctggagccg   2340
gccgacaggt cggccactgg ctcggcgaca atttcgccga ttgggaccac taccggtgga   2400
cgatcgccga gctgcaggaa ttcgcggcgc tgttccagat cccgatggtc ggcagcgaca   2460
tctgcgggta cgacggcaac acgacggaca acctgtgctc cgcgctgggtc ttcctcggcg   2520 ccttctcgcc cttcttccgc gaccactcgg acaaccagtc gccgccgcac gagctgtacc   2580
```

-continued

```
gcactccgca gatcgcggcg gccgcgcgcg ccgccatcga catccgctac cgtctgctcg    2640
actacgcgta cacggtgctg tggacgcaga cccagaccgg cgcgccgatg ctcaacccca    2700
tgttcttcga gtacccggcc gacagcaaca ccgccgacct gcagtaccag ttcttctggg    2760
gcgacagcat catggtcgcg cccgtgaccg acaacgactc gaccaccgtc aacgtctact    2820
tcccgaagga ccagttctac gacttctaca ccggcgcacc tgtgtccggg gagggcaata    2880
ccgtcaccct gaccgacgtc ggcttcgaca ccatcccgct gtacttcaag ggcgggagca    2940
tcgtgcccat gcgcgtgcgc tcggcgaaca cgacggcgga gctgcggcag caggacttcg    3000
tcgtcgtcat cgccccggac agccacggcg acgcgacggg ccagctgtac ctcgacgacg    3060
gcgagagcat caaccagccg cacaccagcg agatccagtt ctcgtaccgc ggaggccatt    3120
tcagcatgac aggcaagttt gactatgatc ccggcaacgt ggtcatcagc cagatcacgc    3180
tgctgggtgc ggacggcgcc ggtaaagggg gttcgtataa cagcaccacc aaggtggcga    3240
cctacaaagt caacgcgaag ttgacgggta aattcgaagc cagcttacac taa          3293
```

<210> SEQ ID NO 14
<211> LENGTH: 1035
<212> TYPE: PRT
<213> ORGANISM: Rasamsonia composticola

<400> SEQUENCE: 14

```
Met Arg Pro Thr Ser Leu Val Lys His Leu Ala Thr Ser Leu Leu
 1               5                  10                  15

Phe Leu Ala Ala Asp Ala Ala Ile Val Arg Arg Asn Gly Ala Ser
                20                  25                  30

Pro Ser Cys Pro Gly Tyr Lys Ala Ser Asn Val Lys Thr Val Asp Gly
            35                  40                  45

Glu Ile Val Ser Ala Asp Leu Asn Leu Ala Gly Pro Ala Cys Asn Val
        50                  55                  60

Tyr Gly Thr Asp Leu Asp Asp Leu Lys Leu Gln Val Glu Tyr Gln Ser
65                  70                  75                  80

Gly Pro Gly Val Arg Ala Asp Cys Leu Leu Pro Phe Asp Val Thr Gly
                85                  90                  95

Thr Val Arg Leu Val Asp Asn Asp Leu Thr Ser Ala Glu Gln Arg Leu
            100                 105                 110

His Val Lys Ile Tyr Asp Ala Ala Glu Gln Val Tyr Gln Val Pro Thr
        115                 120                 125

Ala Val Leu Pro Arg Pro Ser Ser Ala Asn Ile Pro Pro Ala Lys Ser
    130                 135                 140

Asp Leu Lys Phe Ser Met Thr Asn Asp Pro Phe Ser Phe Thr Ile Lys
145                 150                 155                 160

Arg Arg Ser Asn Gly Glu Ile Leu Phe Asp Thr Ser Gly His Pro Leu
                165                 170                 175

Ile Phe Glu Ser Gln Tyr Leu Gly Leu Arg Thr Lys Leu Pro Asp Ser
            180                 185                 190

Pro Asn Ile Tyr Gly Leu Gly Glu His Thr Gly Ser Phe Arg Leu Pro
        195                 200                 205

Thr Lys Asn Tyr Thr Arg Thr Leu Trp Ser Arg Asp Ala Tyr Gly Thr
    210                 215                 220

Pro Lys Asp Thr Asn Leu Tyr Gly Asn His Pro Val Tyr Phe Asp Tyr
225                 230                 235                 240

Arg Gly Ser Asn Gly Thr His Gly Val Phe Leu Leu Asn Ser Asn Gly
                245                 250                 255
```

```
Met Asp Val Asp Ile Asp Val Asp Ser Asp Gly Gln Tyr Leu Gln Tyr
            260                 265                 270

Asn Thr Leu Gly Gly Val Leu Asp Phe Tyr Phe Leu Ser Gly Pro Asp
            275                 280                 285

Pro Lys Ala Val Ala Thr Gln Tyr Ala Glu Thr Val Gly Lys Pro Val
            290                 295                 300

Met Met Pro Tyr Trp Gly Phe Gly Phe His Asn Cys Arg Tyr Gly Tyr
305                 310                 315                 320

Gln Asp Ile Tyr Glu Val Ala Glu Ile Ile Ala Asn Tyr Ser Ala Ala
                325                 330                 335

Asn Ile Pro Leu Glu Thr Gln Trp Thr Asp Ile Asp Tyr Met Asp Leu
            340                 345                 350

Arg Lys Val Phe Thr Leu Asp Pro Tyr Arg Tyr Pro Leu Lys Leu Val
            355                 360                 365

Gln Glu Val Val Ser Tyr Leu His Lys His Asn Gln His Tyr Ile Met
            370                 375                 380

Met Val Asp Pro Ala Val Ala Tyr Gln Asn Tyr Ser Ala Phe Asn Asn
385                 390                 395                 400

Gly Val Ala Ala Asp Ala Phe Leu Lys Phe Ser Asn Gly Ser Ile Tyr
                405                 410                 415

Gln Gly Val Val Trp Pro Gly Pro Thr Ala Phe Pro Asp Trp Phe Ala
            420                 425                 430

Pro Gln Thr Gln Glu Phe Trp Asn Ser Glu Phe Ser Thr Phe Phe Asp
            435                 440                 445

Pro Ala His Gly Val Asp Ile Asp Ala Leu Trp Ile Asp Met Asn Glu
            450                 455                 460

Ala Ser Asn Phe Cys Asp Phe Pro Cys Ser Asn Pro Ala Ala Tyr Ala
465                 470                 475                 480

Ala Ala Asn Gly Asp Pro Pro Thr Pro Pro Val Arg Leu Ser Pro
                485                 490                 495

Pro Arg Pro Ile Pro Gly Phe Gly Pro Asp Phe Gln Pro Thr Cys Val
            500                 505                 510

Ala Thr Val Ser Phe Asp Cys Asp Ala Gln Thr Tyr Phe Gly Glu Asn
            515                 520                 525

Ile Leu Ile Leu Gly Asn Ser Thr Thr Leu Gly Ala Gly Asp Val His
            530                 535                 540

Met Ala Pro Val Met Ser Ala Asn Asn Tyr Pro Ile Trp Gln Leu Thr
545                 550                 555                 560

Val Gln Met Pro Pro Asn Gly Thr Phe Ser Tyr Gln Tyr Val Arg Lys
                565                 570                 575

Glu Ser Asp Gly Ser Tyr Ile Tyr Glu Gln Thr Asn Arg Thr Val Thr
            580                 585                 590

Thr Gly Asp Cys Thr Ser Gly Thr Leu Lys Val Ser Asp Thr Ile Thr
            595                 600                 605

Thr Ser Ser Gly Pro His Lys Arg Ser Glu Leu Arg Pro Leu Val Arg
            610                 615                 620

Ser Pro Phe Pro Ala Glu Asp Leu Thr Arg Arg Gln Ser Gly Ser Met
625                 630                 635                 640

Leu Gly Leu Pro Asn Arg Asn Leu Leu Asn Pro Pro Tyr Thr Ile His
                645                 650                 655

Asn Ala Ala Gly Asn Leu Ser Glu Lys Thr Ile Asn Thr Asp Leu Ile
            660                 665                 670
```

-continued

His Ala Gly Gly Tyr Ala Glu Tyr Asp Thr His Asn Leu Tyr Gly Thr
            675                 680                 685

Met Met Ser Ala Thr Ser Arg Glu Ala Met Leu Asn Arg Arg Pro Ala
690                 695                 700

Val Arg Pro Leu Val Ile Thr Arg Ser Thr Phe Ala Gly Ala Gly Arg
705                 710                 715                 720

Gln Val Gly His Trp Leu Gly Asp Asn Phe Ala Asp Trp Asp His Tyr
            725                 730                 735

Arg Trp Thr Ile Ala Glu Leu Gln Glu Phe Ala Ala Leu Phe Gln Ile
            740                 745                 750

Pro Met Val Gly Ser Asp Ile Cys Gly Tyr Asp Gly Asn Thr Thr Asp
            755                 760                 765

Asn Leu Cys Ser Arg Trp Val Phe Leu Gly Ala Phe Ser Pro Phe Phe
770                 775                 780

Arg Asp His Ser Asp Asn Gln Ser Pro Pro His Glu Leu Tyr Arg Thr
785                 790                 795                 800

Pro Gln Ile Ala Ala Ala Arg Ala Ala Ile Asp Ile Arg Tyr Arg
            805                 810                 815

Leu Leu Asp Tyr Ala Tyr Thr Val Leu Trp Thr Gln Thr Gln Thr Gly
            820                 825                 830

Ala Pro Met Leu Asn Pro Met Phe Phe Glu Tyr Pro Ala Asp Ser Asn
            835                 840                 845

Thr Ala Asp Leu Gln Tyr Gln Phe Phe Trp Gly Asp Ser Ile Met Val
            850                 855                 860

Ala Pro Val Thr Asp Asn Asp Ser Thr Thr Val Asn Val Tyr Phe Pro
865                 870                 875                 880

Lys Asp Gln Phe Tyr Asp Phe Tyr Thr Gly Ala Pro Val Ser Gly Glu
                885                 890                 895

Gly Asn Thr Val Thr Leu Thr Asp Val Gly Phe Asp Thr Ile Pro Leu
            900                 905                 910

Tyr Phe Lys Gly Gly Ser Ile Val Pro Met Arg Val Arg Ser Ala Asn
            915                 920                 925

Thr Thr Ala Glu Leu Arg Gln Gln Asp Phe Val Val Ile Ala Pro
930                 935                 940

Asp Ser His Gly Asp Ala Thr Gly Gln Leu Tyr Leu Asp Asp Gly Glu
945                 950                 955                 960

Ser Ile Asn Gln Pro His Thr Ser Glu Ile Gln Phe Ser Tyr Arg Gly
                965                 970                 975

Gly His Phe Ser Met Thr Gly Lys Phe Asp Tyr Asp Pro Gly Asn Val
            980                 985                 990

Val Ile Ser Gln Ile Thr Leu Leu Gly Ala Asp Gly Ala Gly Lys Gly
            995                 1000                1005

Gly Ser Tyr Asn Ser Thr Thr Lys Val Ala Thr Tyr Lys Val Asn
    1010                1015                1020

Ala Lys Leu Thr Gly Lys Phe Glu Ala Ser Leu His
    1025                1030                1035

<210> SEQ ID NO 15
<211> LENGTH: 1013
<212> TYPE: PRT
<213> ORGANISM: Rasamsonia composticola

<400> SEQUENCE: 15

Ala Ala Ile Val Arg Arg Asn Gly Ala Ser Pro Ser Cys Pro Gly Tyr
1               5                   10                  15

```
Lys Ala Ser Asn Val Lys Thr Val Asp Gly Glu Ile Val Ser Ala Asp
             20                  25                  30

Leu Asn Leu Ala Gly Pro Ala Cys Asn Val Tyr Gly Thr Asp Leu Asp
         35                  40                  45

Asp Leu Lys Leu Gln Val Glu Tyr Gln Ser Gly Pro Gly Val Arg Ala
 50                  55                  60

Asp Cys Leu Leu Pro Phe Asp Val Thr Gly Thr Val Arg Leu Val Asp
 65                  70                  75                  80

Asn Asp Leu Thr Ser Ala Glu Gln Arg Leu His Val Lys Ile Tyr Asp
             85                  90                  95

Ala Ala Glu Gln Val Tyr Gln Val Pro Thr Ala Val Leu Pro Arg Pro
            100                 105                 110

Ser Ser Ala Asn Ile Pro Pro Ala Lys Ser Asp Leu Lys Phe Ser Met
            115                 120                 125

Thr Asn Asp Pro Phe Ser Phe Thr Ile Lys Arg Arg Ser Asn Gly Glu
        130                 135                 140

Ile Leu Phe Asp Thr Ser Gly His Pro Leu Ile Phe Glu Ser Gln Tyr
145                 150                 155                 160

Leu Gly Leu Arg Thr Lys Leu Pro Asp Ser Pro Asn Ile Tyr Gly Leu
                165                 170                 175

Gly Glu His Thr Gly Ser Phe Arg Leu Pro Thr Lys Asn Tyr Thr Arg
            180                 185                 190

Thr Leu Trp Ser Arg Asp Ala Tyr Gly Thr Pro Lys Asp Thr Asn Leu
        195                 200                 205

Tyr Gly Asn His Pro Val Tyr Phe Asp Tyr Arg Gly Ser Asn Gly Thr
210                 215                 220

His Gly Val Phe Leu Leu Asn Ser Asn Gly Met Asp Val Asp Ile Asp
225                 230                 235                 240

Val Asp Ser Asp Gly Gln Tyr Leu Gln Tyr Asn Thr Leu Gly Gly Val
                245                 250                 255

Leu Asp Phe Tyr Phe Leu Ser Gly Pro Asp Pro Lys Ala Val Ala Thr
                260                 265                 270

Gln Tyr Ala Glu Thr Val Gly Lys Pro Val Met Met Pro Tyr Trp Gly
        275                 280                 285

Phe Gly Phe His Asn Cys Arg Tyr Gly Tyr Gln Asp Ile Tyr Glu Val
290                 295                 300

Ala Glu Ile Ile Ala Asn Tyr Ser Ala Ala Asn Ile Pro Leu Glu Thr
305                 310                 315                 320

Gln Trp Thr Asp Ile Asp Tyr Met Asp Leu Arg Lys Val Phe Thr Leu
                325                 330                 335

Asp Pro Tyr Arg Tyr Pro Leu Lys Leu Val Gln Glu Val Ser Tyr
                340                 345                 350

Leu His Lys His Asn Gln His Tyr Ile Met Met Val Asp Pro Ala Val
        355                 360                 365

Ala Tyr Gln Asn Tyr Ser Ala Phe Asn Asn Gly Val Ala Ala Asp Ala
        370                 375                 380

Phe Leu Lys Phe Ser Asn Gly Ser Ile Tyr Gln Gly Val Val Trp Pro
385                 390                 395                 400

Gly Pro Thr Ala Phe Pro Asp Trp Phe Ala Pro Gln Thr Gln Glu Phe
            405                 410                 415

Trp Asn Ser Glu Phe Ser Thr Phe Phe Asp Pro Ala His Gly Val Asp
            420                 425                 430
```

-continued

```
Ile Asp Ala Leu Trp Ile Asp Met Asn Glu Ala Ser Asn Phe Cys Asp
            435                 440                 445

Phe Pro Cys Ser Asn Pro Ala Ala Tyr Ala Ala Asn Gly Asp Pro
450                 455                 460

Pro Thr Pro Pro Pro Val Arg Leu Ser Pro Arg Pro Ile Pro Gly
465                 470                 475                 480

Phe Gly Pro Asp Phe Gln Pro Thr Cys Val Ala Thr Val Ser Phe Asp
                485                 490                 495

Cys Asp Ala Gln Thr Tyr Phe Gly Glu Asn Ile Leu Ile Leu Gly Asn
                500                 505                 510

Ser Thr Thr Leu Gly Ala Gly Asp Val His Met Ala Pro Val Met Ser
            515                 520                 525

Ala Asn Asn Tyr Pro Ile Trp Gln Leu Thr Val Gln Met Pro Pro Asn
530                 535                 540

Gly Thr Phe Ser Tyr Gln Tyr Val Arg Lys Glu Ser Asp Gly Ser Tyr
545                 550                 555                 560

Ile Tyr Glu Gln Thr Asn Arg Thr Val Thr Thr Gly Asp Cys Thr Ser
                565                 570                 575

Gly Thr Leu Lys Val Ser Asp Thr Ile Thr Thr Ser Ser Gly Pro His
            580                 585                 590

Lys Arg Ser Glu Leu Arg Pro Leu Val Arg Ser Pro Phe Pro Ala Glu
                595                 600                 605

Asp Leu Thr Arg Arg Gln Ser Gly Ser Met Leu Gly Leu Pro Asn Arg
            610                 615                 620

Asn Leu Leu Asn Pro Pro Tyr Thr Ile His Asn Ala Ala Gly Asn Leu
625                 630                 635                 640

Ser Glu Lys Thr Ile Asn Thr Asp Leu Ile His Ala Gly Gly Tyr Ala
                645                 650                 655

Glu Tyr Asp Thr His Asn Leu Tyr Gly Thr Met Met Ser Ala Thr Ser
            660                 665                 670

Arg Glu Ala Met Leu Asn Arg Arg Pro Ala Val Arg Pro Leu Val Ile
                675                 680                 685

Thr Arg Ser Thr Phe Ala Gly Ala Gly Arg Gln Val Gly His Trp Leu
            690                 695                 700

Gly Asp Asn Phe Ala Asp Trp Asp His Tyr Arg Trp Thr Ile Ala Glu
705                 710                 715                 720

Leu Gln Glu Phe Ala Ala Leu Phe Gln Ile Pro Met Val Gly Ser Asp
                725                 730                 735

Ile Cys Gly Tyr Asp Gly Asn Thr Thr Asp Asn Leu Cys Ser Arg Trp
            740                 745                 750

Val Phe Leu Gly Ala Phe Ser Pro Phe Phe Arg Asp His Ser Asp Asn
            755                 760                 765

Gln Ser Pro His Glu Leu Tyr Arg Thr Pro Gln Ile Ala Ala Ala
            770                 775                 780

Ala Arg Ala Ala Ile Asp Ile Arg Tyr Arg Leu Leu Asp Tyr Ala Tyr
785                 790                 795                 800

Thr Val Leu Trp Thr Gln Thr Gln Thr Gly Ala Pro Met Leu Asn Pro
                805                 810                 815

Met Phe Phe Glu Tyr Pro Ala Asp Ser Asn Thr Ala Asp Leu Gln Tyr
            820                 825                 830

Gln Phe Phe Trp Gly Asp Ser Ile Met Val Ala Pro Val Thr Asp Asn
            835                 840                 845

Asp Ser Thr Thr Val Asn Val Tyr Phe Pro Lys Asp Gln Phe Tyr Asp
```

```
                  850                 855                 860
Phe Tyr Thr Gly Ala Pro Val Ser Gly Glu Gly Asn Thr Val Thr Leu
865                 870                 875                 880

Thr Asp Val Gly Phe Asp Thr Ile Pro Leu Tyr Phe Lys Gly Gly Ser
                885                 890                 895

Ile Val Pro Met Arg Val Arg Ser Ala Asn Thr Thr Ala Glu Leu Arg
                900                 905                 910

Gln Gln Asp Phe Val Val Ile Ala Pro Asp Ser His Gly Asp Ala
            915                 920                 925

Thr Gly Gln Leu Tyr Leu Asp Asp Gly Glu Ser Ile Asn Gln Pro His
            930                 935                 940

Thr Ser Glu Ile Gln Phe Ser Tyr Arg Gly Gly His Phe Ser Met Thr
945                 950                 955                 960

Gly Lys Phe Asp Tyr Asp Pro Gly Asn Val Val Ile Ser Gln Ile Thr
                965                 970                 975

Leu Leu Gly Ala Asp Gly Ala Gly Lys Gly Gly Ser Tyr Asn Ser Thr
                980                 985                 990

Thr Lys Val Ala Thr Tyr Lys Val Asn Ala Lys Leu Thr Gly Lys Phe
            995                 1000                1005

Glu Ala Ser Leu His
      1010

<210> SEQ ID NO 16
<211> LENGTH: 3162
<212> TYPE: DNA
<213> ORGANISM: Rasamsonia composticola

<400> SEQUENCE: 16
atggcaggct ccgccgccct tgttgccagc ctcgtctggc ttgctcaggc cttcgacgct      60
cttgcaggac cggtcagcag tacgactgcc gcagcaccat ctgctcaatt caccgtcccg     120
gccgctgcgg atgttggggc caacttgctt gccaacatcg acgatcccaa tgccgtcaac     180
gcccaggatg tctgtcccgg ttacacggcg tcgaacgtgc agaacaccga gtctgggttt     240
gtggcgaccc tgacgctggc ggggaaacca tgtaatgtgt acggaacgga cgtggagtcc     300
ctgaacctga cggttgagta ccaagctgcg gatcgactga acatcaatat cgtcccgacg     360
cacgtcgatt cttcaaacca gtcgtggtat ctgcttcccg aaaatgtagt gcccaaaccg     420
ggggtcgatg caggagccca agtcccggag agtgatctcg tcttcagctg gtcgaatgaa     480
ccctccttca atttcaaggt gatccggaaa gccacaggcg acattctctt cgacacggag     540
ggttctgtcc tggtgttcga aaaccagttc atcgagtttg cgagcgctct gccggagaac     600
tacaatctct acggtctggg agagcgtatc catggcctgc gactggggaa caacttcacc     660
gccacgacgt atgccgcgga tagcgcagac cctattgacc ggtgagtatc tgagatcgac     720
tgctcagtct gctctgttgg atctgaaaga agttataaaa ctgacctagc tcaggaacat     780
ctacgggacc catccctttt atctggacac ccggtactac gaggttgatt ccgagcatgg     840
gaggttcacg ttggtgacgg acaacgagac cgatttctcc aaggaatatc tgtcgctctc     900
gcatggagtt ttcctgagaa atgcccacgg acaggaggtg ctgctgcgtc ctcagagcat     960
cacctggcgg acactcggtg gcagcattga tctttacttc tacgccggtc cgacccaggc    1020
cgatgttacc cgcagctacc agaccagcac cgttggcctc ccggcaatgc agcagtactt    1080
cacccctggg catcatcagt gccgctgggg atacagaaac tggtcggagc tagctgatgt    1140
agtggccaat ttcgagaaat cgagatcccc attggaaaat atctggtaag gcatacgcta    1200
```

```
tctgaaagag ttgctgggaa agtgatctga caacttcgtc tctccaggtc ggatattgat   1260
tacatgaacg agtaccgcga ctttgagaac gacccggttc gcttctccta cagcgaggga   1320
gccaaattcc tggaccagct ccacaagagt ggccgtcact acatcccgat tgtggacgcc   1380
gcgatctatg accccaaccc taacaatgac tccgacgcgt aagtctagtc ttgtagggag   1440
gtgatagggg gtggagctga cttctcgatt aggtatgcga catatgatcg aggttctaag   1500
gacgatatct ggttgaagaa tcccgacggc agcgtgtaca tcggagccgt ctggcctggc   1560
tacacagtgt tcaccgattg caccatcca aaagccaacg agtggtgggc aaacgagctg   1620
gctctgtggc acgaaaaggt cgcttttgac ggaatctggc tggacatgaa cgaggtctcg   1680
tccttctgcg ttggcagctg tggaacaggg aacctgaccc tgaatcccgt gcacccgaac   1740
ttcgcgctcc cggagagcc tggagctgtc atctacgact accccgagga cttcaacgtg   1800
acgaatgcca cggcggcggc gtctgcatct gccgcgtcct cgagccaagc tgctgcgaca   1860
gcgacagcta cttcttcgtc cacgactacc agctacctgg tgaccacgcc cactcctgga   1920
gtgcggaatg tcaactaccc tccctatgtg attaatcacg tgcaggaggg tcacgatctc   1980
gctgttcacg ccgtctcgcc caacgcaacc catgtcgatg gtgtgcagga gtacgacgtg   2040
cacaatctct ggggctacca ggagacaaat gcaacctacc atgccctgct gagcatcttc   2100
cccgggaaga gaccgttcat catctcccgt tccacgttcg ccggcagcgg cagatgggcc   2160
ggacactggg gtggcgacaa cgcctcgaaa tgggcgtaca tgttctttc tatcccgcag   2220 gcgctatcgt tctcgctgtt cggcatcccc atgttcggcg tcgacacctg cgggttcaac   2280
ggcaactcgg acgaagagct gtgcaaccgc tggatgcagc tctccgcctt cttcccttc   2340 taccgcaacc acaacgtcct gtcggccatc ccgcaggagc cctatgtctg ggcatccgtc   2400
atcgaggcga gcaagtcggc aatgaggatc cgctacaccc tgctccctta cctctacaca   2460
ctgttctacc tcgcccacac cacggggtcg accgtcatgc gtgccttggc gtgggagttc   2520
cccaacgacc cgtccctcgc tgccgtggac cggcagttcc tcctgggccc gtcgctgatg   2580
gtcgtccccg tgctcgagcc gcaggtcgat accgtcaagg gcgtcttccc gggcgttgcc   2640
cagggccaag tctggtacga ctggtacacg cagaccgcgt tcgacgcgca gccaggcgtg   2700
aacacgacca tctccgcgcc gctgggccac atcccgtgt tcgtccgcgg cgggagcgtg   2760
ctccccatgc agcagccggc actggtgacg cgggacgtgc gcaacagccc ctggtcgctg   2820
ctggtcgcgc tgggcagcga cggcacggcc tcgggacagc tgtacgtgga cgacggcgag   2880
agcatcacac ctccggcgtc cctgcacgtc gacttcgtgg cggccaactt ctcgaccctc   2940
ttcgcgacgg cccgcggtgc gttcaaggac agcaacacgc tggctaacgt cacggtgctg   3000
ggcgtcccag ccgcgccgtc gtctgcagtc acttggaaca acgagacggt tccttcggag   3060
tcggtgtcgt acaatgccac ctccaaagtc ctcgtggtca atggactgca gagtcttacc   3120
cgtgacggag cctggagcag tgactgggtt ctgaagtggt aa                     3162
```

<210> SEQ ID NO 17
<211> LENGTH: 990
<212> TYPE: PRT
<213> ORGANISM: Rasamsonia composticola

<400> SEQUENCE: 17

Met Ala Gly Ser Ala Ala Leu Val Ala Ser Leu Val Trp Leu Ala Gln
1               5                   10                  15

Ala Phe Asp Ala Leu Ala Gly Pro Val Ser Ser Thr Thr Ala Ala Ala

-continued

```
                20                  25                  30
    Pro Ser Ala Gln Phe Thr Val Pro Ala Ala Asp Val Gly Ala Asn
            35                  40                  45
    Leu Leu Ala Asn Ile Asp Pro Asn Ala Val Asn Ala Gln Asp Val
            50                  55                  60
    Cys Pro Gly Tyr Thr Ala Ser Asn Val Gln Asn Thr Glu Ser Gly Phe
    65                  70                  75                  80
    Val Ala Thr Leu Thr Leu Ala Gly Lys Pro Cys Asn Val Tyr Gly Thr
                    85                  90                  95
    Asp Val Glu Ser Leu Asn Leu Thr Val Glu Tyr Gln Ala Ala Asp Arg
                    100                 105                 110
    Leu Asn Ile Asn Ile Val Pro Thr His Val Asp Ser Ser Asn Gln Ser
                    115                 120                 125
    Trp Tyr Leu Leu Pro Glu Asn Val Val Pro Lys Pro Gly Val Asp Ala
                    130                 135                 140
    Gly Ala Gln Val Pro Glu Ser Asp Leu Val Phe Ser Trp Ser Asn Glu
    145                 150                 155                 160
    Pro Ser Phe Asn Phe Lys Val Ile Arg Lys Ala Thr Gly Asp Ile Leu
                    165                 170                 175
    Phe Asp Thr Glu Gly Ser Val Leu Val Phe Glu Asn Gln Phe Ile Glu
                    180                 185                 190
    Phe Ala Ser Ala Leu Pro Glu Asn Tyr Asn Leu Tyr Gly Leu Gly Glu
                    195                 200                 205
    Arg Ile His Gly Leu Arg Leu Gly Asn Asn Phe Thr Ala Thr Thr Tyr
                    210                 215                 220
    Ala Ala Asp Ser Ala Asp Pro Ile Asp Arg Asn Ile Tyr Gly Thr His
    225                 230                 235                 240
    Pro Phe Tyr Leu Asp Thr Arg Tyr Tyr Glu Val Asp Ser Glu His Gly
                    245                 250                 255
    Arg Phe Thr Leu Val Thr Asp Asn Glu Thr Asp Phe Ser Lys Glu Tyr
                    260                 265                 270
    Leu Ser Leu Ser His Gly Val Phe Leu Arg Asn Ala His Gly Gln Glu
                    275                 280                 285
    Val Leu Leu Arg Pro Gln Ser Ile Thr Trp Arg Thr Leu Gly Gly Ser
                    290                 295                 300
    Ile Asp Leu Tyr Phe Tyr Ala Gly Pro Thr Gln Ala Asp Val Thr Arg
    305                 310                 315                 320
    Ser Tyr Gln Thr Ser Thr Val Gly Leu Pro Ala Met Gln Gln Tyr Phe
                    325                 330                 335
    Thr Leu Gly Tyr His Gln Cys Arg Trp Gly Tyr Arg Asn Trp Ser Glu
                    340                 345                 350
    Leu Ala Asp Val Val Ala Asn Phe Glu Lys Phe Glu Ile Pro Leu Glu
                    355                 360                 365
    Asn Ile Trp Ser Asp Ile Asp Tyr Met Asn Glu Tyr Arg Asp Phe Glu
                    370                 375                 380
    Asn Asp Pro Val Arg Phe Ser Tyr Ser Glu Gly Ala Lys Phe Leu Asp
    385                 390                 395                 400
    Gln Leu His Lys Ser Gly Arg His Tyr Ile Pro Ile Val Asp Ala Ala
                    405                 410                 415
    Ile Tyr Asp Pro Asn Pro Asn Asn Asp Ser Asp Ala Tyr Ala Thr Tyr
                    420                 425                 430
    Asp Arg Gly Ser Lys Asp Ile Trp Leu Lys Asn Pro Asp Gly Ser
                    435                 440                 445
```

```
Val Tyr Ile Gly Ala Val Trp Pro Gly Tyr Thr Val Phe Thr Asp Trp
    450                 455                 460
His His Pro Lys Ala Asn Glu Trp Trp Ala Asn Glu Leu Ala Leu Trp
465                 470                 475                 480
His Glu Lys Val Ala Phe Asp Gly Ile Trp Leu Asp Met Asn Glu Val
                485                 490                 495
Ser Ser Phe Cys Val Gly Ser Cys Gly Thr Gly Asn Leu Thr Leu Asn
            500                 505                 510
Pro Val His Pro Asn Phe Ala Leu Pro Gly Glu Pro Gly Ala Val Ile
        515                 520                 525
Tyr Asp Tyr Pro Glu Asp Phe Asn Val Thr Asn Ala Thr Ala Ala Ala
530                 535                 540
Ser Ala Ser Ala Ala Ser Ser Ser Gln Ala Ala Thr Ala Thr Ala Ala
545                 550                 555                 560
Thr Ser Ser Ser Thr Thr Thr Ser Tyr Leu Val Thr Thr Pro Thr Pro
                565                 570                 575
Gly Val Arg Asn Val Asn Tyr Pro Pro Tyr Val Ile Asn His Val Gln
            580                 585                 590
Glu Gly His Asp Leu Ala Val His Ala Val Ser Pro Asn Ala Thr His
        595                 600                 605
Val Asp Gly Val Gln Glu Tyr Asp Val His Asn Leu Trp Gly Tyr Gln
610                 615                 620
Glu Thr Asn Ala Thr Tyr His Ala Leu Leu Ser Ile Phe Pro Gly Lys
625                 630                 635                 640
Arg Pro Phe Ile Ile Ser Arg Ser Thr Phe Ala Gly Ser Gly Arg Trp
                645                 650                 655
Ala Gly His Trp Gly Gly Asp Asn Ala Ser Lys Trp Ala Tyr Met Phe
            660                 665                 670
Phe Ser Ile Pro Gln Ala Leu Ser Phe Ser Leu Phe Gly Ile Pro Met
        675                 680                 685
Phe Gly Val Asp Thr Cys Gly Phe Asn Gly Asn Ser Asp Glu Glu Leu
690                 695                 700
Cys Asn Arg Trp Met Gln Leu Ser Ala Phe Phe Pro Phe Tyr Arg Asn
705                 710                 715                 720
His Asn Val Leu Ser Ala Ile Pro Gln Glu Pro Tyr Val Trp Ala Ser
                725                 730                 735
Val Ile Glu Ala Ser Lys Ser Ala Met Arg Ile Arg Tyr Thr Leu Leu
            740                 745                 750
Pro Tyr Leu Tyr Thr Leu Phe Tyr Leu Ala His Thr Thr Gly Ser Thr
        755                 760                 765
Val Met Arg Ala Leu Ala Trp Glu Phe Pro Asn Asp Pro Ser Leu Ala
770                 775                 780
Ala Val Asp Arg Gln Phe Leu Leu Gly Pro Ser Leu Met Val Val Pro
785                 790                 795                 800
Val Leu Glu Pro Gln Val Asp Thr Val Lys Gly Val Phe Pro Gly Val
                805                 810                 815
Ala Gln Gly Gln Val Trp Tyr Asp Trp Tyr Thr Gln Thr Ala Phe Asp
            820                 825                 830
Ala Gln Pro Gly Val Asn Thr Thr Ile Ser Ala Pro Leu Gly His Ile
        835                 840                 845
Pro Val Phe Val Arg Gly Gly Ser Val Leu Pro Met Gln Gln Pro Ala
    850                 855                 860
```

```
Leu Val Thr Arg Asp Val Arg Asn Ser Pro Trp Ser Leu Leu Val Ala
865                 870                 875                 880

Leu Gly Ser Asp Gly Thr Ala Ser Gly Gln Leu Tyr Val Asp Asp Gly
            885                 890                 895

Glu Ser Ile Thr Pro Pro Ala Ser Leu His Val Asp Phe Val Ala Ala
            900                 905                 910

Asn Phe Ser Thr Leu Phe Ala Thr Ala Arg Gly Ala Phe Lys Asp Ser
            915                 920                 925

Asn Thr Leu Ala Asn Val Thr Val Leu Gly Val Pro Ala Ala Pro Ser
            930                 935                 940

Ser Ala Val Thr Trp Asn Asn Glu Thr Val Pro Ser Glu Ser Val Ser
945                 950                 955                 960

Tyr Asn Ala Thr Ser Lys Val Leu Val Val Asn Gly Leu Gln Ser Leu
                965                 970                 975

Thr Arg Asp Gly Ala Trp Ser Ser Asp Trp Val Leu Lys Trp
            980                 985                 990

<210> SEQ ID NO 18
<211> LENGTH: 973
<212> TYPE: PRT
<213> ORGANISM: Rasamsonia composticola

<400> SEQUENCE: 18

Phe Asp Ala Leu Ala Gly Pro Val Ser Ser Thr Thr Ala Ala Ala Pro
1               5                   10                  15

Ser Ala Gln Phe Thr Val Pro Ala Ala Ala Asp Val Gly Ala Asn Leu
            20                  25                  30

Leu Ala Asn Ile Asp Asp Pro Asn Ala Val Asn Ala Gln Asp Val Cys
        35                  40                  45

Pro Gly Tyr Thr Ala Ser Asn Val Gln Asn Thr Glu Ser Gly Phe Val
    50                  55                  60

Ala Thr Leu Thr Leu Ala Gly Lys Pro Cys Asn Val Tyr Gly Thr Asp
65                  70                  75                  80

Val Glu Ser Leu Asn Leu Thr Val Glu Tyr Gln Ala Ala Asp Arg Leu
                85                  90                  95

Asn Ile Asn Ile Val Pro Thr His Val Asp Ser Ser Asn Gln Ser Trp
            100                 105                 110

Tyr Leu Leu Pro Glu Asn Val Val Pro Lys Pro Gly Val Asp Ala Gly
        115                 120                 125

Ala Gln Val Pro Glu Ser Asp Leu Val Phe Ser Trp Ser Asn Glu Pro
    130                 135                 140

Ser Phe Asn Phe Lys Val Ile Arg Lys Ala Thr Gly Asp Ile Leu Phe
145                 150                 155                 160

Asp Thr Glu Gly Ser Val Leu Val Phe Glu Asn Gln Phe Ile Glu Phe
                165                 170                 175

Ala Ser Ala Leu Pro Glu Asn Tyr Asn Leu Tyr Gly Leu Gly Glu Arg
            180                 185                 190

Ile His Gly Leu Arg Leu Gly Asn Asn Phe Thr Ala Thr Thr Tyr Ala
        195                 200                 205

Ala Asp Ser Ala Asp Pro Ile Asp Arg Asn Ile Tyr Gly Thr His Pro
    210                 215                 220

Phe Tyr Leu Asp Thr Arg Tyr Tyr Glu Val Asp Ser Glu His Gly Arg
225                 230                 235                 240

Phe Thr Leu Val Thr Asp Asn Glu Thr Asp Phe Ser Lys Glu Tyr Leu
                245                 250                 255
```

```
Ser Leu Ser His Gly Val Phe Leu Arg Asn Ala His Gly Gln Glu Val
            260                 265                 270

Leu Leu Arg Pro Gln Ser Ile Thr Trp Arg Thr Leu Gly Ser Ile
        275                 280                 285

Asp Leu Tyr Phe Tyr Ala Gly Pro Thr Gln Ala Asp Val Thr Arg Ser
            290                 295                 300

Tyr Gln Thr Ser Thr Val Gly Leu Pro Ala Met Gln Gln Tyr Phe Thr
305                 310                 315                 320

Leu Gly Tyr His Gln Cys Arg Trp Gly Tyr Arg Asn Trp Ser Glu Leu
                325                 330                 335

Ala Asp Val Val Ala Asn Phe Glu Lys Phe Glu Ile Pro Leu Glu Asn
            340                 345                 350

Ile Trp Ser Asp Ile Asp Tyr Met Asn Glu Tyr Arg Asp Phe Glu Asn
        355                 360                 365

Asp Pro Val Arg Phe Ser Tyr Ser Glu Gly Ala Lys Phe Leu Asp Gln
        370                 375                 380

Leu His Lys Ser Gly Arg His Tyr Ile Pro Ile Val Asp Ala Ala Ile
385                 390                 395                 400

Tyr Asp Pro Asn Pro Asn Asn Asp Ser Asp Ala Tyr Ala Thr Tyr Asp
                405                 410                 415

Arg Gly Ser Lys Asp Asp Ile Trp Leu Lys Asn Pro Asp Gly Ser Val
            420                 425                 430

Tyr Ile Gly Ala Val Trp Pro Gly Tyr Thr Val Phe Thr Asp Trp His
        435                 440                 445

His Pro Lys Ala Asn Glu Trp Trp Ala Asn Glu Leu Ala Leu Trp His
        450                 455                 460

Glu Lys Val Ala Phe Asp Gly Ile Trp Leu Asp Met Asn Glu Val Ser
465                 470                 475                 480

Ser Phe Cys Val Gly Ser Cys Gly Thr Gly Asn Leu Thr Leu Asn Pro
                485                 490                 495

Val His Pro Asn Phe Ala Leu Pro Gly Glu Pro Gly Ala Val Ile Tyr
            500                 505                 510

Asp Tyr Pro Glu Asp Phe Asn Val Thr Asn Ala Thr Ala Ala Ala Ser
        515                 520                 525

Ala Ser Ala Ala Ser Ser Gln Ala Ala Thr Ala Thr Ala Thr
        530                 535                 540

Ser Ser Ser Thr Thr Thr Ser Tyr Leu Val Thr Thr Pro Thr Pro Gly
545                 550                 555                 560

Val Arg Asn Val Asn Tyr Pro Pro Tyr Val Ile Asn His Val Gln Glu
                565                 570                 575

Gly His Asp Leu Ala Val His Ala Val Ser Pro Asn Ala Thr His Val
            580                 585                 590

Asp Gly Val Gln Glu Tyr Asp Val His Asn Leu Trp Gly Tyr Gln Glu
        595                 600                 605

Thr Asn Ala Thr Tyr His Ala Leu Leu Ser Ile Phe Pro Gly Lys Arg
        610                 615                 620

Pro Phe Ile Ile Ser Arg Ser Thr Phe Ala Gly Ser Gly Arg Trp Ala
625                 630                 635                 640

Gly His Trp Gly Gly Asp Asn Ala Ser Lys Trp Ala Tyr Met Phe Phe
                645                 650                 655

Ser Ile Pro Gln Ala Leu Ser Phe Ser Leu Phe Gly Ile Pro Met Phe
            660                 665                 670
```

```
Gly Val Asp Thr Cys Gly Phe Asn Gly Asn Ser Asp Glu Glu Leu Cys
            675                 680                 685

Asn Arg Trp Met Gln Leu Ser Ala Phe Phe Pro Phe Tyr Arg Asn His
        690                 695                 700

Asn Val Leu Ser Ala Ile Pro Gln Glu Pro Tyr Val Trp Ala Ser Val
705                 710                 715                 720

Ile Glu Ala Ser Lys Ser Ala Met Arg Ile Arg Tyr Thr Leu Leu Pro
                725                 730                 735

Tyr Leu Tyr Thr Leu Phe Tyr Leu Ala His Thr Thr Gly Ser Thr Val
            740                 745                 750

Met Arg Ala Leu Ala Trp Glu Phe Pro Asn Asp Pro Ser Leu Ala Ala
        755                 760                 765

Val Asp Arg Gln Phe Leu Leu Gly Pro Ser Leu Met Val Pro Val
770                 775                 780

Leu Glu Pro Gln Val Asp Thr Val Lys Gly Val Phe Pro Gly Val Ala
785                 790                 795                 800

Gln Gly Gln Val Trp Tyr Asp Trp Tyr Thr Gln Thr Ala Phe Asp Ala
                805                 810                 815

Gln Pro Gly Val Asn Thr Thr Ile Ser Ala Pro Leu Gly His Ile Pro
            820                 825                 830

Val Phe Val Arg Gly Gly Ser Val Leu Pro Met Gln Gln Pro Ala Leu
        835                 840                 845

Val Thr Arg Asp Val Arg Asn Ser Pro Trp Ser Leu Leu Val Ala Leu
850                 855                 860

Gly Ser Asp Gly Thr Ala Ser Gly Gln Leu Tyr Val Asp Asp Gly Glu
865                 870                 875                 880

Ser Ile Thr Pro Pro Ala Ser Leu His Val Asp Phe Val Ala Ala Asn
                885                 890                 895

Phe Ser Thr Leu Phe Ala Thr Ala Arg Gly Ala Phe Lys Asp Ser Asn
            900                 905                 910

Thr Leu Ala Asn Val Thr Val Leu Gly Val Pro Ala Ala Pro Ser Ser
        915                 920                 925

Ala Val Thr Trp Asn Asn Glu Thr Val Pro Ser Glu Ser Val Ser Tyr
930                 935                 940

Asn Ala Thr Ser Lys Val Leu Val Val Asn Gly Leu Gln Ser Leu Thr
945                 950                 955                 960

Arg Asp Gly Ala Trp Ser Ser Asp Trp Val Leu Lys Trp
                965                 970

<210> SEQ ID NO 19
<211> LENGTH: 1815
<212> TYPE: DNA
<213> ORGANISM: Bifidobacterium longum

<400> SEQUENCE: 19
atgaccgcaa ataatctcaa tgacgactgg tggaagcagg ccgtcgtcta ccagatctac      60
ccgcgcagct tcaaggacgt taacggcgac ggactcggcg acatcgccgg cgtcaccgag     120
aagatggact acctgaagaa cctcggcgtc gacgcaatct ggctctcccc gttctacccc     180
tccgatctgg cggacggcgg ctacgacgta atcgactacc gcaacgtcga cccgcgccta     240
ggcaccatgg aagacttcga cgcgatggcc aaggccgcgc acgaggccgg catcaaggtg     300
atcgtggaca cgtgcccaa ccacaccgct gacaagcacg tgttcttcca ggaggccctc     360
gccgccgagc ctggctcccc ggcgcgcgac cgctacatct ccgcgacgg ccgcggcgag     420
```

```
catggcgaac tgcccccgaa cgactggcaa tccttcttcg gcggcccggc ctgggcgcgc    480
gtggccgacg gccagtggta tctgcacctg ttcgataagg cgcagccgga cgtcaactgg    540
aagaatccgg acatccacga ggagttcaag aagaccctgc gtttctggtc cgaccacggc    600
accgacgggct tccgcatcga cgtggcgcac ggcctggcca aggacctcga atccaagccg    660
ttggaagagc tcggccgcga atacagcgtg gtcggcgtgc tgaatcatga cttcagccac    720
ccgctgttcg accgtcgcga ggtgcacgat atctaccgcg aatggcgcaa ggtgttcaac    780
gagtacgacc cgccgcgctt tgccgtggcc gaggcgtggg tggtgcccga gcaccagcac    840
ctgtacgctt cgatggacga gctgggccag tccttcaact tcgacttcgc gcaagccaac    900
tggtatgccg acgagttccg cgaggccatc gccgccggac tcaaggcggc ggccgaaacc    960
ggcggttcca ccaccacgtg ggtcatgaac aatcacgacg tgccgcgcag ccctccccgt   1020
tacggcctgc cgcagatcaa gggcgcaccc taccaccagc tgccgcacga ctggctgctg   1080
cgcaacggca ctacctatcc cgaggatcgc gagcttggca ctcgccgcgc ccgcgccgcc   1140
gctttgatgg agctcggcct gcccggcgcc gcctatatct atcagggcga ggagctgggc   1200
ctgtttgagg tggccgatat tccgtgggat cacttggagg atccgaccgc tttccacact   1260
gctcaggcca cgatggacaa gggccgcgac ggctgccgcg tgccgctgcc gtggaccgcc   1320
gccgatgagc cggccttggc cgatttcagc cgtccgactc cggccgatga cggtaccggc   1380
gagaaccatg tgccgctgtg cgccgccggc cagttcggca cgggcgcttc cttcggcttc   1440
tcgccggcta cgcgcgctga gggcgtgacg ccggccgccg acccgcacct gccgcaaccg   1500
ctgtggttca aggattacgc ggtggacgtg gagcaagccg acccggactc gatgctcgcg   1560
ctgtatcgcg ccgcactggc gattcgccag gagtcgctga ccgccacgcg cgacaccacg   1620
gccgagcagg tggacatggg cgacgatgtg gtggcgtaca cccgcgcggc ggttggcggg   1680
cgggtgttca cctcaatcac caacttcggc aatgctccgg tcgcgctgcc cgatggctcc   1740
gtggtgctgg cgtccggccc gctgaccccc gaagcccagc tccccaccga cacttctgcg   1800
tggggttgttc agtag                                                   1815
```

<210> SEQ ID NO 20  
<211> LENGTH: 604  
<212> TYPE: PRT  
<213> ORGANISM: Bifidobacterium longum

<400> SEQUENCE: 20

```
Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Leu
            20                  25                  30

Gly Asp Ile Ala Gly Val Thr Glu Lys Met Asp Tyr Leu Lys Asn Leu
        35                  40                  45

Gly Val Asp Ala Ile Trp Leu Ser Pro Phe Tyr Pro Ser Asp Leu Ala
    50                  55                  60

Asp Gly Gly Tyr Asp Val Ile Asp Tyr Arg Asn Val Asp Pro Arg Leu
65                  70                  75                  80

Gly Thr Met Glu Asp Phe Asp Ala Met Ala Lys Ala Ala His Glu Ala
                85                  90                  95

Gly Ile Lys Val Ile Val Asp Ile Val Pro Asn His Thr Ala Asp Lys
            100                 105                 110

His Val Phe Phe Gln Glu Ala Leu Ala Ala Glu Pro Gly Ser Pro Ala
        115                 120                 125
```

```
Arg Asp Arg Tyr Ile Phe Arg Asp Gly Arg Gly Glu His Gly Glu Leu
130                 135                 140

Pro Pro Asn Asp Trp Gln Ser Phe Phe Gly Gly Pro Ala Trp Ala Arg
145                 150                 155                 160

Val Ala Asp Gly Gln Trp Tyr Leu His Leu Phe Asp Lys Ala Gln Pro
                165                 170                 175

Asp Val Asn Trp Lys Asn Pro Asp Ile His Glu Glu Phe Lys Lys Thr
            180                 185                 190

Leu Arg Phe Trp Ser Asp His Gly Thr Asp Gly Phe Arg Ile Asp Val
        195                 200                 205

Ala His Gly Leu Ala Lys Asp Leu Glu Ser Lys Pro Leu Glu Glu Leu
210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
                245                 250                 255

Lys Val Phe Asn Glu Tyr Asp Pro Pro Arg Phe Ala Val Ala Glu Ala
            260                 265                 270

Trp Val Val Pro Glu His Gln His Leu Tyr Ala Ser Met Asp Glu Leu
        275                 280                 285

Gly Gln Ser Phe Asn Phe Asp Phe Ala Gln Ala Asn Trp Tyr Ala Asp
290                 295                 300

Glu Phe Arg Glu Ala Ile Ala Ala Gly Leu Lys Ala Ala Ala Glu Thr
305                 310                 315                 320

Gly Gly Ser Thr Thr Thr Trp Val Met Asn Asn His Asp Val Pro Arg
                325                 330                 335

Ser Pro Ser Arg Tyr Gly Leu Pro Gln Ile Lys Gly Ala Pro Tyr His
            340                 345                 350

Gln Leu Pro His Asp Trp Leu Leu Arg Asn Gly Thr Thr Tyr Pro Glu
        355                 360                 365

Asp Arg Glu Leu Gly Thr Arg Arg Ala Arg Ala Ala Leu Met Glu
370                 375                 380

Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp His Leu Glu Asp Pro Thr
                405                 410                 415

Ala Phe His Thr Ala Gln Ala Thr Met Asp Lys Gly Arg Asp Gly Cys
            420                 425                 430

Arg Val Pro Leu Pro Trp Thr Ala Asp Glu Pro Ala Leu Ala Asp
        435                 440                 445

Phe Ser Arg Pro Thr Pro Ala Asp Asp Gly Thr Gly Glu Asn His Val
450                 455                 460

Pro Leu Cys Ala Ala Gly Gln Phe Gly Thr Gly Ala Ser Phe Gly Phe
465                 470                 475                 480

Ser Pro Ala Thr Arg Ala Glu Gly Val Thr Pro Ala Ala Asp Pro His
                485                 490                 495

Leu Pro Gln Pro Leu Trp Phe Lys Asp Tyr Ala Val Asp Val Glu Gln
            500                 505                 510

Ala Asp Pro Asp Ser Met Leu Ala Leu Tyr Arg Ala Ala Leu Ala Ile
        515                 520                 525

Arg Gln Glu Ser Leu Thr Ala Thr Arg Asp Thr Thr Ala Glu Gln Val
530                 535                 540
```

Asp Met Gly Asp Asp Val Val Ala Tyr Thr Arg Ala Ala Val Gly Gly
545                 550                 555                 560

Arg Val Phe Thr Ser Ile Thr Asn Phe Gly Asn Ala Pro Val Ala Leu
                565                 570                 575

Pro Asp Gly Ser Val Val Leu Ala Ser Gly Pro Leu Thr Pro Glu Ala
                580                 585                 590

Gln Leu Pro Thr Asp Thr Ser Ala Trp Val Val Gln
        595                 600

<210> SEQ ID NO 21
<211> LENGTH: 1812
<212> TYPE: DNA
<213> ORGANISM: Artificial sequence
<220> FEATURE:
<223> OTHER INFORMATION: BloGlu1_codon-optimized

<400> SEQUENCE: 21

| | | | | |
|---|---|---|---|---|
| gtgacagcaa | ataatcttaa | cgatgattgg | tggaaacaag | cagtggttta ccaaatctac | 60 |
| ccgagatcat | ttaaagacgt | taatggcgac | ggactgggag | atattgcggg cgtgacagag | 120 |
| aaaatggact | atctgaagaa | tctgggagtg | gatgcgattt | ggctgtcacc gttctatccg | 180 |
| agcgatctgg | ctgacggagg | ctacgatgtc | attgattata | gaaatgtgga tccgagactt | 240 |
| ggcacgatgg | aggatttcga | cgcgatggcg | aaggcagccc | atgaagcagg cattaaggtt | 300 |
| attgtcgata | ttgttccgaa | tcatacggcg | gacaaacatg | tgttttttca agaggcactt | 360 |
| gccgctgaac | ctggaagccc | ggctagagat | agatacattt | tcagagatgg cagaggcgaa | 420 |
| cacggcgagc | ttcctcctaa | cgactggcaa | tcattcttcg | gaggccctgc atgggcaaga | 480 |
| gtggcggacg | gccaatggta | cctgcatctt | tttgataagg | cacagccgga tgttaattgg | 540 |
| aaaaatcctg | atattcacga | agagtttaag | aaaacactta | gattctggtc agatcatggc | 600 |
| acggacggat | ttagaattga | tgtcgcacac | ggccttgcga | agatctggga gtcaaaaccg | 660 |
| cttgaggagc | ttggaagaga | atatagcgtg | gttggagttc | tgaatcatga cttcagccac | 720 |
| cctctgtttg | acagaagaga | ggttcatgac | atttatagag | aatggagaaa agttttcaat | 780 |
| gaatatgatc | cgccgagatt | tgcggttgct | gaggcctggg | ttgtgcctga gcatcaacat | 840 |
| ctgtacgctt | caatggacga | gcttggccag | tcattcaact | ttgattttgc ccaagcaaat | 900 |
| tggtatgcag | atgaatttag | agaggctatt | gctgctggcc | tgaaagcagc ggctgaaacg | 960 |
| ggaggatcaa | cgacaacatg | ggttatgaat | aatcacgatg | ttcctagatc accgtcaaga | 1020 |
| tatgccctgc | ctcagattaa | gggcgcaccg | tatcaccagc | ttccgcacga ttggctgctt | 1080 |
| agaaacggca | cgacgtaccc | ggaagataga | gagctgggaa | caagaagagc aagagcagca | 1140 |
| gctctgatgg | aactgggact | gcctggcgca | gcatacatct | atcaaggcga agaacttgga | 1200 |
| cttttcgaag | ttgcagacat | tccgtgggat | catctggaag | atcctacagc atttcacaca | 1260 |
| gcccaggcga | caatggataa | gggcagagac | ggatgtagag | tcccgctgcc gtggacagct | 1320 |
| gccgatgagc | ctgcactggc | agacttctca | agaccgacac | cggccgacga cggaacaggc | 1380 |
| gagaaccatg | tgccgctttg | tgcagccggc | cagtttggca | caggcgctag ctttggattt | 1440 |
| tcaccggcga | cgagagcgga | aggcgtcaca | cctgctgcag | atcctcacct gccgcaacct | 1500 |
| ctgtggttca | aggattatgc | tgttgacgtt | gagcaagcag | acccggactc aatgcttgca | 1560 |
| ctgtatagag | cggccctggc | tattagacaa | gaaagcctta | cggcaacgag agacacgaca | 1620 |
| gcggagcaag | ttgatatggg | cgatgatgtt | gttgcttata | caagaccgcc agttggcgga | 1680 |
| agagtcttta | cgtcaattac | aaattttggc | aatgcaccgg | ttgcacttcc ggatggctca | 1740 |

```
gttgttctgg catcaggccc gcttacacct gaagcacaac tgcctacaga tacgtcagca    1800
tgggtcgttc aa                                                        1812
```

<210> SEQ ID NO 22
<211> LENGTH: 604
<212> TYPE: PRT
<213> ORGANISM: Bifidobacterium longum

<400> SEQUENCE: 22

```
Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Leu
            20                  25                  30

Gly Asp Ile Ala Gly Val Thr Glu Lys Met Asp Tyr Leu Lys Asn Leu
        35                  40                  45

Gly Val Asp Ala Ile Trp Leu Ser Pro Phe Tyr Pro Ser Asp Leu Ala
    50                  55                  60

Asp Gly Gly Tyr Asp Val Ile Asp Tyr Arg Asn Val Asp Pro Arg Leu
65                  70                  75                  80

Gly Thr Met Glu Asp Phe Asp Ala Met Ala Lys Ala His Glu Ala
                85                  90                  95

Gly Ile Lys Val Ile Val Asp Ile Val Pro Asn His Thr Ala Asp Lys
            100                 105                 110

His Val Phe Phe Gln Glu Ala Leu Ala Ala Glu Pro Gly Ser Pro Ala
        115                 120                 125

Arg Asp Arg Tyr Ile Phe Arg Asp Gly Arg Gly Glu His Gly Glu Leu
    130                 135                 140

Pro Pro Asn Asp Trp Gln Ser Phe Phe Gly Gly Pro Ala Trp Ala Arg
145                 150                 155                 160

Val Ala Asp Gly Gln Trp Tyr Leu His Leu Phe Asp Lys Ala Gln Pro
                165                 170                 175

Asp Val Asn Trp Lys Asn Pro Asp Ile His Glu Glu Phe Lys Lys Thr
            180                 185                 190

Leu Arg Phe Trp Ser Asp His Gly Thr Asp Gly Phe Arg Ile Asp Val
        195                 200                 205

Ala His Gly Leu Ala Lys Asp Leu Glu Ser Lys Pro Leu Glu Glu Leu
    210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
                245                 250                 255

Lys Val Phe Asn Glu Tyr Asp Pro Pro Arg Phe Ala Val Ala Glu Ala
            260                 265                 270

Trp Val Val Pro Glu His Gln His Leu Tyr Ala Ser Met Asp Glu Leu
        275                 280                 285

Gly Gln Ser Phe Asn Phe Asp Phe Ala Gln Ala Asn Trp Tyr Ala Asp
    290                 295                 300

Glu Phe Arg Glu Ala Ile Ala Ala Gly Leu Lys Ala Ala Glu Thr
305                 310                 315                 320

Gly Gly Ser Thr Thr Thr Trp Val Met Asn Asn His Asp Val Pro Arg
                325                 330                 335

Ser Pro Ser Arg Tyr Gly Leu Pro Gln Ile Lys Gly Ala Pro Tyr His
            340                 345                 350
```

Gln Leu Pro His Asp Trp Leu Leu Arg Asn Gly Thr Thr Tyr Pro Glu
355                 360                 365

Asp Arg Glu Leu Gly Thr Arg Arg Ala Arg Ala Ala Leu Met Glu
370                 375                 380

Leu Gly Leu Pro Gly Ala Ala Tyr Ile Tyr Gln Gly Glu Leu Gly
385                 390                 395                 400

Leu Phe Glu Val Ala Asp Ile Pro Trp Asp His Leu Glu Asp Pro Thr
            405                 410                 415

Ala Phe His Thr Ala Gln Ala Thr Met Asp Lys Gly Arg Asp Gly Cys
            420                 425                 430

Arg Val Pro Leu Pro Trp Thr Ala Ala Asp Glu Pro Ala Leu Ala Asp
            435                 440                 445

Phe Ser Arg Pro Thr Pro Ala Asp Asp Gly Thr Gly Glu Asn His Val
450                 455                 460

Pro Leu Cys Ala Ala Gly Gln Phe Gly Thr Gly Ala Ser Phe Gly Phe
465                 470                 475                 480

Ser Pro Ala Thr Arg Ala Glu Gly Val Thr Pro Ala Ala Asp Pro His
            485                 490                 495

Leu Pro Gln Pro Leu Trp Phe Lys Asp Tyr Ala Val Asp Val Glu Gln
            500                 505                 510

Ala Asp Pro Asp Ser Met Leu Ala Leu Tyr Arg Ala Ala Leu Ala Ile
515                 520                 525

Arg Gln Glu Ser Leu Thr Ala Thr Arg Asp Thr Thr Ala Glu Gln Val
530                 535                 540

Asp Met Gly Asp Asp Val Val Ala Tyr Thr Arg Ala Ala Val Gly Gly
545                 550                 555                 560

Arg Val Phe Thr Ser Ile Thr Asn Phe Gly Asn Ala Pro Val Ala Leu
            565                 570                 575

Pro Asp Gly Ser Val Val Leu Ala Ser Gly Pro Leu Thr Pro Glu Ala
            580                 585                 590

Gln Leu Pro Thr Asp Thr Ser Ala Trp Val Val Gln
            595                 600

<210> SEQ ID NO 23
<211> LENGTH: 1812
<212> TYPE: DNA
<213> ORGANISM: Artificial sequence
<220> FEATURE:
<223> OTHER INFORMATION: BloGlu2_codon-optimized

<400> SEQUENCE: 23
gtgacggcaa acaatctgaa tgatgattgg tggaaacaag cagtggtcta tcagatttat     60
cctagatcat ttaaggatgt taatggcgac ggcctgggag atattgcagg cgtgacggaa    120
aaaatggatt atctgaagaa tctgggcgtt gacgccattt ggctgtcacc gttttacccg    180
agcgacctgg ccgatggcgg ctatgacgtg attgattata gaatgttgga cccgagactg    240
ggcacgatgg acgattttga cgcaatggct gaagccgcac acgaggctgg cattaaagtt    300
attgttgata ttgtcccgaa ccacacagca gacaagcacg ttttttttcaa agaagcgctg    360 gcaagcgaac tggctcacc ggcgagagac agatacattt ttagagacgg aagaggagag    420
catggcgaac tgcctccgaa cgattggcaa tcattctttg gcggacctgc ttgggctaga    480
gtcccggacg gccaatggta ccttcacctg ttcgataaag ctcagccgga tgtgaattgg    540
aaaaatcctg atatccatga agagtttaag aagacgctta gatttggtc agatcatgga    600 acggatggat tcagaattga tgttgcacac ggacttgcaa aggatcttga atcaaaacct    660

```
cttgaagagc ttggaagaga atactcagtc gttggcgttc ttaatcacga cttttcacac    720
ccgcttttg  acagaagaga ggtgcatgat atttacagag aatggagaaa agttttcaat    780
gaatatacac cgccgagatt cgcagtcgcc gaggcgtggg tggtgcctga acatcagcat    840
ctttatgcat caatggatga acttggccag tcatttaact tcgatttcgc tcaagcaaat    900
tggtacgctg atgaattag  aaaagcaatc gctgccggcc tgaaagcagc ggcagaaaca    960
ggaggaagca cgacaacatg ggtcatgaac aatcatgacg tccctagatc accgtcaaga   1020
tacggccttc ctcaggttaa aggcgcaccg tatcaccaac ttccgcacga ctggctgctg   1080
agagatggca cgacgtatcc ggaggataga aactgggaa  caagaagagc aagagcggct   1140
gccctgatgg agctgggact gcctggagca gcctatatct atcaaggcga ggaacttgga   1200
ctgtttgagg ttgctgacat tccttgggat agactggaag atccgacagc gtttcataca   1260
gctcaggcga caatggacaa gggcagagat ggatgcagag ttccgcttcc gtggacggcg   1320
tcagacgaac cggcacttgc agacttctca agacctgccc ctgcagacga cggcacaggc   1380
gagaatcatg ttcctctgtg cgctgctgga caattcggaa caggcgcttc attcggcttt   1440
agccctgccg ttagagcaga cggagttaca cctgcggccg accgcatct  gcctcaaccg   1500
ctttggttta agattatgc  agtggatgtc gagcaagcag atccggactc aatgtatacg   1560
ctgtatcacg ctgcactggc aattagacaa gaatcactga cagctacaag agatacaaca   1620
gctgagcagg tggacatggg agcagatgtg gttgcatata aagagccgc  ggtcgaagga   1680
agaacattta cgtcagttac gaactttggc acagctccgg tttcactgcc ggaaggctca   1740
gtggtgctga cgagcggacc gcttacgcct gacggacagc tgccgacaga cacaagcgca   1800
tgggttatta ag                                                        1812

<210> SEQ ID NO 24
<211> LENGTH: 604
<212> TYPE: PRT
<213> ORGANISM: Bifidobacterium longum

<400> SEQUENCE: 24

Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Leu
            20                  25                  30

Gly Asp Ile Ala Gly Val Thr Glu Lys Met Asp Tyr Leu Lys Asn Leu
        35                  40                  45

Gly Val Asp Ala Ile Trp Leu Ser Pro Phe Tyr Pro Ser Asp Leu Ala
    50                  55                  60

Asp Gly Gly Tyr Asp Val Ile Asp Tyr Arg Asn Val Asp Pro Arg Leu
65                  70                  75                  80

Gly Thr Met Asp Asp Phe Asp Ala Met Ala Glu Ala His Glu Ala
            85                  90                  95

Gly Ile Lys Val Ile Val Asp Ile Val Pro Asn His Thr Ala Asp Lys
            100                 105                 110

His Val Phe Phe Lys Glu Ala Leu Ala Ser Glu Pro Gly Ser Pro Ala
        115                 120                 125

Arg Asp Arg Tyr Ile Phe Arg Asp Gly Arg Gly Glu His Gly Glu Leu
    130                 135                 140

Pro Pro Asn Asp Trp Gln Ser Phe Phe Gly Gly Pro Ala Trp Ala Arg
145                 150                 155                 160
```

-continued

Val Pro Asp Gly Gln Trp Tyr Leu His Leu Phe Asp Lys Ala Gln Pro
            165                 170                 175

Asp Val Asn Trp Lys Asn Pro Asp Ile His Glu Glu Phe Lys Lys Thr
        180                 185                 190

Leu Arg Phe Trp Ser Asp His Gly Thr Asp Gly Phe Arg Ile Asp Val
    195                 200                 205

Ala His Gly Leu Ala Lys Asp Leu Glu Ser Lys Pro Leu Glu Glu Leu
210                 215                 220

Gly Arg Glu Tyr Ser Val Gly Val Leu Asn His Asp Phe Ser His
225                 230                 235                 240

Pro Leu Phe Asp Arg Arg Glu Val His Asp Ile Tyr Arg Glu Trp Arg
                245                 250                 255

Lys Val Phe Asn Glu Tyr Thr Pro Pro Arg Phe Ala Val Ala Glu Ala
            260                 265                 270

Trp Val Pro Glu His Gln His Leu Tyr Ala Ser Met Asp Glu Leu
        275                 280                 285

Gly Gln Ser Phe Asn Phe Asp Phe Ala Gln Ala Asn Trp Tyr Ala Asp
    290                 295                 300

Glu Phe Arg Lys Ala Ile Ala Ala Gly Leu Lys Ala Ala Glu Thr
305                 310                 315                 320

Gly Gly Ser Thr Thr Thr Trp Val Met Asn Asn His Asp Val Pro Arg
                325                 330                 335

Ser Pro Ser Arg Tyr Gly Leu Pro Gln Val Lys Gly Ala Pro Tyr His
            340                 345                 350

Gln Leu Pro His Asp Trp Leu Leu Arg Asp Gly Thr Thr Tyr Pro Glu
        355                 360                 365

Asp Arg Glu Leu Gly Thr Arg Arg Ala Arg Ala Ala Leu Met Glu
370                 375                 380

Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp Arg Leu Glu Asp Pro Thr
                405                 410                 415

Ala Phe His Thr Ala Gln Ala Thr Met Asp Lys Gly Arg Asp Gly Cys
            420                 425                 430

Arg Val Pro Leu Pro Trp Thr Ala Ser Asp Glu Pro Ala Leu Ala Asp
        435                 440                 445

Phe Ser Arg Pro Ala Pro Ala Asp Asp Gly Thr Gly Glu Asn His Val
    450                 455                 460

Pro Leu Cys Ala Ala Gly Gln Phe Gly Thr Gly Ala Ser Phe Gly Phe
465                 470                 475                 480

Ser Pro Ala Val Arg Ala Asp Gly Val Thr Pro Ala Ala Asp Pro His
                485                 490                 495

Leu Pro Gln Pro Leu Trp Phe Lys Asp Tyr Ala Val Asp Val Glu Gln
            500                 505                 510

Ala Asp Pro Asp Ser Met Tyr Thr Leu Tyr His Ala Ala Leu Ala Ile
        515                 520                 525

Arg Gln Glu Ser Leu Thr Ala Thr Arg Asp Thr Ala Glu Gln Val
530                 535                 540

Asp Met Gly Ala Asp Val Val Ala Tyr Arg Arg Ala Ala Val Glu Gly
545                 550                 555                 560

Arg Thr Phe Thr Ser Val Thr Asn Phe Gly Thr Ala Pro Val Ser Leu
                565                 570                 575

Pro Glu Gly Ser Val Val Leu Thr Ser Gly Pro Leu Thr Pro Asp Gly

```
                580             585             590
Gln Leu Pro Thr Asp Thr Ser Ala Trp Val Ile Lys
        595                 600
```

<210> SEQ ID NO 25
<211> LENGTH: 1815
<212> TYPE: DNA
<213> ORGANISM: Bifidobacterium longum

<400> SEQUENCE: 25

```
atgaccgcca acaacctcaa tgacgactgg tggaagcagg ccgtcgtcta ccagatctac      60
ccgcgcagct tcaaggacgt caacggcgac ggactcggcg acatcgccgg cgtcaccgag     120
aagatggatt acctgaagaa cctcggcgtc gacgcgatct ggctctcccc gttctacccc     180
tcggatctgg cggacggcgg ctacgacgtg atcgactacc gcaacgtcga cccgcgccta     240
ggcaccatgg acgacttcga cgcgatggcc gaggccgcgc acgaggccgg catcaaagtg     300
atcgtggaca tcgtgcccaa ccacaccgcc gacaagcacg tgttcttcaa ggaagccctc     360
gcctccgaac ctggctcccc cgcacgcgat cgctatatct ccgtgacgg ccgcggcgag      420 cacggcgaac tgccgccgaa cgactggcag tccttcttcg gcggcccggc ctgggcgcgc     480
gtgcccgacg gccagtggta cctgcatctg ttcgacaagg cgcagccgga cgtcaactgg     540
aagaatccgg acatccacga ggagttcaaa aagaccctgc gcttctggtc cgaccacggc     600
accgacggct tccgcatcga cgtagcgcac ggcctggcca agaccttga atccaagccg      660 ctggaggagc tcggccgcga atacagcgtg gtcggcgtgc tgaaccacga cttcagccac     720
ccgctgttcg accgccgcga ggtgcacgac atctaccgcg aatggcgcaa ggtgttcaac     780
gaatacactc cgccgcgctt cgccgtggcc gaggcgtggg tggtgcccga gcaccagcac     840
ctgtacgctt cgatggacga gctgggccag tccttcaact tcgacttcgc gcaggccaac     900
tggtatgccg acgagttccg caaggccatc gccgccgggc tcaaggcggc ggccgaaacc     960
ggcggctcca ccaccacgtg ggtcatgaac aatcatgacg tgccgcgcag cccctcccgc    1020
tatggtctgc cgcaggtcaa gggcgcgccg tatcaccagc tgccacacga ctggctgctg    1080
cgcgacggca ccacctaccc ggagaaccgc gaactcggca cccgccgtgc ccgtgccgcc    1140
gcgctgatgg agctcggcct gcccggtgcc gcatacatct atcagggcga ggaactgggc    1200
ctgtttgagg tggccgatat tccgtgggat cacttggagg atccgaccgc cttccacacc    1260
acccgcaaca cgatggacaa gggccgcgac ggctgccgcg tgccgctgcc gtggaccgcc    1320
gccgatgagc cggccttggc cgatttcagc cgtccggctc cggccgatga cggtaccggc    1380
gaaaaccatg tgccgctgtg cgccgccggc cagttcggca cgggcgcttc cttcggcttc    1440
tcccctgcgt tcgcgccga tggcgtgacg ccggccgccg accgcacct gccgcagccg       1500 ctgtggttca aggattacgc ggtggacgtg gagcaagccg acccggactc gatgctcgcg    1560
ctgtatcgcg ccgcactggc gattcgccag gagtcgctga ccgccacgcg cgacaccacg    1620
gccgagcagg tggacatggg cgacgatgtg gtggcgtaca cccgcgcggc ggttggcggg    1680
cgggtgttca cctcaatcac caacttcggc aatgccccgg tcgcgctgcc cgatggctcc    1740
gtggtgctgg cgtccggccc gctgacccccc gaaggccagc tccccaccga cacttctgcg    1800
tgggttatca agtag                                                     1815
```

<210> SEQ ID NO 26
<211> LENGTH: 604
<212> TYPE: PRT

-continued

<213> ORGANISM: Bifidobacterium longum

<400> SEQUENCE: 26

Met Thr Ala Asn Asn Leu Asn Asp Asp Trp Lys Gln Ala Val Val
1               5                   10                  15

Tyr Gln Ile Tyr Pro Arg Ser Phe Lys Asp Val Asn Gly Asp Gly Leu
            20                  25                  30

Gly Asp Ile Ala Gly Val Thr Glu Lys Met Asp Tyr Leu Lys Asn Leu
        35                  40                  45

Gly Val Asp Ala Ile Trp Leu Ser Pro Phe Tyr Pro Ser Asp Leu Ala
    50                  55                  60

Asp Gly Gly Tyr Asp Val Ile Asp Tyr Arg Asn Val Asp Pro Arg Leu
65                  70                  75                  80

Gly Thr Met Asp Asp Phe Asp Ala Met Ala Glu Ala His Glu Ala
            85                  90                  95

Gly Ile Lys Val Ile Val Asp Ile Val Pro Asn His Thr Ala Asp Lys
        100                 105                 110

His Val Phe Phe Lys Glu Ala Leu Ala Ser Glu Pro Gly Ser Pro Ala
    115                 120                 125

Arg Asp Arg Tyr Ile Phe Arg Asp Gly Arg Gly Glu His Gly Glu Leu
130                 135                 140

Pro Pro Asn Asp Trp Gln Ser Phe Phe Gly Gly Pro Ala Trp Ala Arg
145                 150                 155                 160

Val Pro Asp Gly Gln Trp Tyr Leu His Leu Phe Asp Lys Ala Gln Pro
            165                 170                 175

Asp Val Asn Trp Lys Asn Pro Asp Ile His Glu Glu Phe Lys Lys Thr
        180                 185                 190

Leu Arg Phe Trp Ser Asp His Gly Thr Asp Gly Phe Arg Ile Asp Val
    195                 200                 205

Ala His Gly Leu Ala Lys Asp Leu Glu Ser Lys Pro Leu Glu Glu Leu
210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
            245                 250                 255

Lys Val Phe Asn Glu Tyr Thr Pro Pro Arg Phe Ala Val Ala Glu Ala
        260                 265                 270

Trp Val Val Pro Glu His Gln His Leu Tyr Ala Ser Met Asp Glu Leu
    275                 280                 285

Gly Gln Ser Phe Asn Phe Phe Ala Gln Ala Asn Trp Tyr Ala Asp
290                 295                 300

Glu Phe Arg Lys Ala Ile Ala Ala Gly Leu Lys Ala Ala Ala Glu Thr
305                 310                 315                 320

Gly Gly Ser Thr Thr Thr Trp Val Met Asn Asn His Asp Val Pro Arg
            325                 330                 335

Ser Pro Ser Arg Tyr Gly Leu Pro Gln Val Lys Gly Ala Pro Tyr His
        340                 345                 350

Gln Leu Pro His Asp Trp Leu Leu Arg Asp Gly Thr Thr Tyr Pro Glu
    355                 360                 365

Asn Arg Glu Leu Gly Thr Arg Arg Ala Arg Ala Ala Leu Met Glu
370                 375                 380

Leu Gly Leu Pro Gly Ala Ala Tyr Ile Tyr Gln Gly Glu Glu Leu Gly
385                 390                 395                 400

```
Leu Phe Glu Val Ala Asp Ile Pro Trp Asp His Leu Glu Asp Pro Thr
                405                 410                 415
Ala Phe His Thr Thr Arg Asn Thr Met Asp Lys Gly Arg Asp Gly Cys
            420                 425                 430
Arg Val Pro Leu Pro Trp Thr Ala Ala Asp Glu Pro Ala Leu Ala Asp
        435                 440                 445
Phe Ser Arg Pro Ala Pro Ala Asp Asp Gly Thr Gly Glu Asn His Val
    450                 455                 460
Pro Leu Cys Ala Ala Gly Gln Phe Gly Thr Gly Ala Ser Phe Gly Phe
465                 470                 475                 480
Ser Pro Ala Val Arg Ala Asp Gly Val Thr Pro Ala Ala Asp Pro His
                485                 490                 495
Leu Pro Gln Pro Leu Trp Phe Lys Asp Tyr Ala Val Asp Val Glu Gln
            500                 505                 510
Ala Asp Pro Asp Ser Met Leu Ala Leu Tyr Arg Ala Ala Leu Ala Ile
        515                 520                 525
Arg Gln Glu Ser Leu Thr Ala Thr Arg Asp Thr Ala Glu Gln Val
    530                 535                 540
Asp Met Gly Asp Asp Val Val Ala Tyr Thr Arg Ala Ala Val Gly Gly
545                 550                 555                 560
Arg Val Phe Thr Ser Ile Thr Asn Phe Gly Asn Ala Pro Val Ala Leu
                565                 570                 575
Pro Asp Gly Ser Val Val Leu Ala Ser Gly Pro Leu Thr Pro Glu Gly
            580                 585                 590
Gln Leu Pro Thr Asp Thr Ser Ala Trp Val Ile Lys
        595                 600
```

<210> SEQ ID NO 27
<211> LENGTH: 1812
<212> TYPE: DNA
<213> ORGANISM: Artificial sequence
<220> FEATURE:
<223> OTHER INFORMATION: BloGlu3_codon-optimized

<400> SEQUENCE: 27

```
gtgacagcaa acaacctgaa tgacgactgg tggaaacagg ccgtcgtgta tcaaatttac      60
cctagatcat ttaaggacgt taatggcgat ggactgggag atattgcagg cgtcacggag     120
aagatggatt accttaaaaa cctgggcgtt gatgctattt ggctgtcacc gttttacccg     180
tcagacctgg ctgatggcgg ctatgacgtt atcgattata gaaatgtgga tcctagactg     240
ggcacaatgg atgattttga cgcaatggcc gaagccgcgc atgaagcggg aattaaagtt     300
attgttgata tcgttcctaa tcatacagca gataagcatg ttttttttcaa agaagcactg     360
gcctcagaac cgggctcacc tgcaagagat agatacattt tagagacgg aagaggcgaa     420
cacggcgagc tgcctccgaa tgactggcaa tcattttttg gaggacctgc atgggcaaga     480
gtccctgacg acaatggta tctgcacctt ttcgataaag cacaaccgga tgttaattgg     540
aaaaaccctg acatccatga gaatttaag aaaacactga ttttggtc agatcacggc      600
acagacggat ttagaattga tgtggcacat ggacttgcaa agatctgga agcaaaccg      660
ctggaggaac tgggaagaga gtacagcgtt gttggcgttc ttaatcatga cttttcacat     720
ccgctgtttg acagaagaga agtgcatgac atctacagag aatggagaaa ggtgttttaac     780
gaatatacac cgccgagatt tgcagtcgca gaagcatggg tggtgcctga acaccaacat     840
ctgtatgcat caatggacga gctgggccaa tcattcaatt tcgactttgc acaagctaat     900
```

```
tggtatgcag atgagttcag aaaagctatc gctgcgggcc tgaaagcagc agctgagacg    960
ggcggatcaa cgacaacatg ggtcatgaat aatcacgatg ttccgagatc accgtcaaga   1020
tatggcctgc cgcaggttaa gggcgcaccg tatcatcagc ttccgcacga ttggcttctg   1080
agagacggca cgacgtaccc ggagaataga gagctgggaa cgagaagagc aagagcagcg   1140
gcgcttatgg aacttggact gcctggagcg gcttacattt atcagggcga ggagcttggc   1200
cttttttgagg tggcagatat tccttgggat catcttgaag atccgacagc atttcacaca   1260
acaagaaata cgatggataa aggcagagat ggctgcagag tgcctctgcc gtggacagct   1320
gccgatgagc ctgcccttgc cgactttagc agaccggcac ctgccgacga cggaacggga   1380
gagaaccacg ttcctctgtg tgcagcgggc cagtttggca cgggagcatc atttggattc   1440
tcaccggccg ttagagccga tggcgttaca ccggctgcgg acccgcatct gcctcagccg   1500
ctgtggttta aagattatgc agttgacgtt gaacaagccg atcctgattc aatgctggca   1560
ctgtatagag ctgcacttgc tattagacaa gaatcactta cggcaacgag agatacaacg   1620
gcggaacagg tcgacatggg cgatgatgtc gtcgcatata cgagagcggc cgtgggagga   1680
agagttttta caagcattac aaattttggc aacgcacctg tcgcactgcc ggatggcagc   1740
gtcgttctgg cttcaggacc tctgacaccg gagggacaac tgcctacaga cacgtcagct   1800
tgggttatta ag                                                      1812

<210> SEQ ID NO 28
<211> LENGTH: 585
<212> TYPE: PRT
<213> ORGANISM: Bifidobacterium pseudolongum

<400> SEQUENCE: 28

Met Thr Leu Asn Asn Thr His Asp Asp Trp Trp Lys Gln Ala Val Val
1               5                   10                  15

Tyr Gln Val Tyr Pro Arg Ser Phe Arg Asp Ala Asn Gly Asp Gly Leu
            20                  25                  30

Gly Asp Ile Ala Gly Ile Thr Ser Arg Ile Pro Tyr Leu Arg Gln Leu
        35                  40                  45

Gly Val Asp Ala Leu Trp Leu Ser Pro Phe Tyr Pro Ser Glu Leu Ala
    50                  55                  60

Asp Gly Gly Tyr Asp Val Ile Asp Tyr Arg Asn Val Asp Pro Arg Leu
65                  70                  75                  80

Gly Thr Leu Asp Asp Phe Asp Ala Met Val Ala Ala His Ser Ala
                85                  90                  95

Gly Leu Lys Val Val Asp Ile Val Pro Asn His Thr Ser Asn Met
            100                 105                 110

His Pro Trp Phe Gln Glu Ala Leu Ala Ser Ala Pro Gly Ser Pro Ala
        115                 120                 125

Arg Asp Arg Tyr Ile Phe Arg Asp Gly Glu Gly Ala His Gly Glu Leu
    130                 135                 140

Pro Pro Asn Asn Trp Gln Ser Leu Phe Gly Gly Pro Ala Trp Glu Ala
145                 150                 155                 160

Ala Gly Asp Gly Gln Trp Tyr Leu His Leu Phe Thr Lys Glu Gln Pro
                165                 170                 175

Asp Leu Asn Trp Lys Asn Pro Asp Val His Glu Asp Phe Arg Thr Thr
            180                 185                 190

Leu Arg Phe Trp Ser Asp Arg Gly Val Asp Gly Phe Arg Ile Asp Val
        195                 200                 205
```

-continued

Ala His Gly Leu Ala Lys Asp Leu Asp Ser Glu Pro Leu Lys Asp Leu
    210                 215                 220

Glu Arg Phe Pro Val Gly Gly Asn Pro Val Pro Gly His Pro Leu Trp
225                 230                 235                 240

Asp Arg Pro Glu Val His Glu Ile Tyr Arg Glu Trp Asn Lys Val Phe
                245                 250                 255

Asn Glu Tyr Asp Pro Pro Arg Phe Ala Val Gly Glu Ala Trp Val Pro
            260                 265                 270

Ala Glu His Gln His Leu Tyr Ala Ser Lys Asp Glu Leu Gly Gln Val
        275                 280                 285

Phe Asn Phe Glu Phe Ala Lys Ala Asn Trp Phe Ala Asp Asp Phe Arg
290                 295                 300

Leu Ala Ile Glu Glu Gly Leu Ala Ser Ala Asp Glu Ser Lys Ser Thr
305                 310                 315                 320

Thr Thr Trp Val Met Ser Asn His Asp Val Pro Arg His Val Ser Arg
                325                 330                 335

Tyr Gly Leu Pro Gln Val His Thr Arg Gly Tyr His Glu Leu Pro Asn
            340                 345                 350

Asp Trp Leu Leu Arg Asn Gly Thr Thr Tyr Ile Glu Asp Arg Glu Leu
        355                 360                 365

Gly Thr Arg Arg Ala Arg Ala Ala Ile Leu Met Glu Leu Gly Leu Pro
370                 375                 380

Gly Ser Val Tyr Val Tyr Gln Gly Glu Glu Leu Gly Leu Pro Glu Val
385                 390                 395                 400

Ala Thr Ile Pro Trp Asp His Leu Glu Asp Pro Val Ala Phe Asn Thr
                405                 410                 415

Asp His Ser Asp Ala Ala Lys Gly Arg Asp Gly Cys Arg Val Pro Leu
            420                 425                 430

Pro Trp Ser Ala Gln Asp Met Pro Gln Pro Ala Pro Trp Asp Pro Glu
        435                 440                 445

Phe Gly Thr Gly Ala Ser Phe Gly Phe Ser Glu His Ala Gly Gly Arg
450                 455                 460

Ala Ser Ala Asp Pro His Leu Pro Gln Pro Leu Trp Tyr Ala Gly Tyr
465                 470                 475                 480

Ala Ala Asp Met Glu Asp Thr Asp Pro Ala Ser Met Leu Asn Leu Tyr
                485                 490                 495

Arg Arg Ala Met His Trp Arg Gln Glu His Leu Thr Pro Thr Gly Asp
            500                 505                 510

Thr Ser Leu Thr Trp Leu Ser Pro Gln Ser Phe Ala Asp Cys Gly Asp
        515                 520                 525

Asp Val Val Ala Tyr Ala Arg Pro Leu Ala Asp Ser Gly Asp Arg
530                 535                 540

Phe Val Cys Ile Val Asn Phe Gly Ala Ala Ser Ile Glu Leu Pro His
545                 550                 555                 560

Gly Asp Val Met Met Arg Ser Ile Pro Phe Asp Gly Tyr Gln Leu Pro
                565                 570                 575

Ala Asp Ala Ala Val Trp Met Arg Ile
            580                 585

<210> SEQ ID NO 29
<211> LENGTH: 1755
<212> TYPE: DNA
<213> ORGANISM: Artificial sequence
<220> FEATURE:
<223> OTHER INFORMATION: BpsGlu1_codon-optimized

<400> SEQUENCE: 29

```
gtgacactga ataatacaca cgatgactgg tggaaacaag ccgttgtgta tcaagtttat      60
ccgagatcat ttagagacgc taacggcgat ggactgggag acatcgcagg cattacgagc     120
agaatcccgt atcttagaca acttggcgtg gacgcgcttt ggctttcacc gttttatcct     180
agcgagctgg cagacggcgg atatgatgtt attgattaca gaaatgttga cccgagactt     240
ggcacactgg acgactttga tgctatggtg gcggctgccc atagcgcggg actgaaagtt     300
gttgttgata tcgttccgaa tcatacaagc aacatgcacc cttggttcca gaggcgctg      360
gcgagcgcac cgggatcacc tgcgagagat agatacattt tcagagatgg agaaggcgca     420
cacggcgagc ttccgcctaa caattggcaa agcctgtttg gaggaccggc tgggaagca      480
gcaggcgacg gacaatggta cctgcacctt tttacaaaag aacagcctga tctgaattgg     540
aaaaatcctg acgttcacga ggatttcaga acgacactta gattctggtc agacagaggc     600
gttgatggct ttagaatcga cgttgcacat ggacttgcga agacctgga tagcgaaccg      660
ctgaaggatc ttgagagatt cccggtcgga ggaaatccgg ttccgggcca tccgctgtgg     720
gatagacctg aagtgcacga gatttacaga gagtggaata agtctttaa tgaatacgac      780
ccgcctagat tcgctgttgg cgaagcatgg gtgcctgccg aacatcaaca tctttatgcc     840
tcaaaggatg agctgggaca agtgttcaac ttcgaatttg ctaaggcaaa ttggtttgca     900
gatgactta gactggcaat tgaggagggc ctggcctcag cggacgagtc aaaatcaacg      960
acaacatggg ttatgtcaaa tcacgacgtg ccgagacacg tgagcagata tggccttccg    1020
caagttcata cgagaggcta tcacgagctg cctaacgatt ggctgctgag aaatggcaca    1080
acatatattg aagatagaga actgggcaca agaagagcaa gagccgcgat cctgatggaa    1140
cttggacttc ctggatcagt ttatgtttat caaggcgagg agcttggcct gcctgaggtg    1200
gcaacaattc cttgggacca cctggaagat ccggtcgcct tcaacacaga tcactcagat    1260
gcagcaaaag aagagacgg atgtagagtg ccgctgccgt ggtcagctca ggatatgccg     1320
cagcctgcgc cgtgggatcc ggaatttggc acgggcgcat catttggatt ctcagagcat    1380
gccggaggca gagcttcagc agaccgcat ctgccgcaac ctctgtggta tgcaggctat     1440
gctgccgata tggaggatac ggatcctgcg tcaatgctga atctgtatag aagagctatg    1500
cactggagac aggagcatct tacacctaca ggcgatacac cactgacatg gctgtcaccg    1560
caatcattcg cagattgcgg agatgatgtc gtggcatacg caagaccgct ggctgacgat    1620
agcggcgaca gatttgtttg cattgttaac ttcggagcag cgagcatcga actgcctcac    1680
ggagacgtta tgatgagatc aatcccttc gatggatacc agcttcctgc ggacgctgcg     1740
gtgtggatga gaatt                                                   1755
```

<210> SEQ ID NO 30
<211> LENGTH: 585
<212> TYPE: PRT
<213> ORGANISM: Artificial sequence
<220> FEATURE:
<223> OTHER INFORMATION: BpsGlu1 protein_encoded by optimized sequence

<400> SEQUENCE: 30

```
Met Thr Leu Asn Asn Thr His Asp Asp Trp Trp Lys Gln Ala Val Val
1               5                   10                  15
Tyr Gln Val Tyr Pro Arg Ser Phe Arg Asp Ala Asn Gly Asp Gly Leu
            20                  25                  30
```

-continued

```
Gly Asp Ile Ala Gly Ile Thr Ser Arg Ile Pro Tyr Leu Arg Gln Leu
         35                  40                  45

Gly Val Asp Ala Leu Trp Leu Ser Pro Phe Tyr Pro Ser Glu Leu Ala
 50                  55                  60

Asp Gly Gly Tyr Asp Val Ile Asp Tyr Arg Asn Val Asp Pro Arg Leu
 65                  70                  75                  80

Gly Thr Leu Asp Asp Phe Asp Ala Met Val Ala Ala His Ser Ala
                 85                  90                  95

Gly Leu Lys Val Val Asp Ile Val Pro Asn His Thr Ser Asn Met
                100                 105                 110

His Pro Trp Phe Gln Glu Ala Leu Ala Ser Ala Pro Gly Ser Pro Ala
                115                 120                 125

Arg Asp Arg Tyr Ile Phe Arg Asp Gly Glu Gly Ala His Gly Glu Leu
130                 135                 140

Pro Pro Asn Asn Trp Gln Ser Leu Phe Gly Gly Pro Ala Trp Glu Ala
145                 150                 155                 160

Ala Gly Asp Gly Gln Trp Tyr Leu His Leu Phe Thr Lys Glu Gln Pro
                165                 170                 175

Asp Leu Asn Trp Lys Asn Pro Asp Val His Glu Asp Phe Arg Thr Thr
                180                 185                 190

Leu Arg Phe Trp Ser Asp Arg Gly Val Asp Gly Phe Arg Ile Asp Val
    195                 200                 205

Ala His Gly Leu Ala Lys Asp Leu Asp Ser Glu Pro Leu Lys Asp Leu
    210                 215                 220

Glu Arg Phe Pro Val Gly Gly Asn Pro Val Pro Gly His Pro Leu Trp
225                 230                 235                 240

Asp Arg Pro Glu Val His Glu Ile Tyr Arg Glu Trp Asn Lys Val Phe
                245                 250                 255

Asn Glu Tyr Asp Pro Pro Arg Phe Ala Val Gly Glu Ala Trp Val Pro
                260                 265                 270

Ala Glu His Gln His Leu Tyr Ala Ser Lys Asp Glu Leu Gly Gln Val
                275                 280                 285

Phe Asn Phe Glu Phe Ala Lys Ala Asn Trp Phe Ala Asp Asp Phe Arg
    290                 295                 300

Leu Ala Ile Glu Glu Gly Leu Ala Ser Ala Asp Glu Ser Lys Ser Thr
305                 310                 315                 320

Thr Thr Trp Val Met Ser Asn His Asp Val Pro Arg His Val Ser Arg
                325                 330                 335

Tyr Gly Leu Pro Gln Val His Thr Arg Gly Tyr His Glu Leu Pro Asn
                340                 345                 350

Asp Trp Leu Leu Arg Asn Gly Thr Thr Tyr Ile Glu Asp Arg Glu Leu
                355                 360                 365

Gly Thr Arg Arg Ala Arg Ala Ala Ile Leu Met Glu Leu Gly Leu Pro
    370                 375                 380

Gly Ser Val Tyr Val Tyr Gln Gly Glu Glu Leu Gly Leu Pro Glu Val
385                 390                 395                 400

Ala Thr Ile Pro Trp Asp His Leu Glu Asp Pro Val Ala Phe Asn Thr
                405                 410                 415

Asp His Ser Asp Ala Ala Lys Gly Arg Asp Gly Cys Arg Val Pro Leu
                420                 425                 430

Pro Trp Ser Ala Gln Asp Met Pro Gln Pro Ala Pro Trp Asp Pro Glu
    435                 440                 445

Phe Gly Thr Gly Ala Ser Phe Gly Phe Ser Glu His Ala Gly Gly Arg
```

```
            450                 455                 460
Ala Ser Ala Asp Pro His Leu Pro Gln Pro Leu Trp Tyr Ala Gly Tyr
465                 470                 475                 480

Ala Ala Asp Met Glu Asp Thr Asp Pro Ala Ser Met Leu Asn Leu Tyr
            485                 490                 495

Arg Arg Ala Met His Trp Arg Gln Glu His Leu Thr Pro Thr Gly Asp
            500                 505                 510

Thr Ser Leu Thr Trp Leu Ser Pro Gln Ser Phe Ala Asp Cys Gly Asp
            515                 520                 525

Asp Val Val Ala Tyr Ala Arg Pro Leu Ala Asp Asp Ser Gly Asp Arg
            530                 535                 540

Phe Val Cys Ile Val Asn Phe Gly Ala Ala Ser Ile Glu Leu Pro His
545                 550                 555                 560

Gly Asp Val Met Met Arg Ser Ile Pro Phe Asp Gly Tyr Gln Leu Pro
            565                 570                 575

Ala Asp Ala Ala Val Trp Met Arg Ile
            580                 585

<210> SEQ ID NO 31
<211> LENGTH: 1806
<212> TYPE: DNA
<213> ORGANISM: Bifidobacterium thermophilum

<400> SEQUENCE: 31
atggcagaac gcaagtcccc ccagtccgcg caagaatcca cggcatcgga tcgcgccgca      60
gcggcctggt ggcatcaagc ggtggtctat caggtctatc cgcgttcgtt caaggacacc     120
accggttccg gcctcggcga catcgccggt gttaccagcc gatcggcta cctcaagcaa     180 ctgggtgttg acgcgatttg gctcagcccc ttctatccga ccaactcgc cgatggcggg     240 tacgatgtcg atgattaccg caacgtcgac ccgaaactcg gtacgatgga cgatttcgac     300
aaactcgcca aaccgcgcca cgaggccggt atcaagattg tcgtcgatat cgttcccaac     360
cattcttcca acctgcaccc ctggttcaag gccgcgcttg cagctggtcc gggctcgccg     420
gaacgtgacc gctacatctt ccgtgacggc cgcggtgagc atggcgaact gccgcccacc     480
gactgggtgt cccatttcgg cggccccgcg tggacgcgcg tgcctgacgg ccagtggtat     540
ctgcacctgt tcaccgtgga gcagcccgac tggaactgga agaacccgga tgtgcaggcg     600
gacttcatca agaccctgcg ttttttggctt gatcacggcg ctgacggctt ccgtgtcgat     660
gttgcgcacg gctgtgcaa ggacctcgac gcgacaatc tcgaccagtg gagcgtcacc     720
ccgccaagcc tgcccgccga cggcagccat ccgctgtacg accgcgacga cgtgcatcag     780
atttatcgcg agtggcgcaa ggtgttcaac gaatatgatc cgccggcatt cgccgtggcc     840
gaggcgtggg ttaatcccgc gcggcagtat ctgtatgcgt ccgacgatga gctcggtcag     900
gtgttcaact tcgagttcgc gaagaagaac tgggtgcgtg acgacatgca tcaggcgatc     960
gaggaaggtc tcgaggcggc gcgtcgttct ggctctaccg ccacgtgggt gatgagtaat    1020
cacgatgttc cacgtcacgc cagccgttac gcactgccgc aagtgccgag cacgcggcat    1080
catcagttgg cgcatgactg gctgctgcgt gacggcacca gctatcacga ggatcgcgaa    1140
gccggtacgc gccgcgcccg gccgcgatt tgatggagc ttgcgttgcc cggttcggcg    1200
tacctgtacc agggcgaaga gcttggtctg ttcgaggtcg ctgatattcc gtggaacaag    1260
ctcgaggatc cgaccgcgcg caatagcgaa cgtgcggcca aggacaaggg cgcgacgggg    1320
tgccgcgtcc ccctgccgtg ggtcgccgcc gacggggtcg aggggtcgtt cggcttctcg    1380
```

```
cctcgtgtga atccgtggg cgctggcgtt tccgccgatc aggccgggca gccgtcggag    1440
cctgcacacc tgccgcaacc cgcatggttc gctgatttcg ccgccgaccg tgagagcgcg    1500
cagccggagt cgatgttgaa cctgtaccgc agggcgttgg cgttgcgcca tgagctgatg    1560
ccggccgaca caacgctgac ttggctggat gaagaccgcc cgtctgatgc ccggatggc    1620 gctgacggtc agcacggcgg cgtgattgct taccgccggt ccaacggctg ggcgagtgtg    1680
accaatttcg gtgcggaacc tgtcgcattg ccggcgggcg aggtgctgct cacctccggc    1740
gagctgtgct ccgacggccg gctgccgcaa gataccaccg tttggctgcg gttgaaccag    1800
gactga                                                               1806
```

<210> SEQ ID NO 32
<211> LENGTH: 601
<212> TYPE: PRT
<213> ORGANISM: Bifidobacterium thermophilum

<400> SEQUENCE: 32

```
Met Ala Glu Arg Lys Ser Pro Gln Ser Ala Gln Glu Ser Thr Ala Ser
1               5                   10                  15

Asp Arg Ala Ala Ala Trp Trp His Gln Ala Val Val Tyr Gln Val
            20                  25                  30

Tyr Pro Arg Ser Phe Lys Asp Thr Thr Gly Ser Gly Leu Gly Asp Ile
        35                  40                  45

Ala Gly Val Thr Ser Arg Ile Gly Tyr Leu Lys Gln Leu Gly Val Asp
    50                  55                  60

Ala Ile Trp Leu Ser Pro Phe Tyr Pro Ser Gln Leu Ala Asp Gly Gly
65                  70                  75                  80

Tyr Asp Val Asp Asp Tyr Arg Asn Val Asp Pro Lys Leu Gly Thr Met
                85                  90                  95

Asp Asp Phe Asp Lys Leu Ala Lys Thr Ala His Glu Ala Gly Ile Lys
            100                 105                 110

Ile Val Val Asp Ile Val Pro Asn His Ser Ser Asn Leu His Pro Trp
        115                 120                 125

Phe Lys Ala Ala Leu Ala Ala Gly Pro Gly Ser Pro Glu Arg Asp Arg
    130                 135                 140

Tyr Ile Phe Arg Asp Gly Arg Gly Glu His Gly Glu Leu Pro Pro Thr
145                 150                 155                 160

Asp Trp Val Ser His Phe Gly Gly Pro Ala Trp Thr Arg Val Pro Asp
                165                 170                 175

Gly Gln Trp Tyr Leu His Leu Phe Thr Val Glu Gln Pro Asp Trp Asn
            180                 185                 190

Trp Lys Asn Pro Asp Val Gln Ala Asp Phe Ile Lys Thr Leu Arg Phe
        195                 200                 205

Trp Leu Asp His Gly Ala Asp Gly Phe Arg Val Asp Val Ala His Gly
    210                 215                 220

Leu Cys Lys Asp Leu Asp Arg Asp Asn Leu Asp Gln Trp Ser Val Thr
225                 230                 235                 240

Pro Pro Ser Leu Pro Ala Asp Gly Ser His Pro Leu Tyr Asp Arg Asp
                245                 250                 255

Asp Val His Gln Ile Tyr Arg Glu Trp Arg Lys Val Phe Asn Glu Tyr
            260                 265                 270

Asp Pro Pro Ala Phe Ala Val Ala Glu Ala Trp Val Asn Pro Ala Arg
        275                 280                 285
```

```
Gln Tyr Leu Tyr Ala Ser Asp Asp Glu Leu Gly Gln Val Phe Asn Phe
290                 295                 300

Glu Phe Ala Lys Lys Asn Trp Val Arg Asp Asp Met His Gln Ala Ile
305                 310                 315                 320

Glu Glu Gly Leu Glu Ala Ala Arg Arg Ser Gly Ser Thr Ala Thr Trp
                325                 330                 335

Val Met Ser Asn His Asp Val Pro Arg His Ala Ser Arg Tyr Ala Leu
                340                 345                 350

Pro Gln Val Pro Ser Thr Arg His Gln Leu Ala His Asp Trp Leu
                355                 360                 365

Leu Arg Asp Gly Thr Ser Tyr His Glu Asp Arg Glu Ala Gly Thr Arg
370                 375                 380

Arg Ala Arg Ala Ala Ile Leu Met Glu Leu Ala Leu Pro Gly Ser Ala
385                 390                 395                 400

Tyr Leu Tyr Gln Gly Glu Glu Leu Gly Leu Phe Glu Val Ala Asp Ile
                405                 410                 415

Pro Trp Asn Lys Leu Glu Asp Pro Thr Ala Arg Asn Ser Glu Arg Ala
                420                 425                 430

Ala Lys Asp Lys Gly Arg Asp Gly Cys Arg Val Pro Leu Pro Trp Val
                435                 440                 445

Ala Ala Asp Gly Val Glu Gly Ser Phe Gly Phe Ser Pro Arg Val Lys
450                 455                 460

Ser Val Gly Ala Gly Val Ser Ala Asp Gln Ala Gly Gln Pro Ser Glu
465                 470                 475                 480

Pro Ala His Leu Pro Gln Pro Ala Trp Phe Ala Asp Phe Ala Ala Asp
                485                 490                 495

Arg Glu Ser Ala Gln Pro Glu Ser Met Leu Asn Leu Tyr Arg Arg Ala
                500                 505                 510

Leu Ala Leu Arg His Glu Leu Met Pro Ala Asp Thr Thr Leu Thr Trp
                515                 520                 525

Leu Asp Glu Asp Arg Pro Ser Asp Ala Pro Asp Gly Ala Asp Gly Gln
530                 535                 540

His Gly Gly Val Ile Ala Tyr Arg Arg Ser Asn Gly Trp Ala Ser Val
545                 550                 555                 560

Thr Asn Phe Gly Ala Glu Pro Val Ala Leu Pro Ala Gly Glu Val Leu
                565                 570                 575

Leu Thr Ser Gly Glu Leu Cys Ser Asp Gly Arg Leu Pro Gln Asp Thr
                580                 585                 590

Thr Val Trp Leu Arg Leu Asn Gln Asp
                595                 600

<210> SEQ ID NO 33
<211> LENGTH: 1803
<212> TYPE: DNA
<213> ORGANISM: Artificial sequence
<220> FEATURE:
<223> OTHER INFORMATION: BthGlu1_codon-optimized

<400> SEQUENCE: 33
gtggctgaaa gaaaatcacc gcaaagcgca caggaaagca cggcctcaga cagagcagcc      60
gcagcctggt ggcatcaggc cgttgtttat caagtttatc ctagatcatt caaggataca     120
acgggctcag gactgggcga tattgcagga gttacaagca gaatcggcta ccttaagcaa     180
cttggagtcg atgctatttg ctgtcaccg ttttacccgt cacaactggc cgatggcggc     240
tacgatgttg atgactacag aaacgtggat cctaaactgg cacaatgga tgattttgat     300
```

```
aagctggcaa aaacagcaca tgaggcggga atcaagattg ttgttgatat cgttccgaat    360
catagctcaa atctgcatcc gtggtttaaa gcagcactgg cagccggacc gggcagcccg    420
gagagagata gatacatttt cagagacggc agaggcgaac atggcgaact gcctcctaca    480
gactgggttt cacattttgg aggaccggct tggacaagag ttcctgatgg ccagtggtac    540
ctgcatcttt ttacggttga acagcctgat tggaattgga aaaaccctga cgtccaggcg    600
gacttcatta aaacacttag attctggctg gaccatggag cggatggctt tagagttgac    660
gttgcacatg gcctttgtaa ggaccttgac agagacaacc ttgatcagtg gtcagttacg    720
ccgccttcac tgcctgctga cggatcacac ccgctttatg atagagacga cgttcatcag    780
atttatagag aatggagaaa agttttttaac gaatacgatc ctcctgcgtt tgcagtggca    840
gaagcgtggg ttaatccggc tagacaatat ctttatgcaa cgacgacga gctgggacaa    900
gttttcaact ttgaatttgc caaaaagaat tgggtcagag atgatatgca tcaagcgatt    960
gaagaaggcc tggaagctgc tagaagaagc ggcagcacag caacatgggt tatgtcaaac   1020
catgatgtgc cgagacacgc gtcaagatac gcacttcctc aagttccgag cacaagacat   1080
caccaacttg ctcatgactg gcttctgaga acggaacgt cataccacga ggatagagag   1140
gctggaacaa gaagagccag agccgcaatt ctgatggagc tggccctgcc gggatcagca   1200
tatctgtatc agggcgaaga actgggactg tttgaggttg cagacattcc gtggaataag   1260
ctggaagatc cgacagcaag aaattcagaa agagcggcga aagacaaagg aagagatgga   1320
tgtagagtgc cgctgccttg ggtcgctgcc gacggagttg agggctcatt tggattctca   1380
cctagagtta agagcgtcgg agcgggagtt tcagcagacc aggccggaca accgagcgaa   1440
cctgcacatc tgcctcagcc ggcatggttc gccgatttcg cagccgacag agaatcagca   1500
caaccggagt caatgcttaa cctttacaga agagcgcttg ctctgagaca tgaacttatg   1560
cctgccgata cgacactgac atggcttgac gaagatagac cttcagacgc accggacgga   1620
gcagacggac agcatggagg cgttattgca tatagaagat caaacggctg ggcaagcgtt   1680
acaaatttcg gagctgaacc tgtcgcgctt cctgctggcg aggttcttct tacgagcgga   1740
gaactgtgta gcgatggcag acttccgcag gacacaacag tgtggcttag actgaatcag   1800
gat                                                                 1803
```

<210> SEQ ID NO 34
<211> LENGTH: 662
<212> TYPE: PRT
<213> ORGANISM: Bifidobacterium breve

<400> SEQUENCE: 34

```
Met Tyr Phe His Ile Asn His Leu His Asp Thr Val Val Ile Asn Val
1               5                   10                  15

Ile Ser Lys His Gly Phe Thr Val Ala Val Arg Val Leu Leu Asn Pro
            20                  25                  30

Ile Thr Thr Asn Pro Gln Gln Ser Gly Ala Thr His His Val Ser His
        35                  40                  45

Thr Ile Thr His Ala Gln Lys Gly Ile Gly Met Thr Ala Asn Asn Leu
    50                  55                  60

Asn Asp Asp Trp Trp Lys Gln Ala Val Val Tyr Gln Ile Tyr Pro Arg
65                  70                  75                  80

Ser Phe Lys Asp Val Asn Gly Asp Gly Ile Gly Asp Ile Ala Gly Val
                85                  90                  95
```

```
Thr Glu Lys Met Asp Tyr Leu Lys Asn Leu Gly Val Asp Ala Ile Trp
            100                 105                 110

Leu Ser Pro Phe Tyr Pro Ser Asp Leu Ala Asp Gly Gly Tyr Asp Val
        115                 120                 125

Ile Asp Tyr Arg Asn Val Asp Pro Arg Leu Gly Thr Met Asp Asp Phe
130                 135                 140

Asp Ala Met Ala Lys Ala Ala His Glu Ala Gly Ile Lys Val Ile Val
145                 150                 155                 160

Asp Ile Val Pro Asn His Thr Ala Asp Lys His Val Phe Phe Lys Glu
                165                 170                 175

Ala Leu Ala Ala Glu Pro Gly Ser Pro Ala Arg Asp Arg Tyr Ile Phe
            180                 185                 190

Arg Asp Gly Arg Gly Glu His Gly Glu Leu Pro Pro Asn Asp Trp Gln
        195                 200                 205

Ser Phe Phe Gly Gly Pro Ala Trp Ala Arg Val Ala Asp Gly Gln Trp
210                 215                 220

Tyr Leu His Leu Phe Asp Lys Ala Gln Pro Asp Val Asn Trp Lys Asn
225                 230                 235                 240

Pro Asp Ile His Glu Glu Phe Lys Lys Thr Leu Arg Phe Trp Ser Asp
                245                 250                 255

His Gly Thr Asp Gly Phe Arg Ile Asp Val Ala His Gly Leu Ala Lys
            260                 265                 270

Asp Leu Glu Ser Lys Pro Leu Glu Leu Gly Arg Glu Tyr Ser Val
        275                 280                 285

Val Gly Val Leu Asn His Asp Phe Ser His Pro Leu Phe Asp Arg Arg
        290                 295                 300

Glu Val His Asp Ile Tyr Arg Glu Trp Arg Lys Val Phe Asn Glu Tyr
305                 310                 315                 320

Asp Pro Pro Arg Phe Ala Val Ala Glu Ala Trp Val Pro Glu His
                325                 330                 335

Gln His Leu Tyr Ala Ser Met Asp Glu Leu Gly Gln Ser Phe Asn Phe
            340                 345                 350

Asp Phe Ala Gln Ala Ser Trp Tyr Ala Asp Glu Phe Arg Ala Ala Ile
        355                 360                 365

Ala Ala Gly Leu Lys Ala Ala Ala Glu Thr Gly Gly Ser Thr Thr Thr
370                 375                 380

Trp Val Met Asn Asn His Asp Val Pro Arg Ser Pro Ser Arg Tyr Gly
385                 390                 395                 400

Leu Pro Gln Val Lys Gly Ala Pro Tyr His Gln Leu Pro His Asp Trp
                405                 410                 415

Leu Leu Arg Asn Gly Thr Thr Tyr Pro Glu Asp Arg Glu Leu Gly Thr
            420                 425                 430

Arg Arg Ala Arg Ala Ala Leu Met Glu Leu Gly Leu Pro Gly Ala
        435                 440                 445

Ala Tyr Ile Tyr Gln Gly Glu Glu Leu Gly Leu Phe Glu Val Ala Asp
450                 455                 460

Ile Pro Trp Asp Arg Leu Glu Asp Pro Thr Ala Phe His Thr Ala Gln
465                 470                 475                 480

Ala Thr Met Asp Lys Gly Arg Asp Gly Cys Arg Val Pro Ile Pro Trp
                485                 490                 495

Thr Ala Ala Asn Glu Pro Thr Leu Ala Asp Phe Ser Arg Pro Ile Pro
            500                 505                 510

Ala Asp Asp Gly Thr Gly Glu Asn His Val Pro Leu Cys Ala Ala Gly
```

|    |    |    |    |    | 515 |    |    |    |    | 520 |    |    |    |    | 525 |    |    |
| Gln | Phe | Gly | Thr | Gly | Ala | Ser | Phe | Gly | Phe | Ser | Pro | Ala | Thr | Arg | Ala |
|    |    |    | 530 |    |    |    |    | 535 |    |    |    |    | 540 |    |    |

Gln Phe Gly Thr Gly Ala Ser Phe Gly Phe Ser Pro Ala Thr Arg Ala
                530                 535                 540

Glu Gly Val Thr Pro Ala Ala Asp Pro His Leu Pro Gln Pro Leu Trp
545                 550                 555                 560

Phe Lys Asp Tyr Ala Val Asp Val Glu Gln Ala Asp Pro Asp Ser Met
                565                 570                 575

Leu Ala Leu Tyr His Ala Ala Leu Ala Ile Arg Gln Glu Ser Leu Thr
                580                 585                 590

Ala Thr Arg Asp Thr Thr Ala Glu Gln Val Asp Met Gly Pro Asp Val
                595                 600                 605

Val Ala Tyr Thr Arg Ala Ala Val Gly Gly Arg Thr Phe Thr Ser Ile
                610                 615                 620

Thr Asn Phe Gly Thr Glu Pro Val Glu Leu Pro Gly Gly Ser Val Val
625                 630                 635                 640

Leu Thr Ser Gly Pro Leu Thr Pro Asp Gly Gln Leu Pro Thr Asp Thr
                645                 650                 655

Ser Ala Trp Val Ile Lys
                660

<210> SEQ ID NO 35
<211> LENGTH: 1812
<212> TYPE: DNA
<213> ORGANISM: Artificial sequence
<220> FEATURE:
<223> OTHER INFORMATION: BbrGlu2_codon-optimized

<400> SEQUENCE: 35

```
gtgacagcaa ataaccttaa tgacgactgg tggaaacaag cagtggttta ccaaatctat      60
cctagatcat tcaaggatgt taatggcgat ggaattggcg atattgcagg cgttacggaa     120
aaaatggatt acctgaaaaa tctgggagtt gacgctatct ggcttagccc ttttttacccg    180
agcgatctgg ccgacggagg ctatgatgtg attgactata gaaatgttga tccgagactg     240
ggaacgatgg atgatttcga tgcgatggct aaggcggcac atgaagcagg cattaaagtt     300
attgttgata ttgtcccgaa tcatacagct gacaaacatg tcttttttcaa agaagcactt    360
gcagcagaac cgggctcacc tgccagagac agatacatct ttagagatgg aagaggagaa     420
cacggcgaac ttccgcctaa tgactggcaa tcattctttg gcggaccggc atgggctaga     480
gtcgcagatg ccaatggta ccttcatctt ttcgacaagg cgcaacctga tgtcaattgg      540
aaaaaccctg acattcacga gaattcaag aaaacgctga tttttggtc agatcatggc       600
acggatggct tcagaatcga tgtggcacac ggacttgcaa agatctgga agcaaaccg       660
ctggaggaac ttggcagaga atatagcgtg gttggcgttc tgaaccatga ctttcacat      720
ccgctgttcg atagaagaga agttcatgat atctacagag agtggagaaa agtttttaac    780
gaatatgacc cgccgagatt tgccgttgca gaagcatggg tggtgcctga acaccaacac    840
ctgtatgcat caatggacga gctgggacaa tcattcaact ttgattttgc acaggcatca    900
tggtatgccg atgagtttag agctgccatt gccgcaggac ttaaggccgc agcggaaaca    960
ggaggctcaa cgacaacgtg ggtgatgaat aatcacgacg ttcctagaag cccgtcaaga   1020
tatggcctgc cgcaagttaa aggagcacct taccaccagc ttccgcacga ttggcttctg   1080
agaaatggaa caacatatcc ggaagataga gagcttggca cgagaagagc aagagcagcg   1140
gcactgatgg aactgggcct tcctggcgca gcatacattt atcagggcga agaactggga   1200
```

```
ctttttgaag tggcggatat tccgtgggat agacttgagg acccgacagc attccacaca   1260
gcacaagcga caatggataa aggaagagac ggatgcagag tgcctattcc ttggacagct   1320
gcaaatgaac ctacactggc agacttcagc agaccgattc cggcagacga cggaacgggc   1380
gaaaaccatg tcccgctgtg cgctgcagga caattcggca caggagcgtc attcggcttt   1440
agcccggcta caagagccga aggagttaca ccggctgcag atccgcatct gcctcaacct   1500
ctttggttta agattatgc agttgatgtc gagcaggccg accggattc aatgctggca    1560 ctgtatcatg cagcactggc gattagacaa gaatcactta cagcaacaag agacacgacg   1620
gcggaacaag tggatatggg ccctgacgtt gttgcatata cgagagcggc cgtgggcggc   1680
agaacattta catcaattac aaattttgga acggagcctg ttgaactgcc gggaggatca   1740
gttgttctga caagcggacc tctgacaccg gacggccaac tgcctacgga cacatcagct   1800
tgggtcatca aa                                                       1812

<210> SEQ ID NO 36
<211> LENGTH: 604
<212> TYPE: PRT
<213> ORGANISM: Artificial sequence
<220> FEATURE:
<223> OTHER INFORMATION: BbrGlu2 protein_encoded by optimized sequence

<400> SEQUENCE: 36

Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Ile
                20                  25                  30

Gly Asp Ile Ala Gly Val Thr Glu Lys Met Asp Tyr Leu Lys Asn Leu
            35                  40                  45

Gly Val Asp Ala Ile Trp Leu Ser Pro Phe Tyr Pro Ser Asp Leu Ala
        50                  55                  60

Asp Gly Gly Tyr Asp Val Ile Asp Tyr Arg Asn Val Asp Pro Arg Leu
65                  70                  75                  80

Gly Thr Met Asp Asp Phe Asp Ala Met Ala Lys Ala His Glu Ala
                85                  90                  95

Gly Ile Lys Val Ile Val Asp Ile Val Pro Asn His Thr Ala Asp Lys
            100                 105                 110

His Val Phe Phe Lys Glu Ala Leu Ala Ala Glu Pro Gly Ser Pro Ala
        115                 120                 125

Arg Asp Arg Tyr Ile Phe Arg Asp Gly Arg Gly Glu His Gly Glu Leu
    130                 135                 140

Pro Pro Asn Asp Trp Gln Ser Phe Phe Gly Gly Pro Ala Trp Ala Arg
145                 150                 155                 160

Val Ala Asp Gly Gln Trp Tyr Leu His Leu Phe Asp Lys Ala Gln Pro
                165                 170                 175

Asp Val Asn Trp Lys Asn Pro Asp Ile His Glu Glu Phe Lys Lys Thr
            180                 185                 190

Leu Arg Phe Trp Ser Asp His Gly Thr Asp Gly Phe Arg Ile Asp Val
        195                 200                 205

Ala His Gly Leu Ala Lys Asp Leu Glu Ser Lys Pro Leu Glu Glu Leu
    210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
                245                 250                 255
```

```
Lys Val Phe Asn Glu Tyr Asp Pro Arg Phe Ala Val Ala Glu Ala
            260                 265                 270

Trp Val Pro Glu His Gln His Leu Tyr Ala Ser Met Asp Glu Leu
            275                 280                 285

Gly Gln Ser Phe Asn Phe Asp Phe Ala Gln Ala Ser Trp Tyr Ala Asp
    290                 295                 300

Glu Phe Arg Ala Ala Ile Ala Ala Gly Leu Lys Ala Ala Ala Glu Thr
305                 310                 315                 320

Gly Gly Ser Thr Thr Thr Trp Val Met Asn Asn His Asp Val Pro Arg
                325                 330                 335

Ser Pro Ser Arg Tyr Gly Leu Pro Gln Val Lys Gly Ala Pro Tyr His
            340                 345                 350

Gln Leu Pro His Asp Trp Leu Leu Arg Asn Gly Thr Thr Tyr Pro Glu
            355                 360                 365

Asp Arg Glu Leu Gly Thr Arg Arg Ala Arg Ala Ala Leu Met Glu
370                 375                 380

Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp Arg Leu Glu Asp Pro Thr
                405                 410                 415

Ala Phe His Thr Ala Gln Ala Thr Met Asp Lys Gly Arg Asp Gly Cys
            420                 425                 430

Arg Val Pro Ile Pro Trp Thr Ala Ala Asn Glu Pro Thr Leu Ala Asp
            435                 440                 445

Phe Ser Arg Pro Ile Pro Ala Asp Asp Gly Thr Gly Glu Asn His Val
    450                 455                 460

Pro Leu Cys Ala Ala Gly Gln Phe Gly Thr Gly Ala Ser Phe Gly Phe
465                 470                 475                 480

Ser Pro Ala Thr Arg Ala Glu Gly Val Thr Pro Ala Asp Pro His
            485                 490                 495

Leu Pro Gln Pro Leu Trp Phe Lys Asp Tyr Ala Val Asp Val Glu Gln
            500                 505                 510

Ala Asp Pro Asp Ser Met Leu Ala Leu Tyr His Ala Ala Leu Ala Ile
            515                 520                 525

Arg Gln Glu Ser Leu Thr Ala Thr Arg Asp Thr Thr Ala Glu Gln Val
530                 535                 540

Asp Met Gly Pro Asp Val Val Ala Tyr Thr Arg Ala Ala Val Gly Gly
545                 550                 555                 560

Arg Thr Phe Thr Ser Ile Thr Asn Phe Gly Thr Glu Pro Val Glu Leu
                565                 570                 575

Pro Gly Gly Ser Val Val Leu Thr Ser Gly Pro Leu Thr Pro Asp Gly
            580                 585                 590

Gln Leu Pro Thr Asp Thr Ser Ala Trp Val Ile Lys
        595                 600
```

<210> SEQ ID NO 37
<211> LENGTH: 1821
<212> TYPE: DNA
<213> ORGANISM: Bifidobacterium breve

<400> SEQUENCE: 37

```
atgactactt tcaaccgcgc aataattcct gacgccattc gcaccaacgg agccacgccc      60
aacccgtggt ggtcgaatgc ggtggtgtac cagatctacc cgcggtcgtt ccaggacacg     120
```

```
aacggcgatg gtctcggcga cctgaagggc atcacctccc gcctcgacta tcttgccgat      180
ctcggcgtgg atgtgctctg gctctccccg gtctacaggt ccccgcaaga cgacaacggc      240
tacgacatct ccgactaccg ggacatcgac ccgctgttcg gcacgcttga cgacatggac      300
gagctgctgg ccgaagcgca caagcgcggc ctcaagatcg tgatggacct ggtggtcaac      360
cacacctccg acgagcacgc gtggttcgag gcgtcgaagg acaaggacga cccgcacgcc      420
gactggtact ggtggcgtcc cgcccgcccc ggccacgagc cgggcacgcc cggcgccgag      480
ccgaaccagt ggggctccta cttcggcggc tccgcatggg agtacagccc ggagcgcggc      540
gagtactacc tgcaccagtt ctcgaagaag cagcctgatc tcaactggga gaacccggcc      600
gtgcgccgtg cagtgtacga catgatgaat tggtggctcg atcgcggcat cgacggcttc      660
cgtatggacg tcatcaccct tatctccaag cgtacggatg caaacggcag gctccccggc      720
gagtacggtt ccgagctcca tgacctgccg gtggggagg agggctactc cagcccgaat      780
ccgttctgtg ccgacggtcc gcgtcaggac gagttcctcg ccgagatgcg ccgcgaggtg      840
ttcgacgggc gtgacggctt cctcaccgtc ggcgaggccc ccgggatcac cgccgaacgc      900
aacgagcaca tcaccaatcc ggccaatggg gagctggata tgctgttcct gttcgaacat      960
gtcgattttg attgtgatgg cgtcaagtgg aagcctctgc cgctcgattt gccgggattc     1020
aagcggatca tggccggata tcagactgct gtggagaacg tgggctgggc aagcttgttc     1080
actggtaacc acgatcagcc acgtgtggtc tctcgttggg gcgatgactc ctcggaggaa     1140
tcccgcgtgc gctcggccaa agcgcttggc ctgatgttgc acatgcatcg cggcaccccg     1200
tacgtatatc agggtgagga gctgggcatg accaatgctc acttcaccag cctcgatcag     1260
taccgcgacc ttgaatctct caatgcctat cgtcagaggg tcgaggaagc caaggtacaa     1320
tcgccggaat cgatgatggc gggtatcgcc gcgcgcggtc gcgacaattc gcgtacccca     1380
atgcaatggg atggttctgc ctatgccggt ttcaccgcac cggatgcagc gacggagccg     1440
tggatttccg tcaaccccgaa tcatgctgaa atcaatgcgg ccggcgaatt cgacgatcct     1500
gactcggtgt atgccttcta caagaagctc atcgccttgc gccacaacag ttcgattgtg     1560
gcggctggcg agtggcggct gattgatgcg gatgacgcgc atgtatatgc gttcacccgc     1620
acgcttggca acgagcgatt gctggttgtg gttaacctgt ccggccgaac cgtcgacttg     1680
ccgcgtgaat ccaccgagct gattgccggc ggcgtcactg agccagatat cattctctcc     1740
acgtacgacg cccctcacac tgtggtctcc ctcgccaacc gtgagcttga cccgtgggag     1800
gctgctgccg tccagctgta a                                                1821
```

```
<210> SEQ ID NO 38
<211> LENGTH: 419
<212> TYPE: DNA
<213> ORGANISM: Bifidobacterium breve
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
```

-continued

```
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (337)..(338)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (358)..(358)
```

<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t

<400> SEQUENCE: 38

```
mttnradart ngatnwwsna vvyyrsdtng dggdkgtsrd yadgvdvwsv yrsddngyds    60
dyrddgtddm daahkrgkvm dvvnhtsdha waskdkddha dwywwrargh gtganwgsyg   120
gsawysrgyy hskkdnwnav rravydmmnw wdrgdgrmdv tskrtdangr gygshdvggy   180
ssncadgrda mrrvdgrdgt vgagtarnht nangdmhvdd cdgvkwkdgk rmagytavnv   240
gwastgnhdr vvsrwgddss srvrsakagm hmhrgtyvyg gmtnahtsdy rdsnayrrva   300
kvssmmagaa rgrdnsrtmw dgsayagtad aatwsvnnha naagdddsvy aykkarhnss   360
vaagwrdadd ahvyatrtgn rvvvnsgrtv drstaggvtd stydahtvvs anrdwaaav    419
```

<210> SEQ ID NO 39
<211> LENGTH: 1818
<212> TYPE: DNA
<213> ORGANISM: Artificial sequence
<220> FEATURE:
<223> OTHER INFORMATION: BbrGlu5_codon-optimized

<400> SEQUENCE: 39

```
gtgacaacat tcaatagagc aattattccg gatgcgatta gaacaaatgg agccacaccg    60
aatccgtggt ggtcaaacgc agtggtctat caaatctatc cgagatcatt tcaagacaca   120
aacggagacg gccttggcga tcttaaggga atcacatcaa gactggatta tctggctgac   180
cttggagttg atgttctgtg gctgagcccg gtttatagat caccctcaaga cgacaatggc   240
tatgacatca gcgactatag agacattgat cctctgtttg gcacactgga tgatatggac   300
gagctgcttg cagaagcaca taaaagagga cttaaaatcg ttatggacct ggttgtgaac   360
catacatcag atgaacacgc atggtttgaa gcatcaaaag ataaagacga tccgcacgct   420
gactggtatt ggtggagacc tgctagaccg ggccatgaac cgggaacacc tggcgcagag   480
ccgaaccaat ggggctcata ttttggcgga tcagcatggg agtatagccc ggaaagaggc   540
gaatactatc ttcatcagtt ctcaaaaaaa caaccggatc tgaattggga aaatccggcg   600
gtcagaagag cggtgtacga tatgatgaac tggtggctgg atagaggaat tgatggattt   660
agaatggatg ttattacact gatttcaaaa agaacagacg ccaatggaag acttccggga   720
gaatatggat cagaactgca cgaccttcct gtgggcgaag agggctattc atcacctaat   780
ccgttttgcg ccgacggccc gagacaagat gaattccttg ccgaaatgag aagagaagtt   840
tttgacggaa gagatggctt tctgacagtc ggcgaagcac ctggaattac agcagaaaga   900
aacgaacaca ttacaaaccc tgcaaacggc gaacttgata tgctgttcct gttttgaacat   960
gtggactttg attgcgatgg cgttaaatgg aaaccgcttc cgctggatct tcctggcttt  1020
aaaagaatta tggcaggcta tcagacagca gttgaaaatg tcggatgggc atcactgttt  1080
acaggcaatc atgaccaacc gagagttgtc agcagatggg gcgatgactc atcagaggag  1140
agcagagtta gaagcgccaa agcactgggc cttatgctgc acatgcacag aggcacaccg  1200
```

```
tatgtttatc aaggcgagga acttggaatg acaaatgctc attttacgtc acttgaccag    1260
tacagagatc ttgagtcact taatgcttat agacaaagag ttgaagaagc caaggttcag    1320
tcacctgaaa gcatgatggc cggcattgca gctagaggca gagataattc aagaacgccg    1380
atgcaatggg atggaagcgc atacgcaggc tttacggcac ctgacgcagc tacggaaccg    1440
tggatttcag ttaatccgaa tcatgcagaa attaacgcag caggagaatt tgatgacccg    1500
gattcagtct atgcattcta caaaaaactg attgcactga cataatag cagcattgtt      1560 gcagcgggcg aatggagact tatcgatgca gacgatgcac acgtttatgc gtttacaaga    1620
acacttggca cgagagact gcttgtcgtg gttaatctga gcggcagaac agttgatctg     1680
ccgagagagt caacagagct tattgctggc ggcgtgacag aaccggacat tattctttca    1740
acatatgacg cccctcatac agtggtttca ctggcaaata gagagctgga cccgtgggaa    1800
gctgcggcag tgcagctg                                                  1818
```

<210> SEQ ID NO 40
<211> LENGTH: 1570
<212> TYPE: PRT
<213> ORGANISM: Streptococcus sp C150

<400> SEQUENCE: 40

```
Met Lys Lys Asn Trp Val Thr Ile Gly Val Thr Ala Leu Ser Met Val
1               5                   10                  15

Thr Val Ala Gly Gly Thr Leu Leu Glu Asp Gln Gln Val Gln Ala Asp
                20                  25                  30

Glu Gln Asn Ala Ala Asn Gln Ser Gly Asp Ser Ser Gln Asp Leu Leu
            35                  40                  45

Arg Glu Ala Ser Ala Thr Thr Asn Asp Thr Ala Thr Val Ala Pro
    50                  55                  60

Thr Ile Ser Ala Asp Ala Asn Thr Ala Ser Val Asn Ile Pro Val Ala
65                  70                  75                  80

Asp Ala Thr Asn Thr Thr Thr Ala Ala Thr Asp Arg Ala Ala Ala Pro
                85                  90                  95

Thr Thr Thr Ala Ala Thr Val Asp Thr Asn Ser Gly Asn Ala Ala Pro
            100                 105                 110

Ser Thr Asn Val Gln Ala Ala Ala Asp Thr Ser Ala Thr Pro Thr
        115                 120                 125

Asp Thr Asn Thr Asn Thr Asn Ala Ser Val Thr Ala Thr Asp Arg Ala
130                 135                 140

Val Ala Thr Asp Thr Ala Asn Thr Glu Ala Arg Thr Pro Ser Arg Arg
145                 150                 155                 160

Ala Leu Ala Glu Thr Arg Glu Ala Asn Thr Asn Thr Ser Thr Gly Ile
                165                 170                 175

Gln Trp Ile Asn Gly Lys Gln Tyr Tyr Val Asn Ser Asp Gly Ser Val
            180                 185                 190

Arg Lys Asn Phe Val Phe Glu Gln Asp Gly Lys Ser Tyr Tyr Phe Asp
        195                 200                 205

Ala Glu Thr Gly Ala Leu Ala Thr Lys Ser Gln Asp Glu Phe Ser Thr
    210                 215                 220

Glu Pro Ile Lys Ala Ala Val Asp Phe Ser Ser Gly Asn Gln Leu Tyr
225                 230                 235                 240

Lys Asn Asp Asn Lys Ser Leu Asp Gln Leu Asp Thr Phe Ile Thr Ala
                245                 250                 255
```

-continued

```
Asp Ala Trp Tyr Arg Pro Lys Ser Ile Leu Lys Asp Gly Lys Thr Trp
            260                 265                 270

Thr Ala Ser Thr Glu Ala Asp Lys Arg Pro Leu Leu Met Val Trp Trp
        275                 280                 285

Pro Asp Lys Ser Thr Gln Val Asn Tyr Leu Asn Tyr Met Gln Asn Gln
    290                 295                 300

Gly Leu Gly Ala Gly Ser Phe Ser Thr Asn Ser Ser Gln Glu Ser Leu
305                 310                 315                 320

Asn Leu Ala Ala Lys Ala Val Gln Thr Lys Ile Glu Glu Arg Ile Ala
                325                 330                 335

Arg Glu Gly Asn Thr Asn Trp Leu Arg Thr Ser Ile Asp Gln Phe Ile
            340                 345                 350

Lys Thr Gln Pro Gly Trp Asn Ser Ser Thr Glu Asn Ser Ser Tyr Asp
        355                 360                 365

His Leu Gln Gly Gly Gln Leu Leu Phe Asn Asn Ser Lys Gly Asp Thr
    370                 375                 380

Gly Asn Arg Thr Ser Tyr Ala Asn Ser Asp Tyr Arg Leu Leu Asn Arg
385                 390                 395                 400

Thr Pro Thr Asn Gln Ser Gly Thr Arg Lys Tyr Phe Lys Asp Asn Ser
                405                 410                 415

Ile Gly Gly Leu Glu Phe Leu Leu Ala Asn Asp Ile Asp Asn Ser Asn
            420                 425                 430

Pro Ala Val Gln Ala Glu Gln Leu Asn Trp Leu His Phe Met Met Asn
        435                 440                 445

Ile Gly Ser Ile Met Ala Asn Asp Pro Thr Ala Asn Phe Asp Gly Leu
    450                 455                 460

Arg Val Asp Ala Leu Asp Asn Val Asp Ala Asp Leu Leu Gln Ile Ala
465                 470                 475                 480

Ser Asp Tyr Phe Lys Ala Val Tyr Gly Val Asp Lys Ser Glu Ala Asn
                485                 490                 495

Ala Ile Lys His Leu Ser Tyr Leu Glu Ala Trp Ser Ala Asn Asp Pro
            500                 505                 510

Tyr Tyr Asn Lys Asp Thr Lys Gly Ala Gln Leu Pro Ile Asp Asn Ala
        515                 520                 525

Leu Arg Asn Ala Leu Thr Asn Leu Leu Met Arg Asp Lys Asn Thr Arg
    530                 535                 540

Met Gln Leu Gly Asp Met Thr Ala Phe Met Asn Ser Ser Leu Asn Pro
545                 550                 555                 560

Arg Gly Ala Asn Asp Lys Asn Gly Glu Arg Met Ala Asn Tyr Ile Phe
                565                 570                 575

Thr Arg Ala His Asp Thr Glu Ala Gln Thr Ile Ile Gln Arg Ile Ile
            580                 585                 590

Arg Asp Arg Ile Asn Pro Asn Leu Phe Gly Tyr Asn Phe Thr Arg Asp
        595                 600                 605

Glu Ile Lys Lys Ala Phe Glu Ile Tyr Asn Ala Asp Ile Asn Thr Ala
    610                 615                 620

His Lys Thr Tyr Ala Ser Tyr Asn Leu Pro Ser Val Tyr Ala Leu Met
625                 630                 635                 640

Leu Thr Asn Lys Asp Ser Val Thr Arg Val Tyr Tyr Gly Asp Leu Tyr
                645                 650                 655

Arg Glu Asp Gly His Tyr Met Ala Lys Lys Thr Pro Tyr Phe Asp Ala
            660                 665                 670

Ile Asp Thr Leu Leu Arg Ala Arg Ile Lys Tyr Val Ala Gly Gly Gln
```

-continued

```
            675                 680                 685
Asp Met Glu Val Lys Lys Val Gly Asn Asp Gly Leu Leu Thr Ser Val
    690                 695                 700
Arg Tyr Gly Lys Gly Ala Asn Asn Ser Thr Asp Trp Gly Thr Thr Glu
705                 710                 715                 720
Thr Arg Thr Gln Gly Met Gly Val Ile Leu Thr Asn Asn Tyr Asp Phe
                    725                 730                 735
Arg Leu Gly Ser Asn Glu Thr Val Thr Met Asn Met Gly Arg Ala His
                740                 745                 750
Arg Asn Gln Leu Tyr Arg Pro Leu Leu Leu Thr Lys Asp Gly Leu
            755                 760                 765
Ala Thr Tyr Leu Asn Asp Ser Asp Val Pro Ser Asn Leu Leu Lys Arg
    770                 775                 780
Thr Asp Trp Asn Gly Asn Leu Thr Phe Asn Ala Asn Asp Val Phe Gly
785                 790                 795                 800
Val Glu Asn Val Gln Val Ser Gly Tyr Leu Gly Val Trp Val Pro Val
                    805                 810                 815
Gly Ala Lys Ala Asn Gln Asp Ala Arg Thr Gln Pro Ser Asn Arg Ala
                820                  825                830
Asn Ser Asp Gly Gln Val Tyr Lys Ser Ser Ala Ala Leu Asp Ser Gln
            835                 840                 845
Val Met Tyr Glu Ala Phe Ser Asn Phe Gln Ala Phe Ala Asp Asp Gln
    850                 855                 860
Pro Glu Leu Tyr Met Asn Arg Val Leu Ala Lys Asn Thr Asp Leu Leu
865                 870                 875                 880
Lys Ala Trp Gly Val Thr Ser Val Gly Leu Pro Pro Gln Tyr Val Ser
                    885                 890                 895
Ser Lys Asp Gly Thr Phe Leu Asp Ser Thr Ile Asp Asn Gly Tyr Ala
                900                 905                 910
Phe Asp Asp Arg Tyr Asp Met Ala Leu Ser Gln Asn Asn Lys Tyr Gly
            915                 920                 925
Ser Leu Glu Asp Leu Leu Asn Val Leu Arg Ala Leu His Lys Asp Gly
    930                 935                 940
Ile Gln Ala Ile Ala Asp Trp Val Pro Asp Gln Ile Tyr Asn Leu Pro
945                 950                 955                 960
Gly Lys Glu Val Val Asn Ala Thr Arg Val Asn Gly Tyr Gly Tyr His
                    965                 970                 975
Gln Gln Gly Tyr Gln Ile Val Asp Gln Ala Tyr Val Ala Asn Thr Arg
                980                 985                 990
Thr Asp Gly Thr Asp Tyr Gln Gly Arg Tyr Gly Gly Ala Phe Leu Asp
            995                 1000                1005
Glu Leu Lys Ala Lys Tyr Pro Ser Ile Phe Asn Arg Val Gln Ile
    1010                1015                1020
Ser Asn Gly Lys Gln Leu Pro Thr Asn Glu Lys Ile Thr Lys Trp
    1025                1030                1035
Ser Ala Lys Tyr Phe Asn Gly Thr Asn Ile Leu Gly Arg Gly Ile
    1040                1045                1050
Asn Tyr Val Leu Arg Asp Asp Lys Thr Asn Gln Tyr Phe Asn Thr
    1055                1060                1065
Ser Ala Asn Gly Gln Leu Leu Pro Thr Pro Leu Arg Asp Thr Gly
    1070                1075                1080
Ala Ile Thr Ser Thr Gln Val Phe Gln Arg Arg Gly Gln Asp Val
    1085                1090                1095
```

```
Tyr Phe Leu Arg Asp Asn Gln Val Ile Lys Asn Glu Phe Val Gln
    1100            1105                1110

Asp Gly Asn Gly Asn Trp Tyr Tyr Phe Gly Ala Asp Gly Lys Met
    1115            1120                1125

Thr Lys Gly Ala Gln Asn Ile Asn Ser Lys Asp Tyr Tyr Phe Phe
    1130            1135                1140

Asp Asn Gly Val Gln Leu Arg Asn Ala Leu Arg Arg Ala Ser Asn
    1145            1150                1155

Gly Tyr Thr Tyr Tyr Tyr Gly Leu Asp Gly Ala Met Ile Lys Asn
    1160            1165                1170

Ala Phe Val Asp Phe Asp Lys His Gln Gln Val Arg Ala Phe
    1175            1180                1185

Thr Thr Gln Gly Thr Met Val Val Gly Asn Leu His Trp Ser Gly
    1190            1195                1200

His His Phe Tyr Phe Asp Arg Glu Thr Gly Ile Gln Ala Lys Asp
    1205            1210                1215

Arg Ile Val Arg Thr Asp Asp Gly Lys Leu His Tyr Tyr Val Ala
    1220            1225                1230

Gln Thr Gly Asp Met Gly Arg Asn Val Phe Ala Thr Asp Ser Arg
    1235            1240                1245

Thr Gly Lys Arg Tyr Tyr Phe Asp Ala Asp Gly Asn Thr Val Thr
    1250            1255                1260

Gly Ser Arg Val Ile Asp Gly Lys Thr Tyr Tyr Phe Asn Gln Asp
    1265            1270                1275

Gly Ser Val Gly Thr Ala Tyr Ser Asn Arg Ala Asp Ser Ile Ile
    1280            1285                1290

Phe Glu Asn Gly Lys Ala Arg Tyr Ile Thr Pro Ala Gly Glu Ile
    1295            1300                1305

Gly Arg Ser Ile Phe Val Tyr Asn Pro Ala Thr Lys Ala Trp Asn
    1310            1315                1320

Tyr Phe Asp Lys Glu Gly Asn Arg Val Thr Gly Arg Gln Tyr Ile
    1325            1330                1335

Asp Gly Asn Leu Tyr Tyr Phe Lys Glu Asp Gly Ser Gln Val Lys
    1340            1345                1350

Gly Ala Ile Val Glu Glu Asn Gly Ile Lys Tyr Tyr Tyr Glu Pro
    1355            1360                1365

Gly Ser Gly Ile Leu Ala Ser Gly Arg Tyr Leu Gln Val Gly Asp
    1370            1375                1380

Asp Gln Trp Ile Tyr Phe Lys His Asp Gly Ser Leu Ala Ile Gly
    1385            1390                1395

Gln Val Arg Ala Asp Gly Gly Tyr Leu Lys Tyr Phe Asp Lys Asn
    1400            1405                1410

Gly Ile Gln Val Lys Gly Gln Thr Ile Val Glu Asp Gly His Thr
    1415            1420                1425

Tyr Tyr Tyr Asp Ala Asp Ser Gly Ala Leu Val Thr Ser Ser Phe
    1430            1435                1440

Ala Glu Ile Ala Pro Asn Gln Trp Ala Tyr Phe Asn Thr Glu Gly
    1445            1450                1455

Gln Ala Leu Lys Gly Lys Trp Thr Ile Asn Gly Lys Glu Tyr Tyr
    1460            1465                1470

Phe Asp Gln Asn Gly Ile Gln Tyr Lys Gly Lys Ala Val Lys Val
    1475            1480                1485
```

```
Gly Ser Arg Tyr Lys Tyr Tyr Asp Glu Asn Asp Gly Gln Pro Val
    1490            1495                1500

Thr Asn Arg Phe Ala Gln Ile Glu Pro Asn Val Trp Ala Tyr Phe
    1505            1510                1515

Gly Ala Asp Gly Tyr Ala Val Thr Gly Glu Gln Val Ile Asn Gly
    1520            1525                1530

Gln His Leu Tyr Phe Asp Gln Ser Gly Arg Gln Val Lys Gly Ala
    1535            1540                1545

Tyr Val Thr Val Asn Gly Gln Arg Arg Tyr Tyr Asp Ala Asn Thr
    1550            1555                1560

Gly Glu Tyr Ile Pro Gly Arg
    1565            1570

<210> SEQ ID NO 41
<211> LENGTH: 4179
<212> TYPE: DNA
<213> ORGANISM: Streptococcus sp C150

<400> SEQUENCE: 41
atcaatggca aacagtacta tgtaaattcg gacggtagcg tgcgtaagaa tttcgttttt     60
gaacaggatg gtaagagcta ctactttgac gcggaaactg gcgcgctggc cactaaaagc    120
caagatgaat ttagcacgga gccgattaaa gcagcagtgg acttctctag cggcaaccag    180
ctgtacaaaa atgacaacaa atcgctggat cagctggata cgtttatcac cgctgacgca    240
tggtaccgcc ctaagtctat tctgaaggat ggcaaaacct ggaccgcgtc taccgaagct    300
gataagcgtc cgttgctgat ggtgtggtgg ccggacaagt ccacccaagt taactacctg    360
aactacatgc agaaccaggg tttgggtgcg ggtagcttca gcaccaatag cagccaagaa    420
tccctgaatc tggctgcgaa agcagttcag accaagatcg aagaacgcat cgcacgtgag    480
ggtaacacca attggctgcg taccagcatt gaccaattca ttaagacgca gccaggctgg    540
aacagcagca ctgagaatag cagctatgat cacttgcagg gtggtcaact gctgttcaat    600
aacagcaaag gtgatacggg taaccgcacc agctatgcga atagcgacta tcgtctgctg    660
aaccgtaccc caactaatca aagcggcacc cgtaagtact ttaaggataa ttccatcggt    720
ggtctggaat ttctgctggc aaacgacatc gacaacagca accctgccgt tcaggcggag    780
cagctgaact ggctgcactt catgatgaac attggttcta tcatggcgaa tgacccgacg    840
gcgaactttg atggtttgcg tgtggacgcg ttggataacg tggatgcgga cctgttgcag    900
atcgcgagcg attacttcaa ggcagtctac ggtgttgata atccgaggc gaatgcgatc    960
aagcacctga gctatctgga ggcgtggagc gccaatgacc cgtattacaa caaggatacc   1020
aaaggcgcgc aactgccgat tgacaacgcg ctgcgcaacg cactgaccaa cctgttgatg   1080
cgtgacaaga atacgcgcat gcagctgggt gacatgacgg cgtttatgaa tagctctctg   1140
aacccacgtg gtgcgaatga caaaaacggc gagcgtatgg cgaattacat tttcacccgc   1200
gcacacgata ccgaggcgca gaccatcatt cagcgtatta tccgcgatcg tatcaatccg   1260
aacctgtttg gctacaattt caccccgcga gaaatcaaaa aggcgtttga gatctacaac   1320
gcggacatta cacgcgcgca taagacgtac gcgagctaca atctgccgtc cgtctacgca   1380
ctgatgctga cgaataagga cagcgtgacc cgtgtgtatt acggtgacct gtatcgtgag   1440
gacggtcact acatggccaa gaaaacgcct tatttcgatg caatcgatac cctgctgcgt   1500
gcgcgcatca aatacgtggc gggtggtcaa gacatggagg tgaagaaagt tggtaatgac   1560
ggcttgctga cgagcgtccg ctatggcaag ggtgcgaaca atagcaccga ctggggcacg   1620
```

```
actgaaaccc gtacccaagg tatgggcgtt atcctgacga acaactatga tttccgcctg   1680
ggcagcaacg aaaccgtcac gatgaacatg ggccgtgcgc atcgcaatca gctgtatcgt   1740
ccgctgctgc tgacgaccaa ggatggtctg gccacgtacc tgaatgatag cgacgtgcct   1800
tcgaatttgc tgaaacgcac ggactggaat ggtaacttga cctttaatgc caacgatgtg   1860
tttggtgtag agaacgtcca ggtcagcggt tacctgggtg tttgggtacc ggttggtgct   1920
aaagctaacc aggatgcgcg tacccaaccg agcaaccgtg cgaacagcga tggtcaggtc   1980
tataagtcgt ctgcggcatt ggacagccag gtcatgtatg aggcgtttag caattttcag   2040
gcatttgcgg acgatcaacc ggaactgtac atgaaccgcg ttctggcgaa gaacaccgat   2100
ctgctgaaag cgtggggcgt tactagcgtt ggcttgccgc acaatacgt tagcagcaaa   2160 gacggcacct tcctggatag cactattgat aacggctatg cgttcgatga tcgttacgac   2220
atggcgctga gccagaacaa caaatacggt tctctggagg acttgctgaa cgttctgcgc   2280
gctctgcaca agacggtat tcaggcgatt gcggactggg tcccggatca aatctacaat   2340
ttgccgggta agaggttgt taatgcgacg cgtgttaacg gttacggtta ccatcagcag   2400
ggctaccaga ttgttgacca ggcgtacgtt gcaaacaccc gtacgatgg taccgattat   2460 cagggtcgtt acggtggtgc ttttctggac gaactgaagg cgaagtaccc gagcattttc   2520
aatcgtgtcc agattagcaa cggtaaacag ctgccaacca atgagaaaat cacgaaatgg   2580
tccgcgaaat acttcaatgg cacgaacatc ctgggccgtg gtattaacta tgtgctgcgc   2640
gacgacaaga ccaatcagta tttcaacacc agcgcaaacg ccaactgct gccgacgcca   2700 ctgcgcgaca ccggtgccat caccagcacg caagttttcc agcgtcgtgg ccaagacgtc   2760
tattttctgc gtgataacca ggttatcaaa acgagtttg tgcaagatgg taacggtaat   2820
tggtactact tcggtgccga cggtaaaatg acgaaggggtg cacaaaacat caatagcaag   2880
gattactatt tcttcgataa tggcgtccag ctgcgtaatg cgctgcgtcg cgcgtccaat   2940
ggttacacct actattatgg cctggacggt gccatgatca gaacgctttt cgtcgatttt   3000
gatgataagc accaacaggt gcgtgcgttt actacgcagg gcacgatggt ggtcggtaat   3060
ttgcactgga gcggtcacca cttctatttt gaccgcgaaa cgggtatcca agccaaagac   3120
cgcattgtgc gtaccgatga tggcaagctg cactattatg tcgcacaaac cggcgatatg   3180
ggccgcaatg tgtttgcgac cgacagccgc acgggcaagc gctattactt tgatgcggac   3240
ggcaacaccg ttacgggctc ccgtgtcatc gacggcaaga cctactactt caaccaggac   3300
ggttcggtcg gtaccgcgta cagcaatcgt gcggatagca ttatctttga aatggcaag   3360 gctcgctata tcactccggc tggcgagatt ggccgttcca tttttgtcta caacccggcg   3420
accaaagcgt ggaattactt cgacaaggaa ggtaaccgtg tcaccggtcg tcagtatatt   3480
gacggcaatc tgtactactt taaagaggac ggctcccaag tgaaaggtgc gattgttgaa   3540
gagaacggta tcaagtacta ctacgaaccg ggcagcggta tcctggcgag cggtcgttat   3600
ctgcaagtcg gtgacgacca atggatctac ttcaaacacg acggtagcct ggcgatcggt   3660
caggttcgtg cagacggtgg ttacttgaaa tactttgata agaatggcat ccaggtcaag   3720
ggccaaacca ttgtgaggga tggtcatacc tattactacg atgccgactc cggtgctctg   3780
gtgacctcta gcttcgcgga gattgctccg aaccagtggg cctacttcaa taccgagggc   3840
caagccctga gggcaaatg gaccatcaat ggtaaagagt actatttga tcagaacggc   3900 attcagtata aaggcaaggc agttaaggtc ggcagccgtt acaaatacta tgacgagaat   3960
```

-continued

```
gacggtcaac cggtcactaa ccgttttgcc cagattgagc cgaacgtctg ggcgtacttt    4020
ggtgccgatg gctacgcagt tactggcgaa caggtgatta atggccagca cctgtacttc    4080
gatcagtcgg gtcgtcaggt taaaggtgcg tacgtcaccg tgaatggtca acgtcgttac    4140
tacgacgcaa acacgggtga atacattccg ggtcgttaa                           4179
```

<210> SEQ ID NO 42
<211> LENGTH: 1392
<212> TYPE: PRT
<213> ORGANISM: Streptococcus sp C150

<400> SEQUENCE: 42

```
Ile Asn Gly Lys Gln Tyr Tyr Val Asn Ser Asp Gly Ser Val Arg Lys
1               5                   10                  15

Asn Phe Val Phe Glu Gln Asp Gly Lys Ser Tyr Tyr Phe Asp Ala Glu
                20                  25                  30

Thr Gly Ala Leu Ala Thr Lys Ser Gln Asp Glu Phe Ser Thr Glu Pro
            35                  40                  45

Ile Lys Ala Ala Val Asp Phe Ser Ser Gly Asn Gln Leu Tyr Lys Asn
        50                  55                  60

Asp Asn Lys Ser Leu Asp Gln Leu Asp Thr Phe Ile Thr Ala Asp Ala
65                  70                  75                  80

Trp Tyr Arg Pro Lys Ser Ile Leu Lys Asp Gly Lys Thr Trp Thr Ala
                85                  90                  95

Ser Thr Glu Ala Asp Lys Arg Pro Leu Leu Met Val Trp Trp Pro Asp
            100                 105                 110

Lys Ser Thr Gln Val Asn Tyr Leu Asn Tyr Met Gln Asn Gln Gly Leu
        115                 120                 125

Gly Ala Gly Ser Phe Ser Thr Asn Ser Ser Gln Glu Ser Leu Asn Leu
    130                 135                 140

Ala Ala Lys Ala Val Gln Thr Lys Ile Glu Glu Arg Ile Ala Arg Glu
145                 150                 155                 160

Gly Asn Thr Asn Trp Leu Arg Thr Ser Ile Asp Gln Phe Ile Lys Thr
                165                 170                 175

Gln Pro Gly Trp Asn Ser Ser Thr Glu Asn Ser Ser Tyr Asp His Leu
            180                 185                 190

Gln Gly Gly Gln Leu Leu Phe Asn Asn Ser Lys Gly Asp Thr Gly Asn
        195                 200                 205

Arg Thr Ser Tyr Ala Asn Ser Asp Tyr Arg Leu Leu Asn Arg Thr Pro
    210                 215                 220

Thr Asn Gln Ser Gly Thr Arg Lys Tyr Phe Lys Asp Asn Ser Ile Gly
225                 230                 235                 240

Gly Leu Glu Phe Leu Leu Ala Asn Asp Ile Asp Asn Ser Asn Pro Ala
                245                 250                 255

Val Gln Ala Glu Gln Leu Asn Trp Leu His Phe Met Met Asn Ile Gly
            260                 265                 270

Ser Ile Met Ala Asn Asp Pro Thr Ala Asn Phe Asp Gly Leu Arg Val
        275                 280                 285

Asp Ala Leu Asp Asn Val Asp Ala Asp Leu Leu Gln Ile Ala Ser Asp
    290                 295                 300

Tyr Phe Lys Ala Val Tyr Gly Val Asp Lys Ser Glu Ala Asn Ala Ile
305                 310                 315                 320

Lys His Leu Ser Tyr Leu Glu Ala Trp Ser Ala Asn Asp Pro Tyr Tyr
                325                 330                 335
```

```
Asn Lys Asp Thr Lys Gly Ala Gln Leu Pro Ile Asp Asn Ala Leu Arg
                340                 345                 350

Asn Ala Leu Thr Asn Leu Leu Met Arg Asp Lys Asn Thr Arg Met Gln
            355                 360                 365

Leu Gly Asp Met Thr Ala Phe Met Asn Ser Ser Leu Asn Pro Arg Gly
        370                 375                 380

Ala Asn Asp Lys Asn Gly Glu Arg Met Ala Asn Tyr Ile Phe Thr Arg
385                 390                 395                 400

Ala His Asp Thr Glu Ala Gln Thr Ile Ile Gln Arg Ile Ile Arg Asp
                405                 410                 415

Arg Ile Asn Pro Asn Leu Phe Gly Tyr Asn Phe Thr Arg Asp Glu Ile
            420                 425                 430

Lys Lys Ala Phe Glu Ile Tyr Asn Ala Asp Ile Asn Thr Ala His Lys
        435                 440                 445

Thr Tyr Ala Ser Tyr Asn Leu Pro Ser Val Tyr Ala Leu Met Leu Thr
    450                 455                 460

Asn Lys Asp Ser Val Thr Arg Val Tyr Tyr Gly Asp Leu Tyr Arg Glu
465                 470                 475                 480

Asp Gly His Tyr Met Ala Lys Lys Thr Pro Tyr Phe Asp Ala Ile Asp
                485                 490                 495

Thr Leu Leu Arg Ala Arg Ile Lys Tyr Val Ala Gly Gly Gln Asp Met
            500                 505                 510

Glu Val Lys Lys Val Gly Asn Asp Gly Leu Leu Thr Ser Val Arg Tyr
        515                 520                 525

Gly Lys Gly Ala Asn Asn Ser Thr Asp Trp Gly Thr Thr Glu Thr Arg
    530                 535                 540

Thr Gln Gly Met Gly Val Ile Leu Thr Asn Asn Tyr Asp Phe Arg Leu
545                 550                 555                 560

Gly Ser Asn Glu Thr Val Thr Met Asn Met Gly Arg Ala His Arg Asn
                565                 570                 575

Gln Leu Tyr Arg Pro Leu Leu Leu Thr Thr Lys Asp Gly Leu Ala Thr
            580                 585                 590

Tyr Leu Asn Asp Ser Asp Val Pro Ser Asn Leu Leu Lys Arg Thr Asp
        595                 600                 605

Trp Asn Gly Asn Leu Thr Phe Asn Ala Asn Asp Val Phe Gly Val Glu
    610                 615                 620

Asn Val Gln Val Ser Gly Tyr Leu Gly Val Trp Pro Val Gly Ala
625                 630                 635                 640

Lys Ala Asn Gln Asp Ala Arg Thr Gln Pro Ser Asn Arg Ala Asn Ser
                645                 650                 655

Asp Gly Gln Val Tyr Lys Ser Ser Ala Ala Leu Asp Ser Gln Val Met
            660                 665                 670

Tyr Glu Ala Phe Ser Asn Phe Gln Ala Phe Ala Asp Gln Pro Glu
        675                 680                 685

Leu Tyr Met Asn Arg Val Leu Ala Lys Asn Thr Asp Leu Leu Lys Ala
    690                 695                 700

Trp Gly Val Thr Ser Val Gly Leu Pro Pro Gln Tyr Val Ser Ser Lys
705                 710                 715                 720

Asp Gly Thr Phe Leu Asp Ser Thr Ile Asp Asn Gly Tyr Ala Phe Asp
                725                 730                 735

Asp Arg Tyr Asp Met Ala Leu Ser Gln Asn Asn Lys Tyr Gly Ser Leu
            740                 745                 750

Glu Asp Leu Leu Asn Val Leu Arg Ala Leu His Lys Asp Gly Ile Gln
```

```
              755                 760                 765
    Ala Ile Ala Asp Trp Val Pro Asp Gln Ile Tyr Asn Leu Pro Gly Lys
    770                 775                 780

Glu Val Val Asn Ala Thr Arg Val Asn Gly Tyr Gly Tyr His Gln Gln
    785                 790                 795                 800

Gly Tyr Gln Ile Val Asp Gln Ala Tyr Val Ala Asn Thr Arg Thr Asp
                        805                 810                 815

Gly Thr Asp Tyr Gln Gly Arg Tyr Gly Gly Ala Phe Leu Asp Glu Leu
                        820                 825                 830

Lys Ala Lys Tyr Pro Ser Ile Phe Asn Arg Val Gln Ile Ser Asn Gly
                        835                 840                 845

Lys Gln Leu Pro Thr Asn Glu Lys Ile Thr Lys Trp Ser Ala Lys Tyr
    850                 855                 860

Phe Asn Gly Thr Asn Ile Leu Gly Arg Gly Ile Asn Tyr Val Leu Arg
    865                 870                 875                 880

Asp Asp Lys Thr Asn Gln Tyr Phe Asn Thr Ser Ala Asn Gly Gln Leu
                        885                 890                 895

Leu Pro Thr Pro Leu Arg Asp Thr Gly Ala Ile Thr Ser Thr Gln Val
                        900                 905                 910

Phe Gln Arg Arg Gly Gln Asp Val Tyr Phe Leu Arg Asp Asn Gln Val
                        915                 920                 925

Ile Lys Asn Glu Phe Val Gln Asp Gly Asn Gly Asn Trp Tyr Tyr Phe
    930                 935                 940

Gly Ala Asp Gly Lys Met Thr Lys Gly Ala Gln Asn Ile Asn Ser Lys
    945                 950                 955                 960

Asp Tyr Tyr Phe Phe Asp Asn Gly Val Gln Leu Arg Asn Ala Leu Arg
                        965                 970                 975

Arg Ala Ser Asn Gly Tyr Thr Tyr Tyr Gly Leu Asp Gly Ala Met
                        980                 985                 990

Ile Lys Asn Ala Phe Val Asp Phe Asp Asp Lys His Gln Gln Val Arg
                        995                 1000                1005

Ala Phe Thr Thr Gln Gly Thr Met Val Val Gly Asn Leu His Trp
    1010                1015                1020

Ser Gly His His Phe Tyr Phe Asp Arg Glu Thr Gly Ile Gln Ala
    1025                1030                1035

Lys Asp Arg Ile Val Arg Thr Asp Asp Gly Lys Leu His Tyr Tyr
    1040                1045                1050

Val Ala Gln Thr Gly Asp Met Gly Arg Asn Val Phe Ala Thr Asp
    1055                1060                1065

Ser Arg Thr Gly Lys Arg Tyr Tyr Phe Asp Ala Asp Gly Asn Thr
    1070                1075                1080

Val Thr Gly Ser Arg Val Ile Asp Gly Lys Thr Tyr Tyr Phe Asn
    1085                1090                1095

Gln Asp Gly Ser Val Gly Thr Ala Tyr Ser Asn Arg Ala Asp Ser
    1100                1105                1110

Ile Ile Phe Glu Asn Gly Lys Ala Arg Tyr Ile Thr Pro Ala Gly
    1115                1120                1125

Glu Ile Gly Arg Ser Ile Phe Val Tyr Asn Pro Ala Thr Lys Ala
    1130                1135                1140

Trp Asn Tyr Phe Asp Lys Glu Gly Asn Arg Val Thr Gly Arg Gln
    1145                1150                1155

Tyr Ile Asp Gly Asn Leu Tyr Tyr Phe Lys Glu Asp Gly Ser Gln
    1160                1165                1170
```

```
Val Lys Gly Ala Ile Val Glu Glu Asn Gly Ile Lys Tyr Tyr Tyr
    1175            1180            1185

Glu Pro Gly Ser Gly Ile Leu Ala Ser Gly Arg Tyr Leu Gln Val
    1190            1195            1200

Gly Asp Asp Gln Trp Ile Tyr Phe Lys His Asp Gly Ser Leu Ala
    1205            1210            1215

Ile Gly Gln Val Arg Ala Asp Gly Gly Tyr Leu Lys Tyr Phe Asp
    1220            1225            1230

Lys Asn Gly Ile Gln Val Lys Gly Gln Thr Ile Val Glu Asp Gly
    1235            1240            1245

His Thr Tyr Tyr Tyr Asp Ala Asp Ser Gly Ala Leu Val Thr Ser
    1250            1255            1260

Ser Phe Ala Glu Ile Ala Pro Asn Gln Trp Ala Tyr Phe Asn Thr
    1265            1270            1275

Glu Gly Gln Ala Leu Lys Gly Lys Trp Thr Ile Asn Gly Lys Glu
    1280            1285            1290

Tyr Tyr Phe Asp Gln Asn Gly Ile Gln Tyr Lys Gly Lys Ala Val
    1295            1300            1305

Lys Val Gly Ser Arg Tyr Lys Tyr Tyr Asp Glu Asn Asp Gly Gln
    1310            1315            1320

Pro Val Thr Asn Arg Phe Ala Gln Ile Glu Pro Asn Val Trp Ala
    1325            1330            1335

Tyr Phe Gly Ala Asp Gly Tyr Ala Val Thr Gly Glu Gln Val Ile
    1340            1345            1350

Asn Gly Gln His Leu Tyr Phe Asp Gln Ser Gly Arg Gln Val Lys
    1355            1360            1365

Gly Ala Tyr Val Thr Val Asn Gly Gln Arg Arg Tyr Tyr Asp Ala
    1370            1375            1380

Asn Thr Gly Glu Tyr Ile Pro Gly Arg
    1385            1390

<210> SEQ ID NO 43
<211> LENGTH: 1455
<212> TYPE: PRT
<213> ORGANISM: Streptococcus mutans

<400> SEQUENCE: 43

Met Glu Lys Lys Val Arg Phe Lys Leu Arg Lys Val Lys Arg Trp
1               5               10              15

Val Thr Val Ser Val Ala Ser Ala Val Val Thr Leu Thr Ser Leu
                20              25              30

Gly Ser Leu Val Lys Ala Asp Ser Thr Asp Arg Gln Gln Ala Val
            35              40              45

Thr Glu Ser Gln Ala Ser Leu Val Thr Thr Ser Glu Ala Ala Lys Glu
50              55              60

Thr Leu Thr Ala Thr Asp Thr Thr Ala Thr Ser Ala Thr Ser Gln
65              70              75              80

Leu Thr Ala Thr Val Thr Asp Asn Val Ser Thr Thr Asn Gln Ser Thr
                85              90              95

Asn Thr Thr Ala Asn Thr Ala Asn Phe Asp Val Lys Pro Thr Thr Thr
            100             105             110

Ser Glu Gln Ser Lys Thr Asp Asn Ser Asp Lys Ile Ile Ala Thr Ser
        115             120             125

Lys Ala Val Asn Arg Leu Thr Ala Thr Gly Lys Phe Val Pro Ala Asn
```

```
            130                 135                 140
Asn Asn Thr Ala His Pro Lys Thr Val Thr Asp Lys Ile Val Pro Ile
145                 150                 155                 160

Lys Pro Lys Ile Gly Lys Leu Lys Gln Pro Ser Ser Leu Ser Gln Asp
                165                 170                 175

Asp Ile Ala Ala Leu Gly Asn Val Lys Asn Ile Arg Lys Val Asn Gly
                180                 185                 190

Lys Tyr Tyr Tyr Tyr Lys Glu Asp Gly Thr Leu Gln Lys Asn Tyr Ala
                195                 200                 205

Leu Asn Ile Asn Gly Lys Thr Phe Phe Phe Asp Glu Thr Gly Ala Leu
                210                 215                 220

Ser Asn Asn Thr Leu Pro Ser Lys Lys Gly Asn Ile Thr Asn Asn Asp
225                 230                 235                 240

Asn Thr Asn Ser Phe Ala Gln Tyr Asn Gln Val Tyr Ser Thr Asp Ala
                245                 250                 255

Ala Asn Phe Glu His Val Asp His Tyr Leu Thr Ala Glu Ser Trp Tyr
                260                 265                 270

Arg Pro Lys Tyr Ile Leu Lys Asp Gly Lys Thr Trp Thr Gln Ser Thr
                275                 280                 285

Glu Lys Asp Phe Arg Pro Leu Leu Met Thr Trp Trp Pro Asp Gln Glu
                290                 295                 300

Thr Gln Arg Gln Tyr Val Asn Tyr Met Asn Ala Gln Leu Gly Ile His
305                 310                 315                 320

Gln Thr Tyr Asn Thr Ala Thr Ser Pro Leu Gln Leu Asn Leu Ala Ala
                325                 330                 335

Gln Thr Ile Gln Thr Lys Ile Glu Glu Lys Ile Thr Ala Glu Lys Asn
                340                 345                 350

Thr Asn Trp Leu Arg Gln Thr Ile Ser Ala Phe Val Lys Thr Gln Ser
                355                 360                 365

Ala Trp Asn Ser Asp Ser Glu Lys Pro Phe Asp Asp His Leu Gln Lys
370                 375                 380

Gly Ala Leu Leu Tyr Ser Asn Asn Ser Lys Leu Thr Ser Gln Ala Asn
385                 390                 395                 400

Ser Asn Tyr Arg Ile Leu Asn Arg Thr Pro Thr Asn Gln Thr Gly Lys
                405                 410                 415

Lys Asp Pro Arg Tyr Thr Ala Asp Arg Thr Ile Gly Gly Tyr Glu Phe
                420                 425                 430

Leu Leu Ala Asn Asp Val Asp Asn Ser Asn Pro Val Val Gln Ala Glu
                435                 440                 445

Gln Leu Asn Trp Leu His Phe Leu Met Asn Phe Gly Asn Ile Tyr Ala
                450                 455                 460

Asn Asp Pro Asp Ala Asn Phe Asp Ser Ile Arg Val Asp Ala Val Asp
465                 470                 475                 480

Asn Val Asp Ala Asp Leu Leu Gln Ile Ala Gly Asp Tyr Leu Lys Ala
                485                 490                 495

Ala Lys Gly Ile His Lys Asn Asp Lys Ala Ala Asn Asp His Leu Ser
                500                 505                 510

Ile Leu Glu Ala Trp Ser Tyr Asn Asp Thr Pro Tyr Leu His Asp Asp
                515                 520                 525

Gly Asp Asn Met Ile Asn Met Asp Asn Arg Leu Arg Leu Ser Leu Leu
                530                 535                 540

Tyr Ser Leu Ala Lys Pro Leu Asn Gln Arg Ser Gly Met Asn Pro Leu
545                 550                 555                 560
```

-continued

Ile Thr Asn Ser Leu Val Asn Arg Thr Asp Asn Ala Glu Thr Ala
            565                 570                 575

Ala Val Pro Ser Tyr Ser Phe Ile Arg Ala His Asp Ser Glu Val Gln
            580                 585                 590

Asp Leu Ile Arg Asn Ile Ile Arg Ala Glu Ile Asn Pro Asn Val Val
            595                 600                 605

Gly Tyr Ser Phe Thr Met Glu Glu Ile Lys Lys Ala Phe Glu Ile Tyr
            610                 615                 620

Asn Lys Asp Leu Leu Ala Thr Glu Lys Lys Tyr Thr His Tyr Asn Thr
625                 630                 635                 640

Ala Leu Ser Tyr Ala Leu Leu Leu Thr Asn Lys Ser Ser Val Pro Arg
            645                 650                 655

Val Tyr Tyr Gly Asp Met Phe Thr Asp Asp Gly Gln Tyr Met Ala His
            660                 665                 670

Lys Thr Ile Asn Tyr Glu Ala Ile Glu Thr Leu Leu Lys Ala Arg Ile
            675                 680                 685

Lys Tyr Val Ser Gly Gly Gln Ala Met Arg Asn Gln Gln Val Gly Asn
            690                 695                 700

Ser Glu Ile Ile Thr Ser Val Arg Tyr Gly Lys Gly Ala Leu Lys Ala
705                 710                 715                 720

Thr Asp Thr Gly Asp Arg Thr Thr Arg Thr Ser Gly Val Ala Val Ile
            725                 730                 735

Glu Gly Asn Asn Pro Ser Leu Arg Leu Lys Ala Ser Asp Arg Val Val
            740                 745                 750

Val Asn Met Gly Ala Ala His Lys Asn Gln Ala Tyr Arg Pro Leu Leu
            755                 760                 765

Leu Thr Thr Asp Asn Gly Ile Lys Ala Tyr His Ser Asp Gln Glu Ala
            770                 775                 780

Ala Gly Leu Val Arg Tyr Thr Asn Asp Arg Gly Glu Leu Ile Phe Thr
785                 790                 795                 800

Ala Ala Asp Ile Lys Gly Tyr Ala Asn Pro Gln Val Ser Gly Tyr Leu
            805                 810                 815

Gly Val Trp Val Pro Val Gly Ala Ala Ala Asp Gln Asp Val Arg Val
            820                 825                 830

Ala Ala Ser Thr Ala Pro Ser Thr Asp Gly Lys Ser Val His Gln Asn
            835                 840                 845

Ala Ala Leu Asp Ser Arg Val Met Phe Glu Gly Phe Ser Asn Phe Gln
850                 855                 860

Ala Phe Ala Thr Lys Lys Glu Glu Tyr Thr Asn Val Val Ile Ala Lys
865                 870                 875                 880

Asn Val Asp Lys Phe Ala Glu Trp Gly Val Thr Asp Phe Glu Met Ala
            885                 890                 895

Pro Gln Tyr Val Ser Ser Thr Asp Gly Ser Phe Leu Asp Ser Val Ile
            900                 905                 910

Gln Asn Gly Tyr Ala Phe Thr Asp Arg Tyr Asp Leu Gly Ile Ser Lys
            915                 920                 925

Pro Asn Lys Tyr Gly Thr Ala Asp Asp Leu Val Lys Ala Ile Lys Ala
            930                 935                 940

Leu His Ser Lys Gly Ile Lys Val Met Ala Asp Trp Val Pro Asp Gln
945                 950                 955                 960

Met Tyr Ala Phe Pro Glu Lys Glu Val Val Thr Ala Thr Arg Val Asp
            965                 970                 975

-continued

```
Lys Tyr Gly Thr Pro Val Ala Gly Ser Gln Ile Lys Asn Thr Leu Tyr
            980                 985                 990

Val Val Asp Gly Lys Ser Ser Gly Lys Asp Gln Gln Ala Lys Tyr Gly
        995                 1000                1005

Gly Ala Phe Leu Glu Glu Leu Gln Ala Lys Tyr Pro Glu Leu Phe
        1010                1015                1020

Ala Arg Lys Gln Ile Ser Thr Gly Val Pro Met Asp Pro Ser Val
        1025                1030                1035

Lys Ile Lys Gln Trp Ser Ala Lys Tyr Phe Asn Gly Thr Asn Ile
        1040                1045                1050

Leu Gly Arg Gly Ala Gly Tyr Val Leu Lys Asp Gln Ala Thr Asn
        1055                1060                1065

Thr Tyr Phe Ser Leu Val Ser Asp Asn Thr Phe Leu Pro Lys Ser
        1070                1075                1080

Leu Val Asn Pro Asn His Gly Thr Ser Ser Val Thr Gly Leu
        1085                1090                1095

Val Phe Asp Gly Lys Gly Tyr Val Tyr Tyr Ser Thr Ser Gly Tyr
        1100                1105                1110

Gln Ala Lys Asn Thr Phe Ile Ser Leu Gly Asn Asn Trp Tyr Tyr
        1115                1120                1125

Phe Asp Asn Asn Gly Tyr Met Val Thr Gly Ala Gln Ser Ile Asn
        1130                1135                1140

Gly Ala Asn Tyr Tyr Phe Leu Ser Asn Gly Ile Gln Leu Arg Asn
        1145                1150                1155

Ala Ile Tyr Asp Asn Gly Asn Lys Val Leu Ser Tyr Tyr Gly Asn
        1160                1165                1170

Asp Gly Arg Arg Tyr Glu Asn Gly Tyr Tyr Leu Phe Gly Gln Gln
        1175                1180                1185

Trp Arg Tyr Phe Gln Asn Gly Ile Met Ala Val Gly Leu Thr Arg
        1190                1195                1200

Val His Gly Ala Val Gln Tyr Phe Asp Ala Ser Gly Phe Gln Ala
        1205                1210                1215

Lys Gly Gln Phe Ile Thr Thr Ala Asp Gly Lys Leu Arg Tyr Phe
        1220                1225                1230

Asp Arg Asp Ser Gly Asn Gln Ile Ser Asn Arg Phe Val Arg Asn
        1235                1240                1245

Ser Lys Gly Glu Trp Phe Leu Phe Asp His Asn Gly Val Ala Val
        1250                1255                1260

Thr Gly Thr Val Thr Phe Asn Gly Gln Arg Leu Tyr Phe Lys Pro
        1265                1270                1275

Asn Gly Val Gln Ala Lys Gly Glu Phe Ile Arg Asp Ala Asp Gly
        1280                1285                1290

His Leu Arg Tyr Tyr Asp Pro Asn Ser Gly Asn Glu Val Arg Asn
        1295                1300                1305

Arg Phe Val Arg Asn Ser Lys Gly Glu Trp Phe Leu Phe Asp His
        1310                1315                1320

Asn Gly Ile Ala Val Thr Gly Ala Arg Val Val Asn Gly Gln Arg
        1325                1330                1335

Leu Tyr Phe Lys Ser Asn Gly Val Gln Ala Lys Gly Glu Leu Ile
        1340                1345                1350

Thr Glu Arg Lys Gly Arg Ile Lys Tyr Tyr Asp Pro Asn Ser Gly
        1355                1360                1365

Asn Glu Val Arg Asn Arg Tyr Val Arg Thr Ser Ser Gly Asn Trp
```

```
              1370              1375              1380
Tyr Tyr Phe Gly Asn Asp Gly Tyr Ala Leu Ile Gly Trp His Val
    1385              1390              1395

Val Glu Gly Arg Arg Val Tyr Phe Asp Glu Asn Gly Val Tyr Arg
    1400              1405              1410

Tyr Ala Ser His Asp Gln Arg Asn His Trp Asn Tyr Asp Tyr Arg
    1415              1420              1425

Arg Asp Phe Gly Arg Gly Ser Ser Ser Ala Ile Arg Phe Arg His
    1430              1435              1440

Ser Arg Asn Gly Phe Phe Asp Asn Phe Phe Arg Phe
    1445              1450              1455

<210> SEQ ID NO 44
<211> LENGTH: 2715
<212> TYPE: DNA
<213> ORGANISM: Streptococcus mutans

<400> SEQUENCE: 44
gtgaacggca atactacta ctacaaagaa gatggaacat tacagaaaaa ctacgcactg     60
aatatcaacg gcaaaacatt tttctttgat gaaacgggag cgttatccaa taacacattg    120
ccgagcaaaa aaggcaacat cacgaacaac gataacacaa actcctttgc tcaatataac    180
caggtgtact caacggatgc agcgaatttt gaacatgtcg accattatct gacagccgaa    240
tcctggtatc gccctaaata catccttaaa gatggaaaaa catggacgca gtctacagaa    300
aaagacttta gaccgctgct tatgacgtgg tggcctgatc aagaaacaca acgccagtat    360
gtcaattaca tgaacgccca actgggcatc catcagacat ataacacagc aacgagcccg    420
ctgcagctta atttagctgc ccaaacgatc cagacaaaaa tcgaagaaaa aatcacgggct    480 gagaaaaata caaactggtt gagacaaacg atcagcgcat ttgttaaaac acagtctgcg    540
tggaatagcg attctgaaaa accgtttgat gaccatttgc aaaaaggagc attgttgtat    600
tccaacaact caaaactgac gtcccaggca aattcaaact accgtatctt gaaccggaca    660
ccgacgaatc aaacaggcaa aaagatcct agatatacgg cggaccgcac aattggcgga    720
tacgaatttc tgcttgctaa cgatgttgac aattctaacc cggttgtgca agccgaacag    780
ttgaactggc tgcatttct tatgaacttt ggaaacatct acgcgaacga tcctgacgct    840 aatttgatt caattagagt cgatgccgta gacaatgttg atgcagactt attgcaaatc    900
gcgggagatt atcttaaagc agcgaaaggt attcataaaa acgataaagc tgccaatgac    960
catttaagca tcttggaagc atggtcttat aatgatacac cgtacttaca tgatgacgga   1020
gataacatga tcaacatgga caaccgtttg cggctgagcc tgctttattc tttagccaaa   1080
ccgttgaacc agcgtagcgg catgaatcct ctgatcacaa actctcttgt aaatcggacg   1140
gatgacaacg ctgaaacagc agcggttccg tcctattcat ttattagagc ccatgattct   1200
gaagtgcaag accttatcag aaatattatc cgcgcagaaa ttaatcctaa cgtcgtaggc   1260 tactcatttta cgatggaaga aatcaaaaaa gcgtttgaaa tctacaacaa agatttattg   1320
gctacagaga aaaatatac gcattacaac acagcgttaa gctatgctct gcttttaacg   1380
aataaatcaa gcgtgccgag agtctattac ggcgatatgt ttacagatga cggacagtat   1440
atggctcata aaacgatcaa ctacgaagct atcgaaacat tgctgaaagc cagaattaaa   1500
tatgtctctg gtggccaagc catgcgcaac caacaagtgg aaattccgaa attatcacg   1560 tcagtccgtt atggcaaagg agcgcttaaa gctacagata cgggcgacag aacaacgcgc   1620
```

```
acatcaggag tggcagtcat cgaaggcaat aacccgtccc ttagattaaa agcgtcagat      1680
cgcgttgtgg tcaacatggg agctgcccat aaaaatcagg cttatcggcc tcttttattg      1740
acaacggata atggcattaa agcctatcat tcagaccaag aagcagcggg tctggtccgt      1800
tacacgaacg atcggggcga acttatcttt acagctgccg acattaaagg atatgcaaat      1860
cctcaggttt caggctactt aggagtatgg gttcctgtgg gcgcagcggc tgatcaagac      1920
gtcagagtag ccgcatccac ggcgccgtca acagacggaa aaagcgtaca tcagaacgcg      1980
gctctggata gccgcgttat gtttgaaggc ttttctaact ttcaagcctt tgcaacgaaa      2040
aaagaagaat acacaaacgt agttatcgca aaaaatgtag ataaatttgc ggaatgggga      2100
gttacggact ttgaaatggc gccgcagtat gtatcttcca cagatggcag ctttctggac      2160
tctgttatcc aaaacggata tgcatttacg gatagatacg accttggcat ctcaaaacct      2220
aacaaatacg gaacagcgga tgacctggtt aaagccatca agcacttca tagcaaaggc      2280 attaaagtaa tggcagattg ggttccggac cagatgtatg cgtttcctga aaagaagtg       2340 gtcacagcta cgcgcgtaga taaatatggt acgccggttg ctggcagcca aatcaaaaac      2400
acactgtacg tagttgatgg caaatcaagc ggaaaagacc aacaggccaa atatggaggt      2460
gcatttctgg aagaacttca agctaaatac cctgaacttt tgcccgtaa acagatctct       2520 acaggagtgc cgatggaccc gtccgtcaaa atcaaacagt ggtcagcaaa atactttaac      2580
ggcacaaaca tcttaggtcg gggcgcagga tatgtgttga agaccaagc gacaaacacg       2640 tactttagcc tggtgtctga taatacattt ctgccgaaat cacttgtcaa tcctaaccat      2700
ggaacgtctt cctaa                                                       2715
```

<210> SEQ ID NO 45
<211> LENGTH: 904
<212> TYPE: PRT
<213> ORGANISM: Streptococcus mutans

<400> SEQUENCE: 45

```
Val Asn Gly Lys Tyr Tyr Tyr Lys Glu Asp Gly Thr Leu Gln Lys
1               5                   10                  15

Asn Tyr Ala Leu Asn Ile Asn Gly Lys Thr Phe Phe Phe Asp Glu Thr
            20                  25                  30

Gly Ala Leu Ser Asn Asn Thr Leu Pro Ser Lys Lys Gly Asn Ile Thr
        35                  40                  45

Asn Asn Asp Asn Thr Asn Ser Phe Ala Gln Tyr Asn Gln Val Tyr Ser
    50                  55                  60

Thr Asp Ala Ala Asn Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Asp Gln Glu Thr Gln Arg Gln Tyr Val Asn Tyr Met Asn Ala Gln Leu
        115                 120                 125

Gly Ile His Gln Thr Tyr Asn Thr Ala Thr Ser Pro Leu Gln Leu Asn
    130                 135                 140

Leu Ala Ala Gln Thr Ile Gln Thr Lys Ile Glu Glu Lys Ile Thr Ala
145                 150                 155                 160

Glu Lys Asn Thr Asn Trp Leu Arg Gln Thr Ile Ser Ala Phe Val Lys
                165                 170                 175
```

```
Thr Gln Ser Ala Trp Asn Ser Asp Ser Glu Lys Pro Phe Asp Asp His
            180                 185                 190
Leu Gln Lys Gly Ala Leu Leu Tyr Ser Asn Asn Ser Lys Leu Thr Ser
        195                 200                 205
Gln Ala Asn Ser Asn Tyr Arg Ile Leu Asn Arg Thr Pro Thr Asn Gln
    210                 215                 220
Thr Gly Lys Lys Asp Pro Arg Tyr Thr Ala Asp Arg Thr Ile Gly Gly
225                 230                 235                 240
Tyr Glu Phe Leu Leu Ala Asn Asp Val Asp Asn Ser Asn Pro Val Val
                245                 250                 255
Gln Ala Glu Gln Leu Asn Trp Leu His Phe Leu Met Asn Phe Gly Asn
        260                 265                 270
Ile Tyr Ala Asn Asp Pro Asp Ala Asn Phe Asp Ser Ile Arg Val Asp
    275                 280                 285
Ala Val Asp Asn Val Asp Ala Asp Leu Leu Gln Ile Ala Gly Asp Tyr
290                 295                 300
Leu Lys Ala Ala Lys Gly Ile His Lys Asn Asp Lys Ala Ala Asn Asp
305                 310                 315                 320
His Leu Ser Ile Leu Glu Ala Trp Ser Tyr Asn Asp Thr Pro Tyr Leu
                325                 330                 335
His Asp Asp Gly Asp Asn Met Ile Asn Met Asp Asn Arg Leu Arg Leu
                340                 345                 350
Ser Leu Leu Tyr Ser Leu Ala Lys Pro Leu Asn Gln Arg Ser Gly Met
            355                 360                 365
Asn Pro Leu Ile Thr Asn Ser Leu Val Asn Arg Thr Asp Asp Asn Ala
370                 375                 380
Glu Thr Ala Ala Val Pro Ser Tyr Ser Phe Ile Arg Ala His Asp Ser
385                 390                 395                 400
Glu Val Gln Asp Leu Ile Arg Asn Ile Ile Arg Ala Glu Ile Asn Pro
                405                 410                 415
Asn Val Val Gly Tyr Ser Phe Thr Met Glu Glu Ile Lys Lys Ala Phe
                420                 425                 430
Glu Ile Tyr Asn Lys Asp Leu Leu Ala Thr Glu Lys Lys Tyr Thr His
            435                 440                 445
Tyr Asn Thr Ala Leu Ser Tyr Ala Leu Leu Leu Thr Asn Lys Ser Ser
        450                 455                 460
Val Pro Arg Val Tyr Tyr Gly Asp Met Phe Thr Asp Asp Gly Gln Tyr
465                 470                 475                 480
Met Ala His Lys Thr Ile Asn Tyr Glu Ala Ile Glu Thr Leu Leu Lys
                485                 490                 495
Ala Arg Ile Lys Tyr Val Ser Gly Gln Ala Met Arg Asn Gln Gln
        500                 505                 510
Val Gly Asn Ser Glu Ile Ile Thr Ser Val Arg Tyr Gly Lys Gly Ala
    515                 520                 525
Leu Lys Ala Thr Asp Thr Gly Asp Arg Thr Thr Arg Thr Ser Gly Val
530                 535                 540
Ala Val Ile Glu Gly Asn Asn Pro Ser Leu Arg Leu Lys Ala Ser Asp
545                 550                 555                 560
Arg Val Val Val Asn Met Gly Ala Ala His Lys Asn Gln Ala Tyr Arg
                565                 570                 575
Pro Leu Leu Leu Thr Thr Asp Asn Gly Ile Lys Ala Tyr His Ser Asp
            580                 585                 590
Gln Glu Ala Ala Gly Leu Val Arg Tyr Thr Asn Asp Arg Gly Glu Leu
```

```
              595                 600                 605
Ile Phe Thr Ala Ala Asp Ile Lys Gly Tyr Ala Asn Pro Gln Val Ser
610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                    645                 650                 655

His Gln Asn Ala Ala Leu Asp Ser Arg Val Met Phe Glu Gly Phe Ser
                660                 665                 670

Asn Phe Gln Ala Phe Ala Thr Lys Lys Glu Glu Tyr Thr Asn Val Val
            675                 680                 685

Ile Ala Lys Asn Val Asp Lys Phe Ala Glu Trp Gly Val Thr Asp Phe
690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                    725                 730                 735

Ile Ser Lys Pro Asn Lys Tyr Gly Thr Ala Asp Asp Leu Val Lys Ala
                740                 745                 750

Ile Lys Ala Leu His Ser Lys Gly Ile Lys Val Met Ala Asp Trp Val
            755                 760                 765

Pro Asp Gln Met Tyr Ala Phe Pro Glu Lys Glu Val Val Thr Ala Thr
770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                    805                 810                 815

Lys Tyr Gly Gly Ala Phe Leu Glu Glu Leu Gln Ala Lys Tyr Pro Glu
                820                 825                 830

Leu Phe Ala Arg Lys Gln Ile Ser Thr Gly Val Pro Met Asp Pro Ser
            835                 840                 845

Val Lys Ile Lys Gln Trp Ser Ala Lys Tyr Phe Asn Gly Thr Asn Ile
850                 855                 860

Leu Gly Arg Gly Ala Gly Tyr Val Leu Lys Asp Gln Ala Thr Asn Thr
865                 870                 875                 880

Tyr Phe Ser Leu Val Ser Asp Asn Thr Phe Leu Pro Lys Ser Leu Val
                    885                 890                 895

Asn Pro Asn His Gly Thr Ser Ser
                900

<210> SEQ ID NO 46
<211> LENGTH: 1308
<212> TYPE: DNA
<213> ORGANISM: Penicillium marneffei

<400> SEQUENCE: 46
atgaagcaaa ccacttccct cctcctctca gccatcgcgg caaccagcag cttcagcgga      60
ctaacagccg ctcaaaaact cgcctttgcg cacgtcgtcg tcggcaacac tgcagcacac     120
acccaatcca cctgggaaag cgacattact ctcgcccata actccggtct agatgccttt     180
gccttgaacg gtggattccc cgatggcaac atccccgcac aaatcgccaa cgcttttgcg     240
gcttgtgaag ccctttcaaa tggcttcaag ctattcattt cgtttgacta cctcggtggt     300
ggtcagccct ggcctgcctc agaggttgtg tctatgctga agcagtatgc cagttccgat     360
```

```
tgttatttgg cctatgatgg caagcccttt gtctcaactt ttgagggcac cggaaatatt    420
gcggattggg cgcacggagg tcccattcgg tcggcggtgg atgtttactt tgtgccggat    480
tggacgagtt tggggcctgc tgggattaag tcgtatctcg acaatatcga tggattttc    540
agctggaaca tgtggcctgt aggtgcggcc gatatgaccg acgagcctga tttcgaatgg    600
ctcgatgcaa ttgggtccga caagacgtac atgatgggcg tttcgccatg gttcttccac    660
agtgcaagcg gaggcaccga ctgggtctgg cgtggtgatg acctctggga tgaccgatgg    720
attcaagtca cctgcgtcga ccctcaattt gtccaggtcg tcacatggaa cgactggggt    780
gaatcctcct acatcggccc cttcgtgacc gctagcgaag tccccgccgg ctcattagcc    840
tacgtcgaca acatgtcaca ccaaagcttc cttgacttct tgcctttcta catcgccacc    900
ttcaaaggcg acacattcaa catctcccgc gaccagatgc aatactggta ccgcctcgca    960
cccgccgcag caggcagcgc gtgcggcgta tacggcaatg atcccgatca aggccagact   1020
accgttgacg tcaactccat cgttcaggac aaggtgtttt tcagtgcttt gttgacggct   1080
gatgctactg taacggtgca gattggtagt aatgctgcgg tttcatatga tggtgttgct   1140
ggtatgaacc actggagtca ggactttaat ggccagaccg gcgcggttac gtttagtgtt   1200
gtcagggtg gcgctacagt taagagtggt attggagccg agattacggc ttcgacttcg   1260
ttgtcgaatg ggtgcactaa ttacaaccct tgggttggta gtttctaa               1308
```

<210> SEQ ID NO 47
<211> LENGTH: 435
<212> TYPE: PRT
<213> ORGANISM: Penicillium marneffei

<400> SEQUENCE: 47

```
Met Lys Gln Thr Thr Ser Leu Leu Ser Ala Ile Ala Ala Thr Ser
1               5                   10                  15

Ser Phe Ser Gly Leu Thr Ala Ala Gln Lys Leu Ala Phe Ala His Val
                20                  25                  30

Val Val Gly Asn Thr Ala His Thr Gln Ser Thr Trp Glu Ser Asp
        35                  40                  45

Ile Thr Leu Ala His Asn Ser Gly Leu Asp Ala Phe Ala Leu Asn Gly
        50                  55                  60

Gly Phe Pro Asp Gly Asn Ile Pro Ala Gln Ile Ala Asn Ala Phe Ala
65                  70                  75                  80

Ala Cys Glu Ala Leu Ser Asn Gly Phe Lys Leu Phe Ile Ser Phe Asp
                85                  90                  95

Tyr Leu Gly Gly Gly Gln Pro Trp Pro Ala Ser Glu Val Val Ser Met
                100                 105                 110

Leu Lys Gln Tyr Ala Ser Ser Asp Cys Tyr Leu Ala Tyr Asp Gly Lys
        115                 120                 125

Pro Phe Val Ser Thr Phe Glu Gly Thr Gly Asn Ile Ala Asp Trp Ala
130                 135                 140

His Gly Gly Pro Ile Arg Ser Ala Val Asp Val Tyr Phe Val Pro Asp
145                 150                 155                 160

Trp Thr Ser Leu Gly Pro Ala Gly Ile Lys Ser Tyr Leu Asp Asn Ile
                165                 170                 175

Asp Gly Phe Phe Ser Trp Asn Met Trp Pro Val Gly Ala Ala Asp Met
        180                 185                 190

Thr Asp Glu Pro Asp Phe Glu Trp Leu Asp Ala Ile Gly Ser Asp Lys
        195                 200                 205
```

```
Thr Tyr Met Met Gly Val Ser Pro Trp Phe Phe His Ser Ala Ser Gly
    210                 215                 220

Gly Thr Asp Trp Val Trp Arg Gly Asp Asp Leu Trp Asp Asp Arg Trp
225             230                 235                 240

Ile Gln Val Thr Cys Val Asp Pro Gln Phe Val Gln Val Val Thr Trp
                245                 250                 255

Asn Asp Trp Gly Glu Ser Ser Tyr Ile Gly Pro Phe Val Thr Ala Ser
                260                 265                 270

Glu Val Pro Ala Gly Ser Leu Ala Tyr Val Asp Asn Met Ser His Gln
            275                 280                 285

Ser Phe Leu Asp Phe Leu Pro Phe Tyr Ile Ala Thr Phe Lys Gly Asp
    290                 295                 300

Thr Phe Asn Ile Ser Arg Asp Gln Met Gln Tyr Trp Tyr Arg Leu Ala
305                 310                 315                 320

Pro Ala Ala Ala Gly Ser Ala Cys Gly Val Tyr Gly Asn Asp Pro Asp
                325                 330                 335

Gln Gly Gln Thr Thr Val Asp Val Asn Ser Ile Val Gln Asp Lys Val
            340                 345                 350

Phe Phe Ser Ala Leu Leu Thr Ala Asp Ala Thr Val Thr Val Gln Ile
                355                 360                 365

Gly Ser Asn Ala Ala Val Ser Tyr Asp Gly Val Ala Gly Met Asn His
    370                 375                 380

Trp Ser Gln Asp Phe Asn Gly Gln Thr Gly Ala Val Thr Phe Ser Val
385                 390                 395                 400

Val Arg Gly Gly Ala Thr Val Lys Ser Gly Ile Gly Ala Glu Ile Thr
                405                 410                 415

Ala Ser Thr Ser Leu Ser Asn Gly Cys Thr Asn Tyr Asn Pro Trp Val
            420                 425                 430

Gly Ser Phe
        435
```